US008143386B2

(12) United States Patent
Reed et al.

(10) Patent No.: US 8,143,386 B2
(45) Date of Patent: Mar. 27, 2012

(54) **FUSION PROTEINS OF *MYCOBACTERIUM TUBERCULOSIS* ANTIGENS AND THEIR USES**

(75) Inventors: Steven G. Reed, Bellevue, WA (US); Yasir A. Skeiky, Bellevue, WA (US); Davin C. Dillon, Redmond, WA (US); Mark Alderson, Bainbridge Island, WA (US); Antonio Campos-Nero, Bainbridge Island, WA (US)

(73) Assignee: Corixa Corporation, Seattle, WA (US)

( * ) Notice: Subject to any disclaimer, the term of this patent is extended or adjusted under 35 U.S.C. 154(b) by 234 days.

(21) Appl. No.: 11/978,786

(22) Filed: Oct. 29, 2007

(65) Prior Publication Data

US 2009/0281168 A1 Nov. 12, 2009

Related U.S. Application Data

(60) Division of application No. 11/511,587, filed on Aug. 28, 2006, now Pat. No. 7,335,369, which is a continuation of application No. 11/201,519, filed on Aug. 10, 2005, now abandoned, which is a division of application No. 10/359,460, filed on Feb. 5, 2003, now Pat. No. 6,977,069, which is a continuation of application No. 09/287,849, filed on Apr. 7, 1999, now Pat. No. 6,627,198.

(51) Int. Cl.
  *C07H 21/02* (2006.01)
  *C07H 21/04* (2006.01)
  *A61K 39/04* (2006.01)
(52) U.S. Cl. .............. 536/23.7; 536/23.1; 424/184.1; 424/185.1; 424/192.1; 424/200.1; 424/248.1
(58) Field of Classification Search ............ 424/184.1, 424/185.1, 192.1, 200.1, 248.1; 536/23.1, 536/23.7
See application file for complete search history.

(56) References Cited

U.S. PATENT DOCUMENTS

| | | |
|---|---|---|
| 3,943,119 A | 3/1976 | Tsumita et al. |
| 4,235,877 A | 11/1980 | Fullerton |
| 4,436,727 A | 3/1984 | Ribi |
| 4,603,112 A | 7/1986 | Paoletti et al. |
| 4,689,397 A | 8/1987 | Shinnick et al. |
| 4,751,180 A | 6/1988 | Cousens et al. |
| 4,769,330 A | 9/1988 | Paoletti et al. |
| 4,777,127 A | 10/1988 | Suni et al. |
| 4,866,034 A | 9/1989 | Ribi |
| 4,876,089 A | 10/1989 | Luciw et al. |
| 4,877,611 A | 10/1989 | Cantrell |
| 4,879,213 A | 11/1989 | Fox et al. |
| 4,897,268 A | 1/1990 | Tice et al. |
| 4,912,094 A | 3/1990 | Myers et al. |
| 4,935,233 A | 6/1990 | Bell et al. |
| 4,946,778 A | 8/1990 | Ladner et al. |
| 4,952,395 A | 8/1990 | Shinnick et al. |
| 5,108,745 A | 4/1992 | Horwitz |
| 5,145,684 A | 9/1992 | Liversidge et al. |
| 5,240,856 A | 8/1993 | Goffe et al. |
| 5,330,754 A | 7/1994 | Kapoor et al. |
| 5,466,468 A | 11/1995 | Schneider et al. |
| 5,478,726 A | 12/1995 | Shinnick et al. |
| 5,504,005 A | 4/1996 | Bloom et al. |
| 5,543,158 A | 8/1996 | Gref et al. |
| 5,565,213 A | 10/1996 | Nakamori et al. |
| 5,567,434 A | 10/1996 | Szoka |
| 5,580,579 A | 12/1996 | Ruddy et al. |
| 5,583,112 A | 12/1996 | Kensil et al. |
| 5,599,545 A | 2/1997 | Stanford et al. |
| 5,616,500 A | 4/1997 | Steinert et al. |
| 5,639,653 A | 6/1997 | Bloom et al. |
| 5,714,593 A | 2/1998 | Laqueyrerie et al. |
| 5,780,045 A | 7/1998 | McQuinn |
| 5,783,368 A | 7/1998 | Richter et al. |
| 5,795,587 A | 8/1998 | Gao et al. |
| 5,804,212 A | 9/1998 | Illum |
| 5,811,128 A | 9/1998 | Tice et al. |
| 5,814,344 A | 9/1998 | Tice et al. |
| 5,817,473 A | 10/1998 | Das et al. |
| 5,820,883 A | 10/1998 | Tice et al. |
| 5,853,763 A | 12/1998 | Tice et al. |
| 5,856,462 A | 1/1999 | Agrawal |
| 5,928,647 A | 7/1999 | Rock |
| 5,942,252 A | 8/1999 | Tice et al. |
| 5,955,077 A | 9/1999 | Andersen et al. |
| 5,985,287 A | 11/1999 | Tan et al. |
| 6,001,361 A | 12/1999 | Tan et al. |
| 6,034,218 A | 3/2000 | Reed et al. |

(Continued)

FOREIGN PATENT DOCUMENTS

EP 345242 12/1989

(Continued)

OTHER PUBLICATIONS

Girard, M.P., et al. Vaccine, vol. 23, pp. 5725-5731, 2005.*

(Continued)

*Primary Examiner* — Rodney P. Swartz
(74) *Attorney, Agent, or Firm* — Convergent Law Group LLP

(57) ABSTRACT

The present invention relates to fusion proteins containing at least two *Mycobacterium tuberculosis* antigens. In particular, it relates to bi-fusion proteins which contain two individual *M. tuberculosis* antigens, tri-fusion proteins which contain three *M. tuberculosis* antigens, tetra-fusion proteins which contain four *M. tuberculosis* antigens, and penta-fusion proteins which contain five *M. tuberculosis* antigens, and methods for their use in the diagnosis, treatment and prevention of tuberculosis infection.

23 Claims, 68 Drawing Sheets

U.S. PATENT DOCUMENTS

Figure 14A:
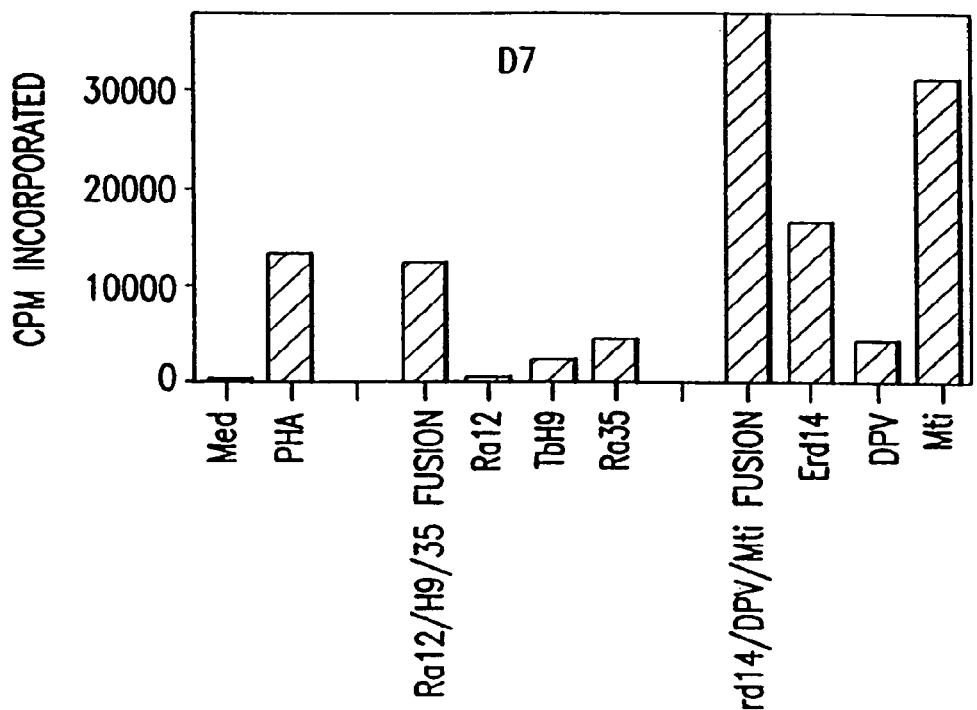
Figure 14B:
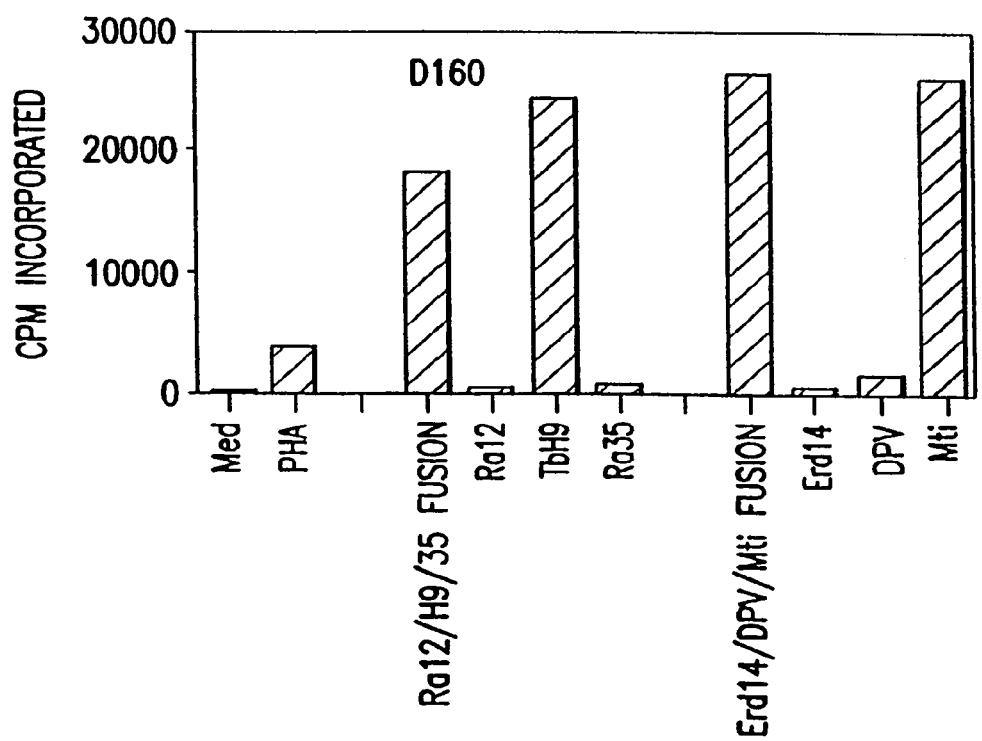
Figure 14C:
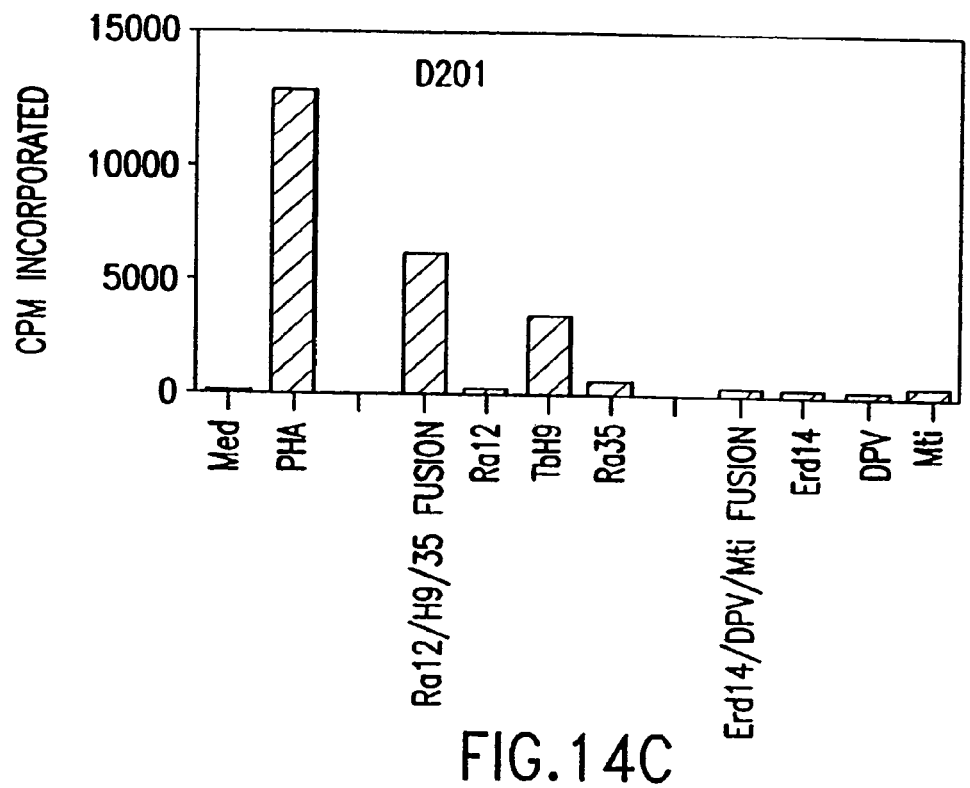
Figure 14D:
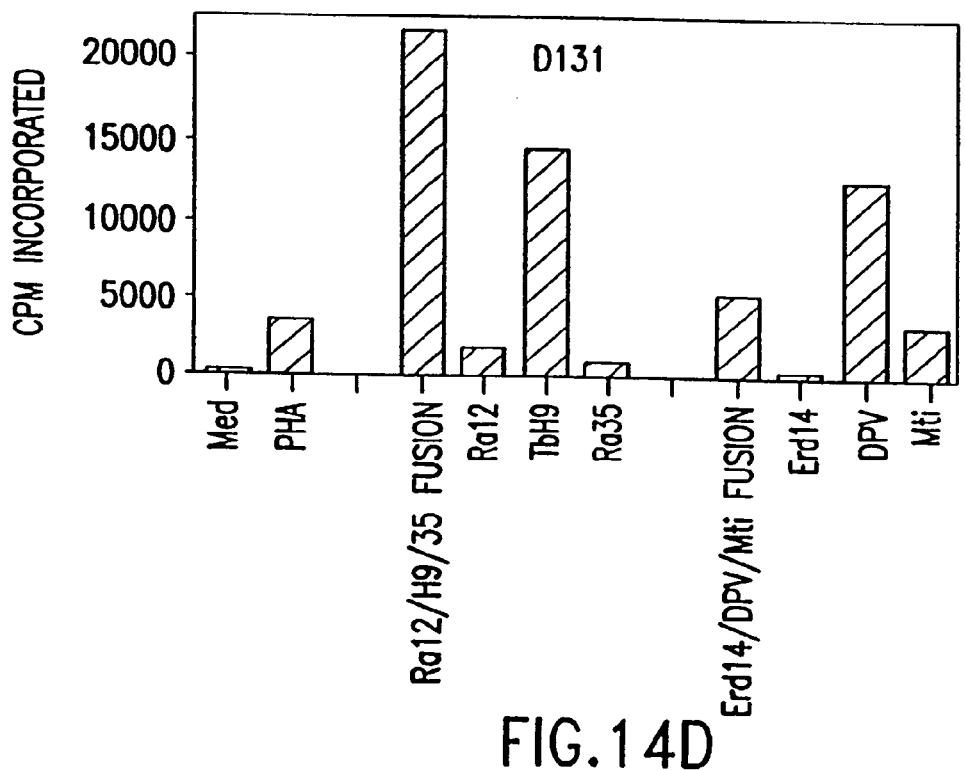
Figure 14E:
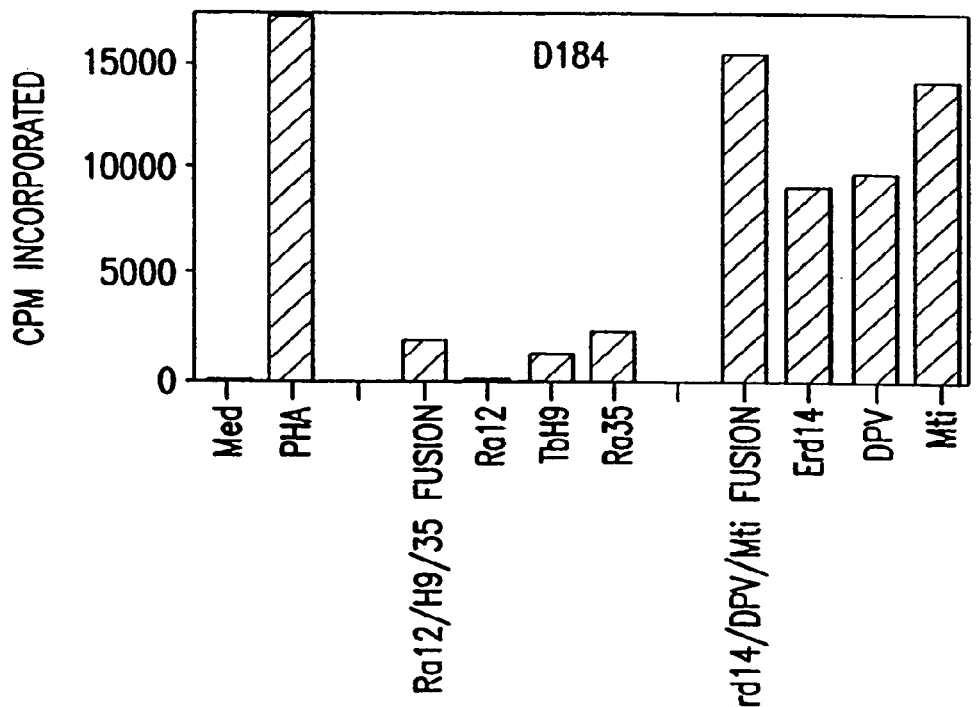
Figure 14F:
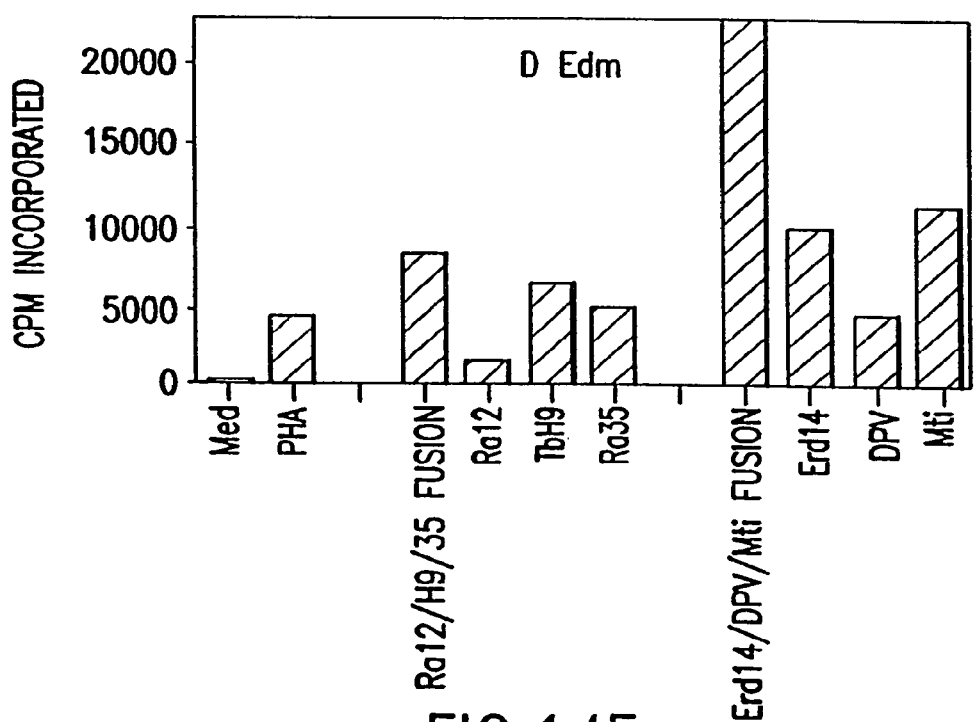
Figure 15A:
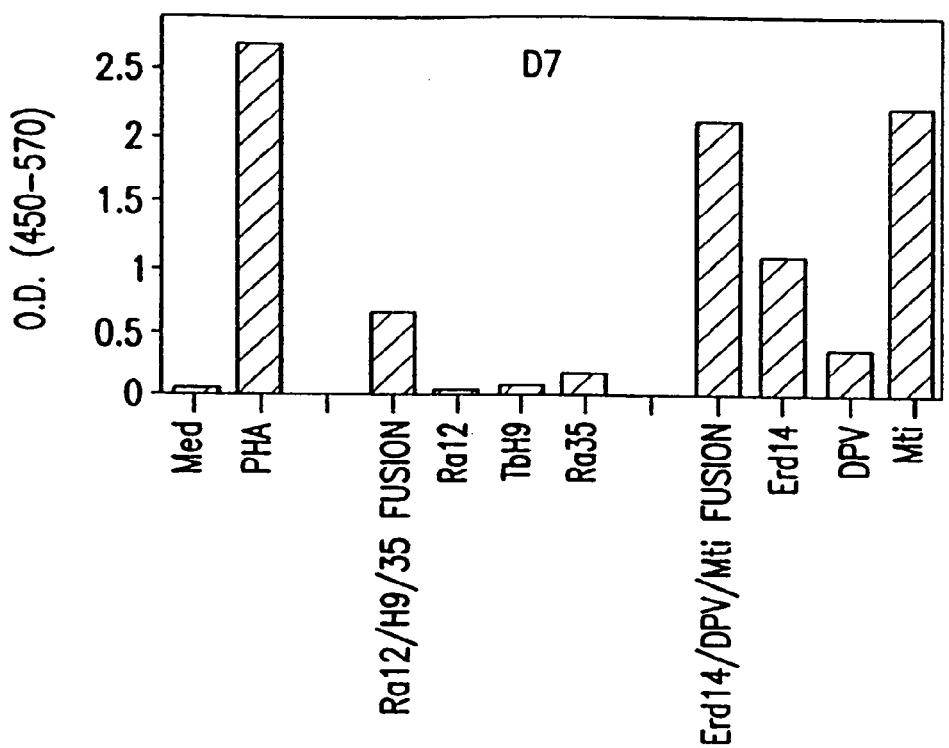
Figure 15B:
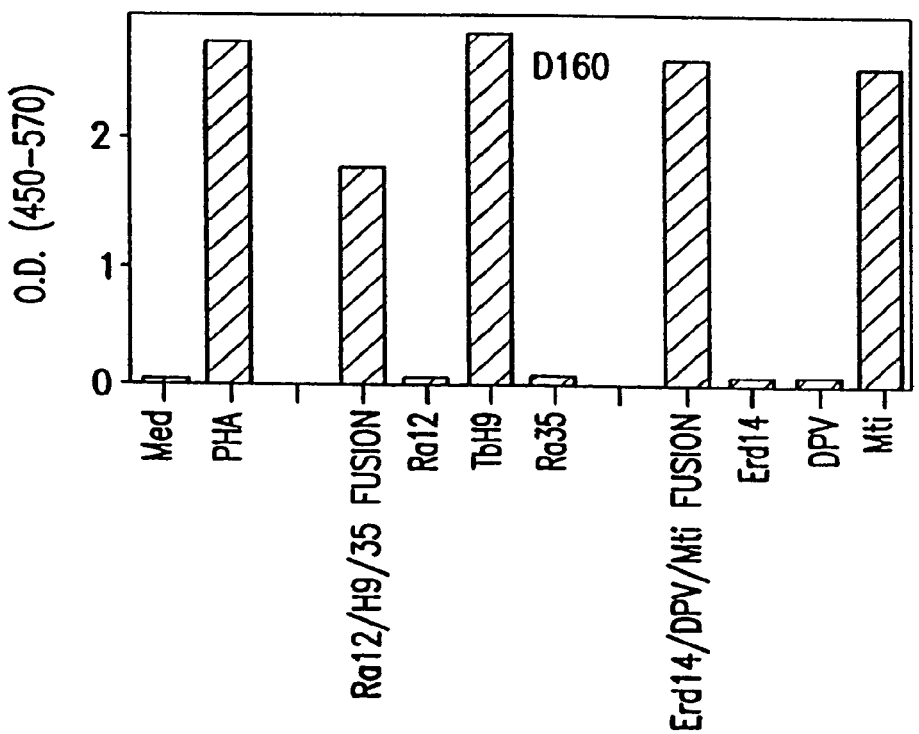
Figure 15C:
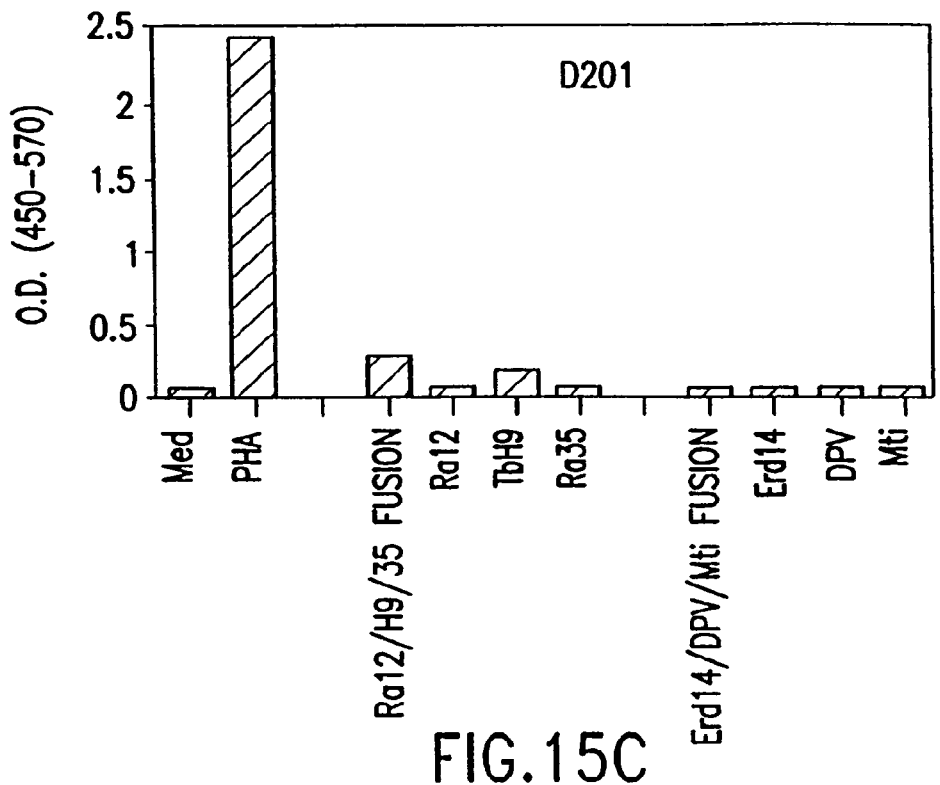
Figure 15D:
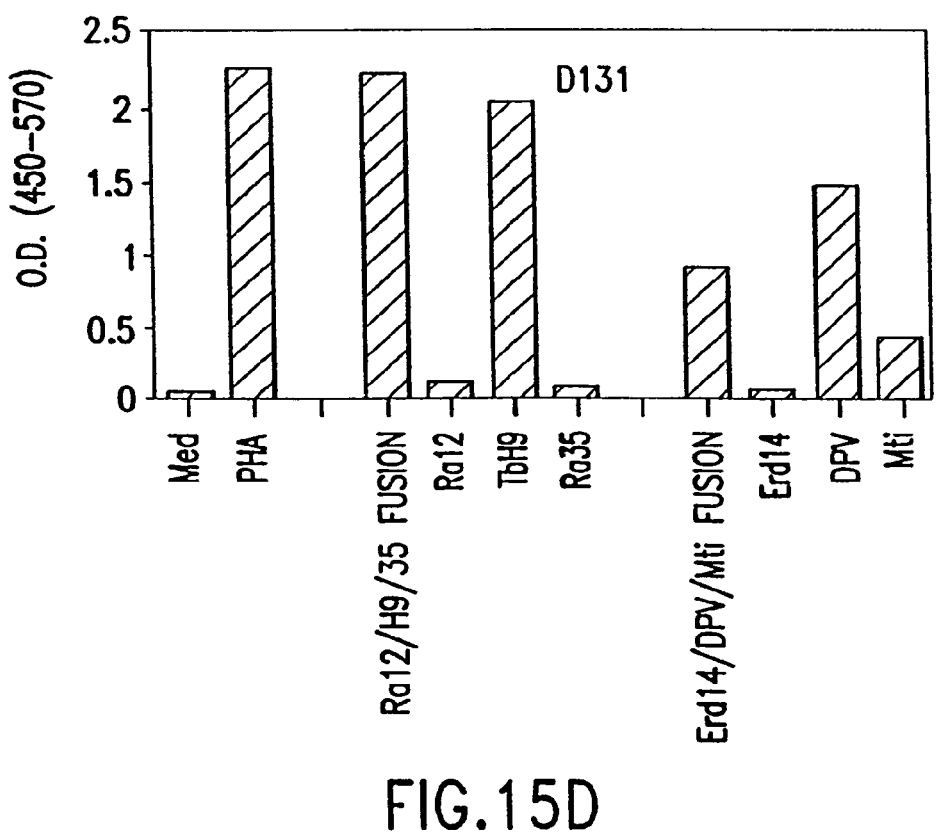
Figure 15E:
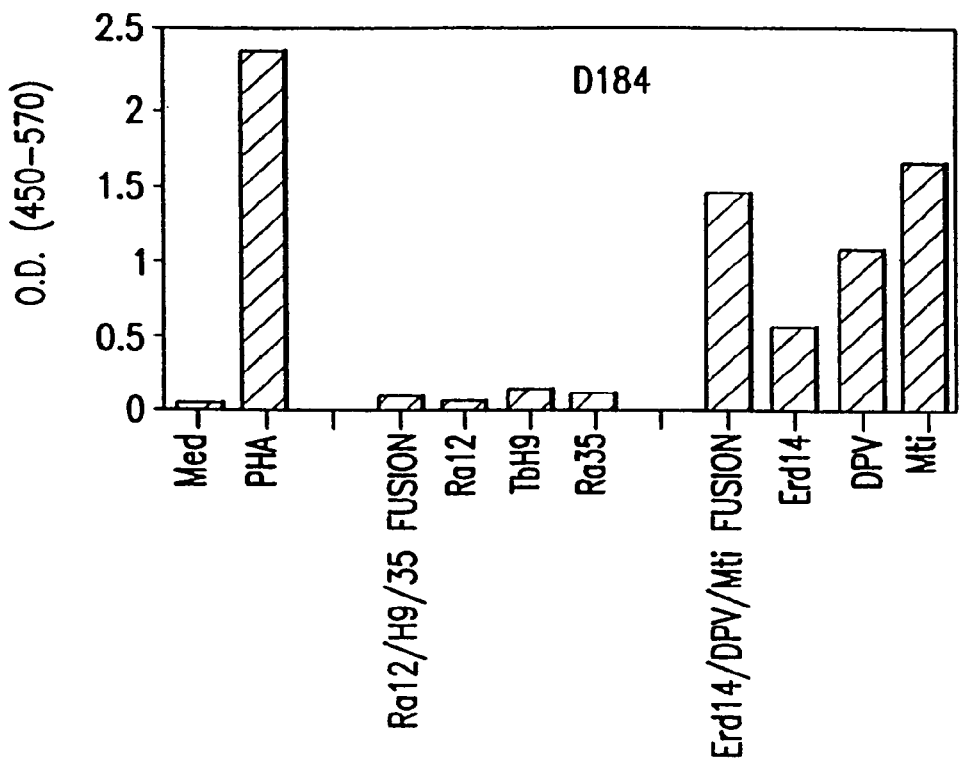
Figure 15F:
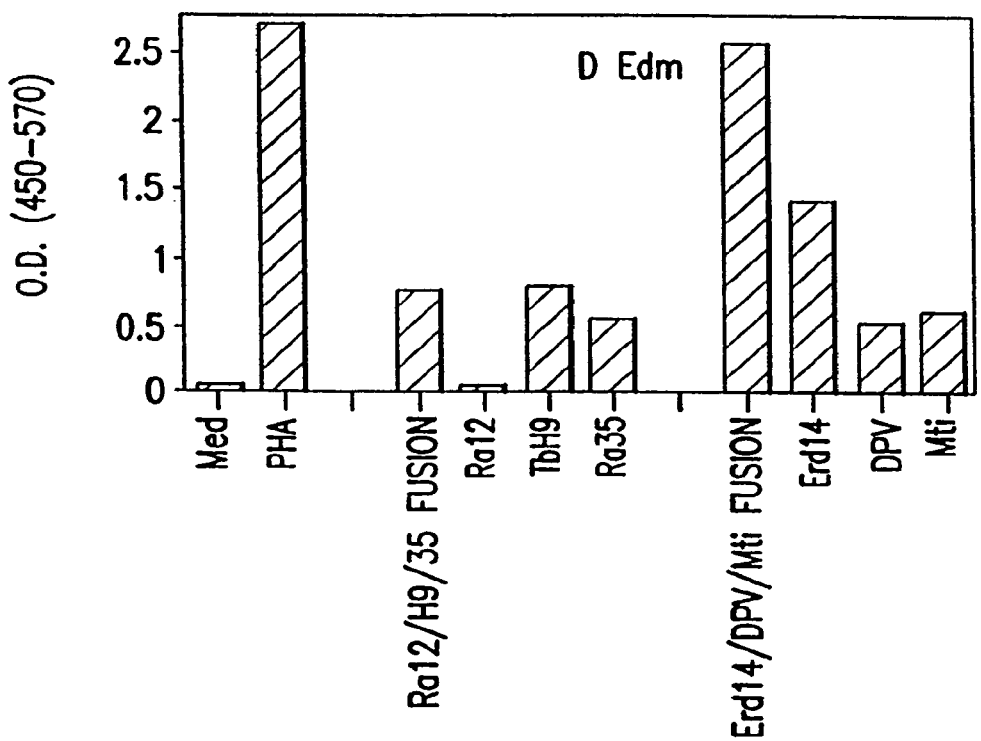
Figure 16A:
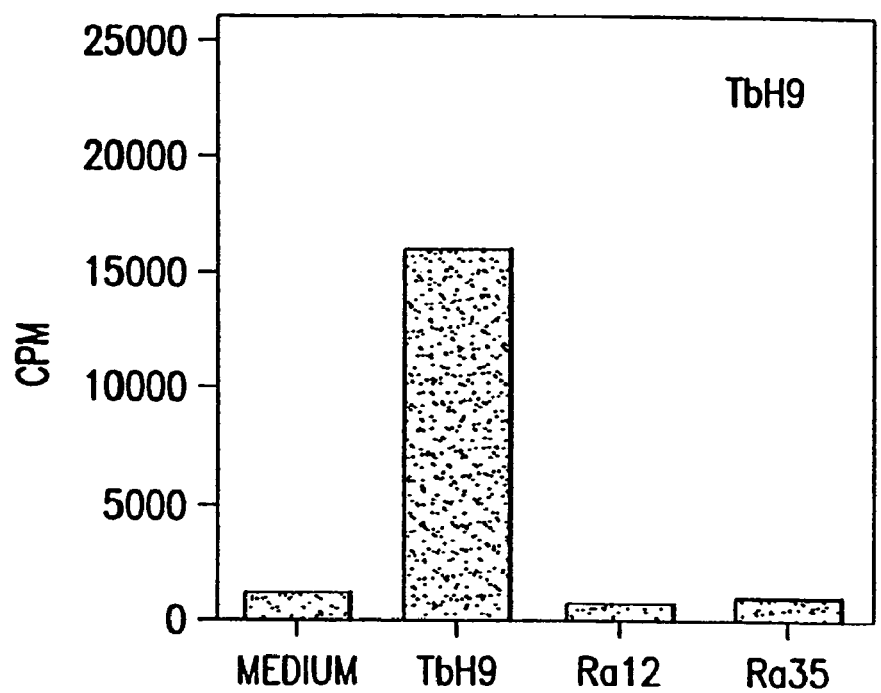
Figure 16B:
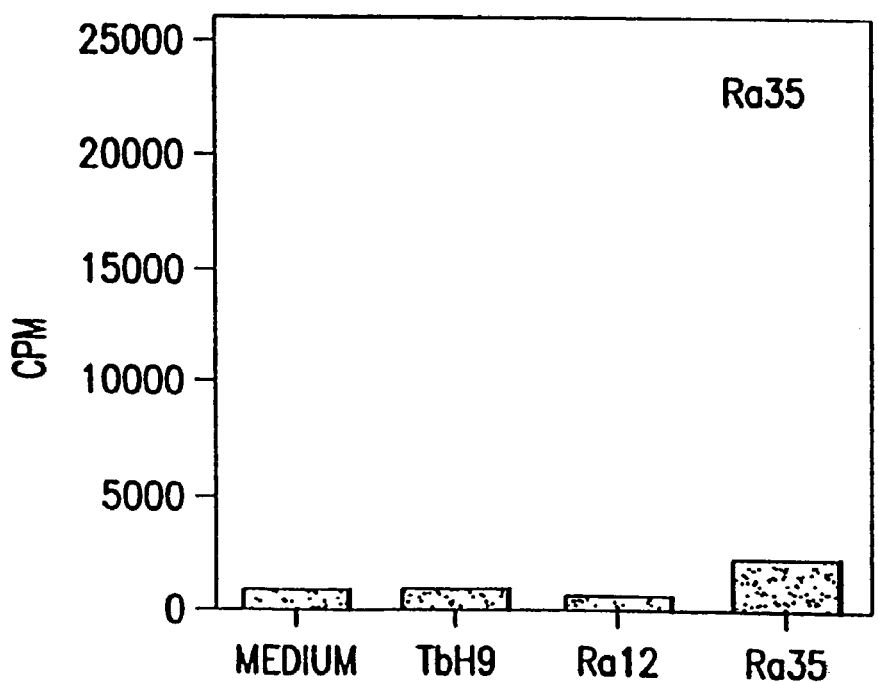
Figure 16C:
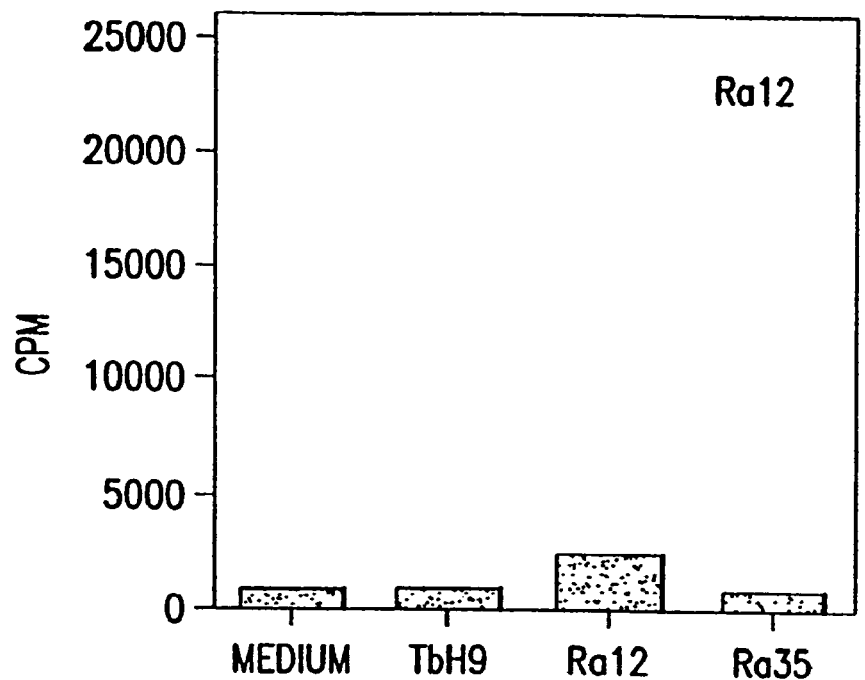
Figure 16D:
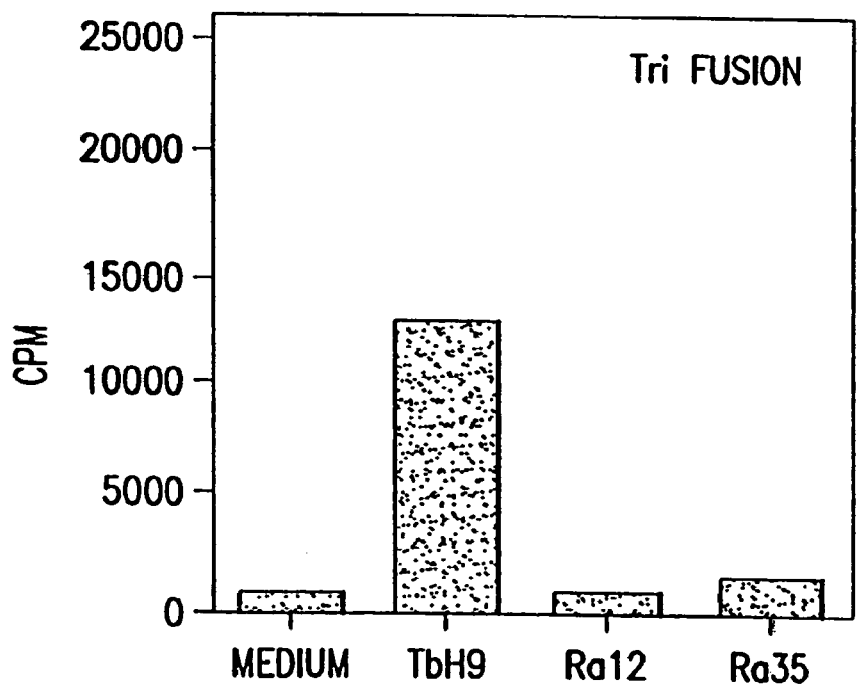
Figure 16E:
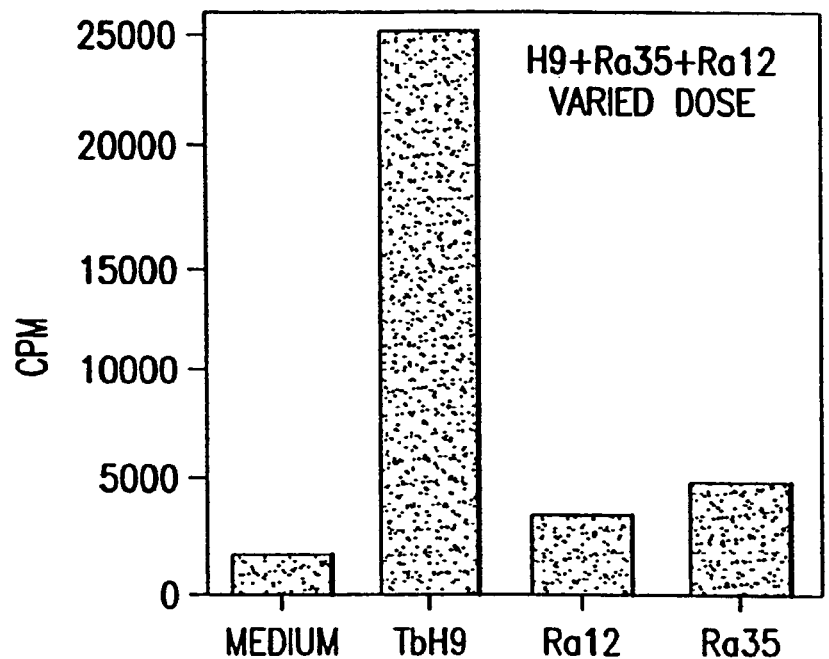
Figure 16F:
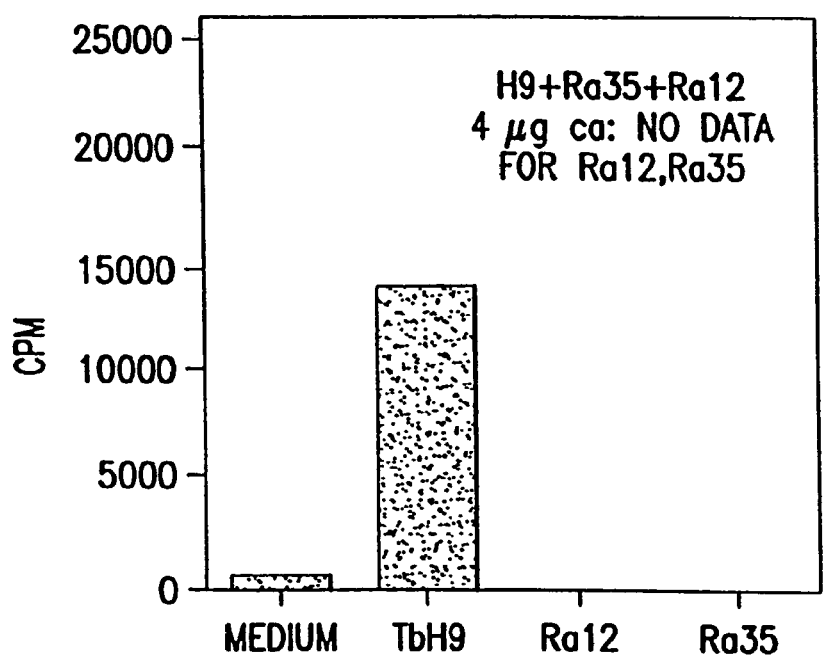

| | | | |
|---|---|---|---|
| 6,037,135 | A | 3/2000 | Kubo et al. |
| 6,113,918 | A | 9/2000 | Johnson et al. |
| 6,290,969 | B1 | 9/2001 | Reed et al. |
| 6,338,852 | B1 | 1/2002 | Reed et al. |
| 6,350,456 | B1 | 2/2002 | Reed et al. |
| 6,355,257 | B1 | 3/2002 | Johnson et al. |
| 6,458,366 | B1 | 10/2002 | Reed et al. |
| 6,465,633 | B1 | 10/2002 | Skeiky |
| 6,544,522 | B1 | 4/2003 | Skeiky et al. |
| 6,555,653 | B2 | 4/2003 | Alderson et al. |
| 6,592,877 | B1 | 7/2003 | Reed et al. |
| 6,613,881 | B1 | 9/2003 | Alderson et al. |
| 6,627,198 | B2 | 9/2003 | Reed et al. |
| 6,949,246 | B2 | 9/2005 | Reed et al. |
| 6,962,710 | B2 | 11/2005 | Reed et al. |
| 6,977,069 | B2 | 12/2005 | Reed et al. |
| 7,026,465 | B2 | 4/2006 | Skeiky et al. |
| 7,064,195 | B2 | 6/2006 | Skeiky et al. |
| 7,083,796 | B2 | 8/2006 | Skeiky et al. |
| 7,087,713 | B2 | 8/2006 | Campos-Neto et al. |
| 7,122,196 | B2 | 10/2006 | Reed et al. |
| 7,186,412 | B1 | 3/2007 | Skeiky et al. |
| 7,261,897 | B2 | 8/2007 | Skeiky et al. |
| 7,311,922 | B1 | 12/2007 | Skeiky et al. |
| 7,335,369 | B2 | 2/2008 | Reed et al. |
| 7,678,375 | B2 | 3/2010 | Skeiky et al. |
| 7,691,993 | B2 | 4/2010 | Skeiky et al. |
| 2006/0193876 | A1 | 8/2006 | Skeiky et al. |
| 2007/0054336 | A1 | 3/2007 | Campos-Neto et al. |
| 2007/0141087 | A1 | 6/2007 | Reed et al. |
| 2008/0176798 | A1 | 7/2008 | Campos-Neto et al. |
| 2008/0199405 | A1 | 8/2008 | Reed et al. |
| 2008/0269151 | A1 | 10/2008 | Skeiky et al. |
| 2008/0317716 | A1 | 12/2008 | Skeiky et al. |
| 2009/0017077 | A1 | 1/2009 | Reed et al. |
| 2009/0018095 | A1 | 1/2009 | Skeiky et al. |
| 2009/0022742 | A1 | 1/2009 | Campos-Neto et al. |
| 2009/0281168 | A1 | 11/2009 | Reed et al. |
| 2009/0306195 | A1 | 12/2009 | Skeiky et al. |
| 2010/0015096 | A1 | 1/2010 | Skeiky et al. |
| 2010/0183657 | A1 | 7/2010 | Skeiky et al. |
| 2010/0183677 | A1 | 7/2010 | Skeiky et al. |

FOREIGN PATENT DOCUMENTS

| | | |
|---|---|---|
| EP | 419355 | 3/1991 |
| EP | 519218 | 12/1992 |
| FR | 2244539 | 4/1975 |
| FR | 2265402 | 10/1975 |
| GB | 2200651 | 8/1988 |
| GB | 2298862 | 9/1996 |
| HU | 158035 | 3/1971 |
| RU | 2024021 | 11/1994 |
| WO | WO 88/05823 | 8/1988 |
| WO | WO 88/06591 | 9/1988 |
| WO | WO 89/01973 | 3/1989 |
| WO | WO 89/06280 | 7/1989 |
| WO | WO 91/02805 | 3/1991 |
| WO | WO 91/04272 | 4/1991 |
| WO | WO 91/14448 | 10/1991 |
| WO | WO 91/18926 | 12/1991 |
| WO | WO 92/04049 | 3/1992 |
| WO | WO 92/07243 | 4/1992 |
| WO | WO 92/14154 | 8/1992 |
| WO | WO 92/14823 | 9/1992 |
| WO | WO 92/16628 | 10/1992 |
| WO | WO 92/21697 | 12/1992 |
| WO | WO 92/21758 | 12/1992 |
| WO | WO 94/00153 | 1/1994 |
| WO | WO 94/00228 | 1/1994 |
| WO | WO 94/00492 | 1/1994 |
| WO | WO 94/00493 | 1/1994 |
| WO | WO 94/14069 | 6/1994 |
| WO | WO 94/20078 | 9/1994 |
| WO | WO 94/23701 | 10/1994 |
| WO | WO 95/01440 | 1/1995 |
| WO | WO 95/01441 | 1/1995 |
| WO | WO 95/14713 | 6/1995 |
| WO | WO 95/17210 | 6/1995 |
| WO | WO 95/17511 | 6/1995 |
| WO | WO 95/31216 | 11/1995 |
| WO | WO 96/02555 | 2/1996 |
| WO | WO 96/06638 | 3/1996 |
| WO | WO 96/15241 | 5/1996 |
| WO | WO 96/23885 | 8/1996 |
| WO | WO 96/28551 | 9/1996 |
| WO | WO 96/33739 | 10/1996 |
| WO | WO 96/38591 | 12/1996 |
| WO | WO 97/09248 | 3/1997 |
| WO | WO 97/09249 | 3/1997 |
| WO | WO 97/09428 | 3/1997 |
| WO | WO 97/09429 | 3/1997 |
| WO | WO 97/24447 | 10/1997 |
| WO | WO 98/07868 | 2/1998 |
| WO | WO 98/16645 | 4/1998 |
| WO | WO 98/16646 | 4/1998 |
| WO | WO 98/44119 | 10/1998 |
| WO | WO 98/53075 | 11/1998 |
| WO | WO 98/53076 | 11/1998 |
| WO | WO 99/09186 | 2/1999 |
| WO | WO 99/33488 | 7/1999 |
| WO | WO 99/42076 | 8/1999 |
| WO | WO 99/42118 | 8/1999 |
| WO | WO 99/51748 | 10/1999 |
| WO | WO 99/52549 | 10/1999 |
| WO | WO 00/09159 | 2/2000 |
| WO | WO 01/24820 | 4/2001 |
| WO | W001/34802 | 5/2001 |
| WO | WO 01/34803 | 5/2001 |
| WO | W001/51633 | 7/2001 |
| WO | WO 01/62893 | 8/2001 |
| WO | W001/73032 | 10/2001 |
| WO | W001/90152 | 11/2001 |
| WO | WO 01/90152 | 11/2001 |
| WO | W001/98460 | 12/2001 |
| WO | WO 2005/076101 | 8/2005 |
| WO | WO 2008/107370 | 9/2008 |

OTHER PUBLICATIONS

Orme, I.M. Vaccine, vol. 24, pp. 2-19, 2006.*

Pal et al., "Immunization with Extracellular Proteins of Mycobacterium tuberculosis Induces Cell-Mediated Immune Responses and Substantial Protective Immunity in a Guinea Pig Model of Pulmonary Tuberculosis"; Infection and Immunity vol. 60, No. 11, pp. 4781-4792 (Nov. 1992).

Philipp et al., An integrated map of the genome of the tubercle bacillus Mycobacterium tuberculosis H37Rv, and comparison with Mycobacterium leprae, Proc. Natl. Acad. Sci, 93:3132-3137 (1996).

Lee et al., Characterization of the Major Membrane Protein of Virulent Mycobacterim tuberculosis, Infection and Immunity, p. 2066-2074 (May 1992).

Tsenova, et al., Evaluation of the Mtb72F Polyprotein Vaccine in a Rabbit Model of Tuberculous Meningitis, Infection and Immunity 74(4):2922-401 (2006).

Vekemans, et al., Immune Responses to Mycobacterial Antigens in the Gambian Population: Implications for Vaccines and Immunodiagostic Test Design, Infection and Immunity 72(1):381-88 (2004).

Von Eschen, et al., The candidate tuberculosis vaccine Mtb72F/AS02A, Human Vaccines 5:7:475-82 (2009).

Altschul, et al., "Gapped BLAST and PSI-BLAST: a new generation of protein database search programs," Nuc. Acids Res. (25):3389-3402 (1977).

Alderson, et al. "Expression Cloning of an Immunodominant Family of *Mycobacterium tuberculosis* Antigens Using Cd4+ T Cells," J. Exp. Med. 191(3): 551-559 (2000).

Andersen and Hansen, "structure and Mapping of Antigenic Domains of Protein Antigen b, a 38,000-Molecular-Weight Protein of *Mycobacterium tuberculosis,* " Infection and Immunity 37(8):2481-2488 (1989).

Andersen and Heron, "Specificity of a Protective Memory Immune Response against *Mycobacterium tuberculosis,* " Infection and Immunity 61(3):844-851 (1993).

Andersen, "Effective Vaccination of Mice against *Mycobacterium tuberculosis* Infection with a Soluble Mixture of Secreted Mycobacterial Proteins," Infections and Immunity 62(6):2536-2544 (1994).

Andersen, et al., "Identification of Immunodominant Antigens of *Mycobacterium tuberculosis,*" Scand. J. Immunol 6:823-831 (1992).

Andersen, et al., "The T Cell Response to Secreted Antigens and *Mycobacterium tuberculosis*," Immunibiol 191:537-547 (1994).

Andersen, et al., "Structure and Mapping of Antigenic Domains of Protein Antigenb, a 38,000-Molecule-Weight Protein of *Mycobacterium tuberculosis,* " Infection and Immunity 57(8):2481-2488 (1989).

Arnon, "Synthetic Peptides as a Basis for Vaccine Design," Molecular Immunology 28(2):209-215 (1991).

Ausubel, et al., "Isolation of Proteins for Microsequence Analysis," Current Protocols in Molecular Biology, Wiley & Sons, NY, pp. 10.19.1-10.19.12 (1993).

Banchereau, et al., "Dendritic cells and the control of immunity," Nature 392:245-251 (1998).

Barnes et al., "Immunoreactivity of a 10-kDa Antigen of *Mycobacterium tuberculosis,* " J. of Immunology 148(6):1835-1840 (1992).

Barrera, et al., Humoral Response to *Mycobacterium Tuberculosis* in Patients with Human Immunodeficienty Virus Infection Tuberde and Lung Disease 73(4):187-91 (1992).

Batzer, et al., "Enhances evolutionary PCR using oligonucleotides with inosine at the 3' terminus" Nuc. Acids Res. 19:5081 (1991).

Berkner, "Development of Adenovirus Vectors for the Expression of Heterologous Genes," Biotechniques 6:616-627 (1988).

Boesen et al., "Human T-Cell Responses to Secreted Antigen Fractions of *Mycobacterium tuberculosis*," Infection and Immunity 63(4):1491-1497 (1995).

Borremans et al., "Cloning, Sequencing Determination, and Exppression of a 32-Kilodalton-Protein Gene of *Mycobacterium tuberculosis,* " Infection and Immunity 57(10):3123-3130 (1989).

Bowie, et al., "Deciphering the Message of Protein Sequences: Tolerance to Amino Acid Substitutions" Science 257:1306-10 (1990).

Brandt, et al. "ESAT-6 subunit vaccination against *Mycobacterium tuberculosis,* " Infection and Immunity 68(2):791-795 (2000).

Brandt, et al. "The Protective Effect of the Mycobacterium bovis BCG Vaccine is increased by Coadministration with *Mycobacterium tuberculosis* 72-Kilodalton Fusion Polyprotein Mtb72F in *M. tuberculosis*-Infected Guinea Pigs" Infection and Immunity 72(11):6622-32 (2004).

Burgess, et al. "Possible Dissociation of the Heparin-binding and Mitogenic Activities of Heparin-Binding (Acidic Fibroblast) Growth Factor-1 from its Receptor-binding Activities by Site-Directed Mutagenesis of a Single Lysine Residue" J. Cell. Biol. 111:2129-2138 (1990).

Cameron, et al., "Identification and characterization of a putative serine expressed in vivo by Micyobacterium avium subsp. Paratuberculosisi," Microbiology 140(8):1977-1982 (1994).

Campos-Neto, et al., "Cutting Edge:CD40 Ligand Is Not Essential for the Development of Cell-Mediated Immunity and Resistance to *Mycobacterium tuberculosis,* " J. Immunol.160(5): 2037-2041 (1988).

Cater and Wells, "Dissecting the catalytic triad of a serine protease," Nature 332: 564-568 (1988).

Carter, "Peptide Analysis Protocols," Methods in Molecular Biology, Chapter 1.1, 36:193-206 (1994).

Chiatra, et al., "Defining putative T cell epitopes from PE and PPE families of protein of *M. tuberculosis* with vaccine potential" Vaccine 23(10):1265-72 (2005).

Chiatra, et al., "HLAA0201-restricted cytotoxix T-cell epitopes in three PE/PPE family of proteins of *M. tuberculosis*" Scand. J. of Immunology 67(4):411-17 (2008).

Chan and Kaufmann, Tuberculosis: Pathogenesis, Protection and Control, Chap. 24, ASM Press (1994).

Chen, et al., "T Cells for Tumor Therapy can be Obtained from Antigen-loaded Sponge Implants" Cancer Res. 54: 1065-1070 (1994).

Cirillo, et al., "Isolation and characterization of the aspartokinase and aspartate semialdehyde dehydrogenase operon from mycobacteria," Molecular Microbiology 11(4): 629-639 (1994).

Cohen, "Naked DNA Points Way to Vaccines" Science 259: 1691-1692 (1993).

Colbere-Garapin, et al., "A New Dominant Hybrid Selective Marker for Higher Eucaryotic Cells," J. Mol. Biol. 150:1-14 (1981).

Cole et al., "Deciphering the biology of *Mycobacterium tuberculosis* from the complete genome sequence," Nature 393: 537-544 (1998).

Coler, et al. "Molecular cloning and immunologic reactivity of a novel low molecular mass abtigen for *Mycobacterium tuberculosis,* " J. Immunol. 161(5):2356-2364 (1998).

Collins, "New Generation of tuberculosis vaccines," Clinical Microbiology Newsletter 23 (3):17-23 (2001).

Content, et al., "The Genes Coding for the Antigen 85 Complexes of *Mycobacterium tuberculosis* and *Mycobacterium bovis* BCG Are Members of a Gene Family: Cloning, Sequence Determination, and Genomic Orginization of the Gene Coding for Antigen 85-C of *M. tuberculosis,* " Infection and Immunity 59:3205-3212 (1991).

Coombes, et al., "Single dose, polymeric, microparticle-based vaccines: the influence of formulation conditions on the magnitude and duration of the immune response to a protein antigen," Vaccine 14:1429-1438 (1996).

Coruzzi, et al., "Tissue-specific and light-regulated expression of a pea nuclear gene encoding the small subunit of ribulose-1,5-biphosphate carboxylase," EMBO 3: 1671-1680 (1984).

Creighton, Protein Structure: A Practical Approach, pp. 184-186 (1989).

Creighton, Proteins: Structures and Molecular Properties, pp. 314-315 (1984).

Daleine, et al., "Preliminary evaluation of a *Mycobacterium tuberculosis* lipoligosaccharide (LOS) antigen in the serological diagnosis of tuberculosis in HIV seropositive and seronegative patients," Tuberde and Lung Disease, 76( 3): 234-39 (1995).

Devereaux, et al., "A Comprehensive System of Sequence Analysis Tools for the VAX," Nuc. Acids Res. 12: 387-395 (1984).

Dillon, et al., "Molecular Characterization and Human T-Cell Responses to a Member of Novel *Mycobacterium tuberculosis* mtb39 Gene Family," Infection and Immunity 67( 6): 2941-2950 (1999).

Doran, et al., "Characertisation of a Novel Repetitive DNA sequence from *Mycrobacerium bovis*," FEMS Microbiology Letters 96: 179-186 (1992).

Eiglmeier, et al., "Use of an ordered cosmid library to deduce the genomic organization of *Mycobacterium leprae*," Mol. Microbiol. 7(2):197-206 (1993).

Fifis, et al., "Purification and Characterization of Major Antigens from a *Mycobacterium bovis* Culture Filtrate," Infection and Immunity 59(3):800-807 (1991).

Fisher-Hoch, et al., "Protection of rhesus monkey from fatal Lassa fever by vaccination with a recombinant vaccinia virus containing the Lassa virus glycoprotein gene" PNAS USA 86: 317-321 (1989).

Flexner, et al., "Vaccinia Virus Expression Vectors" Vaccine 8:17-21 (1989).

Flexner, "Attenuation and immugenicity in primates of vaccinia virus recombinants expression human interleukin-2," Ann. NY. Acad. Sci. 569: 86-103 (1989).

Flynn, et al., "An essential Role for Interferon γ in Resistance to *Mycobacterium tuberculosis* Infection," J. Of Experimental Medicine 178: 2249-2254 (1993).

Fsihi, et al. "The *Mycobacterium leprae* genome: systematic sequence ananlysis indentifies key catabolic enzymes, ATP-dependent transport system and a novel PoIA Locus associated with genomic variability," Molecular Microbiology 16(5:909-919 (1995).

Garcia, "Nucleotide Sequence and Expresion of pneumococcal autolysin gene from its own promoter in *E. coli*," Gene (43):265-292 (1986).

Geysen, et al. "Cognitive features of continuous antigenic determinants," J. Mol. Recognition 1:32-41 (1988).

Goodman-Smitkoff, et al., "Defining minimalrequirements for antibody production to peptide antigens," Vaccine 8: 257-262 (1990).

Grant, et al., "Expression and Secretion Vectors for Yeast, " Methods Enzymol. 153: 516-544 (1987).

Greenspan and Di Cera, "Defining epitopes: It's not as easy as it seems," Nature Biotechnology 17: 936-937 (1999).
Greenway, et al., "Enhancement of protective immune responses to Venezuelan equine encephalitis (VEE) virus with microencapsulated vaccine," Vaccine 13:1411-1420 (1995).
Griffin, et al., "Animal Models of Protective Immunity in Tuberculosis to Evaluate Candidate Vaccines;" Trends in Microbiology 3(11): 417-423 (1995).
Guzman, et al., "Efficient Gene Transfer into Myocardium by Direct Injection of Adenovirus," Cir. Res. 73: 1202-1207 (1993).
Harrison's Principles of Internal Medicine, vol. 1, pp. 1004-1014 (1998).
Harrison's Principles of Internal Medicine, vol.1 pp. 1019-1023 (1998).
Hartman and Mulligan, "Two dominant-acting selectable markers for gene transfer studies in mammalian cells," PNAS USA 85: 8047-51 (1988).
Hendrickson, et al., "Mass Spectrometric Identification of Mtb81, A Novel Serological Marker for Tuberculosis," J. Clin. Microbiol 38(6):2354-2361 (2000).
Higgins and Sharp, "Fast and sensitive multiple sequence alignments on a microcomputer," Cabios 5:151-153 (1989).
Hobbs, McGraw Hill Yearbook of Science and Technology, pages 191-96 (1992).
Horn, et al., "Synthesis of oligonucleotides on cellulose," Nucl. Acids Res. Symposia Series, pp. 225-232 (1980).
Horwitz et al., "Protective immunity against tuberculosis induced by vaccination with major extracellular proteins of *Mycobacterium tuberculosis*," PNAS USA 92:1530-1534 (1995).
Jacobs,"Advances in mycobacterial genetics: new promises for old diseases," Immunobiology 184(2-3):147-156 (1992).
Jurcevic, et al., "T cell responses to a micture of *Mycobacterium tuberculosis* peptide with complementary HLA-DR binding profiles," Clinical and Experimental Immunology 105(3): 416-421 (1996).
Kadival, et al. "Radioimmunoassay of tuberculosis antigen," Indian J. Med. Res. 75:765-770 (1982).
Kalinowski, et al., "Genetic and biochemical analysis of the aspatokinase from *Corynebacterium glutamicum*," Molecular Microbiology 5:1197-1204 (1991).
Kass-Eisler, et al., "Quantitative determination of Adenovirol-mediated gene delivery to rat cardiac myocytes in vitro and in vivo," PNAS USA 90:11498-11502 (1993).
Karlin and Altschul, "Applications and statistics for multiple high-scoring segments in molecular sequences," PNAS USA 90:5873-5787 (1993).
Kaufmann, et al., "Vaccination against tuberculosis and leprosy," Immunobiology 184(2-3): 208-209 (1992).
Khanolkar-Young, et al., "Results of the Third Immunology of Tuberculosis Antimycobaterial Monoclonal Antibody Workshop" Infection and Immunity 60(9):3925-927 (1992).
Kohler and Milstein, "Continuous cultures of fused cells secreting antibodies of predefined sequence," Nature 256:495-497 (1975).
Kolls, "Prolonged and effective blockade of TNF activity through Adenoviral-mediated gene transfer," PNAS USA 91: 215-219 (1994).
Kozak, "Comparison of Initiation of Protein Synthesis in Procaryotes, Eucaryotesm and Organelles;" Microbiological Review, pp. 1-45 (1983).
Kroll, et al., "A Multifunctional Prokaryotic Protein Expression System: Overproduction, Affinity Purification, and Selective Detection," DNA Cell Biol. 12:441-453 (1993).
Labouesse, et al., "Conformational changes in enzyme catalysis," Biochemistry 48:2137-2145 (1962).
Launois, et al., "T-Cell Epitope Mapping of the Major Secreted Mycobacterial Antigen AG85A in Tuberculosis and Leprosy," Infection and Immunity 62:3679-87 (1994).
Lazar, et al., "Transforming Growth Factor-alpha Mutation of Aspartic Acid 47 and Leucine 48 results in Different Biological Activites" Mol. Cell. Biol. 8(3):1247-1252 (1988).
Leao, et al., "Immunological and functional characterization of proteins of the *Mycobacterium tuberculosis* antigen 85 complex using synthetic peptides," J. Gen. Microbiol. 139:1543-1549 (1993).

Lerner, et al., "Cloning and structure of the *Bacillus subtilis* aspartate transcarbamylas gene (pyrB)," J. Biol. Chem. 261(24):11156-11165 (1986).
Lewin, Genes IV, Oxford University Press, pp. 124-26 (1990).
Lewisohn, et al., "Characterization of HumanCD8+ T Cells Reactive with *Mycobacterium tuberculosis*-infected Antigen-presenting Cells," J. Exp. Med. 187(10):1633-1640 (1998).
Li, et al., "Important Role of the Amino Acid Attached to tRNA in Formylation and in Initiation of Protein Synthesis in *Escherichia coli*," J. Biol. Chem., 271:1022-1028 (1996).
Ljungqvist, et al., "Antibody Responses Against *Mycobacterium Tuberculosis* in 11 Strains of Inbred Mice Novel Monoclonal Antibody Specificities Generated by Fusions Using Spleens from BALB B10 and CBA-J Mice," Infections and Immunity 56(8):1994-98 (1988).
Logan and Shenk, "Advenovirus tripartite leader sequence enhances translation of mRNAs late after infection," PNAS USA 81:365-3659 (1984).
Lowrie, et al., "Towards a DNA vaccine against tuberculosis," Vaccine 12(16):1537-1540 (1994).
Lowy, et al., "Isolation of transforming DNA: Cloning the Hamster aprt Gene," Cell 22:817-23 (1990).
Maddox, et al., "Elevated Serum Levels in Human Pregnancy of a Molecule Immunochemically similar to Eosinophil Granule Major Basic Protein," J. Exp. Med. 158:1211-1216 (1983).
Mahairas, et al., "Molecular Analysis of Genetic Differences Between *Mycobacterium bovis* BCG and Virulent *M. bovis*," J. of Bacteriology 178(5): 1274-1282 (1996).
Mahvi, et al., "DNA Cancer Vaccines—A Gene Gun Approach," Imm. And Cell Bio. 75: 456-460 (1997).
Manca, et al., "Molecular cloning, purification, and serological characterization of MPT63, a novel antigen secreted by *Mycobacterium tuberculosis*," Infection and Immunity 65(1):16-23 (1997).
Maratea,et al., "Deletion and fusion analysis of phage phi-X-174 lysis gene E," Gene 40:39-46 (1985).
Mathur and Kolttukudy, "Molecular cloning and sequencing of the gene for mycocerosic acid synthase, a novel fatty acid elongating multifunctional enzyme, from *Mycobacterium tuberculosis* var. bovis Bacillus Calmette-Guerin," J. Biol. Chem. 267:19388-19395 (1992).
Matsumoto, et al., "Cloning and Sequencing of a Unique Antigen MPT70 from *Mycobacterium tuberculosis* H37Rv and Expression in BCG Using *E. coli*-Mycobacteria Shuttle Vector," Scand. J. Immunol. 41:281-287 (1995).
Merrifield, "Solid Phase Peptide Synthesis," J. Am. Chem. Soc. 85:2149 – 2146 (1963).
Moos, Isolation of Proteins for Microsequence Analysis, Current Protocols in Molecular Biology, pp. 10.19.1- 10.19.12 (2000).
Mosmann and Coffan, "Th1 and TH2 Cells: Different Patterns of Lymphokine Secretion Lead to Different Functional Properties," Ann. Rev. Immunol. 7:145-173 (1989).
Murphy, et al., "Geneteic construction, expression and melanoma-selective cytotoxcity of a diphtheria toxin-related alpha-melanocyte stimulating hormone fusion protein," PNAS USA 83:8258-8262 (1986).
Nagai, et al., "Isolation and Partial Characterization of Major Protein Antigens in the Culture Fluid of *Mycobacterium tuberculosis*," Infection and Immunity 59(1):372-382 (1991).
Needleman and Wunsch, "A General Method Applicable to the Search for Similarities in the Amino Acid Sequence of Two Proteins," J. Mol. Biol. 48:443 (1970).
Newport, et al., "A Mutation on the Interferon-γ-Receptor Gene and Susceptibility to Mycobacterial Infection," New Eng. J. of Medicine 335(26):1941-1949 (1996).
Nosoh, et al., Protein Stability and Stabilization through Protein Engineering, chap. 7, p. 197 (1991).
Oettinger, et al., "Cloning and B-cell-epitope mapping of MPT64 from *Mycobacterium tuberculosis* H37Rv," Infection and Immunity 62(5):2058-2064 (1994).
Orme, "Prospects for new vaccines against tuberculosis," Trends in Microbiology 3(10):401-404 (1995).

Ortega, et al., "Single-step purification on DEAE-sephacel of recombinant polypeptides produced in *Escherichia coli*," Biotechnology 10:795-798 (1992).
Pancholi, et al., "Dendritic cells effciently immunoselect mycobacterial-reactive T cells in human blood, including clonable antigen-reactive precursors," Immunology 76(2):217-224 (1992).
Parker, et al., "Targeted Gene Walking Polymerase Chain Reactions," Nuc. Acids Res. 19: 3055-60 (1991).
Paul, Fundamental Immunology, chap. 8, 243-247 (1993).
Porath, et al., "Immobilized Metal Ion Affinity Chromatography," Proto Exp. Purif. 3:263-281 (1992).
Pouthier, et al., "Anti-A60 immunoglobulin G in the serodiagnosis of tuberculosis in HIV-seropositive and seronegative patients," AIDS 8(9):1277-80 (1994).
Reed, et al., "Tuberculosis vaccine development: from mouse to man," Microbes and Infection 7(5-6):992-31 (2005).
Reed, et al., "Defined tuberculosis vaccine, Mtb72F/AS02A, evidence of protection in cynomolgus monkeys," PNAS 106(7):2301-06 (2009).
Rhodes, et al., "Transformations of Maize by the Electroporation of Embryos," Methods Mol. Biol. 55:121-131 (1995).
Rinke De Wit, et al., "A *Mycobacterium leprae*-specific gene encoding an immunologically recognized 45 kDa protein," Mol. Microbiol. 10(4):829-838 (1993).
Rinke De Wit, et al., "Mycobacteria contains two groEL genes: the second *Mycobacterium leprae* groEL gene is arranged in an operon with groES," Mol. Microbiol. 6(14):1995-2007 (1992).
Riveau, et al., "Synthetic peptide vaccines against peptides and biological mediators," Trends in Pharmacological Sciences 11:194-198 (1990).
Roberts, et al., "Prediction of HIV peptide epitopes by a novel algorithm,"AIDS Research and Human Retroviruses 12:593-610 (1996).
Romain, et al., "Identification of a *Mycobacterium bovis* BCG 45/47-Kilodalton Antigen Complex, an Immunodominant Target for Antibody Resonse after Immunization with Living Bacterica," Infection and Immunity 61(2):742-750 (1993).
Romain, et al., "Isolation of a proline-rich mycobacterial protein eliciting delayed-type hypersensitivity reactions only on guinea pigs immunized with living mycobacteria," PNAS USA 90:5322-5326 (1993).
Romain, et al., "Preparation of Tuberculin Antigen L," Ann. Inst. Pasteur/Microbiol. 136B:235-248 (1985).
Romano, et al., "Immunogenicity and protective efficacy of tuberculosis subunit vaccines ecpression PPE44 (Rv2770c)," Vaccine, 26(48):6053-63 (2008).
Rolland, "From Genes to Gene Medicines: Recent Advances in Nonviral Gene Delivery," Crit. Rev. Therap. Drug Carrier Systems 15:143-198 (1998).
Rosenfeld, et al., "Adenovirus-Mediated Transfere of a Recombinant Alpha-1 Antitrypsin Gene to Lung Epithelium in Vivo," Science 252:431-434 (1991).
Rossolini, et al., "Use of deoxyinosine-containing primers versus degenerate primers," Mol. Cell. Probes 8:91-98 (1994).
Sanderson, et al., "Identification of a CD4+ T Cell-stimulating Antigen of Pathogenic Bacteria by Expression Cloning," J. Exp. Med. 182(6):1751-1757 (1995).
Sato, et al., "Immunostimulatory DNA Sequences Necessary for Effective Intradermal Gene Immunization," Science 273:352 (1996).
Scharf, et al., "Heat Stress Promoters and Transcription Factors," Results Probl. Cell Differ. 20:125-162 (1994).
Schorey, "A *Mycobacterium leprae* Gene Encoding a Fibronectin Binding Protein is Used for Efficient Invasion of Epithelial Cells and Schwann Cells," Infection and Immunity 63(7):2652-2657 (1995).
Schinnick, "The 65-Kilodalton Antigen of *Mycobacterium tuberculosis*," J. of Bacteriology 169(3): 1080-1088 (1987).
Singh, et al., "In Vitro Characterization of T Cells from Mycobacterium W-Vaccinated Mice," Infection and Immunity 60(1):257-263 (1992).
Sinha, et al., "Immunological properties of a 30 Kda secretory protein of *Mycobacterium tuberculosis* H37RA," Vaccine 15(6-7): 689-99 (1997).

Simonney, et al., "Analysis of the immunological humoral response to *Mycobacterium tuberculosis* glycolipid antigens (DAT, PGLTb1) for diagnosis of tuberculosis in HIV-seropositive and seronegative patients," Eur. J. of Clin. Microbiology and Infectious Disease 14(10):883-891 (1995).
Skeiky, et al., "Cloning Expression and Immunological Evaluation of Two Putative Secreted Serine Protease Antigens of *Mycrobacterium tuberculosis*," Infectionand Immunity 67(8): 3998-4007 (1999).
Skeiky, et al., "LeIF:a recominant leishmania protein that induces an IL-12 mediiated Th Cytokine profile," J. of Immunology 161:6171-79 (1998).
Skeiky, et al., "Differential immune responses and protective efficacy induces by components of a tuberculosis polyprotein vaccine, Mtb72F, delivered as naked DNA or recombinant protein," J. of Immunology 172(12):7618-28 (2004).
Skorko-Glonek, "Comparison of the structure of wild-type HtrA heat shock protease and mutant HtrA proteins, A Fourier transform infrared spectroscopic study," JBC 270(19): 11140-11146 (1995).
Skuce, et al., "Discrimination of *M. tuberculosis* complex bacterial using novel VNTR-PCR targets," Microbiology 148(2):519-28 (2002).
Sorensen, et al., "Purification and characterization of a low-molecular-mass T-cell antigen secreted by *Mycobacterium tuberculosis*," Infection and Immunity 63(5): 1710-1717 (1995).
Stoute, et al., "A Preliminary Evaluation of a Recombinant Circumsporozoite Protein Vaccine Against Plasmodium Falciparum Malaria," New Engl. J. Med. 336:86-91 (1997).
St. Pierre, et al., "A refined vector system for the in vitro construction of single-copy transcriptional or translational fusions to lacZ," Gene169:65-68 (1996).
Timmerman and Levy, "Dendritic Cell Vaccines for Cancer Immunotherapy," Ann. Rev. Med 50: 507-529 (1999).
Triglia, et al., "A Procedure for in Vitro Amplification of DNA Sequences that Lie Outside the Boundaries of Known Sequences," Nucl. Acids Res. 16:8186 (1988).
Ulmer, et al., "Heterologous Protection Against Influenze by Injection of DNA Encoding a Viral Protein," Science 259:1745-1749 (1993).
Van Pittius, et al., "Evolution and expansion of the *M. tuberculosis* PE and PPE multigene families and their association with the duplication of the ESAT-6 (esx) gene cluster regions," BML Evolutionary Biology 6(1):95 (2006).
Van Soolingen, et al., "Host-Mediated Modification of Pvull Restriction in *Mycobacterium tuberculosis*," J. of Bactreriology 178(1):78-84 (1996).
Vega-Lopez, et al., "Sequence and immunological characterization of a serine-rich antigen from *Mycobacterium leprae*," Infection and Immunity 61(5):2145-2153 (1993).
Verbon, et al., "The 14,000-Molecular-Weight Antigen of *Mycobacterium tuberculosis* Is Related to the Alpha-Crystallin Family of Low-Molecular-Weight Heat Shock Proteins, " J. of Bacteriology 174(4):1352-1359 (1992).
Vordemeier, et al., "Synthetic delivery system for tuberculosis vaccines: immunological evaluation of the *M. tuberculosis* 38 kDa protein entrapped in biodegradable PLG microparticles," Vaccine 13(16):1576-1582 (1995).
Wallis, et al., "Identification of Antigens of *Mycobacterium tuberculosis* Using Human Monoclonal Antibodies," J. Clin. Invest. 84:214-219 (1989).
Wang, et al., "Tuberculosis Vaccines: Past, Present and Future," Expert Rev. Vaccines 1(3):341-54 (2002).
Wang, et al., "A novel method for increasing the expression level of recombinant proteins," Protein Expression and Purification 30(1):124-133 (2003).
Webb, et al., "Molecular Cloning, Expression and Immunogenicity of MTB12," Infection & Immunity 66(9):4208-4214 (1998).
Wiegeshaus, et al., "Evaluation of the protective potency of new tuberculosis vaccines," Reviews of Infectious Diseases 11(Suppl. 2):S484-S490 (1989).
Wieles, et al., "Characterization of a *Mycobacterium leprae* Antigen Related to the Secreted *Mycobacterium tuberculosis* Protein MPT32," Infection and Immunity 62(1):252-258 (1994).

Wigler, et al. "Transformation of mammalian cells with an amplifiable dominant-acting gene," PNAS USA 77:3567-70 (1980).
Wiker and Harboe, "The Antigen 85 Complex: a Major Secretion Product of *Mycobacterium tuberculosis*," Microbiological Reviews 56(4):648-661 (1992).
Winter, "The Expresion of Heat Shock Proteins and Cognate Genes During Plant Development," Results Probl. Cell Differ. 17:85-105 (1991).
Yamaguchi, et al. "Cloning and Characterization of the Gene for Immunogenic Protein MPB64 of *Mycobacterium bovis* BDG," Infection and Immunity 57(1):283-288 (1989).
Young, et al., "Screening of a Recombinant Mycobacterial DNA Library with Polyclonal Antiserum and Molecular Weight Analysis of Expressed Antigens," Infection and Immunity 55(6):1421-1425 (1987).
Zimmerman, et al. "Immunization with peptide heteroconjugates primes a T helper cell type 1-associated antibody (IgG2a) response that recognizes the native epitope on the 38-kDa protein of *Mycobacterium tuberculosis*," Vaccine Res. 5(2):103-118 (1996).
Zitvogel, et al., "Eradiation of established murine tumors using a novel cell-free vaccine: dedritic cell-derived exosomes," Nature Med. 4:594-600 (1998).
Seq_NCBI_AF2122897, 1 page.
Seq_XP002416348_CDC1551, 2 pages.
Seq_NCBI AD000020 gi: 1717739 Dec. 10, 1996, 10 pages.
Seq_NCBI_AL021930.1, 2 pages.
Seq_NCBI_AL021930, 17 pages.
Seq_Database EMBL_U34848 "*Mycobacterium bovis* deletion region 1, 6kDa early secretory antigenic target (esat6) gene".
Seq_Accession No. O05907, Database:stpremb119, publicly available Jul. 1, 1997.
Seq_Accession No. O05908, Database:stpremb119, publicly available Jul. 1, 1997.
Seq_EMBL_MYCY7H7Bc, Accession No. Z95557, May 20, 1997.
Seq_EMBL_MTCY24G1, Accession No. Z83858, Jan. 13, 1997.
Seq_EMBL_MTCY19G5, Accession No. Z77826, Jul. 31, 1996.
Seq_EMBL_MTCY261, Accession No. Z97559, Jul. 10, 1997.
Seq_EMBL_Z78020, XP002224823.
Seq_EMBL_P41403, XP002224824.
Seq_EMBL_Q50596, XP002224822.
Seq_EMBL_Z17372, XP002224825.
Seq_EMBL_U90239, XP002224826.
Seq_EMBL_P97048, XP002224827.
Seq_Accession_No_AU077540.
Seq_EMBL_P15712, (Apr. 1, 1990) "PBP-1 from *M. tuberculosis*" XP002359448.
Seq_Uniprot_Q79FV1.
Seq_Uniprot_O06267.
Seq_Uniprot_P96364.
Seq_Uniprot_O05300.
Seq_Sequence Alignment_SEQ ID No.: n163-*Mycobacterium smegmatis* (Cirillo et al.).
Seq_Sequence Alignment_*Corynebacterium glutamicum*.
Seq_Sequence alignment_*Mycobacterium segmatis*_P41403, created Nov. 1995.
Seq_NCBI_214801_Rv0287 [*Mycobacterium tuberculosisi* H37Rv]).
Seq_EMBL_Q7U0G8-Hypothetical Protein Mb1207c, Oct. 21, 2006 XP002416347.
Seq_EMBL_050430-Hypothetical Protein Mb1207c, Oct. 31, 2006, XP002416348.
Seq_Compugen_Q10813, 1996.
Seq_Compugen_P95242, 1997.
Seq_Compugen_P96363, 1997.
Seq_Compugen_P95243, 1997.
Seq_Compugen_P96361, 1997.
Seq_Compugen_P95012, 1997.
Seq_Compugen_Q49722, 1996.
Seq_EMBL_X84741-Mycobacteriumbovis BCG IS 1081 DNA Sequence, Van Soolingen, D.
Seq_NCBI_CAA17362.
U.S. Appl. No. 09/724,685; filed Oct. 11, 1996.
First Office Action for U.S. Appl. No. 08/658,800.
Second Office Action for U.S. Appl. No. 08/658,800.
First Office Action for U.S. Appl. No. 08/659,683.
Second Office Action for U.S. Appl. No. 08/659,683.
First Office Action for U.S. Appl. No. 08/680,573.
Second Office Action for U.S. Appl. No. 08/680,573.
First Office Action for U.S. Appl. No. 08/680,574.
Second Office Action for U.S. Appl. No. 08/680,574.
First Office Action for U.S. Appl. No. 08/729,622.
Second Office Action for U.S. Appl. No. 08/729,622.
First Office Action for U.S. Appl. No. 08/730,510.
First Office Action for U.S. Appl. No. 08/818,111.
Second Office Action for U.S. Appl. No. 08/818,111.
First Office Action for U.S. Appl. No. 08/818,112.
Second Office Action for U.S. Appl. No. 08/818,112.
First Office Action for U.S. Appl. No. 08/858,998.
First Office Action for U.S. Appl. No. 08/859,381.
First Office Action for U.S. Appl. No. 08/942,341.
First Office Action for U.S. Appl. No. 08/92578.
First Office Action for U.S. Appl. No. 09/056,556.
Second Office Action for U.S. Appl. No. 09/056,556.
First Office Action for U.S. Appl. No. 09/072,967.
First Office Action for U.S. Appl. No. 09/073,009.
Second Office Action for U.S. Appl. No. 09/073,009.
Third Office Action for U.S. Appl. No. 09/073,009.
Fourth Office Action for U.S. Appl. No. 09/073,009.
First Office Action for U.S. Appl. No. 09/073,010.
Second Office Action for U.S. Appl. No. 09/073,010.
Third Office Action for U.S. Appl. No. 09/073,010.
Office Action for U.S. Appl. No. 08/730,510.
Office Action for U.S. Appl. No. 09/470,191.
First Office Action for U.S. Appl. No. 09/072,596.
ORME, Preclinical testing of new vaccines for tuberculosis: A comprehensive review, Vaccine 24:2-19 (2006).
Girard, et al., A review of vacciine research and development: Tuberculosis, Vaccine 23:5725-31 (2006).
Langermans, et al. "Protection of macaques against *Mycobacterium tuberculosis* infection by a subunit vaccine based on a fusion protein of antigen 85B and ESAT-6," Vaccine 23:2740-50 (2005).
Mustafa, et al., "Immunogenicity of *Mycobacterium tuberculosis* Antigens in *Mycobacterium bovis* BCG-Vaccinated and *M. bovis*-Infected Cattle," Infection and Immunity 74(8)4566-72 (2006).
Reece, et al. "Skin Text Performed with Highly Purified *Mycobacterium tuberculosis* Recombinant Protein Triggers Tuberculin Shock in Infected Guinea Pigs," Infection and Immunity 73(6):3301-06 (2005).
Tanghe, et al., "Improved Immunogenicity and Protective Efficacy of a Tuberculosis DNA Vaccine Encoding Ag65 by Protein Boosting," Infection and Immunity 59(5):3041-47 (2001).
Williams, et al., "Evaluation of vaccines in the EU TB Vaccine Cluster using a guinea pig aerosol infection model of tuberculosis," Tuberculosis 85:29-38 (2005).
Final Office Action for U.S. Appl. No. 11/801,112, 2011.
Office Action for U.S. Appl. No. 11/927,566, 2010.
Office Action for U.S. Appl. No. 11/978,786, 2011.
Advisory Action for U.S. Appl. No. 11/981,459, 2011.
Office Action for U.S. Appl. No. 12/490,272, 2011.
Office Action for U.S. Appl. No. 12/698,893, 2010.
Office Action for U.S. Appl. No. 12/698,976, 2010.

* cited by examiner

TCTAGAAATAATTTTGTTTACTTTAAGAAGANATATACATATGCATCACCATCACCATCACACGGCCCCGTCCGATAACTTCCAGCTCTCCCAGGGTGG
                                       M H H H H H H T A A S D N F Q L S Q G G
                                                    ├────── Tb Ra12 ──────
                                                                                                    100

GCAGGGATTCGCCATTCCGATCGGGCAGGCGATGGCGATCGCGGGCCAGATCCGATCGGGTGGGGGGTCACCCACCGTTCATATCGGGCCTACCGCCTTC
 Q G F A I P I G Q A M A I A G Q I R S G G G S P T V H I G P T A F
─────────────────────────────────────── Tb Ra12 ───────────────────────────────────────
                                                                                                    200

CTCGGCTTGGGTGTTGTCGACAACAACGGCAACGGCGCACGAGTCCAACGCGTGGTCGGAGCGCTCCGGCGGCAAGTCTCGGCATCTCCACCGGCGACC
 L G L G V V D N N G N G A R V Q R V V G S A P A A S L G I S T G D
─────────────────────────────────────── Tb Ra12 ───────────────────────────────────────
                                                                                                    300

TGATCACCGCGGTCGACGGCGCCTCCGATCAACTCGGCCACCGGCGATGGCGGACGCGCTTAACGGGCATCATCCCGTGACGTCATCTCGGTGACCTGGCA
 V I T A V D G A P I N S A T A M A D A L N G H H P G D V I S V T W Q
─────────────────────────────────────── Tb Ra12 ───────────────────────────────────────
                                                                                                    400

AACCAAGTCGGGCGGCACGCGTACAGGGAACGTGACATTGGCCGAGGGACCCCCGGCCGAATTCATGGTGGATTTCGGGGCGTTACCACCGGAGATCAAC
 T K S G G T R T G N V T L A E G P P A E F M V D F G A L P P E I N
───────────── Tb Ra12 ─────────────┤   ├───────── Tb H9 ─────────
                                                                                                    500

TCCGCGAGGATGTACGCCGGCCCGGGTTCGGCCCTCGCTGGTGCCCCGGCTCAGATGTGGGACAGCGTGGCGAGTGACCTGTTTTCGGCCGCGTCGGCCT
 S A R M Y A G P G S A S L V A A A C̲ W D S V A S D L F S A A S A
                              ─────── Tb H9 ───────
                                                                                                    600

TTCAGTCGGTCGTCTGGGGTCTCACGGTGGGCGTCGTGGATAGGTTCGTCGGCCGGTCTGATGGTGGCGGCGGCCTCGCCGTATGTGGCCGTGGATGAGCGT
 F Q S V V W G L T V G S W I G S S A G L M V A A S P Y V A W M S V
                              ─────── Tb H9 ───────
                                                                                                    700

CACCGCGGGCAGGCCGAGCTGACCGCCGCCCAGGTCCGGGTTGCTGCGGCGGCCTACGAGACGGCGTATGGGCTGACGGTGCCCCCGCCCGTGATCGCC
 I A G Q A E L T A A Q V R V A A A A Y E T A Y G L T V P P P V I A
                              ─── Tb H9 ───
                                                                                                    800

GAGAACCGTGCTGAACTGATGATTCTGATAGCGACCAACCTCTTGGGGCAAAACACCCCGGCGATCGCGGTCAACGAGGCCGAATACGGCGAGATGTGGG
 E N R A E L M I L I A T N L L G Q N T P A I A V N E A E Y G E M W
                              ─── Tb H9 ───
                                                                                                    900

FIG.1A

```
CCCAAGACCCCGCCGCGATGTTTGGCTACGCCGCGGCGACGGCGACGGCGACGGCGACGTTGCTGCCGTTCGAGGAGGCGCCGGAGATGACCAGCGCGGG
|----|----|----|----|----|----|----|----|----| 1000
 A  Q  D  A  A  A  M  F  G  Y  A  A  A  T  A  T  A  T  A  T  L  L  P  F  E  E  A  P  E  M  T  S  A  G
─────────────────────────── Tb H9 ───────────────────────────

TGGGCTCCTCGAGCAGGCCGCCGCGGTCGAGGAGGCCTCCGACACCGCCGCGGCGAACCAGTTGATGAACAATGTGCCCCAGGCGCCTGCAACAGCTGGCC
|----|----|----|----|----|----|----|----|----| 1100
 G  L  L  E  Q  A  A  A  V  E  E  A  S  D  T  A  A  A  N  Q  L  M  N  N  V  P  Q  A  L  Q  Q  L  A
─────────────────────────── Tb H9 ───────────────────────────

CAGCCCACGCAGGGCACCACGCCTTCTTCCAAGCTGGGTGGCCTGTGGAAGACCGTCTCGCCGCATCGGTCGCCGATCAGCAACATGGTGTCGATGGCCA
|----|----|----|----|----|----|----|----|----| 1200
 Q  P  T  Q  G  T  T  P  S  S  K  L  G  G  L  W  K  T  V  S  P  H  R  S  P  I  S  N  M  V  S  M  A
─────────────────────────── Tb H9 ───────────────────────────

ACAACCACATGTCGATGACCAACTCCGGTGTGTCGATGACCAACACCTTGAGCTCGATGTTGAAGGGCTTTGCCTCCGGCGGCGGCCGCCCAGGCCGTGCA
|----|----|----|----|----|----|----|----|----| 1300
 N  N  H  M  S  M  T  N  S  G  V  S  M  T  N  T  L  S  S  M  L  K  G  F  A  P  A  A  A  A  Q  A  V  Q
─────────────────────────── Tb H9 ───────────────────────────

AACCCCGCGCCCAAAACGGGGTCCGGGCCGATGAGCTCGCTGGGCAGCTCGCTGGGTTCTTCGGGTCTGGGCGGTGGGGTGGCCGCCAACTTGGGTCGGGCG
|----|----|----|----|----|----|----|----|----| 1400
 T  A  A  Q  N  G  V  R  A  M  S  S  L  G  S  S  L  G  S  S  G  L  G  G  V  A  A  N  L  G  R  A
─────────────────────────── Tb H9 ───────────────────────────

GCCTCCGTCGGTTCCTTGTCGGTGCCGCAGGCCTGGGCCGCGGCCAACCAGGCAGTGACCCCGGCGGCGCGGGCCTGCCGCTGACCAGCCTGACCAGCG
|----|----|----|----|----|----|----|----|----| 1500
 A  S  V  G  S  L  S  V  P  Q  A  W  A  A  A  N  Q  A  V  T  P  A  A  R  A  L  P  L  T  S  L  T  S
─────────────────────────── Tb H9 ───────────────────────────

CCGCGGAAAGAGGGCCCCGGGCAGATGCTGGGCCGGCTGCCGGTGGGCCAGATGGGCGCCAGGGCCGGTGGTGGGCTCAGTGGTGTGCTGCGTGTTCCGCC
|----|----|----|----|----|----|----|----|----| 1600
 A  A  E  R  G  P  G  Q  M  L  G  G  L  P  V  G  Q  M  G  A  R  A  G  G  G  L  S  G  V  L  R  V  P  P
─────────────────────────── Tb H9 ───────────────────────────

GCGACCCTATGTGATGCCCGCATTCTCCCGGCAGCCGGCGATATCGCCCCGCCGGCCTTGTCGCAGGACCGGTTCGCCGACTTCCCCGCGCTGCCCCTCGAC
|----|----|----|----|----|----|----|----|----| 1700
 R  P  Y  V  M  P  H  S  P  A  A  G  D  I  A  P  P  A  L  S  Q  D  R  F  A  D  F  P  A  L  P  L  D
──────── Tb H9 ────────|  ──────── Tb Ra35 ────────
```

FIG.1B

```
CCGTCCCCGATGGTCGCCCAAGTGGGGCCCACAGGTGGTCAACATCAACACCAAACTGGGCTACAACAACGCCGTGGGCGCCGGGACCGGCATCGTCATCG
 P  S  A  M  V  A  Q  V  G  P  Q  V  V  N  I  N  T  K  L  G  Y  N  N  A  V  G  A  G  T  G  I  V  I     1800
                                          ──── Tb Ra35 ────

ATCCCAACGGTGTCGTCCTGACCAACAACCACGTGATCGCCGGCGCCCACCGACATCAATGCCTTCAGCGTCGGCTCCGGCCAAACCTACGGCGTCGATGT
 D  P  N  G  V  V  L  T  N  N  H  V  I  A  G  A  T  D  I  N  A  F  S  V  G  S  G  Q  T  Y  G  V  D  V  1900
                                          ──── Tb Ra35 ────

GGTCGGGTATGACCCCACCCAGGATGTCGCCGGTGCCTGCAGCTGCGCGGTGCCGGTGGCCTACCATCGGCGGCCATCGGTGGCGGCGTCGCGGTTGGTGAG
 V  G  Y  D  R  T  Q  D  V  A  V  L  Q  L  R  G  A  G  G  L  P  S  A  A  I  G  G  G  V  A  V  G  E     2000
                                          ──── Tb Ra35 ────

CCCTTCGTCGCGATGGGCAACAGCGGTGGGCAGGGCCGGAACGCCCCGTGCGGTGCCTGGCAGGGTGGTCGCGCCTCGCCCAAACCGTGCAGGCGTCGGATT
 P  F  V  A  M  G  N  S  G  G  Q  G  G  T  P  R  A  V  P  G  R  V  V  A  L  G  Q  T  V  Q  A  S  D     2100
                                          ──── Tb Ra35 ────

CCCTGACCGGTGCCGAAGAGACATTGAACGGGTTGATCCAGTTCGATGCCGCGATCCAGCCCGGTGATTCGGGCGGGGCCGGTCGTCAACGGCCTAGGACA
 S  L  T  G  A  E  E  T  L  N  G  L  I  Q  F  D  A  A  I  Q  P  G  D  S  G  G  P  V  V  N  G  L  G  Q 2200
                                          ──── Tb Ra35 ────

GGTGGTCGGTATGAACACGGCCGCGTCCTAGGATATCCATCACACTGGCGGCCCCTCGAGCAGATCCGGNTGTAACAAAGCCCGAAA
 V  V  G  M  N  T  A  A  S                                                            ───▶ 2267
 ──── Tb Ra35 ───▶
```

FIG.1C

```
GATATACATATGCATCACCATCACCATCACATGGCCACCACCCTTCCCGTTCAGCGCCACCCGCGGTCCCTCTTCCCCGAGTTTTCTGAGCTGTTCGCGG
|————————|————————|————————|————————|————————|————————|————————|————————|————————|————————| 100
    M H H H H H H M A T T L P V Q R H P R S L F P E F S E L F A
             |————————————————— ERD 14 —————————————————
```

```
CCTTCCCGTCATTCGCCGGACTCCCGGCCCACCTTCGACACCCGGTTGATGCGGCTGGAAGACGAGATGAAAGAGGGGCGCTACGAGGTACGCGCGGAGCT
|————————|————————|————————|————————|————————|————————|————————|————————|————————|————————| 200
  A F P S F A G L R P T F D T R L M R L E D E M K E G R Y E V R A E L
                              ————— ERD 14 —————
```

```
TCCCGGGGTCGACCCCGACAAGGACGTCGACATTATGGTCCGCGATGGTCAGCTGACCATCAAGGCCGAGCGCACCGAGCAGAAGGACTTCGACGGTCGC
|————————|————————|————————|————————|————————|————————|————————|————————|————————|————————| 300
  P G V D P D K D V D I M V R D G Q L T I K A E R T E Q K D F D G R
                              ————— ERD 14 —————
```

```
TCGGAATTCGCGTACGGTTCCTTCGTTCGCACGGTGTCGCTGCCGGTAGGTGCTGACGAGGACGACATTAAGGCCACCTACGACAAGGGCATTCTTACTG
|————————|————————|————————|————————|————————|————————|————————|————————|————————|————————| 400
  S E F A Y G S F V R T V S L P V G A D E D D I K A T Y D K G I L T
                              ————— ERD 14 —————
```

```
TGTCCGTGGCGGTTTCGGAAGGGAAGCCAACCGAAAAGCACATTCAGATCCGGTCCACCAACAAGCTTGATCCCGTGGACGCGGTCATTAACACCACCTG
|————————|————————|————————|————————|————————|————————|————————|————————|————————|————————| 500
  V S V A V S E G K P T E K H I Q I R S T N K L D P V D A V I N T T C
           ————— ERD 14 ————————————————  [HindIII]           DPV
```

```
CAATTACGGGCAGGTAGTAGCTGCGCTCAACGCGACGGATCCGGGGGCTGCCGCACAGTTCAACGCCTCACCGGTGGCGCAGTCCTATTTGCGCAATTTC
|————————|————————|————————|————————|————————|————————|————————|————————|————————|————————| 600
  N Y G Q V V A A L N A T D P G A A A Q F N A S P V A Q S Y L R N F
                              ————— DPV —————
```

```
CTCGCCGGCACCGCCACCTCAGCGCGCTGCCATGGCCGCGCCAATTGCAAGCTGTGCCGGGGGCCGGCACAGTACATCGGCCTTGTCGAGTCGGTTGCCGGCT
|————————|————————|————————|————————|————————|————————|————————|————————|————————|————————| 700
  L A A P P P Q R A A M A A Q L Q A V P G A A Q Y I G L V E S V A G
                              ————— DPV —————
```

```
CCTGCAACAACTATGAGCTCATGACGATTAATTACCAGTTCGGGGACGTCGACGCTCATGGCGCCATGATCCGCGCTCAGGCGGCGTCGCTTGAGGCCGA
|————————|————————|————————|————————|————————|————————|————————|————————|————————|————————| 800
  S C N N Y E L M T I N Y Q F G D V D A H G A M I R A Q A A S L E A E
     —— DPV ——[Sac I]                                ————— MTI —————
```

FIG.2A

```
GCATCAGCCCATCGTTCGTCATGTGTTGGCCGCCGGGTGACTTTTGGGGCGGCGCCCGTTCGGTCCCTTGCCAGGAGTTCATTACCCAGTTGGGCCCGTAAC
                                                                                                    900
  H  Q  A  I  V  R  D  V  L  A  A  G  D  F  W  G  G  A  C  S  V  A  C  Q  E  F  I  T  Q  L  G  R  N
                                          MTI

TTCCAGGTGATCTACGAGCAGGCCAACGCCCACGGCCAGAAGGTGCAGGCTGCCGGCAACAACATGGCGCAAACCGACAGCGCCGTCGGCTCCAGCTGGG
                                                                                                    1000
  F  Q  V  I  Y  E  Q  A  N  A  H  G  Q  K  V  Q  A  A  G  N  N  M  A  Q  T  D  S  A  V  G  S  S  W
                                          MTI

CCACTAGTAACGGCCGCCAGTGTGCTGGAATTCTGCAGATATCCATCACACTGGCGGCCGCTCGAGCAGATCCGGCTGCTA
                                                                               1081

A[SpeI]
```

FIG.2B

TGTTCTTCGA CGGCAGGCTG GTGGAGGAAG GGCCCACCGA ACAGCTGTTC TCCTCGCCGA
60

AGCATGCGGA AACCGCCCGA TACGTCGCCG GACTGTCGGG GGACGTCAAG GACGCCAAGC
120

GCGGAAATTG AAGAGCACAG AAAGGTATGG C GTG AAA ATT CGT TTG CAT ACG
172
                                                Val Lys Ile Arg Leu His Thr
                                                 1            5

CTG TTG GCC GTG TTG ACC GCT GCG CCG CTG CTG CTA GCA GCG GCG GGC
220
Leu Leu Ala Val Leu Thr Ala Ala Pro Leu Leu Leu Ala Ala Ala Gly
        10              15                    20

TGT GGC TCG AAA CCA CCG AGC GGT TCG CCT GAA ACG GGC GCC GGC GCC
268
Cys Gly Ser Lys Pro Pro Ser Gly Ser Pro Glu Thr Gly Ala Gly Ala
    25                    30                    35

GGT ACT GTC GCG ACT ACC CCC GCG TCG TCG CCG GTG ACG TTG GCG GAG
316
Gly Thr Val Ala Thr Thr Pro Ala Ser Ser Pro Val Thr Leu Ala Glu
 40                     45                    50                    55

ACC GGT AGC ACG CTG CTC TAC CCG CTG TTC AAC CTG TGG GGT CCG GCC
364
Thr Gly Ser Thr Leu Leu Tyr Pro Leu Phe Asn Leu Trp Gly Pro Ala
               60                    65                    70

TTT CAC GAG AGG TAT CCG AAC GTC ACG ATC ACC GCT CAG GGC ACC GGT
412
Phe His Glu Arg Tyr Pro Asn Val Thr Ile Thr Ala Gln Gly Thr Gly
            75                    80                    85

TCT GGT GCC GGG ATC GCG CAG GCC GCC GCC GGG ACG GTC AAC ATT GGG
460
Ser Gly Ala Gly Ile Ala Gln Ala Ala Ala Gly Thr Val Asn Ile Gly
        90                    95                    100

FIG.3A

```
GCC TCC GAC GCC TAT CTG TCG GAA GGT GAT ATG GCC GCG CAC AAG GGG
    508
Ala Ser Asp Ala Tyr Leu Ser Glu Gly Asp Met Ala Ala His Lys Gly
    105              110             115

CTG ATG AAC ATC GCG CTA GCC ATC TCC GCT CAG CAG GTC AAC TAC AAC
    556
Leu Met Asn Ile Ala Leu Ala Ile Ser Ala Gln Gln Val Asn Tyr Asn
120              125             130             135

CTG CCC GGA GTG AGC GAG CAC CTC AAG CTG AAC GGA AAA GTC CTG GCG
    604
Leu Pro Gly Val Ser Glu His Leu Lys Leu Asn Gly Lys Val Leu Ala
                 140             145             150

GCC ATG TAC CAG GGC ACC ATC AAA ACC TGG GAC GAC CCG CAG ATC GCT
    652
Ala Met Tyr Gln Gly Thr Ile Lys Thr Trp Asp Asp Pro Gln Ile Ala
             155             160             165

GCG CTC AAC CCC GGC GTG AAC CTG CCC GGC ACC GCG GTA GTT CCG CTG
    700
Ala Leu Asn Pro Gly Val Asn Leu Pro Gly Thr Ala Val Val Pro Leu
             170             175             180

CAC CGC TCC GAC GGG TCC GGT GAC ACC TTC TTG TTC ACC CAG TAC CTG
    748
His Arg Ser Asp Gly Ser Gly Asp Thr Phe Leu Phe Thr Gln Tyr Leu
         185             190             195

TCC AAG CAA GAT CCC GAG GGC TGG GGC AAG TCG CCC GGC TTC GGC ACC
    796
Ser Lys Gln Asp Pro Glu Gly Trp Gly Lys Ser Pro Gly Phe Gly Thr
200             205             210             215

ACC GTC GAC TTC CCG GCG GTG CCG GGT GCC CTG GGT GAG AAC GGC AAC
    844
Thr Val Asp Phe Pro Ala Val Pro Gly Ala Leu Gly Glu Asn Gly Asn
                 220             225             230

GGC GGC ATG GTG ACC GGT TGC GCC GAG ACA CCG GGC TGC GTG GCC TAT
    892
Gly Gly Met Val Thr Gly Cys Ala Glu Thr Pro Gly Cys Val Ala Tyr
             235             240             245
```

FIG.3B

```
ATC GGC ATC AGC TTC CTC GAC CAG GCC AGT CAA CGG GGA CTC GGC GAG
    940
Ile Gly Ile Ser Phe Leu Asp Gln Ala Ser Gln Arg Gly Leu Gly Glu
        250                 255                 260

GCC CAA CTA GGC AAT AGC TCT GGC AAT TTC TTG TTG CCC GAC GCG CAA
    988
Ala Gln Leu Gly Asn Ser Ser Gly Asn Phe Leu Leu Pro Asp Ala Gln
        265                 270                 275

AGC ATT CAG GCC GCG GCG GCT GGC TTC GCA TCG AAA ACC CCG GCG AAC
    1036
Ser Ile Gln Ala Ala Ala Ala Gly Phe Ala Ser Lys Thr Pro Ala Asn
280                 285                 290                 295

CAG GCG ATT TCG ATG ATC GAC GGG CCC GCC CCG GAC GGC TAC CCG ATC
    1084
Gln Ala Ile Ser Met Ile Asp Gly Pro Ala Pro Asp Gly Tyr Pro Ile
                300                 305                 310

ATC AAC TAC GAG TAC GCC ATC GTC AAC AAC CGG CAA AAG GAC GCC GCC
    1132
Ile Asn Tyr Glu Tyr Ala Ile Val Asn Asn Arg Gln Lys Asp Ala Ala
        315                 320                 325

ACC GCG CAG ACC TTG CAG GCA TTT CTG CAC TGG GCG ATC ACC GAC GGC
    1180
Thr Ala Gln Thr Leu Gln Ala Phe Leu His Trp Ala Ile Thr Asp Gly
        330                 335                 340

AAC AAG GCC TCG TTC CTC GAC CAG GTT CAT TTC CAG CCG CTG CCG CCC
    1228
Asn Lys Ala Ser Phe Leu Asp Gln Val His Phe Gln Pro Leu Pro Pro
        345                 350                 355

GCG GTG GTG AAG TTG TCT GAC GCG TTG ATC GCG ACG ATT TCC AGC
    1273
Ala Val Val Lys Leu Ser Asp Ala Leu Ile Ala Thr Ile Ser Ser
360                 365                 370

TAGCCTCGTT GACCACCACG CGACAGCAAC CTCCGTCGGG CCATCGGGCT GCTTTGCGGA
    1333

GCATGCTGGC CCGTGCCGGT GAAGTCGGCC GCGCTGGCCC GGCCATCCGG TGGTTGGGTG
    1393
```

FIG.3C

GGATAGGTGC GGTGATCCCG CTGCTTGCGC TGGTCTTGGT GCTGGTGGTG CTGGTCATCG
1453

AGGCGATGGG TGCGATCAGG CTCAACGGGT TGCATTTCTT CACCGCCACC GAATGGAATC
1513

CAGGCAACAC CTACGGCGAA ACCGTTGTCA CCGACGCGTC GCCCATCCGG TCGGCGCCTA
1573

CTACGGGGCG TTGCCGCTGA TCGTCGGGAC GCTGGCGACC TCGGCAATCG CCCTGATCAT
1633

CGCGGTGCCG GTCTCTGTAG GAGCGGCGCT GGTGATCGTG GAACGGCTGC CGAAACGGTT
1693

GGCCGAGGCT GTGGGAATAG TCCTGGAATT GCTCGCCGGA ATCCCCAGCG TGGTCGTCGG
1753

TTTGTGGGGG GCAATGACGT TCGGGCCGTT CATCGCTCAT CACATCGCTC CGGTGATCGC
1813

TCACAACGCT CCCGATGTGC CGGTGCTGAA CTACTTGCCC GGCGACCCGG GCAACGGGGA
1873

GGGCATGTTG GTGTCCGGTC TGGTGTTGGC GGTGATGGTC GTTCCCATTA TCGCCACCAC
1933

CACTCATGAC CTGTTCCGGC AGGTGCCGGT GTTGCCCCGG GAGGGCGCCA TCGGGAATTC
1993

FIG.3D

| | |
|---|---|
| GGTCTTGACC ACCACCTGGG TGTCGAAGTC GGTGCCCGGA TTGAAGTCCA GGTACTCGTG | 60 |
| GGTGGGGCGG GCGAAACAAT AGCGACAAGC ATGCGAGCAG CCGCGGTAGC CGTTGACGGT | 120 |
| GTAGCGAAAC GGCAACGCGG CCGCGTTGGG CACCTTGTTC AGCGCTGATT TGCACAACAC | 180 |
| CTCGTGGAAG GTGATGCCGT CGAATTGTGG CGCGCGAACG CTGCGGACCA GGCCGATCCG | 240 |
| CTGCAACCCG GCAGCGCCCG TCGTCAACGG GCATCCCGTT CACCGCGACG GCTTGCCGGG | 300 |
| CCCAACGCAT ACCATTATTC GAACAACCGT TCTATACTTT GTCAACGCTG GCCGCTACCG | 360 |
| AGCGCCGCAC AGGATGTGAT ATGCCATCTC TGCCCGCACA GACAGGAGCC AGGCCTTATG | 420 |
| ACAGCATTCG GCGTCGAGCC CTACGGGCAG CCGAAGTACC TAGAAATCGC CGGGAAGCGC | 480 |
| ATGGCGTATA TCGACGAAGG CAAGGGTGAC GCCATCGTCT TTCAGCACGG CAACCCCACG | 540 |
| TCGTCTTACT TGTGGCGCAA CATCATGCCG CACTTGGAAG GGCTGGGCCG GCTGGTGGCC | 600 |
| TGCGATCTGA TCGGGATGGG CGCGTCGGAC AAGCTCAGCC CATCGGGACC CGACCGCTAT | 660 |
| AGCTATGGCG AGCAACGAGA CTTTTTGTTC GCGCTCTGGG ATGCGCTCGA CCTCGGCGAC | 720 |
| CACGTGGTAC TGGTGCTGCA CGACTGGGGC TCGGCGCTCG GCTTCGACTG GGCTAACCAG | 780 |
| CATCGCGACC GAGTGCAGGG GATCGCGTTC ATGGAAGCGA TCGTCACCCC GATGACGTGG | 840 |
| GCGGACTGGC CGCCGGCCGT GCGGGGTGTG TTCCAGGGTT TCCGATCGCC TCAAGGCGAG | 900 |
| CCAATGGCGT TGGAGCACAA CATCTTTGTC GAACGGGTGC TGCCCGGGGC GATCCTGCGA | 960 |
| CAGCTCAGCG ACGAGGAAAT GAACCACTAT CGGCGGCCAT TCGTGAACGG CGGCGAGGAC | 1020 |
| CGTCGCCCCA CGTTGTCGTG GCCACGAAAC CTTCCAATCG ACGGTGAGCC CGCCGAGGTC | 1080 |
| GTCGCGTTGG TCAACGAGTA CCGGAGCTGG CTCGAGGAAA CCGACATGCC GAAACTGTTC | 1140 |
| ATCAACGCCG AGCCCGGCGC GATCATCACC GGCCGCATCC GTGACTATGT CAGGAGCTGG | 1200 |
| CCCAACCAGA CCGAAATCAC AGTGCCCGGC GTGCATTTCG TTCAGGAGGA CAGCGATGGC | 1260 |

FIG.4A

```
GTCGTATCGT GGGCGGGCGC TCGGCAGCAT CGGCGACCTG GGAGCGCTCT CATTTCACGA   1320
GACCAAGAAT GTGATTTCCG GCGAAGGCGG CGCCCTGCTT GTCAACTCAT AAGACTTCCT   1380
GCTCCGGGCA GAGATTCTCA GGGAAAAGGG CACCAATCGC AGCCGCTTCC TTCGCAACGA   1440
GGTCGACAAA TATACGTGGC AGGACAAAGG TCTTCCTATT TGCCCAGCGA ATTAGTCGCT   1500
GCCTTTCTAT GGGCTCAGTT CGAGGAAGCC GAGCGGATCA CGCGTATCCG ATTGGACCTA   1560
TGGAACCGGT ATCATGAAAG CTTCGAATCA TTGGAACAGC GGGGCTCCT GCGCCGTCCG     1620
ATCATCCCAC AGGGCTGCTC TCACAACGCC CACATGTACT ACGTGTTACT AGCGCCCAGC   1680
GCCGATCGGG AGGAGGTGCT GGCGCGTCTG ACGAGCGAAG GTATAGGCGC GGTCTTTCAT   1740
TACGTGCCGC TTCACGATTC GCCGGCCGGG CGTCGCT                            1777
```

FIG.4B

TbH-9: protein sequence

Val Ala Trp Met Ser Val Thr Ala Gly Gln Ala Glu Leu Thr Ala Ala
1               5                   10                  15
Gln Val Arg Val Ala Ala Ala Tyr Glu Thr Ala Tyr Gly Leu Thr
            20                  25              30
Val Pro Pro Val Ile Ala Glu Asn Arg Ala Glu Leu Met Ile Leu
        35                  40              45
Ile Ala Thr Asn Leu Leu Gly Gln Asn Thr Pro Ala Ile Ala Val Asn
    50                  55              60
Glu Ala Glu Tyr Gly Glu Met Trp Ala Gln Asp Ala Ala Ala Met Phe
65              70                  75                  80
Gly Tyr Ala Ala Ala Thr Ala Thr Ala Thr Ala Thr Leu Leu Pro Phe
                85              90                  95
Glu Glu Ala Pro Glu Met Thr Ser Ala Gly Gly Leu Leu Glu Gln Ala
            100             105                 110
Ala Ala Val Glu Glu Ala Ser Asp Thr Ala Ala Ala Asn Gln Leu Met
        115                 120                 125
Asn Asn Val Pro Gln Ala Leu Lys Gln Leu Ala Gln Pro Thr Gln Gly
    130                 135                 140
Thr Thr Pro Ser Ser Lys Leu Gly Gly Leu Trp Lys Thr Val Ser Pro
145                 150                 155                 160
His Arg Ser Pro Ile Ser Asn Met Val Ser Met Ala Asn Asn His Met
            165                 170                 175
Ser Met Thr Asn Ser Gly Val Ser Met Thr Asn Thr Leu Ser Ser Met
            180                 185                 190
Leu Lys Gly Phe Ala Pro Ala Ala Ala Gln Ala Val Gln Thr Ala
        195             200                 205
Ala Gln Asn Gly Val Arg Ala Met Ser Ser Leu Gly Ser Ser Leu Gly
        210             215                 220

FIG.4C

```
Ser Ser Gly Leu Gly Gly Gly Val Ala Ala Asn Leu Gly Arg Ala Ala
225             230             235                 240
Ser Val Arg Tyr Gly His Arg Asp Gly Gly Lys Tyr Ala Xaa Ser Gly
                245             250             255
Arg Arg Asn Gly Gly Pro Ala
            260                 Tb38-1: protein sequence
```

```
Thr Asp Ala Ala Thr Leu Ala Gln Glu Ala Gly Asn Phe Glu Arg Ile
1               5               10                  15
Ser Gly Asp Leu Lys Thr Gln Ile Asp Gln Val Glu Ser Thr Ala Gly
                20              25              30
Ser Leu Gln Gly Gln Trp Arg Gly Ala Ala Gly Thr Ala Ala Gln Ala
            35              40              45
Ala Val Val Arg Phe Gln Glu Ala Ala Asn Lys Gln Lys Gln Glu Leu
        50              55              60
Asp Glu Ile Ser Thr Asn Ile Arg Gln Ala Gly Val Gln Tyr Ser Arg
65              70              75                  80

Ala Asp Glu Glu Gln Gln Gln Ala Leu Ser Ser Gln Met Gly Phe
                85              90              95
```

FIG.4D

| | |
|---|---|
| TGGCGAATGG GACGCGCCCT GTAGCGGCGC ATTAAGCGCG GCGGGTGTGG TGGTTACGCG | 60 |
| CAGCGTGACC GCTACACTTG CCAGCGCCCT AGCGCCCGCT CCTTTCGCTT TCTTCCCTTC | 120 |
| CTTTCTCGCC ACGTTCGCCG GCTTTCCCCG TCAAGCTCTA AATCGGGGGC TCCCTTTAGG | 180 |
| GTTCCGATTT AGTGCTTTAC GGCACCTCGA CCCCAAAAAA CTTGATTAGG GTGATGGTTC | 240 |
| ACGTAGTGGG CCATCGCCCT GATAGACGGT TTTTCGCCCT TGACGTTGG AGTCCACGTT | 300 |
| CTTTAATAGT GGACTCTTGT TCCAAACTGG AACAACACTC AACCCTATCT CGGTCTATTC | 360 |
| TTTTGATTTA TAAGGGATTT TGCCGATTTC GGCCTATTGG TTAAAAAATG AGCTGATTTA | 420 |
| ACAAAAATTT AACGCGAATT TTAACAAAAT ATTAACGTTT ACAATTTCAG GTGGCACTTT | 480 |
| TCGGGGAAAT GTGCGCGGAA CCCCTATTTG TTTATTTTTC TAAATACATT CAAATATGTA | 540 |
| TCCGCTCATG AATTAATTCT TAGAAAAACT CATCGAGCAT CAAATGAAAC TGCAATTTAT | 600 |
| TCATATCAGG ATTATCAATA CCATATTTTT GAAAAAGCCG TTTCTGTAAT GAAGGAGAAA | 660 |
| ACTCACCGAG GCAGTTCCAT AGGATGGCAA GATCCTGGTA TCGGTCTGCG ATTCCGACTC | 720 |
| GTCCAACATC AATACAACCT ATTAATTTCC CCTCGTCAAA AATAAGGTTA TCAAGTGAGA | 780 |
| AATCACCATG AGTGACGACT GAATCCGGTG AGAATGGCAA AAGTTTATGC ATTTCTTTCC | 840 |
| AGACTTGTTC AACAGGCCAG CCATTACGCT CGTCATCAAA ATCACTCGCA TCAACCAAAC | 900 |
| CGTTATTCAT TCGTGATTGC GCCTGAGCGA GACGAAATAC GCGATCGCTG TTAAAAGGAC | 960 |
| AATTACAAAC AGGAATCGAA TGCAACCGGC GCAGGAACAC TGCCAGCGCA TCAACAATAT | 1020 |
| TTTCACCTGA ATCAGGATAT TCTTCTAATA CCTGGAATGC TGTTTTCCCG GGGATCGCAG | 1080 |
| TGGTGAGTAA CCATGCATCA TCAGGAGTAC GGATAAAATG CTTGATGGTC GGAAGAGGCA | 1140 |
| TAAATTCCGT CAGCCAGTTT AGTCTGACCA TCTCATCTGT AACATCATTG GCAACGCTAC | 1200 |
| CTTTGCCATG TTTCAGAAAC AACTCTGGCG CATCGGGCTT CCCATACAAT CGATAGATTG | 1260 |

FIG.5A

| | |
|---|---|
| TCGCACCTGA TTGCCCGACA TTATCGCGAG CCCATTTATA CCCATATAAA TCAGCATCCA | 1320 |
| TGTTGGAATT TAATCGCGGC CTAGAGCAAG ACGTTTCCCG TTGAATATGG CTCATAACAC | 1380 |
| CCCTTGTATT ACTGTTTATG TAAGCAGACA GTTTTATTGT TCATGACCAA AATCCCTTAA | 1440 |
| CGTGAGTTTT CGTTCCACTG AGCGTCAGAC CCCGTAGAAA AGATCAAAGG ATCTTCTTGA | 1500 |
| GATCCTTTTT TTCTGCGCGT AATCTGCTGC TTGCAAACAA AAAAACCACC GCTACCAGCG | 1560 |
| GTGGTTTGTT TGCCGGATCA AGAGCTACCA ACTCTTTTTC CGAAGGTAAC TGGCTTCAGC | 1620 |
| AGAGCGCAGA TACCAAATAC TGTCCTTCTA GTGTAGCCGT AGTTAGGCCA CCACTTCAAG | 1680 |
| AACTCTGTAG CACCGCCTAC ATACCTCGCT CTGCTAATCC TGTTACCAGT GGCTGCTGCC | 1740 |
| AGTGGCGATA AGTCGTGTCT TACCGGGTTG GACTCAAGAC GATAGTTACC GGATAAGGCG | 1800 |
| CAGCGGTCGG GCTGAACGGG GGGTTCGTGC ACACAGCCCA GCTTGGAGCG AACGACCTAC | 1860 |
| ACCGAACTGA GATACCTACA GCGTGAGCTA TGAGAAAGCG CCACGCTTCC CGAAGGGAGA | 1920 |
| AAGGCGGACA GGTATCCGGT AAGCGGCAGG GTCGGAACAG GAGAGCGCAC GAGGGAGCTT | 1980 |
| CCAGGGGGAA ACGCCTGGTA TCTTTATAGT CCTGTCGGGT TTCGCCACCT CTGACTTGAG | 2040 |
| CGTCGATTTT TGTGATGCTC GTCAGGGGGG CGGAGCCTAT GGAAAAACGC CAGCAACGCG | 2100 |
| GCCTTTTTAC GGTTCCTGGC CTTTTGCTGG CCTTTTGCTC ACATGTTCTT TCCTGCGTTA | 2160 |
| TCCCCTGATT CTGTGGATAA CCGTATTACC GCCTTTGAGT GAGCTGATAC CGCTCGCCGC | 2220 |
| AGCCGAACGA CCGAGCGCAG CGAGTCAGTG AGCGAGGAAG CGGAAGAGCG CCTGATGCGG | 2280 |
| TATTTTCTCC TTACGCATCT GTGCGGTATT TCACACCGCA TATATGGTGC ACTCTCAGTA | 2340 |
| CAATCTGCTC TGATGCCGCA TAGTTAAGCC AGTATACACT CCGCTATCGC TACGTGACTG | 2400 |
| GGTCATGGCT GCGCCCCGAC ACCCGCCAAC ACCCGCTGAC GCGCCCTGAC GGGCTTGTCT | 2460 |
| GCTCCCGGCA TCCGCTTACA GACAAGCTGT GACCGTCTCC GGGAGCTGCA TGTGTCAGAG | 2520 |
| GTTTTCACCG TCATCACCGA AACGCGCGAG GCAGCTGCGG TAAAGCTCAT CAGCGTGGTC | 2580 |
| GTGAAGCGAT TCACAGATGT CTGCCTGTTC ATCCGCGTCC AGCTCGTTGA GTTTCTCCAG | 2640 |
| AAGCGTTAAT GTCTGGCTTC TGATAAAGCG GGCCATGTTA AGGGCGGTTT TTTCCTGTTT | 2700 |

FIG.5B

```
GGTCACTGAT GCCTCCGTGT AAGGGGGATT TCTGTTCATG GGGGTAATGA TACCGATGAA   2760
ACGAGAGAGG ATGCTCACGA TACGGGTTAC TGATGATGAA CATGCCCGGT TACTGGAACG   2820
TTGTGAGGGT AAACAACTGG CGGTATGGAT GCGGCGGGAC CAGAGAAAAA TCACTCAGGG   2880
TCAATGCCAG CGCTTCGTTA ATACAGATGT AGGTGTTCCA CAGGGTAGCC AGCAGCATCC   2940
TGCGATGCAG ATCCGGAACA TAATGGTGCA GGGCGCTGAC TTCCGCGTTT CCAGACTTTA   3000
CGAAACACGG AAACCGAAGA CCATTCATGT TGTTGCTCAG GTCGCAGACG TTTTGCAGCA   3060
GCAGTCGCTT CACGTTCGCT CGCGTATCGG TGATTCATTC TGCTAACCAG TAAGGCAACC   3120
CCGCCAGCCT AGCCGGGTCC TCAACGACAG GAGCACGATC ATGCGCACCC GTGGGGCCGC   3180
CATGCCGGCG ATAATGGCCT GCTTCTCGCC GAAACGTTTG GTGGCGGGAC CAGTGACGAA   3240
GGCTTGAGCG AGGGCGTGCA AGATTCCGAA TACCGCAAGC GACAGGCCGA TCATCGTCGC   3300
GCTCCAGCGA AAGCGGTCCT CGCCGAAAAT GACCCAGAGC GCTGCCGGCA CCTGTCCTAC   3360
GAGTTGCATG ATAAAGAAGA CAGTCATAAG TGCGGCGACG ATAGTCATGC CCCGCGCCCA   3420
CCGGAAGGAG CTGACTGGGT TGAAGGCTCT CAAGGGCATC GGTCGAGATC CCGGTGCCTA   3480
ATGAGTGAGC TAACTTACAT TAATTGCGTT GCGCTCACTG CCCGCTTTCC AGTCGGGAAA   3540
CCTGTCGTGC CAGCTGCATT AATGAATCGG CCAACGCGCG GGGAGAGGCG GTTTGCGTAT   3600
TGGGCGCCAG GGTGGTTTTT CTTTTCACCA GTGAGACGGG CAACAGCTGA TTGCCCTTCA   3660
CCGCCTGGCC CTGAGAGAGT TGCAGCAAGC GGTCCACGCT GGTTTGCCCC AGCAGGCGAA   3720
AATCCTGTTT GATGGTGGTT AACGGCGGGA TATAACATGA GCTGTCTTCG GTATCGTCGT   3780
ATCCCACTAC CGAGATATCC GCACCAACGC GCAGCCCGGA CTCGGTAATG GCGCGCATTG   3840
CGCCCAGCGC CATCTGATCG TTGGCAACCA GCATCGCAGT GGGAACGATG CCCTCATTCA   3900
GCATTTGCAT GGTTTGTTGA AAACCGGACA TGGCACTCCA GTCGCCTTCC CGTTCCGCTA   3960
TCGGCTGAAT TTGATTGCGA GTGAGATATT TATGCCAGCC AGCCAGACGC AGACGCGCCG   4020
AGACAGAACT TAATGGGCCC GCTAACAGCG CGATTTGCTG GTGACCCAAT GCGACCAGAT   4080
GCTCCACGCC CAGTCGCGTA CCGTCTTCAT GGGAGAAAAT AATACTGTTG ATGGGTGTCT   4140
```

FIG.5C

| | |
|---|---|
| GGTCAGAGAC ATCAAGAAAT AACGCCGGAA CATTAGTGCA GGCAGCTTCC ACAGCAATGG | 4200 |
| CATCCTGGTC ATCCAGCGGA TAGTTAATGA TCAGCCCACT GACGCGTTGC GCGAGAAGAT | 4260 |
| TGTGCACCGC CGCTTTACAG GCTTCGACGC CGCTTCGTTC TACCATCGAC ACCACCACGC | 4320 |
| TGGCACCCAG TTGATCGGCG CGAGATTTAA TCGCCGCGAC AATTTGCGAC GGCGCGTGCA | 4380 |
| GGGCCAGACT GGAGGTGGCA ACGCCAATCA GCAACGACTG TTTGCCCGCC AGTTGTTGTG | 4440 |
| CCACGCGGTT GGGAATGTAA TTCAGCTCCG CCATCGCCGC TTCCACTTTT TCCCGCGTTT | 4500 |
| TCGCAGAAAC GTGGCTGGCC TGGTTCACCA CGCGGGAAAC GGTCTGATAA GAGACACCGG | 4560 |
| CATACTCTGC GACATCGTAT AACGTTACTG GTTTCACATT CACCACCCTG AATTGACTCT | 4620 |
| CTTCCGGGCG CTATCATGCC ATACCGCGAA AGGTTTTGCG CCATTCGATG GTGTCCGGGA | 4680 |
| TCTCGACGCT CTCCCTTATG CGACTCCTGC ATTAGGAAGC AGCCCAGTAG TAGGTTGAGG | 4740 |
| CCGTTGAGCA CCGCCGCCGC AAGGAATGGT GCATGCAAGG AGATGGCGCC CAACAGTCCC | 4800 |
| CCGGCCACGG GGCCTGCCAC CATACCCACG CCGAAACAAG CGCTCATGAG CCCGAAGTGG | 4860 |
| CGAGCCCGAT CTTCCCCATC GGTGATGTCG GCGATATAGG CGCCAGCAAC CGCACCTGTG | 4920 |
| GCGCCGGTGA TGCCGGCCAC GATGCGTCCG GCGTAGAGGA TCGAGATCTC GATCCCGCGA | 4980 |
| AATTAATACG ACTCACTATA GGGGAATTGT GAGCGGATAA CAATTCCCCT CTAGAAATAA | 5040 |
| TTTTGTTTAA CTTTAAGAAG GAGATATACA TATGGGCCAT CATCATCATC ATCACGTGAT | 5100 |
| CGACATCATC GGGACCAGCC CCACATCCTG GAACAGGCG GCGGCGGAGG CGGTCCAGCG | 5160 |
| GGCGCGGGAT AGCGTCGATG ACATCCGCGT CGCTCGGGTC ATTGAGCAGG ACATGGCCGT | 5220 |
| GGACAGCGCC GGCAAGATCA CCTACCGCAT CAAGCTCGAA GTGTCGTTCA AGATGAGGCC | 5280 |
| GGCGCAACCG AGGGGCTCGA AACCACCGAG CGGTTCGCCT GAAACGGGCG CCGGCGCCGG | 5340 |
| TACTGTCGCG ACTACCCCCG CGTCGTCGCC GGTGACGTTG GCGGAGACCG GTAGCACGCT | 5400 |
| GCTCTACCCG CTGTTCAACC TGTGGGGTCC GGCCTTTCAC GAGAGGTATC CGAACGTCAC | 5460 |
| GATCACCGCT CAGGGCACCG GTTCTGGTGC CGGGATCGCG CAGGCCGCCG CCGGGACGGT | 5520 |
| CAACATTGGG GCCTCCGACG CCTATCTGTC GGAAGGTGAT ATGGCCGCGC ACAAGGGGCT | 5580 |

FIG.5D

```
GATGAACATC GCGCTAGCCA TCTCCGCTCA GCAGGTCAAC TACAACCTGC CCGGAGTGAG    5640

CGAGCACCTC AAGCTGAACG GAAAAGTCCT GGCGGCCATG TACCAGGGCA CCATCAAAAC    5700

CTGGGACGAC CCGCAGATCG CTGCGCTCAA CCCCGGCGTG AACCTGCCCG GCACCGCGGT    5760

AGTTCCGCTG CACCGCTCCG ACGGGTCCGG TGACACCTTC TTGTTCACCC AGTACCTGTC    5820

CAAGCAAGAT CCCGAGGGCT GGGGCAAGTC GCCCGGCTTC GGCACCACCG TCGACTTCCC    5880

GGCCGTGCCG GGTGCGCTGG GTGAGAACGG CAACGGCCGC ATGGTGACCG GTTGCGCCGA    5940

GACACCGGGC TGCGTGGCCT ATATCGGCAT CAGCTTCCTC GACCAGGCCA GTCAACGGGG    6000

ACTCGGCGAG GCCCAACTAG GCAATAGCTC TGGCAATTTC TTGTTGCCCG ACGCGCAAAG    6060

CATTCAGGCC GCGGCGGCTG GCTTCGCATC GAAAACCCCG GCGAACCAGG CGATTTCGAT    6120

GATCGACGGG CCCGCCCCGG ACGGCTACCC GATCATCAAC TACGAGTACG CCATCGTCAA    6180

CAACCGGCAA AAGGACGCCG CCACCGCGCA GACCTTGCAG GCATTTCTGC ACTGGGCGAT    6240

CACCGACGGC AACAAGGCCT CGTTCCTCGA CCAGGTTCAT TTCCAGCCGC TGCCGCCCGC    6300

GGTGGTGAAG TTGTCTGACG CGTTGATCGC GACGATTTCC AGCGCTGAGA TGAAGACCGA    6360

TGCCGCTACC CTCGCGCAGG AGGCAGGTAA TTTCGAGCGG ATCTCCGGCG ACCTGAAAAC    6420

CCAGATCGAC CAGGTGGAGT CGACGGCAGG TTCGTTGCAG GGCCAGTGGC GCGGCGCGGC    6480

GGGGACGGCC GCCCAGGCCG CGGTGGTGCG CTTCCAAGAA GCAGCCAATA AGCAGAAGCA    6540

GGAACTCGAC GAGATCTCGA CGAATATTCG TCAGGCCGGC GTCCAATACT CGAGGGCCGA    6600

CGAGGAGCAG CAGCAGGCGC TGTCCTCGCA AATGGGCTTT GTGCCCACAA CGGCCGCCTC    6660

GCCGCCGTCG ACCGCTGCAG CGCCACCCGC ACCGGCGACA CCTGTTGCCC CCCACCACC    6720

GGCCGCCGCC AACACGCCGA ATGCCCAGCC GGGCGATCCC AACGCAGCAC CTCCGCCGGC    6780

CGACCCGAAC GCACCGCCGC CACCTGTCAT TGCCCCAAAC GCACCCCAAC CTGTCCGGAT    6840

CGACAACCCG GTTGGAGGAT TCAGCTTCGC GCTGCCTGCT GGCTGGGTGG AGTCTGACGC    6900

CGCCCACTTC GACTACGGTT CAGCACTCCT CAGCAAAACC ACCGGGGACC CGCCATTTCC    6960

CGGACAGCCG CCGCCGGTGG CCAATGACAC CCGTATCGTG CTCGGCCGGC TAGACCAAAA    7020
```

FIG.5E

```
GCTTTACGCC AGCGCCGAAG CCACCGACTC CAAGGCCGCG GCCCGGTTGG GCTCGGACAT    7080

GGGTGAGTTC TATATGCCCT ACCCGGGCAC CCGGATCAAC CAGGAAACCG TCTCGCTTGA    7140

CGCCAACGGG GTGTCTGGAA GCGCGTCGTA TTACGAAGTC AAGTTCAGCG ATCCGAGTAA    7200

GCCGAACGGC CAGATCTGGA CGGGCGTAAT CGGCTCGCCC GCGGCGAACG CACCGGACGC    7260

CGGGCCCCCT CAGCGCTGGT TTGTGGTATG GCTCGGGACC GCCAACAACC CGGTGGACAA    7320

GGGCGCGGCC AAGGCGCTGG CCGAATCGAT CCGGCCTTTG GTCGCCCCGC CGCCGGCGCC    7380

GGCACCGGCT CCTGCAGAGC CCGCTCCGGC GCCGGCGCCG GCCGGGGAAG TCGCTCCTAC    7440

CCCGACGACA CCGACACCGC AGCGGACCTT ACCGGCCTGA GAATTCTGCA GATATCCATC    7500

ACACTGGCGG CCGCTCGAGC ACCACCACCA CCACCACTGA GATCCGGCTG CTAACAAAGC    7560

CCGAAAGGAA GCTGAGTTGG CTGCTGCCAC CGCTGAGCAA TAACTAGCAT AACCCCTTGG    7620

GGCCTCTAAA CGGGTCTTGA GGGGTTTTTT GCTGAAAGGA GGAACTATAT CCGGAT        7676
```

FIG.5F

Met Gly His His His His His Val Ile Asp Ile Ile Gly Thr Ser
1           5             10            15
Pro Thr Ser Trp Glu Gln Ala Ala Glu Ala Val Gln Arg Ala Arg
          20          25          30
Asp Ser Val Asp Asp Ile Arg Val Ala Arg Val Ile Glu Gln Asp Met
        35          40          45
Ala Val Asp Ser Ala Gly Lys Ile Thr Tyr Arg Ile Lys Leu Glu Val
    50              55              60
Ser Phe Lys Met Arg Pro Ala Gln Pro Arg Gly Ser Lys Pro Pro Ser
65          70              75              80
Gly Ser Pro Glu Thr Gly Ala Gly Ala Gly Thr Val Ala Thr Thr Pro
            85              90              95
Ala Ser Ser Pro Val Thr Leu Ala Glu Thr Gly Ser Thr Leu Leu Tyr
        100             105             110
Pro Leu Phe Asn Leu Trp Gly Pro Ala Phe His Glu Arg Tyr Pro Asn
        115             120             125
Val Thr Ile Thr Ala Gln Gly Thr Gly Ser Gly Ala Gly Ile Ala Gln
    130             135             140
Ala Ala Ala Gly Thr Val Asn Ile Gly Ala Ser Asp Ala Tyr Leu Ser
145             150             155             160
Glu Gly Asp Met Ala Ala His Lys Gly Leu Met Asn Ile Ala Leu Ala
            165             170             175
Ile Ser Ala Gln Gln Val Asn Tyr Asn Leu Pro Gly Val Ser Glu His
        180             185             190
Leu Lys Leu Asn Gly Lys Val Leu Ala Ala Met Tyr Gln Gly Thr Ile
        195             200             205
Lys Thr Trp Asp Asp Pro Gln Ile Ala Ala Leu Asn Pro Gly Val Asn
210             215             220

FIG.5G

Leu Pro Gly Thr Ala Val Val Pro Leu His Arg Ser Asp Gly Ser Gly
225                 230                 235                 240
Asp Thr Phe Leu Phe Thr Gln Tyr Leu Ser Lys Gln Asp Pro Glu Gly
            245                 250                 255
Trp Gly Lys Ser Pro Gly Phe Gly Thr Thr Val Asp Phe Pro Ala Val
                260                 265                 270
Pro Gly Ala Leu Gly Glu Asn Gly Asn Gly Gly Met Val Thr Gly Cys
            275                 280                 285
Ala Glu Thr Pro Gly Cys Val Ala Tyr Ile Gly Ile Ser Phe Leu Asp
    290                 295                 300
Gln Ala Ser Gln Arg Gly Leu Gly Glu Ala Gln Leu Gly Asn Ser Ser
305                 310                 315                 320
Gly Asn Phe Leu Leu Pro Asp Ala Gln Ser Ile Gln Ala Ala Ala Ala
                325                 330                 335
Gly Phe Ala Ser Lys Thr Pro Ala Asn Gln Ala Ile Ser Met Ile Asp
                340                 345                 350
Gly Pro Ala Pro Asp Gly Tyr Pro Ile Ile Asn Tyr Glu Tyr Ala Ile
            355                 360                 365
Val Asn Asn Arg Gln Lys Asp Ala Ala Thr Ala Gln Thr Leu Gln Ala
    370                 375                 380
Phe Leu His Trp Ala Ile Thr Asp Gly Asn Lys Ala Ser Phe Leu Asp
385                 390                 395                 400
Gln Val His Phe Gln Pro Leu Pro Pro Ala Val Val Lys Leu Ser Asp
                405                 410                 415
Ala Leu Ile Ala Thr Ile Ser Ser Ala Glu Met Lys Thr Asp Ala Ala
            420                 425                 430
Thr Leu Ala Gln Glu Ala Gly Asn Phe Glu Arg Ile Ser Gly Asp Leu
        435                 440                 445
Lys Thr Gln Ile Asp Gln Val Glu Ser Thr Ala Gly Ser Leu Gln Gly
    450                 455                 460
Gln Trp Arg Gly Ala Ala Gly Thr Ala Ala Gln Ala Ala Val Val Arg
465                 470                 475                 480

FIG.5H

```
Phe Gln Glu Ala Ala Asn Lys Gln Lys Gln Glu Leu Asp Glu Ile Ser
                485             490             495
Thr Asn Ile Arg Gln Ala Gly Val Gln Tyr Ser Arg Ala Asp Glu Glu
            500             505             510
Gln Gln Gln Ala Leu Ser Ser Gln Met Gly Phe Val Pro Thr Thr Ala
        515             520             525
Ala Ser Pro Pro Ser Thr Ala Ala Ala Pro Pro Ala Pro Ala Thr Pro
    530             535             540
Val Ala Pro Pro Pro Ala Ala Ala Asn Thr Pro Asn Ala Gln Pro
545             550             555             560
Gly Asp Pro Asn Ala Ala Pro Pro Ala Asp Pro Asn Ala Pro Pro
            565             570             575
Pro Pro Val Ile Ala Pro Asn Ala Pro Gln Pro Val Arg Ile Asp Asn
        580             585             590
Pro Val Gly Gly Phe Ser Phe Ala Leu Pro Ala Gly Trp Val Glu Ser
        595             600             605
Asp Ala Ala His Phe Asp Tyr Gly Ser Ala Leu Leu Ser Lys Thr Thr
    610             615             620
Gly Asp Pro Pro Phe Pro Gly Gln Pro Pro Val Ala Asn Asp Thr
625             630             635             640
Arg Ile Val Leu Gly Arg Leu Asp Gln Lys Leu Tyr Ala Ser Ala Glu
            645             650             655
Ala Thr Asp Ser Lys Ala Ala Ala Arg Leu Gly Ser Asp Met Gly Glu
            660             665             670
Phe Tyr Met Pro Tyr Pro Gly Thr Arg Ile Asn Gln Glu Thr Val Ser
        675             680             685
Leu Asp Ala Asn Gly Val Ser Gly Ser Ala Ser Tyr Tyr Glu Val Lys
    690             695             700
Phe Ser Asp Pro Ser Lys Pro Asn Gly Gln Ile Trp Thr Gly Val Ile
705             710             715             720
Gly Ser Pro Ala Ala Asn Ala Pro Asp Ala Gly Pro Pro Gln Arg Trp
            725             730             735
```

FIG.5I

Phe Val Val Trp Leu Gly Thr Ala Asn Asn Pro Val Asp Lys Gly Ala
            740                     745                 750
Ala Lys Ala Leu Ala Glu Ser Ile Arg Pro Leu Val Ala Pro Pro Pro
        755                 760                 765
Ala Pro Ala Pro Ala Pro Ala Glu Pro Ala Pro Ala Pro Ala Pro Ala
    770             775                 780
Gly Glu Val Ala Pro Thr Pro Thr Thr Pro Thr Pro Gln Arg Thr Leu
785                 790             795                     800
Pro Ala
    802

```
ATGCCCGCAGGCCTGCTCAGCGGGATGGCTTTGGCCAGCCTTGCGGCCCGTGGCACCGGGGGCCTGGGCGGCACCAGGAGCGGCACTGACGGCCAAGAGGACGGCCGAAACCC
+---------+---------+---------+---------+---------+---------+---------+---------+---------+---------+---------+   2520
TACGGCGTCCGGACGAGTCGCCCCTACCGAAACGCGCTGGAGCTGCGGGCATCGCCGACCCGCCGCCGGCACCCGCCTGCGGCCTCGCCGGTGGTCCTCGGCCGGGCGTTTGGG
                                            ─── mTCC2 ───
M   P   A   G   L   L   S   G   M   A   L   A   S   L   A   A   R   G   T   T   G   G   G   T   R   S   G   T   S   T   D   G   Q   E   D   G   R   K   P

CCGGTAGTTGTGATTAGAGAGCAGCCCCCGCCGGGAAACCCCCCGCGGTAAGATATC
+---------+---------+---------+---------+---------+------   2577
GGCCATCAACACTAATCTCTCGTCGGGGGCGGCCCTTTGGGGGGCGCCATTCTATAG
─── mTCC2 ───                                       ┌──┐
                                                    │RV│
                                                    └──┘
P   V   V   V   I   R   E   Q   P   P   P   G   N   P   P   R   D   I
```

FIG.6F

```
CATATGCATCACCATCACCATCACATGGCCACCACCCTTCCCGTTCAGCGCCACCCGGCGGTCCCTCTTCCCCGAGTTTTCTGAGCTGTTCGCGGCCTTCC
||||||||||||||||||||||||||||||||||||||||||||||||||||||||||||||||||||||||||||||||||||||||||||||||||| 100
GTATACGTAGTGGTAGTGGTAGTGTACCGGTGGTGGGAAGGGCAAGTCGCGGTGGGCCCAGGGAGAAGGGGCTCAAAAGACTCGACAAGCGCCGGAAGG
```
  H  M  H  H  H  H  H  M  A  T  T  L  P  V  Q  R  H  P  R  S  L  F  P  E  F  S  E  L  F  A  A  F

```
CGTCATTCCCCGGACTCCGGCCCACCTTCGACACCCGGTTGATGCGGCTGGAAGACGAGATGCCCGACGGGGCGCTACGAGGTACGCGCGGAGCTTCCCCG
||||||||||||||||||||||||||||||||||||||||||||||||||||||||||||||||||||||||||||||||||||||||||||||||||| 200
GCAGTAAGGGGCCTGAGGCCGGGTGGAAGCTGTGGGCCAACTACGCCGACCTTCTGCTCTACTTTCTCCCCGCGATGCTCCATGCGCGCCTCGAAGGGCC
```
  P  S  F  A  G  L  R  P  T  F  D  T  R  L  M  R  L  E  D  E  M  K  E  G  R  Y  E  V  R  A  E  L  P  G

```
GGTCGACCCCGACAAGGACGTCGACATTATGGTCCGCGATGGTCAGCTGACCATCAAGGCCGAGCGCACCGAGCAGAAGGACTTCGACGGTCGCTCGGAA
||||||||||||||||||||||||||||||||||||||||||||||||||||||||||||||||||||||||||||||||||||||||||||||||||| 300
CCAGCTGGGGCTGTTCCTGCAGCTGTAATACCAGGCGCTACCAGTCGACTGGTAGTTCCGGCTCGCGTGGCTCGTCTTCCTGAAGCTGCCAGCGAGCCTT
```
  V  D  P  D  K  D  V  D  I  M  V  R  D  G  Q  L  T  I  K  A  E  R  T  E  Q  K  D  F  D  G  R  S  E

```
TTCGCGTACGGTTCCTTCGTTCGCACGGTGTGCTGCCGGTAGGTGCTGACGAGGACGACATTAAGGCCACCTACGACAAGGGCATTCTTACTGTGTCGG
||||||||||||||||||||||||||||||||||||||||||||||||||||||||||||||||||||||||||||||||||||||||||||||||| 400
AAGCGCATGCCAAGGAAGCAAGCGTGCCACAGCGACGGCCATCCACGACTGCTCCTGCTGTAATTCCGGTGGATGCTGTTCCCGTAAGAATGACACAGCC
```
  F  A  Y  G  S  F  V  R  T  V  S  L  P  V  G  A  D  E  D  D  I  K  A  T  Y  D  K  G  I  L  T  V  S

```
TGGCGGTTTCGGAAGGGAAGCCAACCGAAAAGCACATTCAGATCCGGTCCACCAACAAGCTTGATCCCGTGGACGCGGTCATTAACACCACCTGCAATTA
||||||||||||||||||||||||||||||||||||||||||||||||||||||||||||||||||||||||||||||||||||||||||||||||||| 500
ACCGCCAAAGCCTTCCCTTCGGTTGGCTTTTCGTGTAAGTCTAGGCCAGGTGGTTGTTCGAACTAGGGCACCTGCCCCAGTAATTGTGGTGGACGTTAAT
```
  V  A  V  S  E  G  K  P  T  E  K  H  I  Q  I  R  S  T  N  K  L  D  P  V  D  A  V  I  N  T  T  C  N  Y

```
CGGGCAGGTAGTAGCTGCGCTCAACGCGACGGATCCGGGGGCTGCCGCACAGTTCAACGCCCTCACCGGTGGCGCAGTCCTATTTGCGCAATTTCCTCGCC
||||||||||||||||||||||||||||||||||||||||||||||||||||||||||||||||||||||||||||||||||||||||||||||||||| 600
GCCCGTCCATCATCGACGCGAGTTGCGCTGCCTAGGCCCCCGACGGCGTGTCAAGTTGCGGAGTGGCCACCGCGTCAGGATAAACGCGTTAAAGGAGCGG
```
  G  Q  V  V  A  A  L  N  A  T  D  P  G  A  A  Q  F  N  A  S  P  V  A  Q  S  Y  L  R  N  F  L  A

```
GCACCGGCCACCTCAGCCGCCTGCCATGGCCGCGCAATTGCAAGCTGTGCCGGGGGCGGCACAGTACATCGGCCTTGTCGAGTCGGTTGCCGGCTCCTGCA
||||||||||||||||||||||||||||||||||||||||||||||||||||||||||||||||||||||||||||||||||||||||||||||||||| 700
CGTGGCCGGTGGAGTCGGCGGACGGTACCGGCGCCGTTAAACGTTCGACACGGCCCCCGCCGTGTCATGTAGCCGGAACAGCTCAGCCAACGGCCGAGGACGT
```
  A  P  P  P  Q  R  A  A  M  A  A  Q  L  Q  A  V  P  G  A  A  Q  Y  I  G  L  V  E  S  V  A  G  S  C

FIG.7A

```
ACAACTATGAGCTCATGACGATTAATTACCAGTTCGGGGACGTCGACCCTCATGGCCCCATGATCCGCGCTCAGGCGGCGTCGCTTGAGGCGGAGCATCA
||||||||||||||||||||||||||||||||||||||||||||||||||||||||||||||||||||||||||||||||||||||||||||||||||  800
TGTTGATACTCGAGTACTGCTAATTAATGGTCAAGCCCCTGCAGCTGCGAGTACCGCGGTACTAGGCGCGAGTCCGCCGCAGCCAACTCCGCCTCCTAGT
   N  N  Y  E  L  M  T  I  N  Y  Q  F  G  D  V  D  A  H  G  A  M  I  R  A  Q  A  A  S  L  E  A  E  H  Q
```

```
GGCCATCGTTCGTGATGTGTTGGCCGCGGGTGACTTTTGGGGCGGCGCCGGTTCGGTGGCTTGCCAGGAGTTCATTACCCAGTTGGGCCGTAACTTCCAG
||||||||||||||||||||||||||||||||||||||||||||||||||||||||||||||||||||||||||||||||||||||||||||||||||  900
CCGGTAGCAAGCACTACACAACCGGCGCCCACTGAAAACCCCGCCGCGGCCAAGCCACCGAACGGTCCTCAAGTAATGGGTCAACCCGGCATTGAAGGTC
    A  I  V  R  D  V  L  A  A  G  D  F  W  G  G  A  G  S  V  A  C  Q  E  F  I  T  Q  L  G  R  N  F  Q
```

```
GTGATCTACGAGCAGGCCAACGCCCACGGGCAGAAGGTGCAGGCTGCCGGCAACAACATGGCGCAAACCGACAGCGCCGTCGGCTCCAGCTGGGCCACTA
||||||||||||||||||||||||||||||||||||||||||||||||||||||||||||||||||||||||||||||||||||||||||||||||||  1000
CACTAGATGCTCGTCCGGTTGCGGGTGCCCGTCTTCCACGTCCGACGGCCGTTGTTGTACCGCGTTTGGCTGTCGCGGCAGCCGAGGTCGACCCGGTGAT
    V  I  Y  E  Q  A  N  A  H  G  Q  K  V  Q  A  A  G  N  N  M  A  Q  T  D  S  A  V  G  S  S  W  A  T
```

```
GTATGAGCCTTTTGGATGCTCATATCCCACAGTTGGTGGCCTCCCAGTCGGCGTTTGCCGCCAAGGCGGGGCTGATGCGGCACACGATCGGTCAGGCCGA
||||||||||||||||||||||||||||||||||||||||||||||||||||||||||||||||||||||||||||||||||||||||||||||||||  1100
CATACTCGGAAAACCTACGAGTATAGGGTGTCAACCACCGGAGGGTCAGCCGCAAACGGCGGTTCCGCCCCGACTACGCCGTGTGCTAGCCAGTCCGGCT
    S  M  S  L  L  D  A  H  I  P  Q  L  V  A  S  Q  S  A  F  A  A  K  A  G  L  M  R  H  T  I  G  Q  A  E
```

```
GCAGGCGGCGATGTCGGCTCAGGCGTTTCACCAGGGGGAGTCGTCGGCGGCGTTTCAGGCCGCCCATGCCCGGTTTGTGGCGGCGGCCGCCAAAGTCAAC
||||||||||||||||||||||||||||||||||||||||||||||||||||||||||||||||||||||||||||||||||||||||||||||||||  1200
CGTCCGCCGCTACAGCCGAGTCCGCAAAGTGGTCCCCCTCAGCAGCCGCCGCAAAGTCCGGCGGGTACGGGCCAAACACCGCCGCCGGCGGTTTCAGTTG
    Q  A  A  M  S  A  Q  A  F  H  Q  G  E  S  S  A  A  F  Q  A  A  H  A  R  F  V  A  A  A  K  V  N
```

```
ACCTTGTTCGATGTCGCGCCAGGCGAATCTGGGTGAGGCCGCCGGTACCTATGTGGCCGCCGATGCTGCGGCCGCGTCGACCTATACCGGGTTCGATATC
||||||||||||||||||||||||||||||||||||||||||||||||||||||||||||||||||||||||||||||||||||||||||||||||||— 1299
TGGAACAAGCTACAGCGCCGTCCGCTTAGACCCACTCCGGCGGCCATGGATACACCGGCGGCTACGACGCCGGCGCAGCTGGATATGGCCCAAGCTATAG
    T  L  L  D  V  A  Q  A  N  L  G  E  A  A  G  T  Y  V  A  A  D  A  A  A  S  T  Y  T  G  F  D  I
```

FIG.7B

FIG. 8A

```
         10         20         30         40         50         60         70         80         90        100
CATATGCATCACCATCACCATCACGATCCCGTGGACGCGGTCATTAACACCACCTGCAATTACGGGGCAGGTAGTAGCTGCCCTCAACGCGACGGATCCGG
||||||||||||||||||||||||||||||||||||||||||||||||||||||||||||||||||||||||||||||||||||||||||||||||||
GTATACGTAGTGGTAGTGGTAGTGCTAGGGCACCTGCGCCAGTAATTGTGGTGGACGTTAATGCCCGTCCATCATCGACGGGAGTTGCCTGCCTAGCGCC

|—— Met/HIS TAG ——|
  H  H  H  H  H  H  D  P  V  D  A  V  I  N  T  T  C  N  Y  G  Q  V  V  A  A  L  N  A  T  D  P
                                                           |———————— DPV ————————

110        120        130        140        150        160        170        180        190        200
CGGCTGCCCACACAGTTCAACGCCTCACCGGTGGCCAGTACATCGGGCTATTTGGCGCATCCTCCCCGCACCGCCACCTCAGCGCCTGCCATGGCCGCAATT
||||||||||||||||||||||||||||||||||||||||||||||||||||||||||||||||||||||||||||||||||||||||||||||||||||
CCCGACGGGTGTGTCAAGTTGCGGAGTGGCCACCGGTCATGTAGCCCGATAAACCGCGTAGGAGGGGCGTGGCGGTGGAGTCGCGGACGGTACCGGCGTTAA

G  A  A  A  Q  F  N  A  S  P  V  A  Q  S  Y  L  R  N  F  L  A  A  P  P  P  Q  R  A  A  M  A  A  Q  L
                                              |———————— DPV ————————

210        220        230        240        250        260        270        280        290        300
GCAAGCTGTGCCGGGGGCGGGCACAGTACATCGGGCTCATGATCCCGCGCTCGAGTCGTTGCCGGATCCGTTGCACAACTATGAGCTCATGACGATTAATTACCAGTTCGGG
|||||||||||||||||||||||||||||||||||||||||||||||||||||||||||||||||||||||||||||||||||||||||||||||||||
CGTTCGACACGGCCCCCGCCCGTGTCATGTAGCCCGAGTCAGCAGGGCGACGAGCTCAGCAACGGCCTAGGCAACAGCCTGGACACCGCCGACTATACTCGAGTACTGCTAATTAATGGTCAAGCCC

Q  A  V  P  G  A  A  A  Q  Y  I  G  L  V  E  S  V  A  G  S  C  N  N  Y  E  L  M  T  I  N  Y  Q  F  G
                 |———————— DPV ————————                                        |  Sac I  |
                                                                               |———— MT I ————

310        320        330        340        350        360        370        380        390        400
GACGTCGACGCGCTCATGGGCGCCATGATCCGCGCTCAGGCGGCGGCCTCGTTGAGCGGAGCATCAGGCCCATCCGTTCCTGATGTGTTGGCCGCGGGGTGACTTTT
|||||||||||||||||||||||||||||||||||||||||||||||||||||||||||||||||||||||||||||||||||||||||||||||||||
CTGCAGCTGCGCGAGTACCCGCGGTAGCCGCGGTACTAGGCGCGAGTCCGCCGCCGGAGCAACTCGCCTCGTAGTCCGGTAGGATGGCAAGGACTACACAACGGCGCCCCACTGAAAA

```
                                                                                    1700
CCACCCCGATACGGGGAATTGGAGGTGATCGCGCTCTACATTGCATCCATCGGAGACCGGGAGCATTGGGCTCGGGATCACGAACACGGCCAGCACCTGGCA
GGTGGGGCTATCCCCCTTAACCTGCACTAGCGCGAGATGTAACGTAGGTAGCGCCTGCCGCTGCCGGTCGTAACGGCCGAGCCGCTAGTCGTTGTGCCGGTCTCGGACCGT
                                                     ————————— mTCC2 —————————
  P  I  P  I  G  E  L  D  V  I  A  L  Y  I  A  S  I  A  T  G  S  I  A  L  A  I  I  T  N  T  A  R  P  W  H

1800
CATCGGCCTATACGGGGAAGCGGAACGCGGCCGTCGCAGCATCCACTGAGTTCGGCCGACCGATGCCCGAGCCGGAGCCGGAGCCGGACTGGGGCCCCTTCGGG
GTAGCCGGATATGCCCTTCGCCGCCTTGCGCGGCGGCCAGCGTCGTAGGTGACGTCAAGCCGGCTGGCTAGCCGGAGCCGCGAGCCCGCCGGGAAGCCC
                                                     ————————— mTCC2 —————————
  I  G  L  Y  G  N  A  G  G  L  G  P  T  Q  G  H  P  L  S  S  A  T  D  E  P  E  P  H  W  G  P  F  G

1900
GGGCCCGGCGGCGGCGTGCCCGGCGTCGCCACGCGCCGCCAGCATTAGTCGGACCGTTGTCGGGTGCCGCCACAGCAGCTGCTGAACAGCCAGGGCGTGTGACCGGGCCGTGCCCGGCGCGGGCCCTCTAGGTCGAGC
CCGCGCCGCCGCCGCGCCGCCAGCGGTGCGCGGCGGTCGTAATCAGCCTGGCAACAGCTTGTCGGTCCCGCACGACTTGTCGGTCCCGCCGCCGCGCCCGGGAGATCCAGCTCG
                                                     ————————— mTCC2 —————————
  G  A  A  P  V  S  A  G  V  G  H  A  A  L  V  G  A  L  S  V  P  H  S  W  T  T  A  A  P  E  I  Q  L

2000
CCGTTCAGGCGCAACACCCACCTTCAGCTCCAGCGGCGGCGCGGCCGCCACCCGACGGCGCGCCCACGCGGCTAAACCGGATCCGGCAGGCCTGCTCAGCCGGGATGCCTTTGCCGAG
GGCAAGTCCGCTTGTGCGGTGGAAGTCGAGGTCGCGCCGCCGACTTTGCCCTAGGCCCTGGCCTTGCCCGGGGATTTGCCCTACGGCGCCTCCGAGTCGCCCCTACCGAAACCGCTC
                                                     ————————— mTCC2 —————————
  A  V  Q  A  T  P  T  F  S  S  S  A  G  A  D  P  T  A  L  N  G  M  P  A  G  L  L  S  G  M  A  L  A  S
```

```
CCTGCCCCCACGGGGCCACGACGGGCCGTGGCCGGCACCAGCACTGACGGGCACCCGGTAGCGGCCAAGAGGACGGGCCCCAAACCCCGTAGTTGTGATTAGA
+---+---+---+---+---+---+---+---+---+---+---+---+---+---+---+---+---+---+---+---+  2100
GGACGGGGCGTGCCTGCTGCCCACCGGCCGTGGTCGTGACTGCCCGTAGGCCATCGCCGGTTCTCGCCGGTTTGGGCGGCCATCAACACTAATCT
                                                    ─────── mTCC2 ────────
L A A R G T T G G G G T R S G T S T D G Q E D G R K P P V V V I R

2168
GAGCAGCCCCCCGGAAACCCCCGCGTAAGATTTCTAAATCCATCACACTGGGGGCCGCTCGAG
+---+---+---+---+---+---+---+---+---+---+---+---+
CTCGTCGGGGGGCCTTTGGGGGCGCATTCTAAAGATTTAGGTAGTGTGACCCCGGCCGAGCTC
── mTCC2 ──                                    ┌──────────────┬──────┐
                                               │ pET polylinker│ XhoI │
                                               └──────────────┴──────┘
E Q P P P G N P P R    D F I H H T G G R S S
```

FIG.8F

```
CATATGCATCACCATCACCATCACCGATCCCGTGGACGCCGTCATTAACACCACCTGCAATTACGGGCACCTAGTAGCTGCGCTCAACGCGACGGATCCGG
|++++++++|++++++++|++++++++|++++++++|++++++++|++++++++|++++++++|++++++++|++++++++|++++++++| 100
GTATACGTAGTGGTAGTGGTAGTGGCTAGGGCACCTGCGGCCAGTAATTGTGGTGGACGTTAATGCCCGTCCATCATCGACGCGAGTTGCGCTGCCTAGGCC
   H  M  H  H  H  H  H  H  D  P  V  D  A  V  I  N  T  T  C  N  Y  G  Q  V  V  A  A  L  N  A  T  D  P
```

```
GGGCTGCCGGCACAGTTCAACGCCTCACCCGTGGCCCAGTCCTATTTGCGCAATTTCCTCGCCGGCACCGCCACCTCAGCGCGCTGCCATGGCCGCGCCAATT
|++++++++|++++++++|++++++++|++++++++|++++++++|++++++++|++++++++|++++++++|++++++++|++++++++| 200
CCCGACGGCCGTGTCAAGTTGCGGAGTGGGCCACCGGGTCAGGATAAACGCGTTAAAGGAGCGGCCGTGGCGGTGGAGTCGCGCGACGGTACCGGCGCGTTAA
   G  A  A  A  Q  F  N  A  S  P  V  A  Q  S  Y  L  R  N  F  L  A  A  P  P  P  Q  R  A  A  M  A  A  Q  L
```

```
GCAAGCTCTGCCGGGGGCCGGCACAGTACATCGGCCTTGTCGAGTCGGTTGCCGGCTCCTGCAACAACTATGAGCTCATGACGATTAATTACCAGTTCGGG
|++++++++|++++++++|++++++++|++++++++|++++++++|++++++++|++++++++|++++++++|++++++++|++++++++| 300
CGTTCGACACGGCCCCCCGGCCGTGTCATGTAGCCGGAACAGCTCAGCCAACGGCCGAGGACGTTGTTGATACTCGAGTACTGCTAATTAATGGTCAAGCCC
   Q  A  V  P  G  A  A  Q  Y  I  G  L  V  E  S  V  A  G  S  C  N  N  Y  E  L  M  T  I  N  Y  Q  F  G
```

```
GACGTCGACGCTCATGGCGGCCATGATCCGCGCTCAGGCGGCGTCCCTTGAGGCGGAGCATCAGGCCATCGTTCGTGATGTGTTGGCCGCGGGTGACTTTT
|++++++++|++++++++|++++++++|++++++++|++++++++|++++++++|++++++++|++++++++|++++++++|++++++++| 400
CTGCAGCTGCGAGTACCGCCGGTACTAGGCGCGAGTCCGCCGCAGCGAACTCCGCCTCGTAGTCCGGTAGCAAGCACTACACAACCGGCGCCCACTGAAAA
   D  V  D  A  H  G  A  M  I  R  A  Q  A  A  S  L  E  A  E  H  Q  A  I  V  R  D  V  L  A  A  G  D  F
```

```
GGGGCGGCGCCGGTTCGGTGGCTTGCCAGGAGTTCATTACCAGTTGGGCCGTAACTTCCAGGTGATCTACGAGCAGGCCAAGCGCCCACGGGCAGAAGGT
|++++++++|++++++++|++++++++|++++++++|++++++++|++++++++|++++++++|++++++++|++++++++|++++++++| 500
CCCCGCCGCGGCCAAGCCACCGAACGGTCCTCAAGTAATGGTCAACCCGGCATTGAAGGTCCACTAGATGCTCGTCCGGTTCGCGGGTGCCCGTCTTCCA
   W  G  G  A  G  S  V  A  C  Q  E  F  I  T  Q  L  G  R  N  F  Q  V  I  Y  E  Q  A  N  A  H  G  Q  K  V
```

```
GCAGCCTGCCGGCAACAACATGGCGCAAACCGACAGCGCCGTCGGCTCCAGCTGGGCCACTAGTATGAGCCTTTTGGATGCTCATATCCCACAGTTGGTG
|++++++++|++++++++|++++++++|++++++++|++++++++|++++++++|++++++++|++++++++|++++++++|++++++++| 600
CGTCGGACGGCCGTTGTTGTACCGCGTTTGGCTGTCGCGGCAGCCGAGGTCGACCCGGTGATCATACTCGGAAAACCTACGAGTATAGGGTGTCAACCAC
   Q  A  A  G  N  N  M  A  Q  T  D  S  A  V  G  S  S  W  A  T  S  M  S  L  L  D  A  H  I  P  Q  L  V
```

```
GCCTCCCAGTCGGCGTTTGCCGCCAAGGCGGGGCTGATGCGGCACACGATCGGTCAGGCCGAGCAGGCGGCGATGTCGGCTGAGGCGTTTCACCAGGGG
|++++++++|++++++++|++++++++|++++++++|++++++++|++++++++|++++++++|++++++++|++++++++|++++++++| 700
CGGAGGGTCAGCCGCAAACGGCGGTTCCCGCCCCGACTACGCCGTGTGCTAGCCAGTCCGGCTCGTCCGCCGCTACCAGCCGAGTCCGCAAAGTGGTCCCCC
   A  S  Q  S  A  F  A  A  K  A  G  L  M  R  H  T  I  G  Q  A  E  Q  A  A  M  S  A  Q  A  F  H  Q  G
```

FIG.9A

```
AGTCGTCGGCGGCCTTTCAGGCCGCCCATGCCCGGTTTGTGGCGGCCGCCGCCAAAGTCAACACCTTGTTGGATGTCGCGCAGGCGAATCTGGTTGAGGC
++++++++|++++++++|++++++++|++++++++|++++++++|++++++++|++++++++|++++++++|++++++++|++++++++|++++++++| 800
TCAGCAGCCGCCGGAAAGTCCGGCGGGTACGGGCCAAACACCGCCGCCGGCGGTTTCAGTTGTGGAACAACCTACAGCGCGTCCGCTTAGACCCACTCCG
  E  S  S  A  A  F  Q  A  A  H  A  R  F  V  A  A  A  A  K  V  N  T  L  L  D  V  A  Q  A  N  L  G  E  A
```

```
CGCCGGTACCTATGTGGCCGCCGATGCTGCGGCCGCGTCGACCTATACCGGGTTCGATATCCATCACACTGGCGGCCGCCTCGACCAGATCCGGCTGCTAA
++++++++|++++++++|++++++++|++++++++|++++++++|++++++++|++++++++|++++++++|++++++++|++++++++|++++++++| 900
GCGGCCATGGATACACCGGCGGCTACGACGCCGGCGCAGCTGGATATGGCCCAAGCTATAGGTAGTGTGACCGCCGGCGGAGCTCGTATAGGCCGACGATT
   A  G  T  Y  V  A  A  D  A  A  A  A  S  T  Y  T  G  F  D  I  H  H  T  G  G  R  S  S  R  S  G  C
```

```
CAAAGCCCGAAAGGAAGCTGA
++++++++|++++++++|— 921
GTTTCGGGCTTTCCTTCGACT
  Q  S  P  K  G  S
```

FIG.9B

```
CATATGCATCACCATCACCATCACATGGTGGATTTCGGGGCGTTACCACCGGAGATCAACTCCGCGAGGATGTACGCCCGCCCGGGTTCGGCCTCGCTGG
|++++++++|++++++++|++++++++|++++++++|++++++++|++++++++|++++++++|++++++++|++++++++|++++++++| 100
GTATACGTACTGGTAGTGGTAGTGTACCACCTAAAGCCCCGCAATGGTGGCCTCTAGTTGAGGCGCTCCTACATGCGGCCGGGCCCAAGCCGGAGCGACC
  H  M  H  H  H  H  H  H  M  V  D  F  G  A  L  P  P  E  I  N  S  A  R  M  Y  A  G  P  G  S  A  S  L
```

```
TGGCCCGCGGCTCAGATGTGGGACAGCGTGGCGAGTGACCTGTTTTCGGCCGCGTCGGCGTTTCAGTCGGTGGTCTGGGGTCTGACGGTGGGGTCGTGGAT
|++++++++|++++++++|++++++++|++++++++|++++++++|++++++++|++++++++|++++++++|++++++++|++++++++| 200
ACCGGCGCCGAGTCTACACCCTGTCGCACCGCTCACTGGACAAAAGCCGGCGCAGCCGCAAAGTCAGCCACCAGACCCCAGACTGCCACCCCAGCACCTA
   V  A  A  A  Q  M  W  D  S  V  A  S  D  L  F  S  A  A  S  A  F  Q  S  V  V  W  G  L  T  V  G  S  W  I
```

```
AGCTTCGTCGGCGGGTCTGATGGTGGCGGCGGCCTCGCCGTATGTGGCGTGGATGAGCGTCACGGCGGGCAGGCCGAGCTGACCGCCGCCCAGGTCCGG
|++++++++|++++++++|++++++++|++++++++|++++++++|++++++++|++++++++|++++++++|++++++++|++++++++| 300
TCGAAGCAGCCGCCCAGACTACCACCGCCGCCGGAGCGGCATACACCGCACCTACTCGCAGTGGCGCCCCGTCCGGCTCGACTGGCGGCGGGTCCAGGCC
   G  S  S  A  G  L  M  V  A  A  A  S  P  Y  V  A  W  M  S  V  T  A  G  Q  A  E  L  T  A  A  Q  V  R
```

```
GTTGCTGCGGCCGGCCTACGAGACGGCGTATGGGCTGACGGTGCCCCCGCCCGGTGATCGCCGAGAACCGTGCTGAACTGATGATTCTGATAGCGACCAACC
|++++++++|++++++++|++++++++|++++++++|++++++++|++++++++|++++++++|++++++++|++++++++|++++++++| 400
CAACGACGCCGGCCGGATGCTCTGCCGGCATACCCGACTGCCACGGGGCGGCCACTAGCGGCTCTTGGCACGACTTGACTACTAAGACTATCGCTGGTTGG
   V  A  A  A  A  Y  E  T  A  Y  G  L  T  V  P  P  P  V  I  A  E  N  R  A  E  L  M  I  L  I  A  T  N
```

```
TCTTGGGGCAAAACACCCCGGCCGATCGCGGTCAACGAGGCCGAATACGGCGAGATGTGGGCCCAAGACGCCGCCGCGATGTTTGGCTACGCCGCGGCGAC
|++++++++|++++++++|++++++++|++++++++|++++++++|++++++++|++++++++|++++++++|++++++++|++++++++| 500
AGAACCCCGTTTTGTGGGGCCGCTAGCGCCAGTTGCTCCGGCTTATGCCGCTCTACACCCGGGTTCTGCGGCGGCGCTACAAACCGATGCGGCGCCGCTG
   L  L  G  Q  N  T  P  A  I  A  V  N  E  A  E  Y  G  E  M  W  A  Q  D  A  A  A  M  F  G  Y  A  A  A  T
```

```
GGCGACGGCCACGGCGACCTTGCTGCCGTTCGAGGAGGCGCCGGAGATGACCAGCGCGGGTGGGCTCCTCGAGCAGGCCGCCGCGGTCGAGGAGGCCTCC
|++++++++|++++++++|++++++++|++++++++|++++++++|++++++++|++++++++|++++++++|++++++++|++++++++| 600
CCGCTGCCGCTGCCGCTGCCAACGACGGCAAGCTCCTCCGCGGCCTCTACTGGTCGCGCCCACCCGAGGAGCTCGTCCGGCGGCGGCCAGCTCCTCCGGAGG
     A  T  A  T  L  L  P  F  E  E  A  P  E  M  T  S  A  G  G  L  L  E  Q  A  A  A  V  E  E  A  S
```

```
GACACCGCCGCGGCGAACCAGTTGATGAACAATGTGCCCCAGGCGCTGCAACAGCTGGCCCAGCCCACGCAGGGCACCACGCCTTCTTCCAAGCTGGGTG
|++++++++|++++++++|++++++++|++++++++|++++++++|++++++++|++++++++|++++++++|++++++++|++++++++| 701
CTGTGGCGGCGCCGCTTGGTCAACTACTTGTTACACGGGGTCCGCGACGTTGTCGACCGGGTCGGGTGCGTCCCGTGGTGCGGAAGAAGGTTCGACCCAC
   D  T  A  A  A  N  Q  L  M  N  N  V  P  Q  A  L  Q  Q  L  A  Q  P  T  Q  G  T  T  P  S  S  K  L  G
```

FIG.10A

```
GCCTGTGGAAGACGGTCTCGCCCGCATCGGTCGCCCATCAGCAACATGGTGTCGATGGCCAACAACCACATGTCCATGACCAACTCGGGTGTGTCGATGAC
++++++++++++++++++++++++++++++++++++++++++++++++++++++++++++++++++++++++++++++++++++++++++++++++++ 800
CGGACACCTTCTGCCAGAGCGGCGTAGCCAGCGGCTAGTCGTTGTACCACAGCTACCGGTTGTTGGTGTACAGCTACTGGTTGAGCCCACACAGCTACTG
  G  I  W  K  I  V  S  P  H  R  S  P  I  S  N  M  V  S  M  A  N  N  H  M  S  M  T  N  S  G  V  S  M  T

CAACACCTTGACCTCCATGTTGAAGGGCTTTGCTCCGCCGGCGGCCGCCCCAGCCCGTGCAAACCCCGGCCCAAAACGGGGTCCGGGCGATGAGCTCGCTG
++++++++++++++++++++++++++++++++++++++++++++++++++++++++++++++++++++++++++++++++++++++++++++++++++ 900
GTTGTGGAACTGGAGGTACAACTTCCCGAAACGAGGCGGCCGCCGGCGGGTCGGGCACGTTTGGCGCCGGCGTTTTGCCCCAGGCCCGCTACTCGAGCGAC
  N  T  L  S  S  M  L  K  G  F  A  P  A  A  A  A  Q  A  V  Q  T  A  A  Q  N  G  V  R  A  M  S  S  L

GGCAGCTCGCTGGGTTCTTCGGGTCTGGGCGGTGGCGTGGCCCCCAACTTGGGTCGGGCGGCCTCGGTCGGTTCGTTGTCGGTGCCGCAGGCCTGGGCCG
++++++++++++++++++++++++++++++++++++++++++++++++++++++++++++++++++++++++++++++++++++++++++++++++++ 1000
CCGTCGAGCGACCCAAGAAGCCCAGACCCGCCACCCCACCGGCGGTTGAACCCAGCCCCGCGGAGCCAGCCAAGCAACAGCCACGGCGTCCGGACCCGGC
  G  S  S  L  G  S  S  G  L  G  G  V  A  A  N  L  G  R  A  A  S  V  G  S  L  S  V  P  Q  A  W  A

CGGCCAACCAGGCAGTCACCCCGGCGGCGCGGGCGCTGCCGCTGACCAGCCTGACCAGCGCCGCGGAAAGAGGGCCCGGGCAGATGCTGGGCGGGCTGCC
++++++++++++++++++++++++++++++++++++++++++++++++++++++++++++++++++++++++++++++++++++++++++++++++++ 1100
GCCGGTTGGTCCGTCAGTGGGGCCGCCGCGCCCGCGACGGCGACTGGTCGGACTGGTCGCGGCGCCTTTCTCCCGGGCCCGTCTACGACCCGCCCGACGG
  A  A  N  Q  A  V  T  P  A  A  R  A  L  P  L  T  S  L  T  S  A  A  E  R  G  P  G  Q  M  L  G  L  P

GGTGGGGCAGATGGGCGCCAGGGCCGGTGGTGGGCTCAGTGGTGTGCTGCGTGTTCCCCCGCGACCCTATGTGATGCCGCATTCTCCGGCAGCCGGCAAG
++++++++++++++++++++++++++++++++++++++++++++++++++++++++++++++++++++++++++++++++++++++++++++++++++ 1200
CCACCCCGTCTACCCGCGGTCCCGGCCACCACCCGAGTCACCACACGACGCACAAGGCGCGCCTGGGATACACTACGGCGTAAGAGGCCGTCGGCCGTTC
  V  G  Q  M  G  A  R  A  G  G  G  L  S  G  V  L  R  V  P  P  R  P  Y  V  M  P  H  S  P  A  A  G  K

CTTGATCCCGTGGACGCCGTCATTAACACCACCTGCAATTACGGGCAGGTAGTAGCTGCCCTCAACGCGACGGATCCGGGGGCTGCCGCACAGTTCAACG
++++++++++++++++++++++++++++++++++++++++++++++++++++++++++++++++++++++++++++++++++++++++++++++++++ 1300
GAACTAGGGCACCTGCGCCAGTAATTGTGGTGGACGTTAATGCCCGTCCATCATCGACGCGAGTTGCGCTGCCTAGGCCCCCGACGGCGTGTCAAGTTGC
  L  D  P  V  D  A  V  I  N  T  T  C  N  Y  G  Q  V  V  A  A  L  N  A  T  D  P  G  A  A  A  Q  F  N

CCTCACCGGTGCCCAGTCCTATTTGCGCAATTTCCTCGCCGCACCGCCACCTCAGCGCGCTGCCATGGCCGCGCAATTGCAAGCTGTGCCGGGGGCGGC
++++++++++++++++++++++++++++++++++++++++++++++++++++++++++++++++++++++++++++++++++++++++++++++++++ 1400
GGAGTGGCCACCCCGTCAGGATAAACGCGTTAAAGGAGCGGCGTGGCGGTGGAGTCGCGCGACGGTACCGGCGCGTTAACGTTCGACACGGAAAAAGCCG
  A  S  P  V  A  Q  S  Y  L  R  N  F  L  A  A  P  P  P  Q  R  A  A  M  A  A  Q  L  Q  A  V  P  G  A  A
```

FIG.10B

```
ACAGTACATCGGCCTTGTCGAGTCGGTTGCCGGCTCCTGCAACAACTATGAGCTCATGACGATTAATTACCAGTTCGGGGACGTCGACGCTCATGGCGCC
++++++++|++++++++|++++++++|++++++++|++++++++|++++++++|++++++++|++++++++|++++++++|++++++++| 1500
TGTCATGTAGCCGGAACAGCTCAGCCAACGGCCGAGGACGTTGTTGATACTCGAGTACTGCTAATTAATGGTCAAGCCCCTGCAGCTGCGAGTACCGCGG
  Q  Y  I  G  L  V  E  S  V  A  G  S  C  N  N  Y  E  L  M  T  I  N  Y  Q  F  G  D  V  D  A  H  G  A
```

```
ATGATCCGCGCTCAGGCGGCGTCGCTTGAGGCGGAGCATCAGGCCATCGTTCGTGATGTGTTGGCCGCCGGCTGACTTTTGGGGCCGGCCCCGGTTCGTGG
++++++++|++++++++|++++++++|++++++++|++++++++|++++++++|++++++++|++++++++|++++++++|++++++++| 1600
TACTAGGCGCGAGTCCGCCGCAGCGAACTCCGCCTCGTAGTCCGGTAGCAAGCACTACACAACCGGCGCCCACTGAAAACCCCGGCCGCGGCCAAGCCACC
  M  I  R  A  Q  A  A  S  L  E  A  E  H  Q  A  I  V  R  D  V  L  A  A  G  D  F  W  G  G  A  G  S  V
```

```
CTTGCCAGGAGTTCATTACCCAGTTGGGCCGTAACTTCCAGGTGATCTACGAGCAGGCCAACGCCCACGGGCAGAAGGTGCAGGCTGCCGGCAACAACAT
++++++++|++++++++|++++++++|++++++++|++++++++|++++++++|++++++++|++++++++|++++++++|++++++++| 1700
GAACGGTCCTCAAGTAATGGGTCAACCCGGCATTGAAGGTCCACTAGATGCTCGTCCCGTTGCGGGTGCCCGTCTTCCACGTCCGACGGCCGTTGTTGTA
  A  C  Q  E  F  I  T  Q  L  G  R  N  F  Q  V  I  Y  E  Q  A  N  A  H  G  Q  K  V  Q  A  A  G  N  N  M
```

```
GGCGCAAACCGACAGCGCCGTCGGCTCCAGCTGGGCCACTAGTAACGGCCGCCAGTGTGCTGGAATTCTGCAGATATCCATCACACTGGCGGCCGCTCGA
++++++++|++++++++|++++++++|++++++++|++++++++|++++++++|++++++++|++++++++|++++++++|++++++++| 1800
CCGCGTTTGGCTGTCGCGGCAGCCGAGGTCGACCCGGTGATCATTGCCGGCGGTCACACGACCTTAAGACGTCTATAGGTAGTGTGACCGCCGGCGAGCT
  A  Q  T  D  S  A  V  G  S  S  W  A  T  S  N  G  R  Q  C  A  G  I  L  Q  I  S  I  T  L  A  A  A  R
```

FIG.10C

```
CATATGCATCACCATCACCATCACATGCCCACCACCCTTCCCGTTCAGCGCCACCCGCGGTCCCTCTTCCCCGAGTTTTCTGAGCCTGTTCGCGGCCTTCC
||||||||||||||||||||||||||||||||||||||||||||||||||||||||||||||||||||||||||||||||||||||||||||||||||| 100
GTATACGTAGTGGTAGTGGTAGTGTACCGGTGGTGGGAACGGCAAGTCGCGGTGGGCCCAGGGAGAAGGGGCTCAAAAGACTCGACAAGCGCCGGAAGG
  H  M  H  H  H  H  H  H  M  A  T  T  I  P  V  Q  R  H  P  R  S  I  F  P  F  F  S  F  I  F  A  A  F
```
```
CGTCATTCGCCCGGACTCCGGCCCACCTTCGACACCCCGTTGATGCGGCTGGAAGACGAGATGAAAGAGGGGCGCTACGAGGTACGCGCGGAGCTTCCCGG
||||||||||||||||||||||||||||||||||||||||||||||||||||||||||||||||||||||||||||||||||||||||||||||||||| 200
GCAGTAAGCGGCCTGAGGCCGGGTGGAAGCTGTGGGCCAACTACGCCGACCTTCTGCTCTACTTTCTCCCCGCGATGCTCCATGCGCGCCTCGAAGGGCC
  P  S  F  A  G  L  R  P  T  F  D  T  R  L  M  R  L  E  D  E  M  K  E  G  R  Y  E  V  R  A  E  L  P  G
```
```
GGTCGACCCCGACAAGGACGTCGACATTATGGTCCGCGATGGTCAGCTGACCATCAAGGCCGAGCGCACCGAGCAGAAGGACTTCGACGGTCGCTCGGAA
||||||||||||||||||||||||||||||||||||||||||||||||||||||||||||||||||||||||||||||||||||||||||||||||||| 300
CCAGCTGGGGCTGTTCCTGCAGCTGTAATACCAGGCGCTACCAGTCGACTGGTAGTTCCGGCTCGCGTGGCTCGTCTTCCTGAAGCTGCCAGCGAGCCTT
   V  D  P  D  K  D  V  D  I  M  V  R  D  G  Q  L  T  I  K  A  E  R  T  E  Q  K  D  F  D  G  R  S  E
```
```
TTCCCGTACGGTTCCTTCGTTCGCACGGTGTCCCTGCCCGGTAGCGTGCTGACGAGGACGACATTAAGGCCACCTACGACAAGGGCATTCTTACTGTGTCGG
||||||||||||||||||||||||||||||||||||||||||||||||||||||||||||||||||||||||||||||||||||||||||||||||||| 400
AAGGGCATGCCAAGGAAGCAAGCGTGCCACAGCGACGGCCATCCACGACTGCTCCTGCTGTAATTCCGGTGGATGCTGTTCCCGTAAGAATGACACAGCC
   F  A  Y  G  S  F  V  R  T  V  S  L  P  V  G  A  D  E  D  D  I  K  A  T  Y  D  K  G  I  L  T  V  S
```
```
TGGCGGTTTCGGAAGGGAAGCCAACCGAAAAGCACATTCAGATCCGGTCCACCAACAAGCTTGATCCCGTGGACGCGGTCATTAACACCACCTGCAATTA
||||||||||||||||||||||||||||||||||||||||||||||||||||||||||||||||||||||||||||||||||||||||||||||||||| 500
ACCGCCAAAGCCTTCCCTTCGGTTGGCTTTTCGTGTAAGTCTAGGCCAGGTGGTTGTTCGAACTAGGGCACCTGCGCCAGTAATTGTGGTGGACGTTAAT
   V  A  V  S  E  G  K  P  T  E  K  H  I  Q  I  R  S  T  N  K  L  D  P  V  D  A  V  I  N  T  T  C  N  Y
```
```
CGGGCAGCTAGTAGCTCGCCTCAACGCGACGGATCCGGGGGCTGCCGCAGAGTTCAACGCCTCACCGGTGGCGCAGTCCTATTTGCGCAATTTCCTCGCC
||||||||||||||||||||||||||||||||||||||||||||||||||||||||||||||||||||||||||||||||||||||||||||||||||| 600
GCCCGTCGATCATCGACGCGAGTTGCGCTGCCTAGGCCCCCGACGGCGTGTCAAGTTGCGGAGTGGCCACCGCGTCAGGATAAACGCGTTAAAGGAGCGG
    G  Q  V  V  A  A  L  N  A  T  D  P  G  A  A  Q  F  N  A  S  P  V  A  Q  S  Y  L  R  N  F  L  A
```
```
GCACCGCCACCTCAGCGCGCCTGCCATGGCCGCGGCAATTGCAAGCTGTGCCGGGGCGCCGCACAGTACATCGGCCTTGTCGAGTCGGTTGCCGGCTCCTGCA
||||||||||||||||||||||||||||||||||||||||||||||||||||||||||||||||||||||||||||||||||||||||||||||||||| 700
CGTGGCGGTGGAGTCGCGCGGACGGTACCGGCGCGTTAACGTTCGACACGGCCCCGCCGTGTCATGTAGCCGGAACAGCTCAGCCAACGGCCGAGGACGT
   A  P  P  P  Q  R  A  A  M  A  A  Q  L  Q  A  V  P  G  A  A  Q  Y  I  G  L  V  E  S  V  A  G  S  C
```

FIG.11A

```
ACAACTATGAGCTCATGACGATTAATTACCAGTTCGGGGACGTCGACGCTCATGGCCCCATGATCCCCGCTCAGGCGGCCTCGCTTGAGGCGGAGCATCA
||||||||||||||||||||||||||||||||||||||||||||||||||||||||||||||||||||||||||||||||||||||||||||||||||  800
TGTTGATACTCGAGTACTGCTAATTAATGGTCAAGCCCCTGCAGCTGCGAGTACCGGGGTACTAGGCGCGAGTCCGCCGCAGCGAACTCCGCCTCGTAGT
  N N Y E L M T I N Y Q F G D V D A H G A M I R A Q A A S L E A E H Q
```

```
GGCCATCGTTCGTGATGTGTTGGGCGCGGGTGACTTTTGGGGCGGCGCCGGTTCGGTGGCTTGCCAGGAGTTCATTACCCAGTTGGGCCGTAACTTCCAG
||||||||||||||||||||||||||||||||||||||||||||||||||||||||||||||||||||||||||||||||||||||||||||||||||  900
CCGGTAGCAAGCACTACACAACCCGCGCCCACTGAAAACCCCGCCGCGGCCAAGCCACCGAACCGTCCTCAAGTAATGGGTCAACCCGGCATTGAAGGTC
   A I V R D V L A A G D F W G G A G S V A C Q E F I T Q L G R N F Q
```

```
GTGATCTACGAGCAGGCCAACGCCCACGGGCAGAAGGTGCAGGCTGCCGGCAACAACATGGCCCAAACCGACAGCGCCGTGGGCTCCAGCTGGGCCACTA
||||||||||||||||||||||||||||||||||||||||||||||||||||||||||||||||||||||||||||||||||||||||||||||||||  1000
CACTAGATGCTCGTCCGGTTGCGGGTGCCCGTCTTCCACGTCCGACGGCCGTTGTTGTACCCGGTTTGGCTGTCGCGGCAGCCGAGGTCGACCCGGTGAT
   V I Y E Q A N A H G Q K V Q A A G N N M A Q T D S A V G S S W A T
```

```
GTAACGGCCGCCAGTGTGCTGGAATTCTGCAGATATCCATCACACTGGCGGCCGCTCGAGCAGATCCGGCTGCTAACAAAGCCCGAAAGGAAGCTGAGTT
||||||||||||||||||||||||||||||||||||||||||||||||||||||||||||||||||||||||||||||||||||||||||||||||||  1100
CATTGCCGGCGGTCACACGACCTTAAGACGTCTATAGGTAGTGTGACCGCCGGCGAGCTCGTCTAGGCCGACGATTGTTTCGGGCTTTCCTTCGACTCAA
   S N G R Q C A G I L Q I S I T L A A A R A D P A A N K A R K E A E L
```

```
GGCT
||||  1104
CCGA
 A
```

FIG. 11B

```
CATATGCATCACCATCACCATCACATGGTGGATTTCGGGGCGTTACCACCCGAGATCAACTCCGCGAGGATGTACGCCCGGCCCGGGTTCGCCCTCGCTGG
++++++++++++++++++++++++++++++++++++++++++++++++++++++++++++++++++++++++++++++++++++++++++++++++++++ 100
GTATACGTAGTGGTAGTGGTAGTGTACCACCTAAAGCCCCGCAATGGTGGCCTCTAGTTGAGGCGCTCCTACATGCGGCCGGGCCCAAGCCCGAGCGACC
  H  M  H  H  H  H  H  H  M  V  D  F  G  A  L  P  P  I  N  S  A  R  M  Y  A  G  P  G  S  A  S  L
```

```
TGCCCGCGGCTCAGATGTGGGACAGCGTGGCGAGTGACCTGTTTTCGGCCGCGTCGGCGTTCAGTGGTGGTCTGGGGTCTGACGGTGGGGTCGTGGAT
++++++++++++++++++++++++++++++++++++++++++++++++++++++++++++++++++++++++++++++++++++++++++++++++ 200
ACGGGCGCCGAGTCTACACCCTGTCGCACCGCTCACTGGACAAAAGCCGGCGCAGCCGCAAAGTCAGCCACCAGACCCCAGACTGCCACCCCAGCACCTA
  V  A  A  A  Q  M  W  D  S  V  A  S  D  L  F  S  A  A  S  A  F  Q  S  V  V  W  G  L  V  G  S  W  I
```

```
AGGTTCCTCGGCGGGTCTGATGGTGGCGGCGGCCTCGCCGTATGTGGCGTGGATGAGCGTCACCGCGGGGCAGGCCGAGCTGACCGCCGCCCAGGTCCGG
++++++++++++++++++++++++++++++++++++++++++++++++++++++++++++++++++++++++++++++++++++++++++++++++++ 300
TCCAAGCAGCCGCCCAGACTACCACCGCCGCCCGGAGCGGCATACACCGCACCTACTCGCAGTGGCGCCCCGTCCGGCTCGACTGGCGGCGGGTCCAGGCC
  G  S  S  A  G  L  M  V  A  A  A  S  P  Y  V  A  W  M  S  V  T  A  G  Q  A  E  L  T  A  A  Q  V  R
```

```
GTTGCTGCGGCCGCCTACGAGACGGCGTATGGGCTGACGGTGCCCCCGCCCGTGATCGCCGAGAACCGTGCTGAACTGATGATTCTGATAGCGACCAACC
++++++++++++++++++++++++++++++++++++++++++++++++++++++++++++++++++++++++++++++++++++++++++++++++++ 400
CAACGACGCCGGCGGATGCTCTGCCGCATACCCGACTGCCACGGGGGCGGCCACTAGCGGCTCTTGGCACGACTTGACTACTAAGACTATCGCTGGTTGG
  V  A  A  A  A  Y  E  T  A  Y  G  L  T  V  P  P  P  V  I  A  E  N  R  A  E  L  M  I  L  I  A  T  N
```

```
TCTTGGGGCAAAACACCCCGGCCGATCGCGGTCAACGAGGCCGAATACGGCGAGATGTGGGCCCAAGACGCCGCCGCGATGTTTGGCTACGCCGCGGCGAC
++++++++++++++++++++++++++++++++++++++++++++++++++++++++++++++++++++++++++++++++++++++++++++++++++ 500
AGAACCCCGTTTTGTGGGGCCGCTAGCGCCAGTTGCTCCGGCTTATGCCGCTCTACACCCGGGTTCTGCGGCGGCGCTACAAACCGATGCGGCGCCGCTG
   L  L  G  Q  N  T  P  A  I  A  V  N  E  A  E  Y  G  E  M  W  A  Q  D  A  A  A  M  F  G  Y  A  A  A  T
```

```
GGCGACGGCGACGGCGAACGTTGCTGCCGTTCGAGGACGCGCCGGAGATGACCAGCGCGGTGGGCTCCTCGAGCAGGCCGCCGCCGGTCGAGGAGGCCTCC
++++++++++++++++++++++++++++++++++++++++++++++++++++++++++++++++++++++++++++++++++++++++++++++++++ 600
CCGCTGCCGCTGCCGCTGCAACGACGGCAAGCTCCTCCGCGGCCTCTACTGGTCGCGCCCACCCGAGGAGCTCGTCCGGCGGCGCCAGCTCCTCCGGAGG
   A  T  A  T  A  T  L  L  P  F  E  E  A  P  E  M  T  S  A  G  G  L  L  E  Q  A  A  A  V  E  E  A  S
```

```
GACACCGCCGCGGCGAACCAGTTGATGAACAATGTGCCCCAGGCGCTGCAACAGCTGGCCCAGCCCACGCAGGGCACCACGCCTTCTTCCAAGCTGGGTG
++++++++++++++++++++++++++++++++++++++++++++++++++++++++++++++++++++++++++++++++++++++++++++++++++ 700
CTGTGGCGGCGCCGCTTGGTCAACTACTTGTTACACGGGGTCGGCGACGTTGTCGACCGGGTCGGGTGCGTCCCGTGGTGCGGAAGAAGGTTCGACCCAC
   D  T  A  A  A  N  Q  L  M  N  N  V  P  Q  A  L  Q  Q  L  A  Q  P  T  Q  G  T  T  P  S  S  K  L  G
```

FIG.12A

```
CCCTGTGGAAGACGGTCTCGCCGCATCGGTCGCCCATCAGCAACATGGTGTCGATGGCCAACAACCACATGTCGATGACCAACTCGGGTGTGTCGATGAC
||||||||||||||||||||||||||||||||||||||||||||||||||||||||||||||||||||||||||||||||||||||||||||||||||| 800
GGGACACCTTCTGCCAGAGCGGCGTAGCCAGCGGCTAGTCGTTGTACCACAGCTACCGGTTGTTGGTGTACAGCTACTGGTTGAGCCCACACAGCTACTG
  G L W K T V S P H R S P I S N M V S M A N N H M S M T N S G V S M T

CAACACCTTGAGCTCGATGTTGAAGGGCTTTGCTCCCGCCGCCGCCCGCCCAGGCCGTGCCAAACCGCGGCGCCAAAACGGGGTCCGGGCCGATGAGCTCGCTG
||||||||||||||||||||||||||||||||||||||||||||||||||||||||||||||||||||||||||||||||||||||||||||||||||| 900
GTTGTGGAACTCGAGCTACAACTTCCCGAAACGAGGCCGCCGGCGCGGGTCCGGCACGGTTTGGCGCCGCGGTTTTGCCCCAGGCCCGGCTACTCGAGCGAC
   N T L S S M L K G F A P A A A A Q A V Q T A A Q N G V R A M S S L

GGCAGCTCCCTGGGTTCTTCGGGTCTGGGCGGTGGCGTGGCCGCCAACTTGGGTCGGGCGGCCCTCGGTCGGTTCGTTGTCGGTGCCGCAGGCCTGGGCCG
||||||||||||||||||||||||||||||||||||||||||||||||||||||||||||||||||||||||||||||||||||||||||||||||||| 1000
CCGTCGAGGGACCCAAGAAGCCCAGACCCGCCACCCCACCGGCGGTTGAACCCAGCCCGCCGGAGCCAGCCAAGCAACAGCCACGGCGTCCGGACCCGGC
   G S S L G S S G L G G G V A A N L G R A A S V G S L S V P Q A W A

CGGCCAACCAGGCAGTCACCCCGGCGGCGCGGGCGCTGCCCCTGACCAGCCTGACCAGCGCCGCGGAAAGAGGGCCCGGGCAGATGCTGGGCGGGCTGCC
||||||||||||||||||||||||||||||||||||||||||||||||||||||||||||||||||||||||||||||||||||||||||||||||||| 1100
GCCGGTTGGTCCGTCAGTGGGGCCGCCGCGCCCCGCACGGCGACTGGTCGGACTGGTCGCGGCGCCTTTCTCCCGGGCCCGTCTACGACCCGCCCGACGG
  A A N Q A V T P A A R A L P L T S L T S A A E R G P G Q M L G G L P

GGTCCGGCAGATGGCGCCCAGGGCCGGTGGTGGGCTCAGTGGTGTGCTGCGTGTTCCGCCGCGACCCTATGTGATGCCGCATTCTCCGGCAGCCGGCGAT
||||||||||||||||||||||||||||||||||||||||||||||||||||||||||||||||||||||||||||||||||||||||||||||||||| 1200
CCAGCCCGTCTACCCGCGGTCCCGGCCACCACCCGAGTCACCACACGACGCACAAGGCGGCGCTGGATACACTACGGCGTAAGAGGCCGTCGGCCCCTA
    V G Q M G A R A G G G L S G V L R V P P R P Y V M P H S P A A G D

ATCGCCCCGCCGGCCTTGTCGCAGGACCGGTTCGCCGACTTCCCGCGGCTGCCCCTCGACCCGTCGGCGATGGTCGCCCAAGTGGGGCCACAGGTGGTCA
||||||||||||||||||||||||||||||||||||||||||||||||||||||||||||||||||||||||||||||||||||||||||||||||||| 1300
TAGCGGGGCGGCCGGAACAGCGTCCTGGCCAAGCGGCTGAAGGGCGCGACGGGGAGCTGGGCAGGCCCTACCAGCGGGTTCACCCCGGTGTCCACCAGT
   I A P P A L S Q D R F A D F P A L P L D P S A M V A Q V G P Q V V

ACATCAACACCAAACTGGGCTACAACAACGCCGTGGGCGCCGGGACCGGCATCGTCATCGATCCCAACGGTGTCGTGCTGACCAACAACCACGTGATCGC
||||||||||||||||||||||||||||||||||||||||||||||||||||||||||||||||||||||||||||||||||||||||||||||||||| 1400
TGTAGTTGTGGTTTGACCCGATGTTGTTGCGGCACCCGCGGCCCTGGCCGTAGCAGTAGCTAGGGTTGCCACAGCACGACTGGTTGTTGGTGCACTAGCG
   N I N T K L G Y N N A V G A G T G I V I D P N G V V L T N N H V I A
```

FIG.12B

```
GCGGCCCACCGACATCAATGCGTTCAGCGTCGGCTCCGGCCAAACCTACGGCGTCGATGTGGTCGGGTATGACCGCACCCAGGATGTCGCCGTCCTGCAG
+++++++++|+++++++++|+++++++++|+++++++++|+++++++++|+++++++++|+++++++++|+++++++++|+++++++++|+++++++++| 1500
CCCGCCGTGGCTGTAGTTACGCAAGTCGCAGCCGAGGCCGGTTTGGATGCCGCAGCTACACCAGCCCATACTGGCGTGGGTCCTACAGCGCCACGACGTC
  G  A  T  D  I  N  A  F  S  V  G  S  G  Q  T  Y  G  V  D  V  V  G  Y  D  R  T  Q  D  V  A  V  L  Q
```

```
CTGCGCGGTGCCGGTGCCCTGCCGTCGGCGCCGATCGGTGGCGGCGTCCCGGTTGGTGAGCCCGTCCTCGCCGATGGGCAACAGCGGTGGGCAGGGCCGAA
+++++++++|+++++++++|+++++++++|+++++++++|+++++++++|+++++++++|+++++++++|+++++++++|+++++++++|+++++++++| 1600
GACGCGCCACGGCCACCGGACGGCAGCCGCCGGGATCGGTGGCCGGGAGGGCCAACCACTCGGGCAGCAGCGCCTACCCGTTGTCGCCACCCGTCCCGGCTT
  L  R  G  A  G  G  L  P  S  A  A  I  G  G  G  V  A  V  G  E  P  V  V  A  M  G  N  S  G  G  Q  G  G
```

```
CCGCCCGTCCGGTGCCCTGGCAGGGTGGTCGCCCTCGGCCAAACCGTGCAGGCGTCGGATTCGCTGACCGGTGCCGAAGAGACATTGAACGGGTTGATCCA
+++++++++|+++++++++|+++++++++|+++++++++|+++++++++|+++++++++|+++++++++|+++++++++|+++++++++|+++++++++| 1700
GCGGGGCACGCCACGGACCGTCCCACCAGCCGCAGCCGGTTTGGCACGTCCGCAGCCTAAGCGACTGGCCACGGCTTCTCTGTAACTTGCCCAACTAGGT
  T  P  R  A  V  P  G  R  V  V  A  L  G  Q  T  V  Q  A  S  D  S  L  T  G  A  E  E  T  L  N  G  L  I  Q
```

```
GGTCGATGCCGCGATCCAGCCCGGTGATTCGGGCGGCCCCGTCGTCAACGGCCTAGGACAGGTGGTCGGTATGAACACGGCCGCGTCCTAGGATATC
+++++++++|+++++++++|+++++++++|+++++++++|+++++++++|+++++++++|+++++++++|+++++++++|+++++++++|++++++→ 1797
CAAGCTACGGCGCCTAGGTCGGGCCACTAAGCCCGCCGGGGCAGCAGTTGCCGGATCCTGTCCACCAGCCATACTTGTGCCGGCGCAGGATCCTATAG
  F  D  A  A  I  Q  P  G  D  S  G  G  P  V  V  N  G  L  G  Q  V  V  G  M  N  T  A  A  S     D  I
```

FIG.12C

```
                                                  Mlu113 I
                                                    Soc II
          Mlu I                                     Sst II
           PliM I
            Van91 I    Eco47 III          SgrA I  Bcl I  Sal I
```

FIG.13A

```
                    Eco52 I                                                                 Clr9 I
                    Xma III                                                                 Xma I
                    |             EcoR I           Bam HI                                   | Sma I
                    |             |                |                                        | | Bgl I
                    |             |                |                                        | | |
TGGCCCAGGGACCCCCCGGCCGAATTCGACGACGACGACAAGGATCCACCTGACCCGCATCAGCCGGACATGACGAAAGGCTATTGCCCCGGGTGGCCCGATG
++++++++++|++++++++++|++++++++++|++++++++++|++++++++++|++++++++++|++++++++++|++++++++++|++++++++++|  500
ACCGGCTCCCTGGGGGCCGGCTTAAGCTGCTGCTGCTGTTCCTAGGTGGACTGGGCGTAGTCGGCCTGTACTGCTTTCCGATAACGGGGCCCACCGGCTAC

L A E G P P A E F D D D D K D P P D P H Q P D M T K G Y C P G G R W
    W P R D P R P N S T T T T R I H L T R I S R T   R K A L A R V A D
      G R G T P G R I R R R R Q G S T   P A S A G H D E R L L P G W P M

GGGTTTTGGCGACTTGGCCCGTGTGCGACGGCGAGAAGTACCCCGACGGCTCGTTTTGGCACCAGTGGATGCAAACGTGGTTTACCGGCCCACAGTTTTAC
++++++++++|++++++++++|++++++++++|++++++++++|++++++++++|++++++++++|++++++++++|++++++++++|++++++++++|  600
CCCAAAACCGCTGAACCGGCACACGCTGCCGCTCTTCATGGGGCTGCCGAGCAAAACCGTGGTCACCTACGTTTGCACCAAATGGCCGGGTGTCAAAATG

G F G D L A V C D G E K Y P D G S F W H Q W M Q T W F T G P Q F Y
     G V L A T W P C A T A R S T P T A R F G T S G C K R G L P A H S F T
       G F W R L G R V R R R E V P R R L V L A P V D A N V V Y R P T V L

Dra III
                              PflM I
            RleA I            Van91 I                                              EcoR I
            |                 |                                                    |
TTCGATTGTGTCAGCGGCGGTGAGCCCCTCCCCGGCCCGCCGCCACCGGGTGGTTGCGGTGGGGCAATTCCCTCCGAGCAGCCCAACGCTCCCTGAGAAT
++++++++++|++++++++++|++++++++++|++++++++++|++++++++++|++++++++++|++++++++++|++++++++++|++++++++++| 700
AAGCTAACACAGTCGCCGCCACTCGGGGAGGGGCCGGGCGGCGGTGGCCCACCAACGCCACCCCGTTAAGGGAGGCTCGTCGGGTTGCGAGGGACTCTTA

F D C V S G G E P L P G P P P P G G C G G A I P S E Q P N A P   E
     S I V S A A V S P S P A R R H R V V A V G Q F R P S S P T L P E N
       L R L C Q R R   A P P R P A A T G W L R W G N S V R A A Q R S L R I

TC
→702
AG

F
S
→
```

FIG.13B

# FUSION PROTEINS OF *MYCOBACTERIUM TUBERCULOSIS* ANTIGENS AND THEIR USES

The present application is a division of U.S. patent application Ser. No. 11/511,587, now U.S. Pat. No. 7,335,369, filed Aug. 28, 2006, which is a continuation of U.S. patent application Ser. No. 11/201,519, filed Aug. 10, 2005, now abandoned, which is a division of U.S. patent application Ser. No. 10/359,460, filed Feb. 5, 2003, now U.S. Pat. No. 6,977,069, which is continuation of U.S. patent application Ser. No. 09/287,849, filed Apr. 7, 1999, now U.S. Pat. No. 6,627,198, each of which is incorporated by reference in the entirety.

1. INTRODUCTION

The present invention relates to fusion proteins containing at least two *Mycobacterium tuberculosis* antigens. In particular, it relates to bi-fusion proteins which contain two individual *M. tuberculosis* antigens, tri-fusion proteins which contain three *M. tuberculosis* antigens, tetra-fusion proteins which contain four *M. tuberculosis* antigens, and penta-fusion proteins which contain five *M. tuberculosis* antigens, and methods for their use in the diagnosis, treatment and prevention of tuberculosis infection.

2. BACKGROUND OF THE INVENTION

Tuberculosis is a chronic infectious disease caused by infection with *M. tuberculosis*. It is a major disease in developing countries, as well as an increasing problem in developed areas of the world, with about 8 million new cases and 3 million deaths each year. Although the infection may be asymptomatic for a considerable period of time, the disease is most commonly manifested as an acute inflammation of the lungs, resulting in fever and a nonproductive cough. If untreated, serious complications and death typically result.

Although tuberculosis can generally be controlled using extended antibiotic therapy, such treatment is not sufficient to prevent the spread of the disease. Infected individuals may be asymptomatic, but contagious, for some time. In addition, although compliance with the treatment regimen is critical, patient behavior is difficult to monitor. Some patients do not complete the course of treatment, which can lead to ineffective treatment and the development of drug resistance.

In order to control the spread of tuberculosis, effective vaccination and accurate early diagnosis of the disease are of utmost importance. Currently, vaccination with live bacteria is the most efficient method for inducing protective immunity. The most common *Mycobacterium* employed for this purpose is *Bacillus* Calmette-Guerin (BCG), an avirulent strain of *M. bovis*. However, the safety and efficacy of BCG is a source of controversy and some countries, such as the United States, do not vaccinate the general public with this agent.

Diagnosis of tuberculosis is commonly achieved using a skin test, which involves intradermal exposure to tuberculin PPD (protein-purified derivative). Antigen-specific T cell responses result in measurable induration at the injection site by 48-72 hours after injection, which indicates exposure to Mycobacterial antigens. Sensitivity and specificity have, however, been a problem with this test, and individuals vaccinated with BCG cannot be distinguished from infected individuals.

While macrophages have been shown to act as the principal effectors of *M. tuberculosis* immunity, T cells are the predominant inducers of such immunity. The essential role of T cells in protection against *M. tuberculosis* infection is illustrated by the frequent occurrence of *M. tuberculosis* in Acquired Immunodeficiency Syndrome patients, due to the depletion of CD4+ T cells associated with human immunodeficiency virus (HIV) infection. *Mycobacterium*-reactive CD4+ T cells have been shown to be potent producers of gamma-interferon (IFN-γ), which, in turn, has been shown to trigger the anti-mycobacterial effects of macrophages in mice. While the role of IFN-γ in humans is less clear, studies have shown that 1,25-dihydroxy-vitamin D3, either alone or in combination with IFN-γ or tumor necrosis factor-alpha, activates human macrophages to inhibit *M. tuberculosis* infection. Furthermore, it is known that IFN-γ stimulates human macrophages to make 1,25-dihydroxy-vitamin D3. Similarly, interleukin-12 (IL-12) has been shown to play a role in stimulating resistance to *M. tuberculosis* infection. For a review of the immunology of *M. tuberculosis* infection, see Chan and Kaufmann, 1994, *Tuberculosis: Pathogenesis, Protection and Control*, Bloom (ed.), ASM Press, Washington, D.C.

Accordingly, there is a need for improved vaccines, and improved methods for diagnosis, preventing and treating tuberculosis.

3. SUMMARY OF THE INVENTION

The present invention relates to fusion proteins of *M. tuberculosis* antigens. In particular, it relates to fusion polypeptides that contain two or more *M. tuberculosis* antigens, polynucleotides encoding such polypeptides, methods of using the polypeptides and polynucleotides in the diagnosis, treatment and prevention of *M. tuberculosis* infection.

The present invention is based, in part, on the inventors' discovery that polynucleotides which contain two to five *M. tuberculosis* coding sequences produce recombinant fusion proteins that retain the immunogenicity and antigenicity of their individual components. The fusion proteins described herein induced both T cell and B cell responses, as measured by T cell proliferation, cytokine production, and antibody production. Furthermore, a fusion protein was used as an immunogen with adjuvants in vivo to elicit both cell-mediated and humoral immunity to *M. tuberculosis*. Additionally, a fusion protein was made by a fusion construct and used in a vaccine formulation with an adjuvant to afford long-term protection in animals against the development of tuberculosis. The fusion protein was a more effective immunogen than a mixture of its individual protein components.

In a specific embodiment of the invention, the isolated or purified *M. tuberculosis* polypeptides of the invention may be formulated as pharmaceutical compositions for administration into a subject in the prevention and/or treatment of *M. tuberculosis* infection. The immunogenicity of the fusion protein may be enhanced by the inclusion of an adjuvant.

In another aspect of the invention, the isolated or purified polynucleotides are used to produce recombinant fusion polypeptide antigens in vitro. Alternatively, the polynucleotides may be administered directly into a subject as DNA vaccines to cause antigen expression in the subject, and the subsequent induction of an anti-*M. tuberculosis* immune response.

It is also an object of the invention that the polypeptides be used in in vitro assays for detecting humoral antibodies or cell-mediated immunity against *M. tuberculosis* for diagnosis of infection or monitor of disease progression. Additionally, the polypeptides may be used as an in vivo diagnostic agent in the form of an intradermal skin test. Alternatively, the polypeptides may be used as immunogens to generate anti-*M.*

*tuberculosis* antibodies in a non-human animal. The antibodies can be used to detect the target antigens in vivo and in vitro.

4. BRIEF DESCRIPTION OF THE DRAWINGS

FIGS. 1A-1C: The nucleotide sequence (SEQ ID NO:1) and amino acid sequence (SEQ ID NO:2) of tri-fusion protein Ra12-TbH9-Ra35 (designated Mtb32-Mtb39 fusion).

FIGS. 2A and 2B: The nucleotide sequence (SEQ ID NO:3) and amino acid sequence (SEQ ID NO:4) of tri-fusion protein Erd14-DPV-MTI.

FIG. 3A-3D: The nucleotide sequence (SEQ ID NO:5) and amino acid sequence (SEQ ID NO:6) of tri-fusion protein TbRa3-38 kD-Tb38-1.

FIG. 4A-4D: The nucleotide sequence (SEQ ID NO:7) and amino acid sequence (SEQ ID NO:8) of bi-fusion protein TbH9-Tb38-1.

FIG. 5A-5J: The nucleotide sequence (SEQ ID NO:9) and amino acid sequence (SEQ ID NO:10) of tetra-fusion protein TbRa3-38 kD-Tb38-1-DPEP (designated TbF-2).

FIGS. 6A-6F: The nucleotide sequence (SEQ ID NO:11) and amino acid sequence (SEQ ID NO:12) of penta-fusion protein Erd14-DPV-MTI-MSL-MTCC2 (designated Mtb88f).

FIGS. 7A and 7B: The nucleotide sequence (SEQ ID NO:13) and amino acid sequence (SEQ ID NO:14) of tetra-fusion protein Erd14-DPV-MTI-MSL (designated Mtb46f).

FIGS. 8A-8F: Nucleotide sequence (SEQ ID NO:15) encoding: tetra-fusion protein DPV-MTI-MSL-MTCC2 (designated Mtb71f) with initial histidine tag (SEQ ID NO:16) and artificial sequence of SEQ ID NO:17.

FIGS. 9A and 9B: The nucleotide sequence (SEQ ID NO:18) and amino acid sequence (SEQ ID NOS:19 and 20) of tri-fusion protein DPV-MTI-MSL (designated Mtb31f).

FIGS. 10A-10C: The nucleotide sequence (SEQ ID NO:21) and amino acid sequence (SEQ ID NO:22) of tri-fusion protein TbH9-DPV-MTI (designated Mtb61f).

FIG. 11A and 11B: The nucleotide sequence (SEQ ID NO:23) and amino acid sequence (SEQ ID NO:24) of tri-fusion protein Erd14-DPV-MTI (designated Mtb36f).

FIGS. 12A-12C: The nucleotide sequence (SEQ ID NO:25) and amino acid sequence (SEQ ID NO:26) of bi-fusion protein TbH9-Ra35 (designated Mtb59f).

FIG. 13A and 13B: The nucleotide sequence (SEQ ID NO:27) and amino acid sequences from three reading frames (SEQ ID NOS:28, 29-33 and 34-39, respectively) of bi-fusion protein Ra12-DPPD (designated Mtb24).

FIG. 14A-14F: T cell proliferation responses of six PPD+ subjects when stimulated with two fusion proteins and their individual components.

FIG. 15A-15F: IFN-γ production of six PPD+ subjects when stimulated with two fusion proteins and their individual components.

FIG. 16A-16F: T cell proliferation of mice immunized with a fusion protein or its individual components and an adjuvant.

Figure 17:
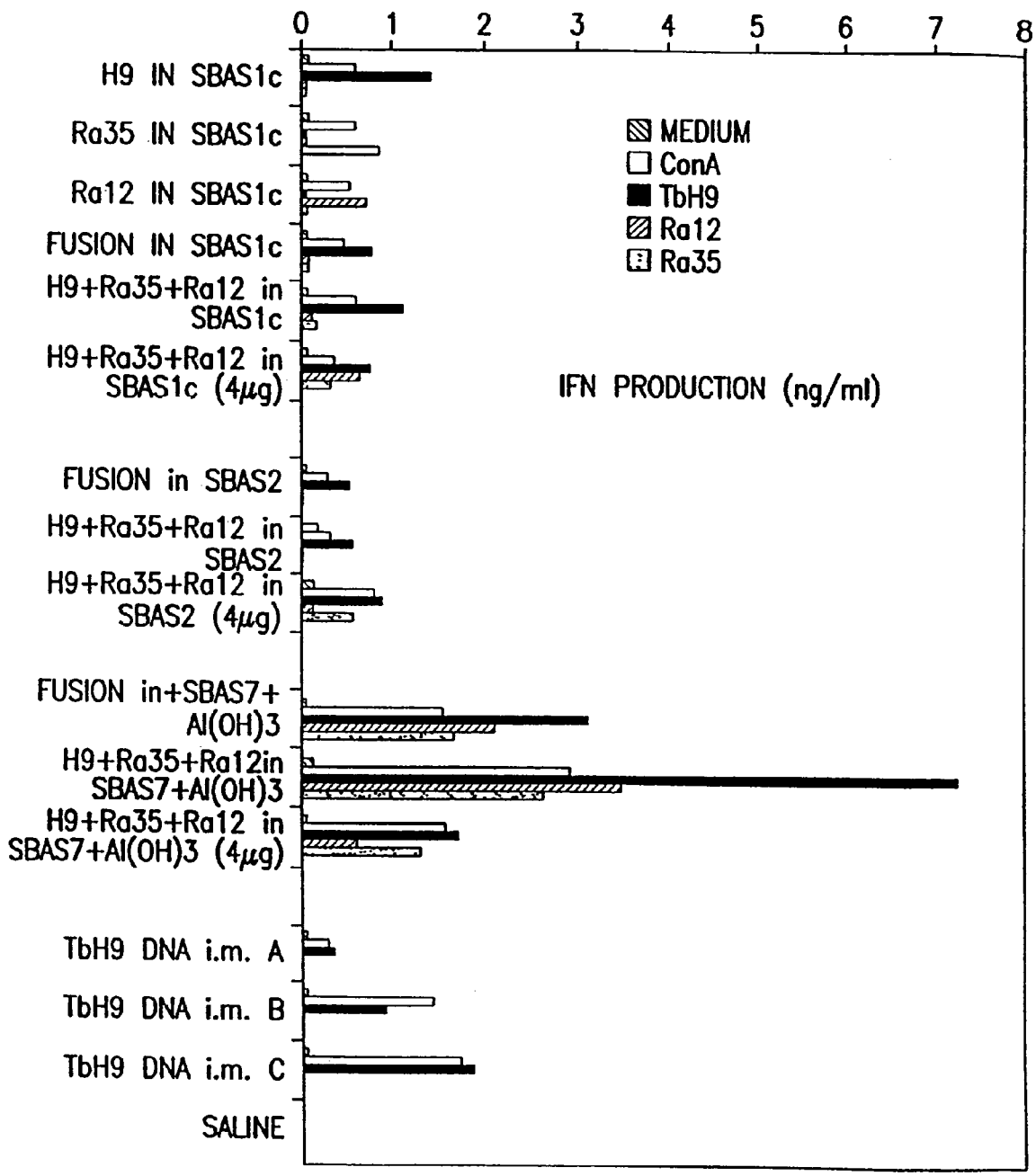

FIG. 17: IFN-γ production of mice immunized with a fusion protein or its individual components and an adjuvant.

Figure 18:
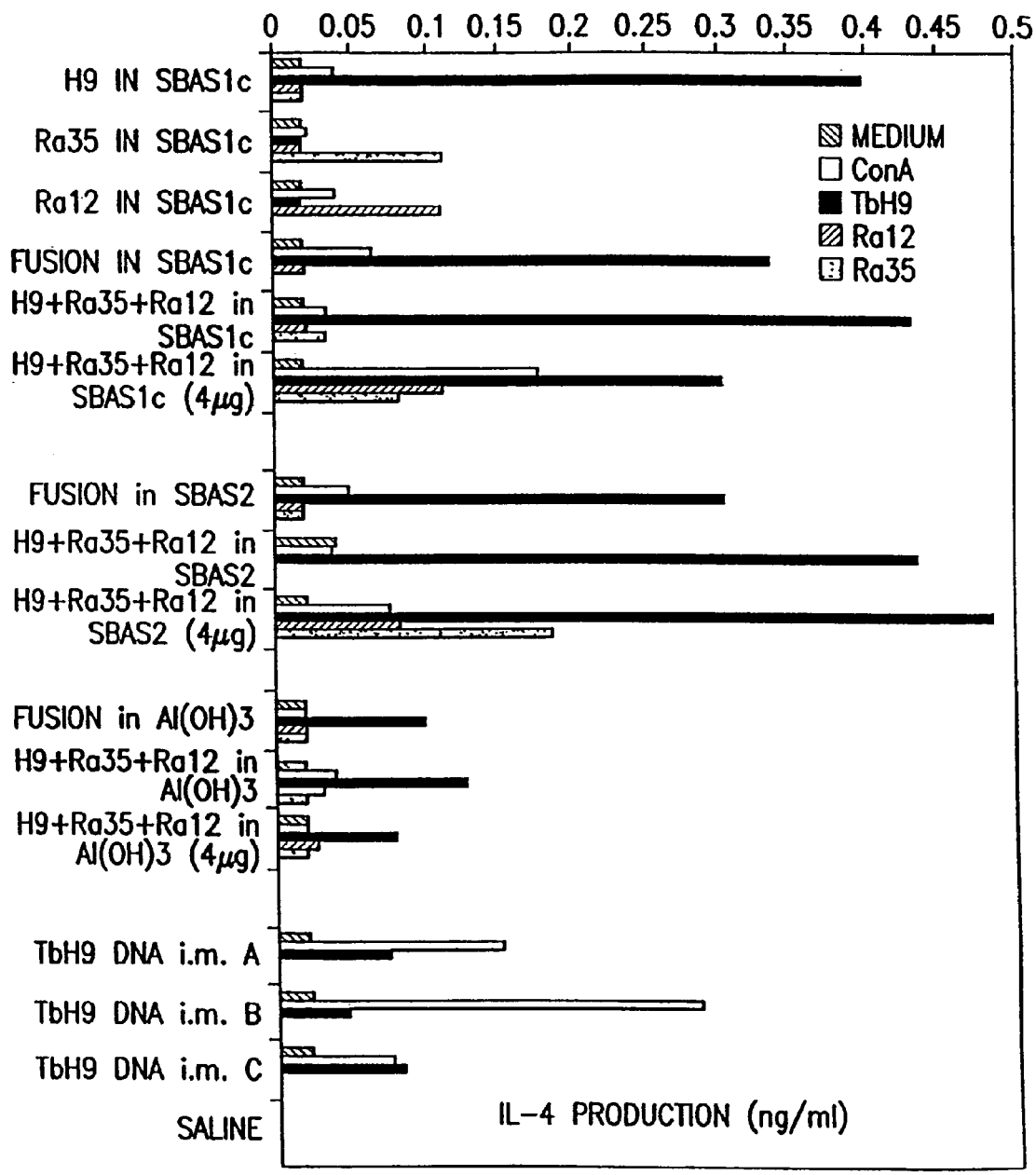
Figure 19A:
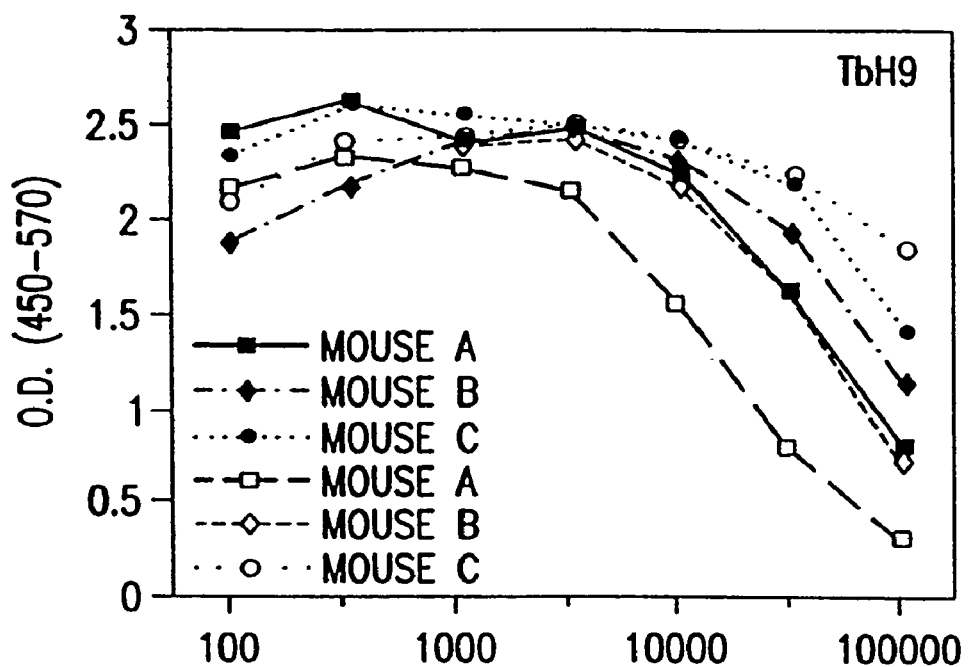
Figure 19B:
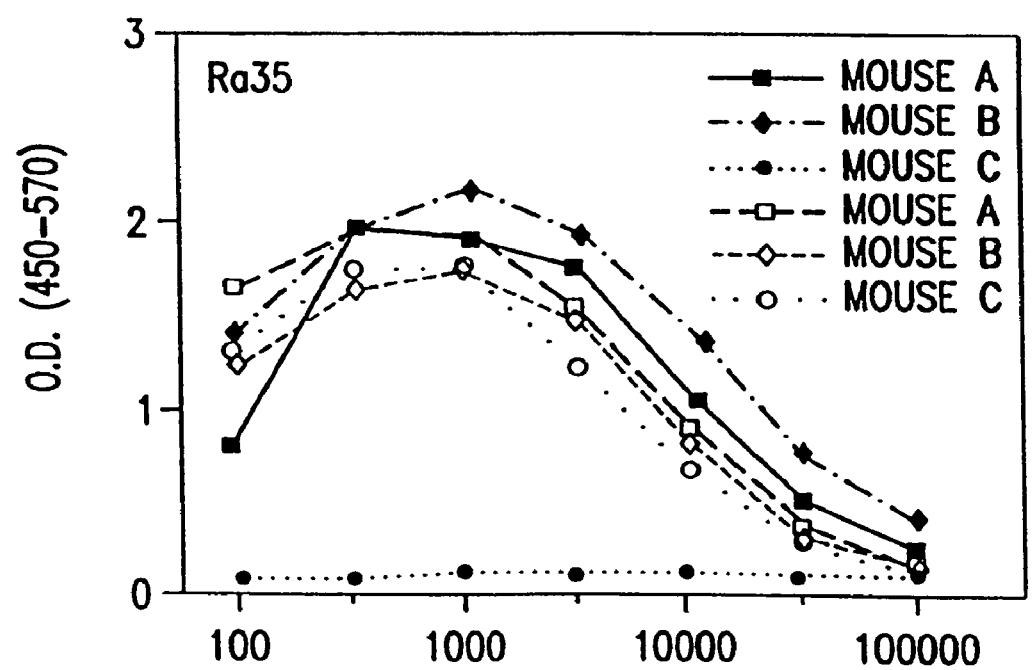
Figure 19C:
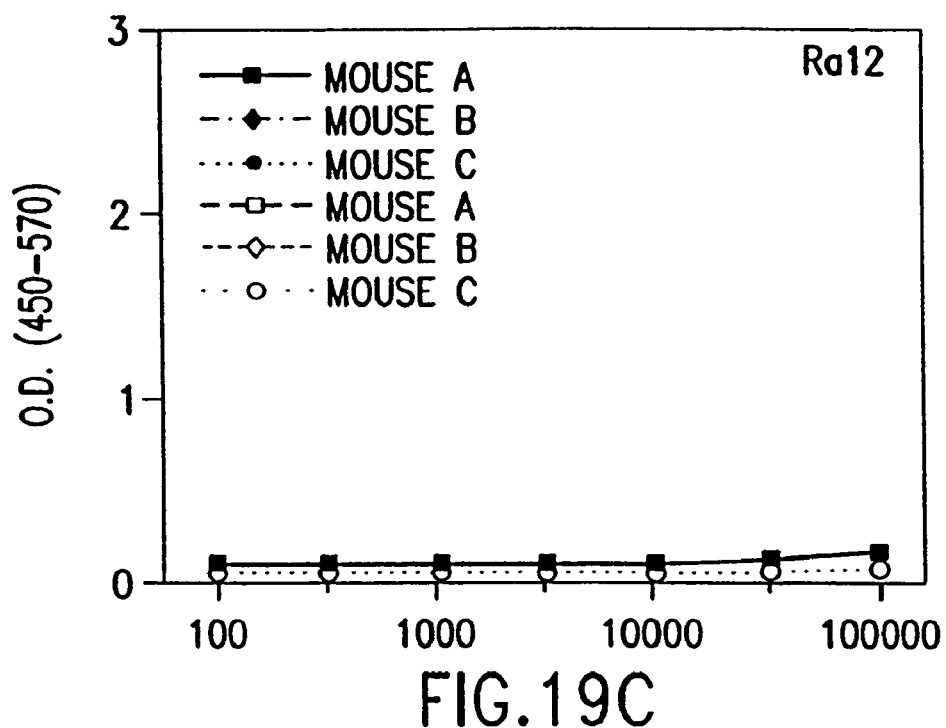
Figure 19D:
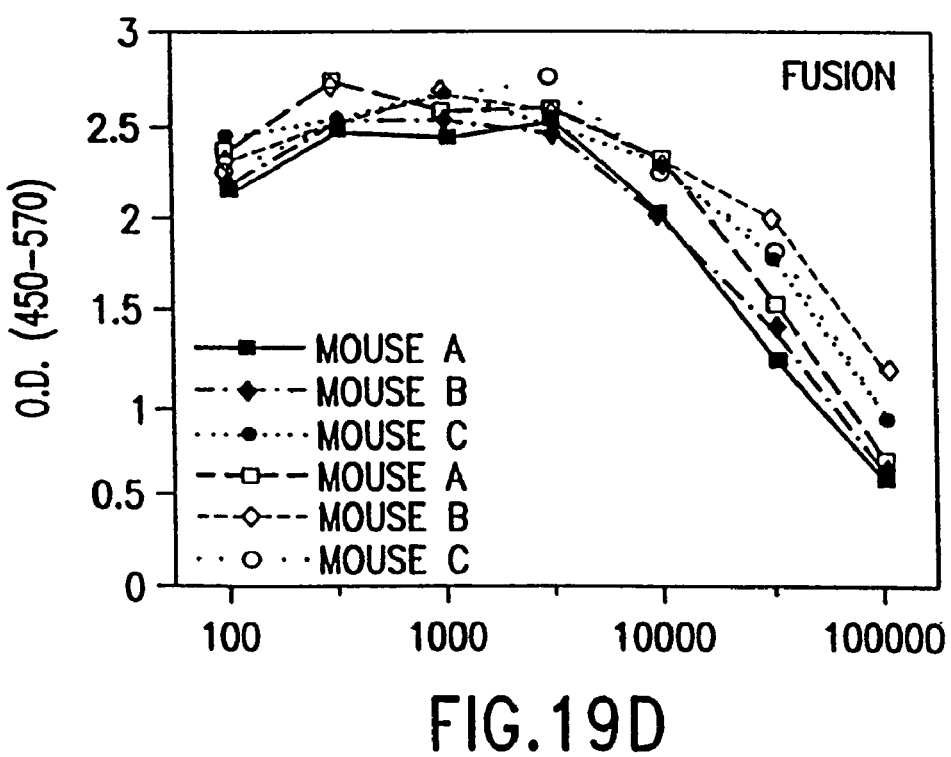
Figure 19E:
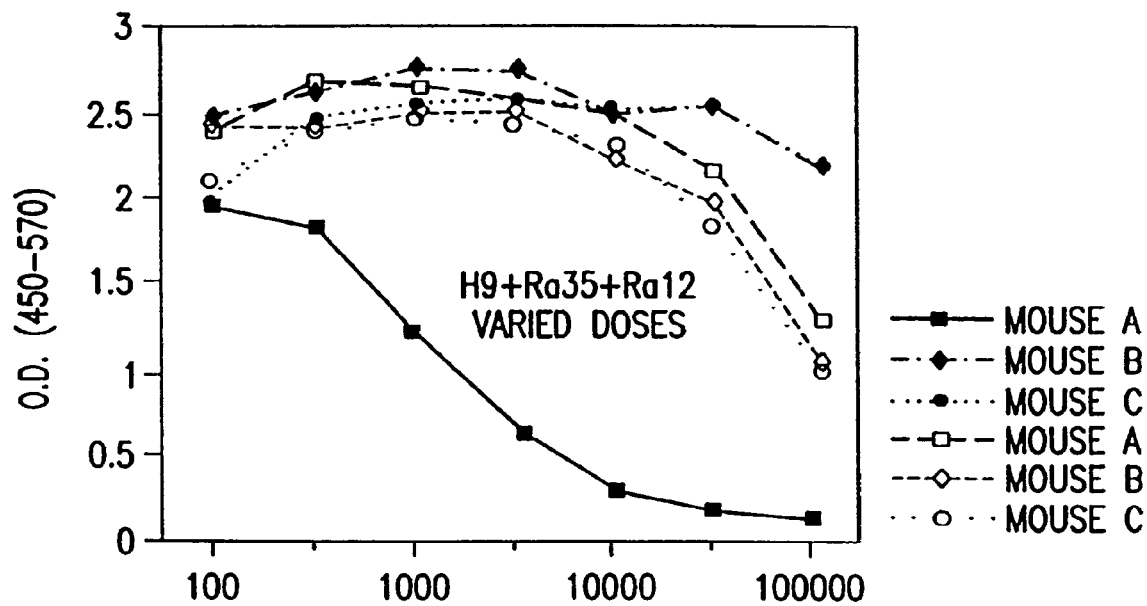
Figure 19F:
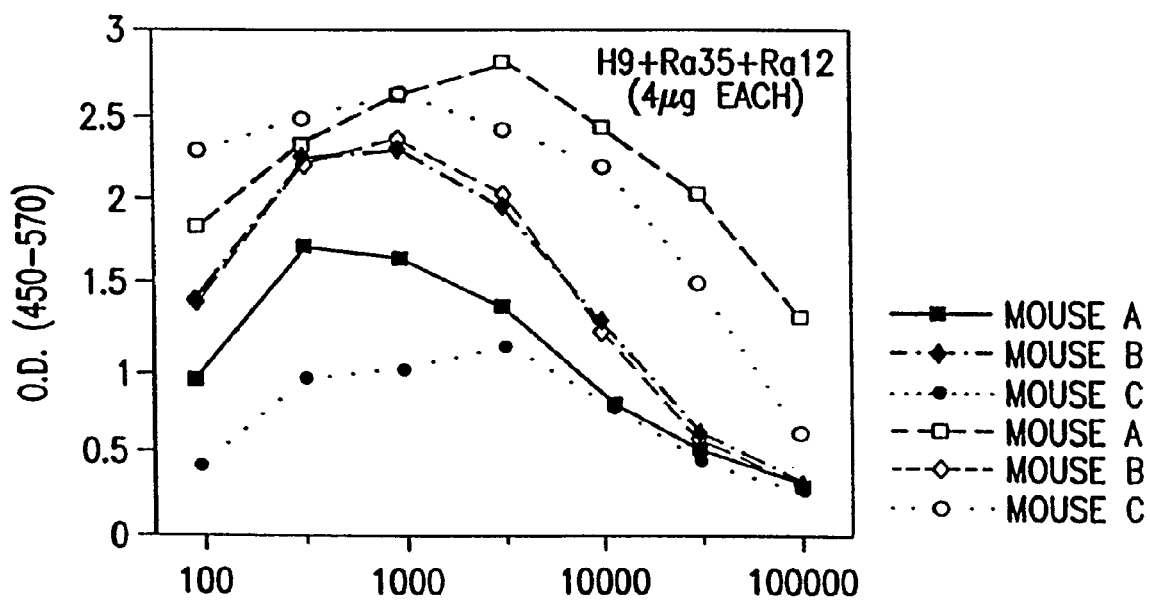

FIG. 18: IL4 production of mice immunized with a fusion protein or its individual components and an adjuvant.

FIG. 19A-19F: Serum antibody concentrations of mice immunized with a fusion protein or its individual components and an adjuvant.

Figure 20A:
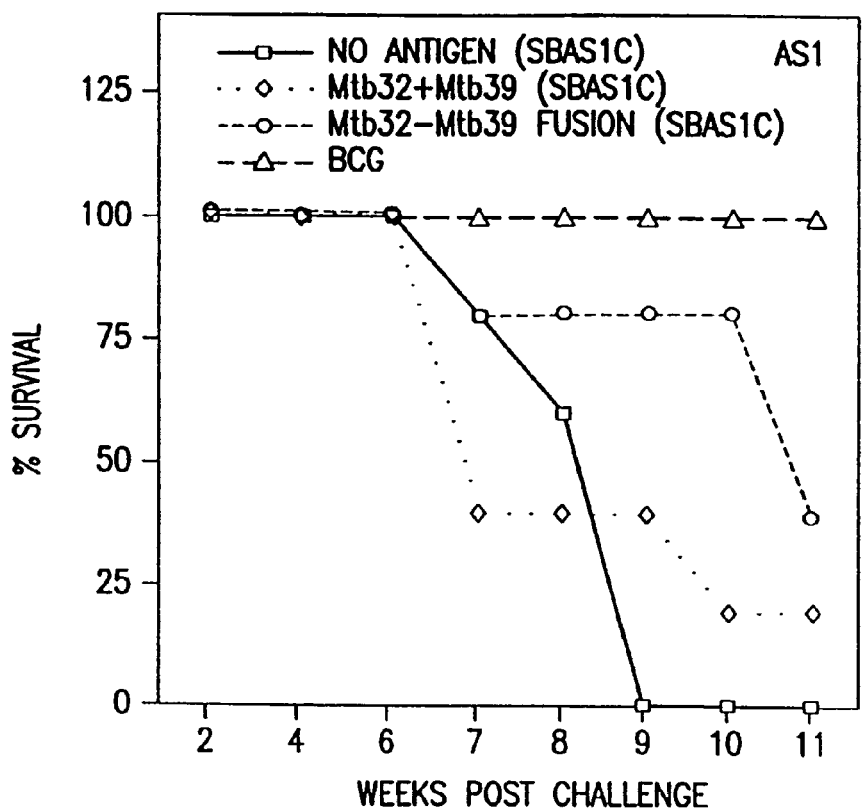
Figure 20B:
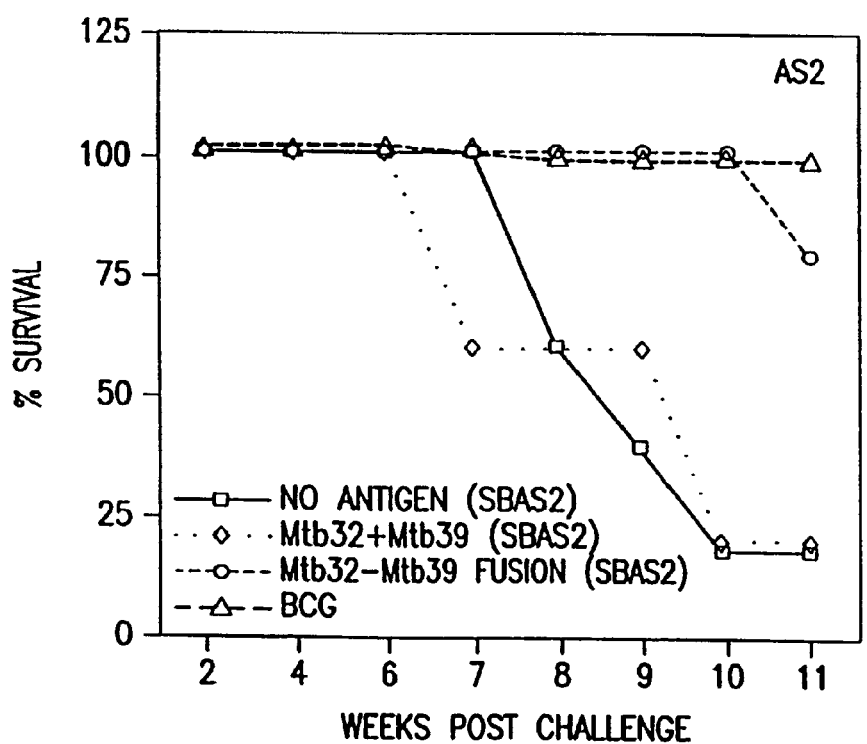
Figure 20C:
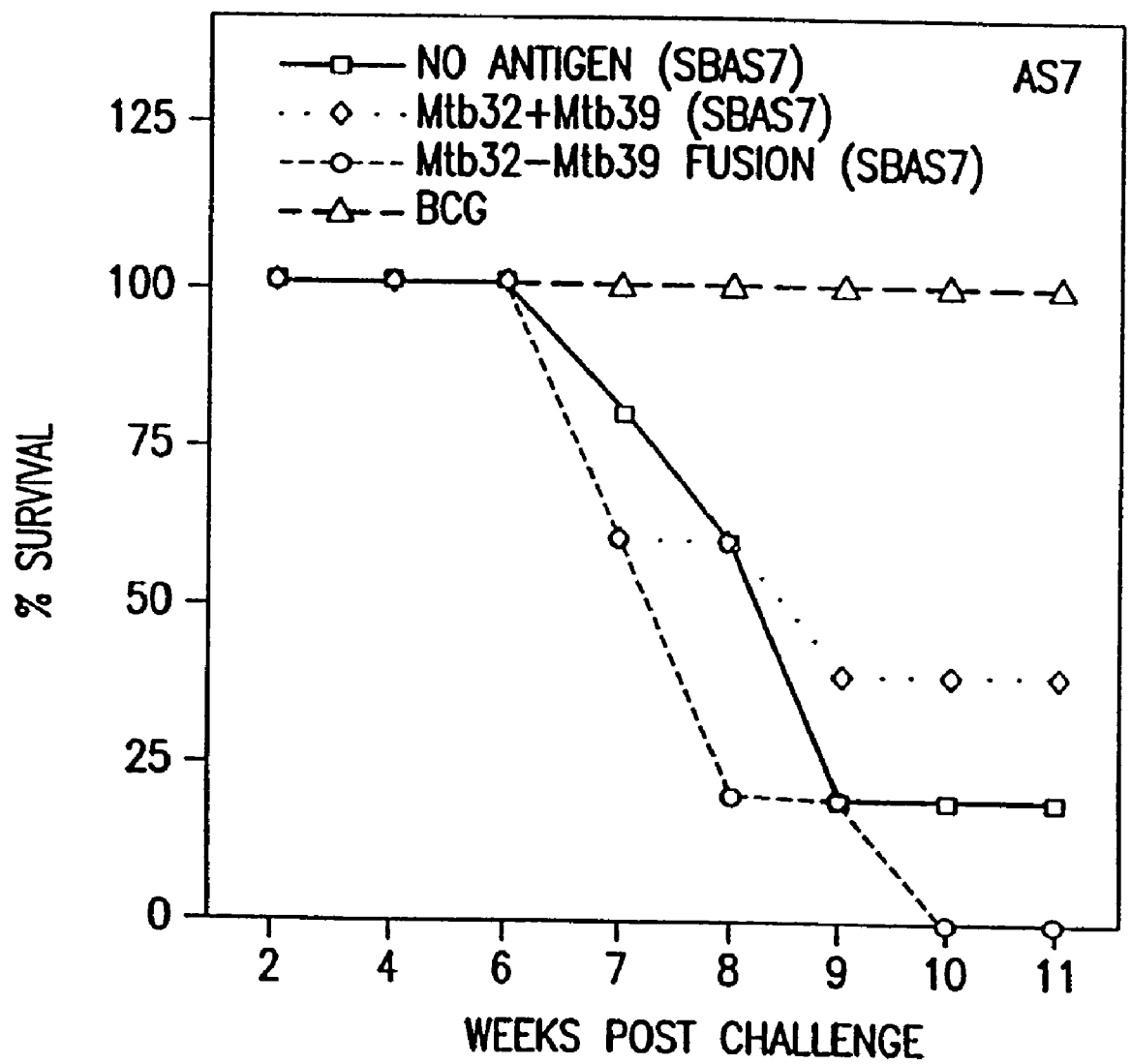

FIG. 20A-20C: Survival of guinea pigs after aerosol challenge of *M. tuberculosis*. Fusion protein, Mtb32-Mtb39 fusion or a mixture of Mtb32A and Mtb39A, were formulated in adjuvant SBAS1c (20A), SBAS2 (20B) or SBAS7 (20C), and used as an immunogen in guinea pigs prior to challenge with bacteria. BCG is the positive control.

Figure 21A:
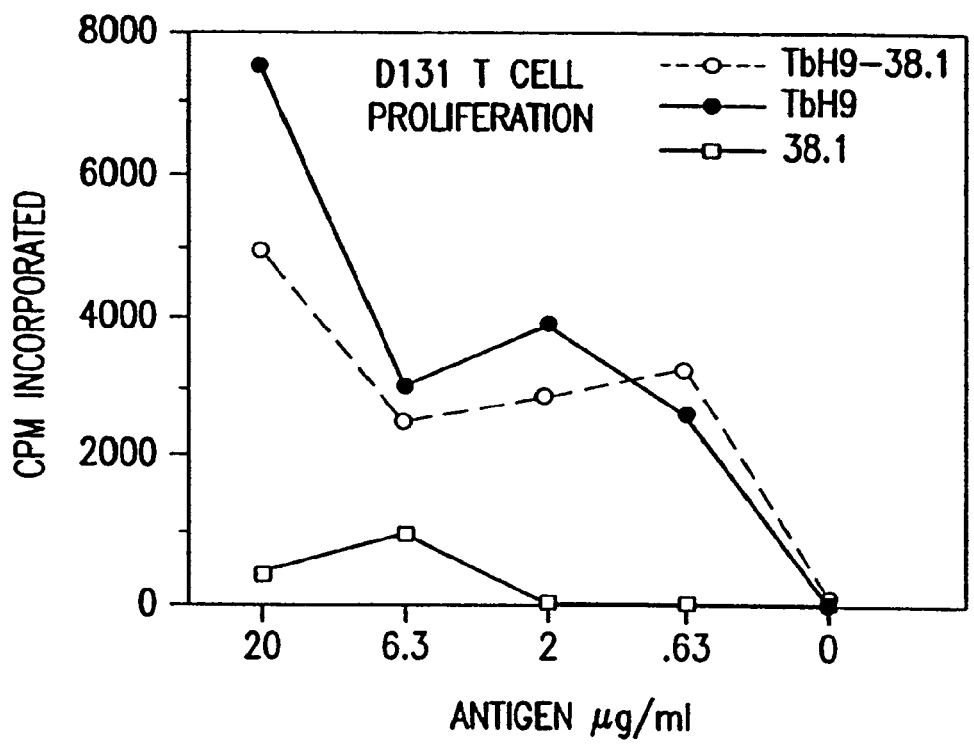
Figure 21B:
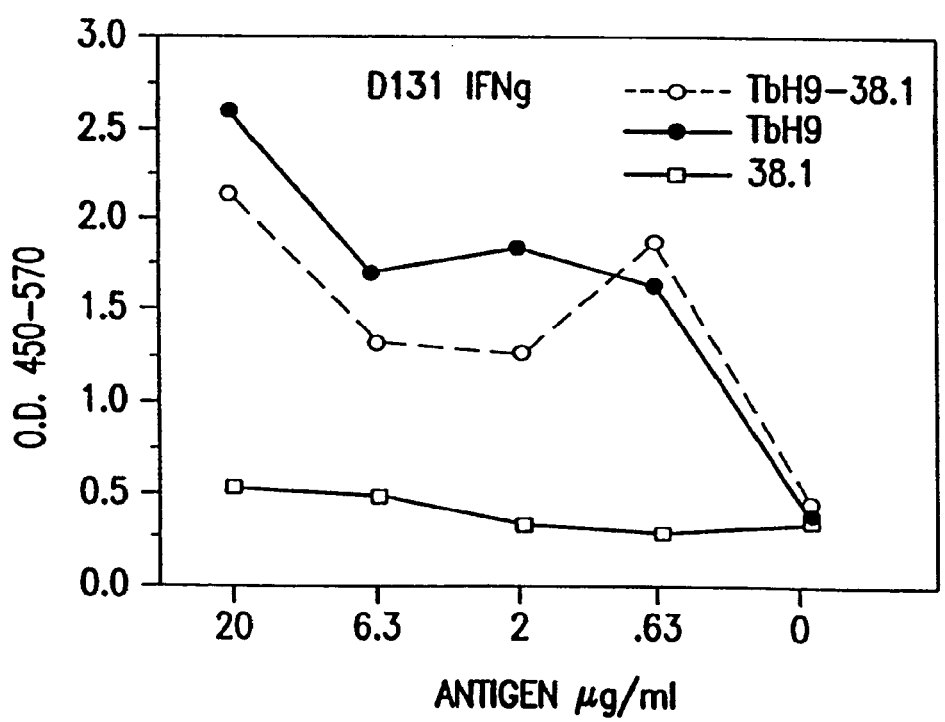

FIGS. 21A and 21B: Stimulation of proliferation and IFN-γ production in TbH9-specific T cells by the fusion protein TbH9-Tb38-1.

Figure 22A:
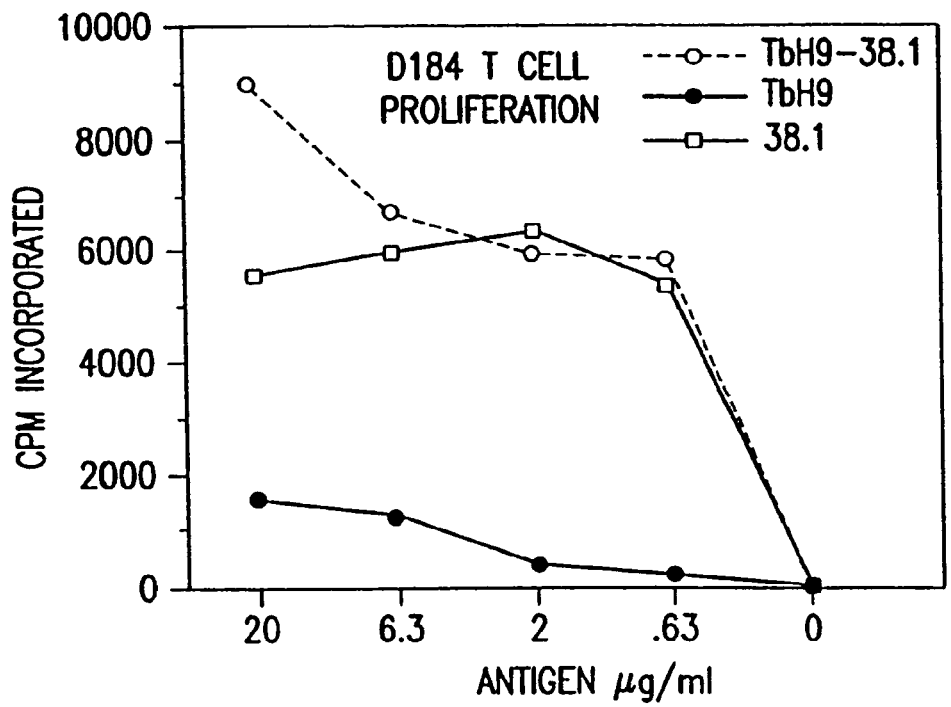
Figure 22B:
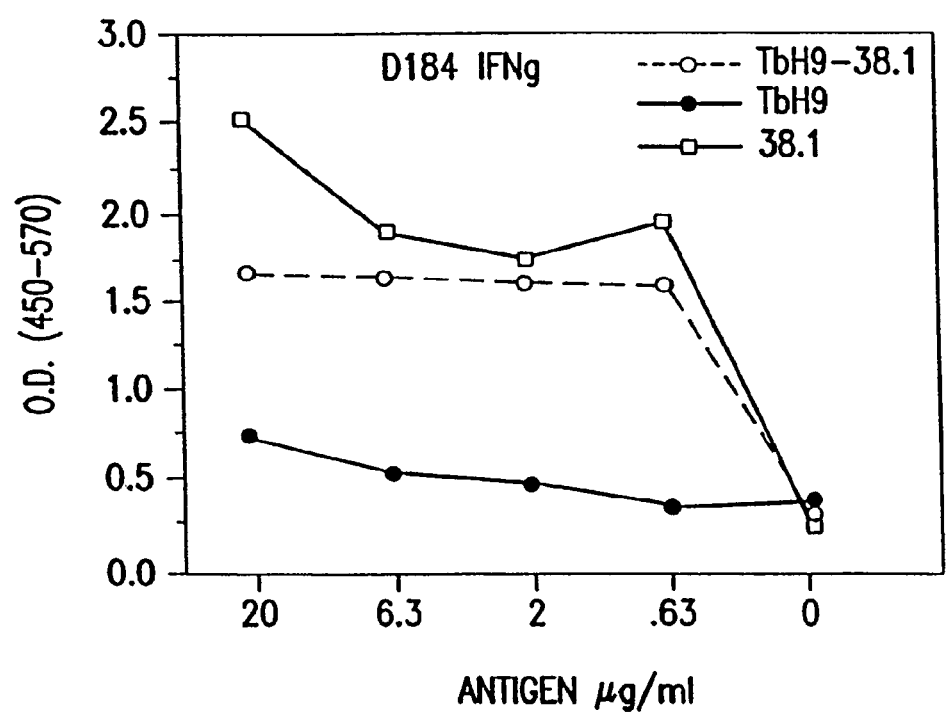

FIGS. 22A and 22B: Stimulation of proliferation and IFN-γ production in Th38-1-specific T cells by the fusion protein TbH9-Tb38-1.

Figure 23A:
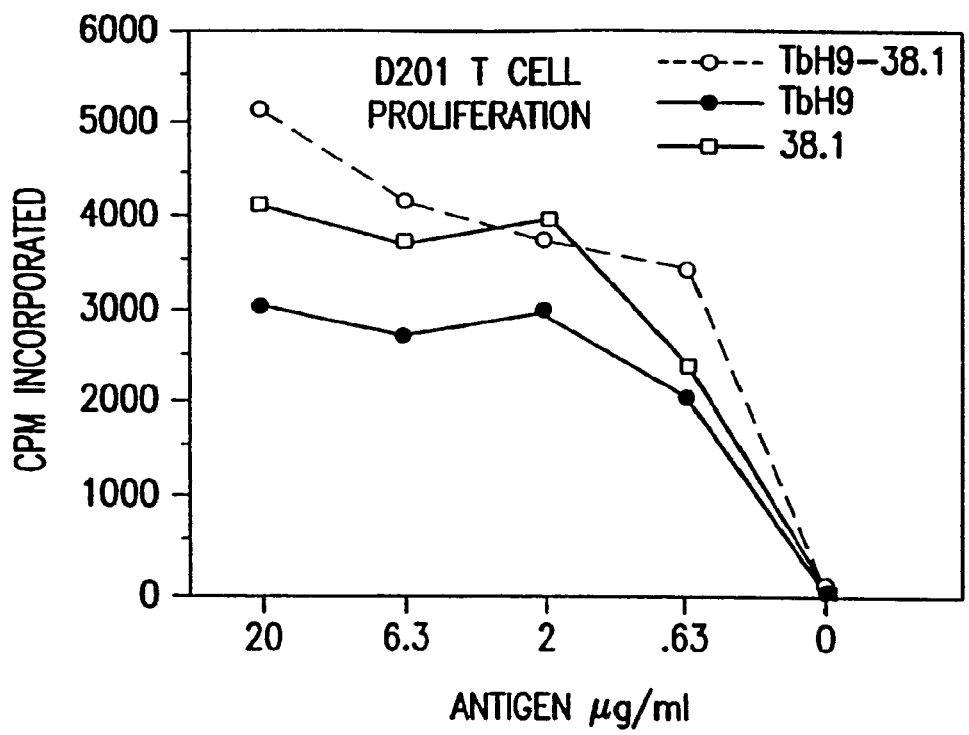
Figure 23B:
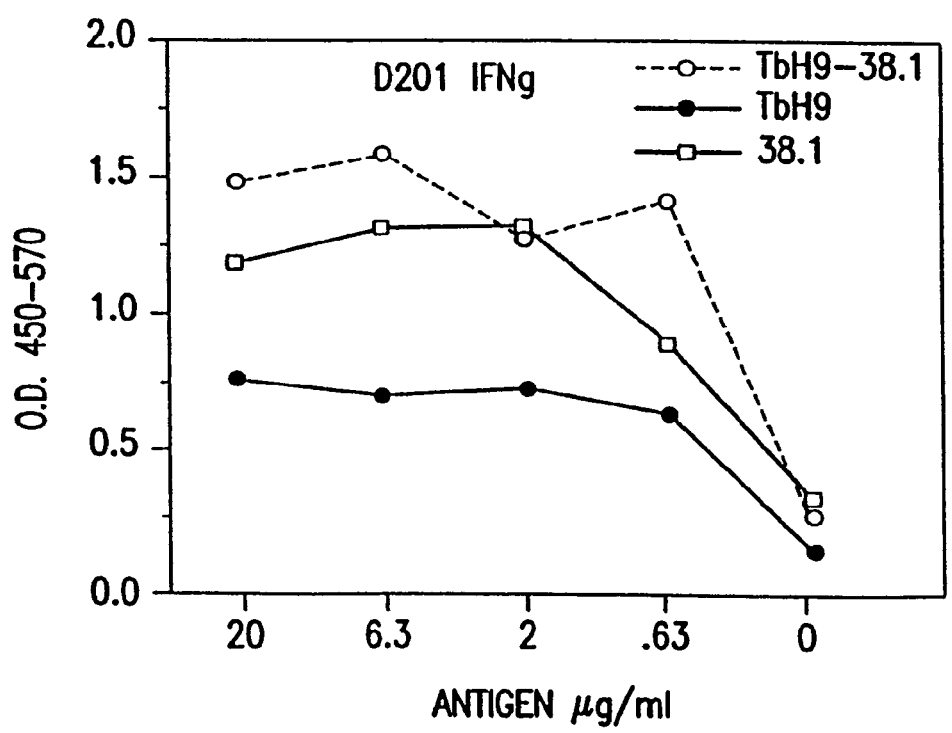

FIGS. 23A and 23B: Stimulation of proliferation and IFN-γ production in T cells previously shown to respond to both TbH-9 and Tb38-1 antigens by the fusion protein TbH9-Tb38-1.

5. DETAILED DESCRIPTION OF THE INVENTION

The present invention relates to antigens useful for the treatment and prevention of tuberculosis, polynucleotides encoding such antigens, and methods for their use. The antigens of the present invention are fusion polypeptides of *M. tuberculosis* antigens and variants thereof. More specifically, the antigens of the present invention comprise at least two polypeptides of *M. tuberculosis* that are fused into a larger fusion polypeptide molecule. The antigens of the present invention may further comprise other components designed to enhance the immunogenicity of the antigens or to improve these antigens in other aspects, for example, the isolation of these antigens through addition of a stretch of histidine residues at one end of the antigen.

5.1. *M. tuberculosis* Specific Antigens

The antigens of the present invention are exemplified in FIGS. 1A through 13B, including homologues and variants of those antigens. These antigens may be modified, for example, by adding linker peptide sequences as described below. These linker peptides may be inserted between one or more polypeptides which make up each of the fusion proteins presented in FIGS. 1A through 13B. Other antigens of the present invention are antigens described in FIGS. 1A through 13B which have been linked to a known antigen of *M. tuberculosis*, such as the previously described 38 kD (SEQ ID NO:40) antigen (Andersen and Hansen, 1989, Infect. Immun. 57:2481-2488; Genbank Accession No. M30046).

5.2. Immunogenicity Assays

Antigens described herein, and immunogenic portions thereof, have the ability to induce an immunogenic response. More specifically, the antigens have the ability to induce proliferation and/or cytokine production (i.e., interferon-γ and/or interleukin-12 production) in T cells, NK cells, B cells and/or macrophages derived from an *M. tuberculosis*-immune individual. The selection of cell type for use in evaluating an immunogenic response to a antigen will depend-on the desired response. For example, interleukin-12 production is most readily evaluated using preparations containing B cells and/or macrophages. An *M. tuberculosis*-immune individual is one who is considered to be resistant to the development of tuberculosis by virtue of having mounted an effective T cell response to *M. tuberculosis* (i.e., substantially free of disease symptoms). Such individuals may be identified based on a strongly positive (i.e., greater than about 10 mm diameter induration) intradermal skin test response to tuberculosis proteins (PPD) and an absence of any signs or symptoms of tuberculosis disease. T cells, NK cells, B cells and macrophages derived from *M. tuberculosis*-immune individuals may be prepared using methods known to those of ordinary skill in the art. For example, a preparation of PBMCs (i.e., peripheral blood mononuclear cells) may be employed without further separation of component cells. PBMCs may generally be prepared, for example, using density centrifugation through "FICOLL" (Winthrop Laboratories, NY). T cells for use in the assays described herein may also be purified directly from PBMCs. Alternatively, an enriched T cell line reactive against mycobacterial proteins, or T cell clones reactive to individual mycobacterial proteins, may be employed. Such T cell clones may be generated by, for example, culturing PBMCs from *M. tuberculosis*-immune individuals with mycobacterial proteins for a period of 2-4 weeks. This allows expansion of only the mycobacterial protein-specific T cells, resulting in a line composed solely of such cells. These cells may then be cloned and tested with individual proteins, using methods known to those of ordinary skill in the art, to more accurately define individual T cell specificity. In general, antigens that test positive in assays for proliferation and/or cytokine production (i.e., interferon-γ and/or interleukin-12 production) performed using T cells, NK cells, B cells and/or macrophages derived from an *M. tuberculosis*-immune individual are considered immunogenic. Such assays may be performed, for example, using the representative procedures described below. Immunogenic portions of such antigens may be identified using similar assays, and may be present within the polypeptides described herein.

The ability of a polypeptide (e.g., an immunogenic antigen, or a portion or other variant thereof) to induce cell proliferation is evaluated by contacting the cells (e.g., T cells and/or NK cells) with the polypeptide and measuring the proliferation of the cells. In general, the amount of polypeptide that is sufficient for evaluation of about $10^5$ cells ranges from about 10 ng/ml to about 100 μg/mL and preferably is about 10 μg/mL. The incubation of polypeptide with cells is typically performed at 37° C. for about six days. Following incubation with polypeptide, the cells are assayed for a proliferative response, which may be evaluated by methods known to those of ordinary skill in the art, such as exposing cells to a pulse of radiolabeled thymidine and measuring the incorporation of label into cellular DNA. In general, a polypeptide that results in at least a three fold increase in proliferation above background (i.e., the proliferation observed for cells cultured without polypeptide) is considered to be able to induce proliferation.

The ability of a polypeptide to stimulate the production of interferon-γ and/or interleukin-12 in cells may be evaluated by contacting the cells with the polypeptide and measuring the level of interferon-γ or interleukin-12 produced by the cells. In general, the amount of polypeptide that is sufficient for the evaluation of about $10^5$ cells ranges from about 10 ng/mL to about 100 μg/mL and preferably is about 10 μg/mL. The polypeptide may be, but need not be, immobilized on a solid support, such as a bead or a biodegradable microsphere, such as those described in U.S. Pat. Nos. 4,897,268 and 5,075,109. The incubation of polypeptide with the cells is typically performed at 37° C. for about six days.

Following incubation with polypeptide, the cells are assayed for interferon-γ and/or interleukin-12 (or one or more subunits thereof), which may be evaluated by methods known to those of ordinary skill in the art, such as an enzyme-linked immunosorbent assay (ELISA) or, in the case of IL-12 P70 subunit, a bioassay such as an assay measuring proliferation of T cells. In general, a polypeptide that results in the production of at least 50 pg of interferon-γ per mL of cultured supernatant (containing $10^4$-$10^5$ T cells per mL) is considered able to stimulate the production of interferon-γ. A polypeptide that stimulates the production of at least 10 pg/mL of IL-12 P70 subunit, and/or at least 100 pg/mL of IL-12 P40 subunit, per $10^5$ macrophages or B cells (or per $3\times10^5$ PBMC) is considered able to stimulate the production of IL-12.

In general, immunogenic antigens are those antigens that stimulate proliferation and/or cytokine production (i.e., interferon-γ and/or interleukin-12 production) in T cells, NK cells, B cells and/or macrophages derived from at least about 25% of *M. tuberculosis*-immune individuals. Among these immunogenic antigens, polypeptides having superior therapeutic properties may be distinguished based on the magnitude of the responses in the above assays and based on the percentage of individuals for which a response is observed. In addition, antigens having superior therapeutic properties will not stimulate proliferation and/or cytokine production in vitro in cells derived from more than about 25% of individuals who are not *M. tuberculosis*-immune, thereby eliminating responses that are not specifically due to *M. tuberculosis*-responsive cells. Those antigens that induce a response in a high percentage of T cell, NK cell, B cell and/or macrophage preparations from *M. tuberculosis*-immune individuals (with a low incidence of responses in cell preparations from other individuals) have superior therapeutic properties.

Antigens with superior therapeutic properties may also be identified based on their ability to diminish the severity of *M. tuberculosis* infection in experimental animals, when administered as a vaccine. Suitable vaccine preparations for use on experimental animals are described in detail below. Efficacy may be determined based on the ability of the antigen to provide at least about a 50% reduction in bacterial numbers and/or at least about a 40% decrease in mortality following experimental infection. Suitable experimental animals include mice, guinea pigs and primates.

5.3. Isolation of Coding Sequences

The present invention also relates to nucleic acid molecules that encode fusion polypeptides of *M. tuberculosis*. In a specific embodiment by way of example in Section 6, infra, thirteen *M. tuberculosis* fusion coding sequences were constructed. In accordance with the invention, any nucleotide sequence which encodes the amino acid sequence of the fusion protein can be used to generate recombinant molecules which direct the expression of the coding sequence.

In order to clone full-length coding sequences or homologous variants to generate the fusion polynucleotides, labeled DNA probes designed from any portion of the nucleotide sequences or their complements disclosed herein may be used to screen a genomic or cDNA library made from various strains of *M. tuberculosis* to identify the coding sequence of each individual component. Isolation of coding sequences may also be carried out by the polymerase chain reactions (PCR) using two degenerate oligonucleotide primer pools designed on the basis of the coding sequences disclosed herein.

The invention also relates to isolated or purified polynucleotides complementary to the nucleotide sequences of SEQ ID NOS:1, 3, 5, 7, 9, 11, 13, 15, 18, 21, 23, 25 and 27, and polynucleotides that selectively hybridize to such complementary sequences. In a preferred embodiment, a polynucleotide which hybridizes to the sequence of SEQ ID NOS:1, 3, 5, 7, 9, 11, 13, 15, 18, 21, 23, 25 and 27 or its complementary sequence under conditions of low stringency and encodes a protein that retains the immunogenicity of the fusion proteins of SEQ ID NOS:2, 4, 6, 8, 10, 12, 14, 16, 19, 22, 24, 26 and 28 is provided. By way of example and not limitation, exemplary conditions of low stringency are as follows (see also Shilo and Weinberg, 1981, Proc. Natl. Acad. Sci. USA 78:6789-6792): Filters containing DNA are pretreated for 6 h at 40° C. in a solution containing 35% formamide, 5×SSC, 50 mM Tris-HC1 (pH 7.5), 5 mM EDTA, 0.1% PVP, 0.1% Ficoll, 1%

BSA, and 500 μg/mL denatured salmon sperm DNA. Hybridizations are carried out in the same solution with the following modifications: 0.02% PVP, 0.02% Ficoll, 0.2% BSA, 100 μg/mL salmon sperm DNA, 10% (wt/vol) dextran sulfate, and 5-20×10$^6$ cpm $^{32}$P-labeled probe is used. Filters are incubated in hybridization mixture for 18-20 h at 40° C., and then washed for 1.5 h at 55° C. in a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography. If necessary, filters are washed for a third time at 65-68° C. and re-exposed to film. Other conditions of low stringency which may be used are well known in the art (e.g., as employed for cross-species hybridizations).

In another preferred embodiment, a polynucleotide which hybridizes to the coding sequence of SEQ ID NOS:1, 3, 5, 7, 9, 11, 13, 15, 18, 21, 23, 25 and 27 or its complementary sequence under conditions of high stringency and encodes a protein that retains the immunogenicity of the fusion proteins of SEQ ID NOS:2, 4, 6, 8, 10, 12, 14, 16, 19, 22, 24, 26 and 28 is provided. By way of example and not limitation, exemplary conditions of high stringency are as follows: Prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 μg/mL denatured salmon sperm DNA. Filters are hybridized for 48 h at 65° C. in prehybridization mixture containing 100 μg/mL denatured salmon sperm DNA and 5-20×10$^6$ cpm of $^{32}$P-labeled probe. Washing of filters is done at 37° C. for 1 h in a solution containing 2×SSC, 0.01% PVP, 0.01% Ficoll, and 0.01% BSA. This is followed by a wash in 0.1×SSC at 50° C. for 45 min before autoradiography. Other conditions of high stringency which may be used are well known in the art.

In yet another preferred embodiment, a polynucleotide which hybridizes to the coding sequence of SEQ ID NOS:1, 3, 5, 7, 9, 11, 13, 15, 18, 21, 23, 25 and 27 or its complementary sequence under conditions of moderate stringency and encodes a protein that retains the immunogenicity of the fusion proteins of SEQ ID NOS:2, 4, 6, 8, 10, 12, 14, 16, 19, 22, 24, 26 and 28 is provided. Exemplary conditions of moderate stringency are as follows: Filters containing DNA are pretreated for 6 h at 55° C. in a solution containing 6×SSC, 5× Denhart's solution, 0.5% SDS and 100 μg/mL denatured salmon sperm DNA. Hybridizations are carried out in the same solution and 5-20 ×10$^6$ cpm $^{32}$P-labeled probe is used. Filters are incubated in hybridization mixture for 18-20 h at 55° C., and then washed twice for 30 minutes at 60° C. in a solution containing 1×SSC and 0.1% SDS. Filters are blotted dry and exposed for autoradiography. Other conditions of moderate stringency which may be used are well-known in the art. Washing of filters is done at 37° C. for 1 h in a solution containing 2×SSC, 0.1% SDS.

5.4. Polypeptides Encoded by the Coding Sequences

In accordance with the invention, a polynucleotide of the invention which encodes a fusion protein, fragments thereof, or functional equivalents thereof may be used to generate recombinant nucleic acid molecules that direct the expression of the fusion protein, fragments thereof, or functional equivalents thereof, in appropriate host cells. The fusion polypeptide products encoded by such polynucleotides may be altered by molecular manipulation of the coding sequence.

Due to the inherent degeneracy of the genetic code, other DNA sequences which encode substantially the same or a functionally equivalent amino acid sequence, may be used in the practice of the invention for the expression of the fusion polypeptides. Such DNA sequences include those which are capable of hybridizing to the coding sequences or their complements disclosed herein under low, moderate or high stringency conditions described in Sections 5.3, supra.

Altered nucleotide sequences which may be used in accordance with the invention include deletions, additions or substitutions of different nucleotide residues resulting in a sequence that encodes the same or a functionally equivalent gene product. The gene product itself may contain deletions, additions or substitutions of amino acid residues, which result in a silent change thus producing a functionally equivalent antigenic epitope. Such conservative amino acid substitutions may be made on the basis of similarity in polarity, charge, solubility, hydrophobicity, hydrophilicity, and/or the amphipathic nature of the residues involved. For example, negatively charged amino acids include aspartic acid and glutamic acid; positively charged amino acids include lysine, histidine and arginine; amino acids with uncharged polar head groups having similar hydrophilicity values include the following: glycine, asparagine, glutamine, serine, threonine and tyrosine; and amino acids with nonpolar head groups include alanine, valine, isoleucine, leucine, phenylalanine, proline, methionine and tryptophan.

The nucleotide sequences of the invention may be engineered in order to alter the fusion protein coding sequence for a variety of ends, including but not limited to, alterations which modify processing and expression of the gene product. For example, mutations may be introduced using techniques which are well known in the art, e.g., site-directed mutagenesis, to insert new restriction sites, to alter glycosylation patterns, phosphorylation, etc.

In an alternate embodiment of the invention, the coding sequence of a fusion protein could be synthesized in whole or in part, using chemical methods well known in the art. See, e.g., Caruthers et al., 1980, *Nuc. Acids Res. Symp. Ser.* 7:215-233; Crea and Horn, 180, *Nuc. Acids Res.* 9(10):2331; Matteucci and Caruthers, 1980, *Tetrahedron Letter* 21:719; and Chow and Kempe, 1981, *Nuc. Acids Res.* 9(12):2807-2817. Alternatively, the polypeptide itself could be produced using chemical methods to synthesize an amino acid sequence in whole or in part. For example, peptides can be synthesized by solid phase techniques, cleaved from the resin, and purified by preparative high performance liquid chromatography. (See Creighton, 1983, *Proteins Structures And Molecular Principles*, W.H. Freeman and Co., N.Y. pp. 50-60). The composition of the synthetic polypeptides may be confirmed by amino acid analysis or sequencing (e.g., the Edman degradation procedure; see Creighton, 1983, *Proteins, Structures and Molecular Principles*, W.H. Freeman and Co., N.Y., pp. 34-49).

Additionally, the coding sequence of a fusion protein can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including but not limited to, chemical mutagenesis, in vitro site-directed mutagenesis (Hutchinson, C., et al., 1978, J. Biol. Chem. 253:6551), use of TAB® linkers (Pharmacia), and the like. It is important that the manipulations do not destroy immunogenicity of the fusion polypeptides.

In addition, nonclassical amino acids or chemical amino acid analogs can be introduced as a substitution or addition into the sequence. Non-classical amino acids include, but are not limited to, the D-isomers of the common amino acids, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogs in general. Furthermore, the amino acid can be D (dextrorotary) or L (levorotary).

In a specific embodiment, the coding sequences of each antigen in the fusion protein are joined at their amino- or carboxy-terminus via a peptide bond in any order. Alternatively, a peptide linker sequence may be employed to separate the individual polypeptides that make up a fusion polypeptide by a distance sufficient to ensure that each polypeptide folds into a secondary and tertiary structure that maximizes its antigenic effectiveness for preventing and treating tuberculosis. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., Gene 40:39-46, 1985; Murphy et al., Proc. Natl. Acad. Sci. USA 83:8258-8262, 1986; U.S. Pat. No. 4,935,233 and U.S. Pat. No. 4,751,180. The linker sequence may be from 1 to about 50 amino acids in length. Peptide sequences are not required when the first and second polypeptides have non-essential N-terminal amino acid regions that can be used to separate the functional domains and prevent steric interference. For example, the antigens in a fusion protein may be connected by a flexible polylinker such as Gly-Cys-Gly or Gly-Gly-Gly-Gly-Ser repeated 1 to 3 times (SEQ ID NOS: 41-43 and 44-46, respectively) (Bird et al., 1988, Science 242:423-426; Chaudhary et al., 1990, Proc. Natl. Acad. Sci. U.S.A. 87:1066-1070).

In one embodiment, such a protein is produced by recombinant expression of a nucleic acid encoding the protein. Such a fusion product can be made by ligating the appropriate nucleic acid sequences encoding the desired amino acid sequences to each other by methods known in the art, in the proper coding frame, and expressing the product by methods known in the art. Alternatively, such a product may be made by protein synthetic techniques, e.g., by use of a peptide synthesizer. Coding sequences for other molecules such as a cytokine or an adjuvant can be added to the fusion polynucleotide as well.

5.5. Production of Fusion Proteins

In order to produce a *M. tuberculosis* fusion protein of the invention, the nucleotide sequence coding for the protein, or a functional equivalent, is inserted into an appropriate expression vector, i.e., a vector which contains the necessary elements for the transcription and translation of the inserted coding sequence. The host cells or cell lines transfected or transformed with recombinant expression vectors can be used for a variety of purposes. These include, but are not limited to, large scale production of the fusion protein.

Methods which are well known to those skilled in the art can be used to construct expression vectors containing a fusion coding sequence and appropriate transcriptional/translational control signals. These methods include in vitro recombinant DNA techniques, synthetic techniques and in vivo recombination/genetic recombination. (See, e.g., the techniques described in Sambrook et al., 1989, Molecular Cloning A Laboratory Manual, Cold Spring Harbor Laboratory, N.Y. and Ausubel et al., 1989, Current Protocols in Molecular Biology, Greene Publishing Associates and Wiley Interscience, N.Y.). RNA capable of encoding a polypeptide may also be chemically synthesized (Gait, ed, 1984, Oligonucleotide Synthesis, IRL Press, Oxford).

5.5.1. Expression Systems

A variety of host-expression vector systems may be utilized to express a fusion protein coding sequence. These include, but are not limited to, microorganisms such as bacteria (e.g., *E. coli, B. subtilis*) transformed with recombinant bacteriophage DNA, plasmid DNA or cosmid DNA expression vectors containing a coding sequence; yeast (e.g., *Saccharomycdes, Pichia*) transformed with recombinant yeast expression vectors containing a coding sequence; insect cell systems infected with recombinant virus expression vectors (e.g., baculovirus) containing a coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing a coding sequence; or mammalian cell systems (e.g., COS, CHO, BHK, 293, 3T3 cells). The expression elements of these systems vary in their strength and specificities.

Depending on the host/vector system utilized, any of a number of suitable transcription and translation elements, including constitutive and inducible promoters, may be used in the expression vector. For example, when cloning in bacterial systems, inducible promoters such as pL of bacteriophage λ, plac, ptrp, ptac (ptrp-lac hybrid promoter; cytomegalovirus promoter) and the like may be used; when cloning in insect cell systems, promoters such as the baculovirus polyhedron promoter may be used; when cloning in plant cell systems, promoters derived from the genome of plant cells (e.g., heat shock promoters; the promoter for the small subunit of RUBISCO; the promoter for the chlorophyll α/β, binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5K promoter) may be used; when generating cell lines that contain multiple copies of a the antigen coding sequence, SV40-, BPV- and EBV-based vectors may be used with an appropriate selectable marker.

Bacterial systems are preferred for the expression of *M. tuberculosis* antigens. For in vivo delivery, a bacterium such as *Bacillus*-Calmette-Guerrin may be engineered to express a fusion polypeptide of the invention on its cell surface. A number of other bacterial expression vectors may be advantageously selected depending upon the use intended for the expressed products. For example, when large quantities of the fusion protein are to be produced for formulation of pharmaceutical compositions, vectors which direct the expression of high levels of fusion protein products that are readily purified may be desirable. Such vectors include, but are not limited to, the *E. coli* expression vector pUR278 (Ruther et al., 1983, EMBO J. 2:1791), in which a coding sequence may be ligated into the vector in frame with the lacZ coding region so that a hybrid protein is produced; pIN vectors (Inouye and Inouye, 1985, Nucleic Acids Res. 13:3101-3109, Van Heeke and Schuster, 1989, J. Biol. Chem. 264:5503-5509); and the like. pGEX vectors may also be used to express foreign polypeptides as fusion proteins with glutathione S-transferase (GST). In general, such fusion proteins are soluble and can be purified easily from lysed cells by adsorption to glutathione-agarose beads followed by elution in the presence of free glutathione. The pGEX vectors are designed to include thrombin or factor Xa protease cleavage sites so that the cloned fusion polypeptide of interest can be released from the GST moiety.

5.5.2. Protein Purification

Once a recombinant protein is expressed, it can be identified by assays based on the physical or functional properties of the product, including radioactive labeling of the product followed by analysis by gel electrophoresis, radioimmunoassay, ELISA, bioassays, etc.

Once the encoded protein is identified, it may be isolated and purified by standard methods including chromatography (e.g., high performance liquid chromatography, ion exchange, affinity, and sizing column chromatography), centrifugation, differential solubility, or by any other standard technique for the purification of proteins. The actual conditions used will depend, in part, on factors such as net charge, hydrophobicity, hydrophilicity, etc., and will be apparent to those having skill in the art. The functional properties may be evaluated using any suitable assay such as antibody binding, induction of T cell proliferation, stimulation of cytokine production such as IL2, IL4 and IFN-γ. For the practice of the present invention, it is preferred that each fusion protein is at least 80% purified from other proteins. It is more preferred that they are at least 90% purified. For in vivo administration, it is preferred that the proteins are greater than 95% purified.

5.6. Uses of the Fusion Protein Coding Sequence

The fusion protein coding sequence of the invention may be used to encode a protein product for use as an immunogen to induce and/or enhance immune responses to *M. tuberculosis*. In addition, such coding sequence may be ligated with a coding sequence of another molecule such as cytokine or an adjuvant. Such polynucleotides may be used in vivo as a DNA vaccine (U.S. Pat. Nos. 5,589,466; 5,679,647; 5,703,055). In this embodiment of the invention, the polynucleotide expresses its encoded protein in a recipient to directly induce an immune response. The polynucleotide may be injected into a naive subject to prime an immune response to its encoded product, or administered to an infected or immunized subject to enhance the secondary immune responses.

In a preferred embodiment, a therapeutic composition comprises a fusion protein coding sequence or fragments thereof that is part of an expression vector. In particular, such a polynucleotide contains a promoter operably linked to the coding region, said promoter being inducible or constitutive, and, optionally, tissue-specific. In another embodiment, a polynucleotide contains a coding sequence flanked by regions that promote homologous recombination at a desired site in the genome, thus providing for intrachromosomal expression of the coding sequence (Koller and Smithies, 1989, Proc. Natl. Acad. Sci. USA 86:8932-8935; Zijlstra et al., 1989, Nature 342:435-438).

Delivery of the nucleic acid into a subject may be either direct, in which case the subject is directly exposed to the nucleic acid or nucleic acid-carrying vector, or indirect, in which case, cells are first transformed with the nucleic acid in vitro, then transplanted into the subject. These two approaches are known, respectively, as in vivo or ex vivo gene transfer.

In a specific embodiment, the nucleic acid is directly administered in vivo, where it is expressed to produce the encoded fusion protein product. This can be accomplished by any of numerous methods known in the art, e.g., by constructing it as part of an appropriate nucleic acid expression vector and administering it so that it becomes intracellular, e.g., by infection using a defective or attenuated retroviral or other viral vector (see, U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules (U.S. Pat. Nos. 5,407,609; 5,853,763; 5,814,344 and 5,820,883), or by administering it in linkage to a peptide which is known to enter the nucleus, by administering it in linkage to a ligand subject to receptor-mediated endocytosis (see, e.g., Wu and Wu, 1987, J. Biol. Chem. 262:4429-4432) which can be used to target cell types specifically expressing the receptors, etc. In another embodiment, a nucleic acid-ligand complex can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180 dated Apr. 16, 1992; WO 92/22635 dated Dec. 23, 1992; WO92/20316 dated Nov. 26, 1992; WO93/14188 dated Jul. 22, 1993; WO 93/20221 dated Oct. 14, 1993). Alternatively, the nucleic acid can be introduced intracellularly and incorporated within host cell DNA for expression, by homologous recombination (Koller and Smithies, 1989, Proc. Natl. Acad. Sci. USA 86:8932-8935; Zijlstra et al., 1989, Nature 342:435-438).

In a specific embodiment, a viral vector such as a retroviral vector can be used (see, Miller et al., 1993, Meth. Enzymol. 217:581-599). Retroviral vectors have been modified to delete retroviral sequences that are not necessary for packaging of the viral genome and integration into host cell DNA. A fusion coding sequence is cloned into the vector, which facilitates delivery of the nucleic acid into a recipient. More detail about retroviral vectors can be found in Boesen et al., 1994, Biotherapy 6:291-302, which describes the use of a retroviral vector to deliver the mdr1 gene to hematopoietic stem cells in order to make the stem cells more resistant to chemotherapy. Other references illustrating the use of retroviral vectors in gene therapy are: Clowes et al., 1994, J. Clin. Invest. 93:644-651; Kiem et al., 1994, Blood 83:1467-1473; Salmons and Gunzberg, 1993, Human Gene Therapy 4:129-141; and Grossman and Wilson, 1993, Curr. Opin. in Genetics and Devel. 3:110-114.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Adeno-associated virus (AAV) has also been proposed for use in in vivo gene transfer (Walsh et al., 1993, Proc. Soc. Exp. Biol. Med. 204:289-300.

Another approach involves transferring a construct to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a subject.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see e.g., Loeffler and Behr, 1993, Meth. Enzymol. 217:599-618; Cohen et al., 1993, Meth. Enzymol. 217:618-644; Cline, 1985, Pharmac. Ther. 29:69-92) and may be used in accordance with the present invention.

The polynucleotides of the invention may also be used in the diagnosis of tuberculosis for detection of polynucleotide sequences specific to *M. tuberculosis* in a patient. Such detection may be accomplished, for example, by isolating polynucleotides from a biological sample obtained from a patient suspected of being infected with the bacteria. Upon isolation of polynucleotides from the biological sample, a labeled polynucleotide of the invention that is complementary to one or more of the polynucleotides, will be allowed to hybridize to polynucleotides in the biological sample using techniques of nucleic acid hybridization known to those of ordinary skill in the art.

For example, such hybridization may be carried out in solution or with one hybridization partner on a solid support.

5.7. Therapeutic and Prophylactic Uses of the Fusion Protein

Purified or partially purified fusion proteins or fragments thereof may be formulated as a vaccine or therapeutic composition. Such composition may include adjuvants to enhance immune responses. In addition, such proteins may be further suspended in an oil emulsion to cause a slower release of the proteins in vivo upon injection. The optimal ratios of each component in the formulation may be determined by techniques well known to those skilled in the art.

Any of a variety of adjuvants may be employed in the vaccines of this invention to enhance the immune response. Most adjuvants contain a substance designed to protect the antigen from rapid catabolism, such as aluminum hydroxide or mineral oil, and a specific or nonspecific stimulator of immune responses, such as lipid A, *Bortadella pertussis* or *Mycobacterium tuberculosis*. Suitable adjuvants are commercially available and include, for example, Freund's Incomplete Adjuvant and Freund's Complete Adjuvant (Difco Laboratories) and Merck Adjuvant 65 (Merck and Company, Inc., Rahway, N.J.). Other suitable adjuvants include alum, biodegradable microspheres, monophosphoryl lipid A, quil A, SBAS1c, SBAS2 (Ling et al., 1997, Vaccine 15:1562-1567), SBAS7, $Al(OH)_3$ and CpG oligonucleotide (WO96/02555).

In the vaccines of the present invention, it is preferred that the adjuvant induces an immune response comprising Th1 aspects. Suitable adjuvant systems include, for example, a combination of monophosphoryl lipid A, preferably 3-de-O-acylated monophosphoryl lipid A (3D-MPL) together with an aluminum salt. An enhanced system involves the combination of a monophosphoryl lipid A and a saponin derivative, particularly the combination of 3D-MLP and the saponin QS21 as disclosed in WO 94/00153, or a less reactogenic composition where the QS21 is quenched with cholesterol as disclosed in WO 96/33739. Previous experiments have demonstrated a clear synergistic effect of combinations of 3D-MLP and QS21 in the induction of both humoral and Th1 type cellular immune responses. A particularly potent adjuvant formation involving QS21, 3D-MLP and tocopherol in an oil-in-water emulsion is described in WO 95/17210 and is a preferred formulation.

Formulations containing an antigen of the present invention may be administered to a subject per se or in the form of a pharmaceutical or therapeutic composition. Pharmaceutical compositions comprising the proteins may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries which facilitate processing of the polypeptides into preparations which can be used pharmaceutically. Proper formulation is dependent upon the route of administration chosen.

For topical administration, the proteins may be formulated as solutions, gels, ointments, creams, suspensions, etc. as are well-known in the art.

Systemic formulations include those designed for administration by injection, e.g. subcutaneous, intravenous, intramuscular, intrathecal or intraperitoneal injection, as well as those designed for transdermal, transmucosal, oral or pulmonary administration.

For injection, the proteins may be formulated in aqueous solutions, preferably in physiologically compatible buffers such as Hanks's solution, Ringer's solution, or physiological saline buffer. The solution may contain formulatory agents such as suspending, stabilizing and/or dispersing agents. Alternatively, the proteins may be in powder form for constitution with a suitable vehicle, e.g., sterile pyrogen-free water, before use.

For transmucosal administration, penetrants appropriate to the barrier to be permeated are used in the formulation. Such penetrants are generally known in the art.

For oral administration, a composition can be readily formulated by combining the proteins with pharmaceutically acceptable carriers well known in the art. Such carriers enable the proteins to be formulated as tablets, pills, dragees, capsules, liquids, gels, syrups, slurries, suspensions and the like, for oral ingestion by a subject to be treated. For oral solid formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents may be added, such as the cross-linked polyvinylpyrrolidone, agar, or alginic acid or a salt thereof such as sodium alginate.

If desired, solid dosage forms may be sugar-coated or enteric-coated using standard techniques.

For oral liquid preparations such as, for example, suspensions, elixirs and solutions, suitable carriers, excipients or diluents include water, glycols, oils, alcohols, etc. Additionally, flavoring agents, preservatives, coloring agents and the like may be added.

For buccal administration, the proteins may take the form of tablets, lozenges, etc. formulated in conventional manner.

For administration by inhalation, the proteins for use according to the present invention are conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the proteins and a suitable powder base such as lactose or starch.

The proteins may also be formulated in rectal or vaginal compositions such as suppositories or retention enemas, e.g., containing conventional suppository bases such as cocoa butter or other glycerides.

In addition to the formulations described previously, the proteins may also be formulated as a depot preparation. Such long acting formulations may be administered by implantation (for example subcutaneously or intramuscularly) or by intramuscular injection. Thus, for example, the proteins may be formulated with suitable polymeric or hydrophobic materials (for example as an emulsion in an acceptable oil) or ion exchange resins, or as sparingly soluble derivatives, for example, as a sparingly soluble salt. Alternatively, other pharmaceutical delivery systems may be employed. Liposomes and emulsions are well known examples of delivery vehicles that may be used to deliver an antigen. Certain organic solvents such as dimethylsulfoxide also may be employed, although usually at the cost of greater toxicity. The fusion proteins may also be encapsulated in microspheres (U.S. Pat. Nos. 5,407,609; 5,853,763; 5,814,344 and 5,820,883). Additionally, the proteins may be delivered using a sustained-release system, such as semipermeable matrices of solid polymers containing the therapeutic or vaccinating agent. Various sustained-release materials have been established and are well known by those skilled in the art. Sustained-release capsules may, depending on their chemical nature, release the proteins for a few weeks up to over 100 days. Depending on the chemical nature and the biological stability of the reagent, additional strategies for protein stabilization may be employed.

Determination of an effective amount of the fusion protein for inducing an immune response in a subject is well within the capabilities of those skilled in the art, especially in light of the detailed disclosure provided herein.

An effective dose can be estimated initially from in vitro assays. For example, a dose can be formulated in animal models to achieve an induction of an immune response using techniques that are well known in the art. One having ordinary skill in the art could readily optimize administration to humans based on animal data. Dosage amount and interval may be adjusted individually. For example, when used as a vaccine, the polypeptides and/or polynucleotides of the invention may be administered in about 1 to 3 doses for a 1-36 week period. Preferably, 3 doses are administered, at intervals of about 3-4 months, and booster vaccinations may be given periodically thereafter. Alternate protocols may be appropriate for individual patients. A suitable dose is an amount of polypeptide or DNA that, when administered as described above, is capable of raising an immune response in an immunized patient sufficient to protect the patient from *M. tuberculosis* infection for at least 1-2 years. In general, the amount of polypeptide present in a dose (or produced in situ by the DNA in a dose) ranges from about 1 pg to about 100 mg per kg of host, typically from about 10 pg to about 1 mg, and preferably from about 100 pg to about 1 µg. Suitable dose range will vary with the size of the patient, but will typically range from about 0.1 mL to about 5 mL.

5.8 Diagnostic Uses of the Fusion Protein

The fusion polypeptides of the invention are useful in the diagnosis of tuberculosis infection in vitro and in vivo. The ability of a polypeptide of the invention to induce cell proliferation or cytokine production can be assayed by the methods disclosed in Section 5.2, supra.

In another aspect, this invention provides methods for using one or more of the fusion polypeptides to diagnose tuberculosis using a skin test in vivo. As used herein, a skin test is any assay performed directly on a patient in which a delayed-type hypersensitivity (DTH) reaction (such as swelling, reddening or dermatitis) is measured following intradermal injection of one or more polypeptides as described above. Such injection may be achieved using any suitable device sufficient to contact the polypeptide with dermal cells of the patient, such as, for example, a tuberculin syringe or 1 mL syringe. Preferably, the reaction is measured at least about 48 hours after injection, more preferably about 48 to about 72 hours after injection.

The DTH reaction is a cell-mediated immune response, which is greater in patients that have been exposed previously to the test antigen (i.e., the immunogenic portion of the polypeptide employed, or a variant thereof). The response may be measured visually, using a ruler. In general, a response that is greater than about 0.5 cm in diameter, preferably greater than about 1.0 cm in diameter, is a positive response, indicative of tuberculosis infection, which may or may not be manifested as an active disease.

The fusion polypeptides of this invention are preferably formulated, for use in a skin test, as pharmaceutical compositions containing a polypeptide and a physiologically acceptable carrier. Such compositions typically contain one or more of the above polypeptides in an amount ranging from about 1 µg to about 100 µg, preferably from about 10 µg to about 50 µg in a volume of 0.1 mL. Preferably, the carrier employed in such pharmaceutical compositions is a saline solution with appropriate preservatives, such as phenol and/or Tween 80™.

In another aspect, the present invention provides methods for using the polypeptides to diagnose tuberculosis. In this aspect methods are provided for detecting *M. tuberculosis* infection in a biological sample using the fusion polypeptides alone or in combination. As used herein, a "biological sample" is any antibody-containing sample obtained from a patient. Preferably, the sample is whole blood, sputum, serum, plasma, saliva cerebrospinal fluid or urine. More preferably, the sample is a blood, serum or plasma sample obtained from a patient or a blood supply. The polypeptide(s) are used in an assay, as described below, to determine the presence or absence of antibodies to the polypeptide(s) in the sample relative to a predetermined cut-off value. The presence of such antibodies indicates previous sensitization to mycobacterial antigens which may be indicative of tuberculosis.

In embodiments in which more than one fusion polypeptide is employed, the polypeptides used are preferably complementary (i.e., one component polypeptide will tend to detect infection in samples where the infection would not be detected by another component polypeptide). Complementary polypeptides may generally be identified by using each polypeptide individually to evaluate serum samples obtained from a series of patients known to be infected with *M. tuberculosis*. After determining which samples test positive (as described below) with each polypeptide, combinations of two or more fusion polypeptides may be formulated that are capable of detecting infection in most, or all, of the samples tested. Such polypeptides are complementary. Approximately 25-30% of sera from tuberculosis-infected individuals are negative for antibodies to any single protein. Complementary polypeptides may, therefore, be used in combination to improve sensitivity 3 of a diagnostic test.

There are a variety of assay formats known to those of ordinary skill in the art for using one or more polypeptides to detect antibodies in a sample. See, e.g., Harlow and Lane, *Antibodies: A Laboratory Manual*, Cold Spring Harbor Laboratory, 1988, which is incorporated herein by reference. In a preferred embodiment, the assay involves the use of polypeptide immobilized on a solid support to bind to and remove the antibody from the sample. The bound antibody may then be detected using a detection reagent that contains a reporter group. Suitable detection reagents include antibodies that bind to the antibody/polypeptide complex and free polypeptide labeled with a reporter group (e.g., in a semi-competitive assay). Alternatively, a competitive assay may be utilized, in which an antibody that binds to the polypeptide is labeled with a reporter group and allowed to bind to the immobilized antigen after incubation of the antigen with the sample. The extent to which components of the sample inhibit the binding of the labeled antibody to the polypeptide is indicative of the reactivity of the sample with the immobilized polypeptide.

The solid support may be any solid material known to those of ordinary skill in the art to which the antigen may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681.

The polypeptides may be bound to the solid support using a variety of techniques known to those of ordinary skill in the art. In the context of the present invention, the term "bound" refers to both noncovalent association, such as adsorption, and covalent attachment (which may be a direct linkage between the antigen and functional groups on the support or may be a linkage by way of a cross-linking agent). Binding by adsorption to a well in a microtiter plate or to a membrane is preferred. In such cases, adsorption may be achieved by contacting the polypeptide, in a suitable buffer, with the solid support for a suitable amount of time. The contact time varies with temperature, but is typically between about 1 hour and 1 day. In general, contacting a well of a plastic microtiter plate (such as polystyrene or polyvinylchloride) with an amount of polypeptide ranging from about 10 ng to about 1 Mg, and preferably about 100 ng, is sufficient to bind an adequate amount of antigen. Covalent attachment of polypeptide to a solid support may generally be achieved by first reacting the support with a bifunctional reagent that will react with both the support and a functional group, such as a hydroxyl or amino group, on the polypeptide. For example, the polypeptide may be bound to supports having an appropriate polymer coating using benzoquinone or by condensation of an aldehyde group on the support with an amine and an active hydrogen on the polypeptide (see, e.g., Pierce Immunotechnology Catalog and Handbook. 1991, at A12-A13).

In certain embodiments, the assay is an enzyme linked immunosorbent 1 assay (ELISA). This assay may be performed by first contacting a fusion polypeptide antigen that has been immobilized on a solid support, commonly the well of a microtiter plate, with the sample, such that antibodies to the polypeptide within the sample are allowed to bind to the immobilized polypeptide. Unbound sample is then removed from the immobilized polypeptide and a detection reagent capable of binding to the immobilized antibody-polypeptide complex is added. The amount of detection reagent that remains bound to the solid support is then determined using a method appropriate for the specific detection reagent.

More specifically, once the polypeptide is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.) may be employed. The immobilized polypeptide is then incubated with the sample, and antibody is allowed to bind to the antigen. The sample may be diluted with a suitable diluent, such as phosphate-buffered saline (PBS) prior to incubation. In general, an appropriate contact time is that period of time that is sufficient to detect the presence of antibody within a *M. tuberculosis*-infected sample. Preferably, the contact time is sufficient to achieve a level of binding that is at least 95% of that achieved at equilibrium between bound and unbound antibody. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. Detection reagent may then be added to the solid support. An appropriate detection reagent is any compound that binds to the immobilized antibody-polypeptide complex and that can be detected by any of a variety of means known to those in the art. Preferably, the detection reagent contains a binding agent (for example, Protein A, Protein G, lectin or free antigen) conjugated to a reporter group. Preferred reporter groups include enzymes (such as horseradish peroxidase), substrates, cofactors, inhibitors, dyes, radionuclides, luminescent groups, fluorescent groups, biotin and colloidal particles, such as colloidal gold and selenium. The conjugation of binding agent to reporter group may be achieved using standard methods known to those of ordinary skill in the art. Common binding agents may also be purchased conjugated to a variety of reporter groups from many commercial sources (e.g. Zymed Laboratories, San Francisco, Calif., and Pierce, Rockford. Ill.).

The detection reagent is then incubated with the immobilized antibody-polypeptide complex for an amount of time sufficient to detect the bound antibody. An appropriate amount of time may generally be determined from the manufacturer's instructions or by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of anti-*M. tuberculosis* antibodies in the sample, the signal detected from the reporter group that remains bound to the solid support is generally compared to a signal that corresponds to a predetermined cut-off value. In one preferred embodiment, the cut-off value is the average mean signal obtained when the immobilized antigen is incubated with samples from an uninfected patient. In general, a sample generating a signal that is three standard deviations above the predetermined cut-off value is considered positive for tuberculosis. In an alternate preferred embodiment, the cut-off value is determined using a Receiver Operator Curve. according to the method of Sackett et al., 1985, *Clinical Epidemiology: A Basic Science for Clinical Medicine*, Little Brown and Co., pp. 106-107. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e. the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for tuberculosis.

In a related embodiment, the assay is performed in a rapid flow-through or strip test format, wherein the antigen is immobilized on a membrane, such as nitrocellulose. In the flow-through test, antibodies within the sample bind to the immobilized polypeptide as the sample passes through the membrane. A detection reagent (e.g., protein A-colloidal gold) then binds to the antibody-polypeptide complex as the solution containing the detection reagent flows through the membrane. The detection of bound detection reagent may then be performed as described above. In the strip test format, one end of the membrane to which polypeptide is bound is immersed in a solution containing the sample. The sample migrates along the membrane through a region containing detection reagent and to the area of immobilized polypeptide. Concentration of detection reagent at the polypeptide indicates the presence of anti-*M. tuberculosis* antibodies in the sample. Typically, the concentration of detection reagent at that site generates a pattern, such as a line, that can be read visually. The absence of such a pattern indicates a negative result. In general, the amount of polypeptide immobilized on the membrane is selected to generate a visually discernible pattern when the biological sample contains a level of antibodies that would be sufficient to generate a positive signal in an ELISA, as discussed above. Preferably, the amount of polypeptide immobilized on the membrane ranges from about 5 ng to about 1 μg, and more preferably from about 50 ng to about 500 ng. Such tests can typically be performed with a very small amount (e.g., one drop) of patient serum or blood.

The invention having been described, the following examples are offered by way of illustration and not limitation.

6. EXAMPLE

Fusion Proteins of *M. tuberculosis* Antigens Retain Immunogenicity of the Individual Components 6.1. Materials and Methods 6.1.1. Construction of Fusion Proteins Coding sequences of *M. tuberculosis* antigens were modified by PCR in order to facilitate their fusion and subsequent expression of fusion protein. DNA amplification was performed using 10 μl 10×Pfu buffer, 2 μl 10 mM dNTPs, 2 μl each of the PCR primers at 10 μM concentration, 81.5 μl water, 1.5 μl Pfu DNA polymerase (Stratagene, La Jolla, Calif.) and 1 μl DNA at either 70 ng/μl (for ThRa3 antigen) or 50 ng/μl (for 38 kD and Tb38-1 antigens). For TbRa3 antigen, denaturation at 94° C. was performed for 2 min, followed by 40 cycles of 96° C. for 15 sec and 72° C. for 1 min, and lastly by 72° C. for 4 min. For 38 kD antigen, denaturation at 96° C. was performed for 2 min, followed by 40 cycles of 96° C. for 30 sec, 68° C. for 15 sec and 72° C. for 3 min and finally by 72° C. for 4 min. For Tb38-1 antigen, denaturation at 94° C. for 2 min was followed by 10 cycles of 96° C. for 15 sec, 68° C. for 15 sec and 72° C. for 1.5 min, 30 cycles of 96° C. for 15 sec, 64° C. for 15 sec and 72° C. for 1.5, and finally by 72° C. for 4 min.

Following digestion with a restriction endonuclease to yield the desired cohesive or blunt ends, a polynucleotide specific for each fusion polypeptide was ligated into an expression plasmid. Each resulting plasmid contained the coding sequences of the individual antigens of each fusion polypeptide. The expression vectors used were pET-12b and pT7^L2 IL 1.

Three coding sequences for antigens Ra12, TbH9 and Ra35 were ligated to encode one fusion protein (SEQ ID NOS:1 and 2) (FIGS. 1A-1C). Another three coding sequences for antigens Erd14, DPV and MTI were ligated to encode a second fusion protein (SEQ ID NOS:3 and 4) (FIGS. 2A and 2B). Three coding sequences for antigens TbRa3, 38 kD and Tb38-1 were ligated to encode one fusion protein (SEQ ID NOS:5 and 6) (FIG. 3A-3D). Two coding sequences for antigens TbH9 and Tb38-1 were ligated to encode one fusion protein (SEQ ID NOS:7 and 8) (FIG. 4A-4D). Four coding sequences for antigens TbRa3, 38 kD, Tb38-1 and DPEP were ligated to encode one fusion protein (SEQ ID NOS:9 and 10) (FIGS. 5A-5J). Five coding sequences for antigens Erd14, DPV, MTI, MSL and MTCC2 were ligated to encode one fusion protein (SEQ ID NOS:11 and 12) (FIGS. 6A-6F). Four coding sequences for antigens Erd14, DPV, MTI and MSL were ligated to encode one fusion protein (SEQ ID NOS:13 and 14) (FIGS. 7A and 7B). Four coding sequences for antigens DPV, MTI, MSL and MTCC2 were ligated to encode one fusion protein (SEQ ID NOS:15 and 16) (FIGS. 8A and 8F). Three coding sequences for antigens DPV, MTI and MSL were ligated to encode one fusion protein (SEQ ID NOS:18 and 19) (FIGS. 9A and 9B). Three coding sequences for antigens TbH9, DPV and MTI were ligated to encode one fusion protein (SEQ ID NOS:21 and 22) (FIGS. 10A-10C). Three coding sequences for antigens Erd14, DPV and MTI were ligated to encode one fusion protein (SEQ ID NOS:23 and 24) (FIGS. 11A and 11B). Two coding sequences for antigens TbH9 and Ra35 were ligated to encode one fusion protein (SEQ ID NOS:25 and 26) (FIGS. 12A-12C). Two coding sequences for antigens Ra12 and DPPD were ligated to encode one fusion protein (SEQ ID NOS:27 and 28) (FIGS. 13A and 13B).

The recombinant proteins were expressed in *E. coli* with six histidine residues at the amino-terminal portion using the pET plasmid vector (pET-17b) and a T7 RNA polymerase expression system (Novagen, Madison, Wis.). *E. coli* strain BL21 (DE3) pLysE (Novagen) was used for high level expression. The recombinant (His-Tag) fusion proteins were purified from the soluble supernatant or the insoluble inclusion body of 500 ml of IPTG induced batch cultures by affinity chromatography using the one step QIAexpress Ni-NTA Agarose matrix (QIAGEN, Chatsworth, Calif.) in the presence of 8M urea. Briefly, 20 ml of an overnight saturated culture of BL21 containing the pET construct was added into 500 ml of 2×YT media containing 50 μg/ml ampicillin and 34 μg/ml chloramphenicol, grown at 37° C. with shaking. The bacterial cultures were induced with 2 mM IPTG at an OD 560 of 0.3 and grown for an additional 3 h (OD=1.3 to 1.9). Cells were harvested from 500 ml batch cultures by centrifugation and resuspended in 20 ml of binding buffer (0.1 M sodium phosphate, pH 8.0; 10 mM Tris-HCl, pH 8.0) containing 2 mM PMSF and 20 μg/ml leupeptin plus one complete protease inhibitor tablet (Boehringer Mannheim) per 25 ml. *E. coli* was lysed by freeze-thaw followed by brief sonication, then spun at 12 k rpm for 30 min to pellet the inclusion bodies.

The inclusion bodies were washed three times in 1% CHAPS in 10 mM Tris-HCl (pH 8.0). This step greatly reduced the level of contaminating LPS. The inclusion body was finally solubilized in 20 ml of binding buffer containing 8 M urea or 8M urea was added directly into the soluble supernatant. Recombinant fusion proteins with His-Tag residues were batch bound to Ni-NTA agarose resin (5 ml resin per 500 ml inductions) by rocking at room temperature for 1 h and the complex passed over a column. The flow through was passed twice over the same column and the column washed three times with 30 ml each of wash buffer (0.1 M sodium phosphate and 10 mM Tris-HCL, pH 6.3) also containing 8 M urea. Bound protein was eluted with 30 ml of 150 mM immidazole in wash buffer and 5 ml fractions collected. Fractions containing each recombinant fusion protein were pooled, dialyzed against 10 mM TrisHCl (pH 8.0) bound one more time to the Ni-NTA matrix, eluted and dialyzed in 10 mM Tris-HCL (pH 7.8). The yield of recombinant protein varies from 25-150 mg per liter of induced bacterial culture with greater than 98% purity. Recombinant proteins were assayed for endotoxin contamination using the *Limulus* assay (BioWhittaker) and were shown to contain<10 E.U.Img.

6.1.2. T-Cell Proliferation Assay

Purified fusion polypeptides were tested for the ability to induce T-cell proliferation in peripheral blood mononuclear cell (PBMC) preparations. The PBMCs from donors known to be PPD skin test positive and whose T-cells were shown to proliferate in response to PPD and crude soluble proteins from *M. tuberculosis* were cultured in RPMI 1640 supplemented with 10% pooled human serum and 50 µg/ml gentamicin. Purified polypeptides were added in duplicate at concentrations of 0.5 to 10 μg/ml. After six days of culture in 96-well round-bottom plates in a volume of 200 μl, 50 μl of medium was removed from each well for determination of IFN-γ levels, as described below in Section 6.1.3. The plates were then pulsed with 1 μCi/well of tritiated thymidine for a further 18 hours, harvested and tritium uptake determined using a gas scintillation counter. Fractions that resulted in proliferation in both replicates three fold greater than the proliferation observed in cells cultured in medium alone were considered positive.

6.1.3. Interferon-γ Assay

Spleens from mice were removed asceptically and single cell suspension prepared in complete RPMI following lysis of red blood cells. 100 μl of cells ($2\times10^{-5}$ cells) were plated per well in a 96-well flat bottom microtiter plate. Cultures were stimulated with the indicated recombinant proteins for 24 h and the supernatant assayed for IFN-γ.

The levels of supernatant IFN-γ was analysed by sandwich ELISA, using antibody pairs and procedures available from PharMingen. Standard curves were generated using recombinant mouse cytokines. ELISA plates (Corning) were coated with 50 μl/well (1 μg/ml, in 0.1 M bicarbonate coating buffer, pH9.6) of a cytokine capture mAb (rat anti-mouse IFN-γ (PharMingen; Cat. # 18181D)), and incubated for 4 h at room temp. Shake out plate contents and block with PBS-0.05% Tween, 1.0% BSA (200 μl/well) overnight at 4° C. and washed for 6× in PBS-0.1% Tween. Standards (mouse IFN-γ) and supernatant samples diluted in PBS-0.05% Tween, 0.1% BSA were then added for 2 hr at room temp. The plates were washed as above and then incubated for 2 hr at room temperature with 100 μl/well of a second Ab (biotin rat a mouse IFN-γ (Cat. # 18112D; PharMingen) at 0.5 μg/ml diluted in PBS-0.05% Tween, 0.1% BSA. After washing, plates were incubated with 100 μl/well of streptavidin-HRP (Zymed) at a 1:2500 dilution in PBS-0.05% Tween, 0.1% BSA at room temp for 1 hr. The plates were washed one last time and developed with 100 μl/well TMB substrate (3,3',5,5'-tetramethylbenzidine, Kirkegaard and Perry, Gaithersburg, Md.) and the reaction stopped after color developed, with $H_2SO_4$, 50 μl/well. Absorbance (OD) were determined at 450 nm using 570 nm as a reference wavelength and the cytokine concentration evaluated using the standard curve.

6.2. Results 6.2.1. Tri-Fusion Proteins Induced Immune Responses

Three coding sequences for *M. tuberculosis* antigens were inserted into an expression vector for the production of a fusion protein. The antigens designated Ra12, TbH9 and Ra35 were produced as one recombinant fusion protein (FIGS. 1A-1C). Antigens Erd14, DPV and MTI were produced as a second fusion protein (FIGS. 2A and 2B). The two fusion proteins were affinity purified for use in in vitro and in vivo assays.

The two fusion proteins were tested for their ability to stimulate T cell responses from six $PPD^+$ subjects. When T cell proliferation was measured, both fusion proteins exhibited a similar reactivity pattern as their individual components (FIGS. 14A-14F). A similar result was obtained when IFN-γ production was measured (FIGS. 15A-15F). For example, subject D160 responded to antigens TbH9 and MTI individually. Subject D160 also responded to the fusion proteins that contained these antigens (FIGS. 14B and 15B).

In contrast, no T cell response from D160 was observed to other antigens individually.

Another subject, D201, who did not react with antigens Erd14, DPV or MTI individually, was also unresponsive to the fusion protein containing these antigens. It should be noted that when the T cell responses to the individual components of the two fusion proteins were not particularly strong, the fusion proteins stimulated responses that were equal to or higher than that induced by the individual antigens in most cases.

The Ra12-TbH9-Ra35 tri-fusion protein was also tested as an immunogen in vivo.

In these experiments, the fusion protein was injected into the footpads of mice for immunization. Each group of three mice received the protein in a different adjuvant formulation: SBAS1c, SBAS2 (Ling et al., 1997, Vaccine 15:1562-1567), SBAS7 and $AL(OH)_3$. After two subcutaneous immunizations at three week intervals, the animals were sacrificed one week later, and their draining lymph nodes were harvested for use as responder cells in T cell proliferation and cytokine production assays. Regardless which adjuvant was used in the immunization, strong T cell proliferation responses were induced against TbH9 when it was used as an individual antigen (FIG. 16A). Weaker responses were induced against Ra35 and Ra12 (FIGS. 16B and 16C). When the Ra12-TbH9-Ra35 fusion protein was used as immunogen, a response similar to that against the individual components was observed.

When cytokine production was measured, adjuvants SBAS1c and SBAS2 produced similar IFN-γ (FIG. 17) and ILK responses (FIG. 18). However, the combination of SBAS7 and aluminum hydroxide produced the strongest IFN-γ responses and the lowest level of IL-4 production for all three antigens. With respect to the humoral antibody response in vivo, FIG. 19A-19F shows that the fusion protein elicited both $IgG_1$ and $IgG_{2a}$ antigen-specific responses when it was used with any of the three adjuvants.

Additionally, C57BL/6 mice were immunized with an expression construct containing Ra12-TbH9-Ra35 (Mtb32-Mtb39 fusion) coding sequence as DNA vaccine. The immunized animals exhibited significant protection against tuberculosis upon a subsequent aerosol challenge of live bacteria.

Based on these results, a fusion construct of Mtb32-Mtb39 coding sequence was made, and its encoded product tested in a guinea pig long term protection model. In these studies, guinea pigs were immunized with a single recombinant fusion protein or a mixture of Mtb32A (Ra35) and Mtb39A (TbH9) proteins in formulations containing an adjuvant. FIGS. 20A-20C shows that guinea pigs immunized with the fusion protein in SBAS1c or SBAS2 were better protected against the development of tuberculosis upon subsequent challenge, as compared to animals immunized with the two antigens in a mixture in the same adjuvant formulation. The fusion proteins in SBAS2 formulation afforded the greatest protection in the animals. Thus, fusion proteins of various *M. tuberculosis* antigens may be used as more effective immunogens in vaccine formulations than a mixture of the individual components.

6.2.2. Bi-Fusion Protein Induced Immune Responses

A bi-fusion fusion protein containing the TbH-9 and Tb38-1 antigens without a hinge sequence was produced by recombinant methods. The ability of the TbH9-Tb38-1 fusion protein to induce T cell proliferation and IFN-γ production was examined. PBMC from three donors were employed: one donor had been previously shown to respond to TbH9 but not to Tb38-1 (donor 131); one had been shown to respond to Tb38-1 but not to TbH9 (donor 184); and one had been shown to respond to both antigens (donor 201). The results of these studies demonstrate the functional activity of both the antigens in the fusion protein (FIGS. 21A and 21B, 22A and 22B, and 23A and 23B).

6.2.3. A Tetra-Fusion Protein Reacted with Tuberculosis Patient Sera

A fusion protein containing TbRa3, 38 KD antigen, Tb38-1 and DPEP was produced by recombinant methods. The reactivity of this tetra-fusion protein referred to as TbF-2 with sera from *M. tuberculosis*-infected patients was examined by ELISA. The results of these studies (Table 1) demonstrate that all four antigens function independently in the fusion protein.

One of skill in the art will appreciate that the order of the individual antigens within each fusion protein may be changed and that comparable activity would be expected provided that each of the epitopes is still functionally available. In addition, truncated forms of the proteins containing active epitopes may be used in the construction of fusion proteins.

The present invention is not to be limited in scope by the exemplified embodiments which are intended as illustrations of single aspects of the invention, and any clones, nucleotide or amino acid sequences which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims. It is also to be understood that all base pair sizes given for nucleotides are approximate and are used for purposes of description.

All publications cited herein are incorporated by reference in their entirety.

TABLE 1

REACTIVITY OF TBF-2 FUSION PROTEIN WITH TB AND NORMAL SERA

| | | TbF | | TbF-2 | | ELISA Reactivity | | | |
|---|---|---|---|---|---|---|---|---|---|
| Serum ID | Status | OD450 | Status | OD450 | Status | 38 kD | TbRa3 | Tb38-I | DPEP |
| B931-40 | TB | 0.57 | + | 0.321 | + | − | + | − | + |
| B931-41 | TB | 0.601 | + | 0.396 | + | + | + | + | − |
| B931-109 | TB | 0.494 | + | 0.404 | + | + | + | ±± | − |
| B931-132 | TB | 1.502 | + | 1.292 | + | + | + | + | ±± |
| 5004 | TB | 1.806 | + | 1.666 | + | ±± | ±± | + | − |
| 15004 | TB | 2.862 | + | 2.468 | + | + | + | + | − |
| 39004 | TB | 2.443 | + | 1.722 | + | + | + | + | − |
| 68004 | TB | 2.871 | + | 2.575 | + | + | + | + | − |
| 99004 | TB | 0.691 | + | 0.971 | + | − | ±± | + | − |
| 107004 | TB | 0.875 | + | 0.732 | + | − | ±± | + | − |
| 92004 | TB | 1.632 | + | 1.394 | + | + | ±± | ±± | − |
| 97004 | TB | 1.491 | + | 1.979 | + | + | ±± | − | + |
| 118004 | TB | 3.182 | + | 3.045 | + | + | ±± | − | − |
| 173004 | TB | 3.644 | + | 3.578 | + | + | + | + | − |
| 175004 | TB | 3.332 | + | 2.916 | + | + | + | − | − |
| 274004 | TB | 3.696 | + | 3.716 | + | − | + | − | + |
| 276004 | TB | 3.243 | + | 2.56 | + | − | − | + | − |
| 282004 | TB | 1.249 | + | 1.234 | + | + | − | − | − |
| 289004 | TB | 1.373 | + | 1.17 | + | − | + | − | − |
| 308004 | TB | 3.708 | + | 3.355 | + | − | − | + | − |
| 314004 | TB | 1.663 | + | 1.399 | + | − | − | + | − |
| 317004 | TB | 1.163 | + | 0.92 | + | + | − | − | − |
| 312004 | TB | 1.709 | + | 1.453 | + | − | + | − | − |
| 380004 | TB | 0.238 | − | 0.461 | + | − | ±± | − | + |
| 451004 | TB | 0.18 | − | 0.2 | − | − | − | − | ±± |
| 478004 | TB | 0.188 | − | 0.469 | + | − | − | − | ±± |
| 410004 | TB | 0.384 | + | 2.392 | + | ±± | − | − | + |
| 411004 | TB | 0.306 | + | 0.874 | + | − | + | − | + |
| 421004 | TB | 0.357 | + | 1.456 | + | − | + | − | + |
| 528004 | TB | 0.047 | − | 0.196 | − | − | − | − | + |
| A6-87 | Normal | 0.094 | − | 0.063 | − | − | − | − | − |
| A6-88 | Normal | 0.214 | − | 0.19 | − | − | − | − | − |
| A6-89 | Normal | 0.248 | − | 0.125 | − | − | − | − | − |
| A6-90 | Normal | 0.179 | − | 0.206 | − | − | − | − | − |

TABLE 1-continued

REACTIVITY OF TBF-2 FUSION PROTEIN WITH TB AND NORMAL SERA

| Serum ID | TbF | | TbF-2 | | ELISA Reactivity | | | |
| | Status | OD450 | Status | OD450 | Status | 38 kD | TbRa3 | Tb38-I | DPEP |
|---|---|---|---|---|---|---|---|---|---|
| A6-91 | Normal | 0.135 | – | 0.151 | – | – | – | – | – |
| A6-92 | Normal | 0.064 | – | 0.097 | – | – | – | – | – |
| A6-93 | Normal | 0.072 | – | 0.098 | – | – | – | – | – |
| A6-94 | Normal | 0.072 | – | 0.064 | – | – | – | – | – |
| A6-95 | Normal | 0.125 | – | 0.159 | – | – | – | – | – |
| A6-96 | Normal | 0.121 | – | 0.12 | – | – | – | – | – |
| Cut-off | | 0.284 | | 0.266 | | | | | |

SEQUENCE LISTING

<160> NUMBER OF SEQ ID NOS: 46

<210> SEQ ID NO 1
<211> LENGTH: 2287
<212> TYPE: DNA
<213> ORGANISM: Artificial Sequence
<220> FEATURE:
<223> OTHER INFORMATION: Description of Artificial Sequence:tri-fusion
      protein Ra12-TbH9-Ra35 (designated Mtb32-Mtb39
      fusion)
<221> NAME/KEY: modified_base
<222> LOCATION: (30)
<223> OTHER INFORMATION: n = g, a, c or t
<221> NAME/KEY: modified_base
<222> LOCATION: (33)
<223> OTHER INFORMATION: n = g, a, c or t
<221> NAME/KEY: CDS
<222> LOCATION: (42)..(2231)
<221> NAME/KEY: modified_base
<222> LOCATION: (2270)
<223> OTHER INFORMATION: n = g, a, c or t

<400> SEQUENCE: 1

```
tctagaaata attttgttta ctttaagaan ganatataca t atg cat cac cat cac      56
                                              Met His His His His
                                                1               5 cat cac acg gcc gcg tcc gat aac ttc cag ctg tcc cag ggt ggg cag       104
His His Thr Ala Ala Ser Asp Asn Phe Gln Leu Ser Gln Gly Gly Gln
             10                  15                  20 gga ttc gcc att ccg atc ggg cag gcg atg gcg atc gcg ggc cag atc       152
Gly Phe Ala Ile Pro Ile Gly Gln Ala Met Ala Ile Ala Gly Gln Ile
         25                  30                  35 cga tcg ggt ggg ggg tca ccc acc gtt cat atc ggg cct acc gcc ttc       200
Arg Ser Gly Gly Gly Ser Pro Thr Val His Ile Gly Pro Thr Ala Phe
     40                  45                  50 ctc ggc ttg ggt gtt gtc gac aac aac ggc aac ggc gca cga gtc caa       248
Leu Gly Leu Gly Val Val Asp Asn Asn Gly Asn Gly Ala Arg Val Gln
 55                  60                  65 cgc gtg gtc ggg agc gct ccg gcg gca agt ctc ggc atc tcc acc ggc       296
Arg Val Val Gly Ser Ala Pro Ala Ala Ser Leu Gly Ile Ser Thr Gly
 70                  75                  80                  85 gac gtg atc acc gcg gtc gac ggc gct ccg atc aac tcg gcc acc gcg       344
Asp Val Ile Thr Ala Val Asp Gly Ala Pro Ile Asn Ser Ala Thr Ala
             90                  95                 100 atg gcg gac gcg ctt aac ggg cat cat ccc ggt gac gtc atc tcg gtg       392
Met Ala Asp Ala Leu Asn Gly His His Pro Gly Asp Val Ile Ser Val
            105                 110                 115 acc tgg caa acc aag tcg ggc ggc acg cgt aca ggg aac gtg aca ttg       440
Thr Trp Gln Thr Lys Ser Gly Gly Thr Arg Thr Gly Asn Val Thr Leu
        120                 125                 130 gcc gag gga ccc ccg gcc gaa ttc atg gtg gat ttc ggg gcg tta cca       488
Ala Glu Gly Pro Pro Ala Glu Phe Met Val Asp Phe Gly Ala Leu Pro
    135                 140                 145 ccg gag atc aac tcc gcg agg atg tac gcc ggc ccg ggt tcg gcc tcg       536
Pro Glu Ile Asn Ser Ala Arg Met Tyr Ala Gly Pro Gly Ser Ala Ser
150                 155                 160                 165 ctg gtg gcc gcg gct cag atg tgg gac agc gtg gcg agt gac ctg ttt       584
Leu Val Ala Ala Ala Gln Met Trp Asp Ser Val Ala Ser Asp Leu Phe
            170                 175                 180 tcg gcc gcg tcg gcg ttt cag tcg gtg gtc tgg ggt ctg acg gtg ggg       632
Ser Ala Ala Ser Ala Phe Gln Ser Val Val Trp Gly Leu Thr Val Gly
            185                 190                 195 tcg tgg ata ggt tcg tcg gcg ggt ctg atg gtg gcg gcg gcc tcg ccg       680
```

```
                                                    -continued

Ser Trp Ile Gly Ser Ser Ala Gly Leu Met Val Ala Ala Ala Ser Pro
        200             205             210 tat gtg gcg tgg atg agc gtc acc gcg ggg cag gcc gag ctg acc gcc    728
Tyr Val Ala Trp Met Ser Val Thr Ala Gly Gln Ala Glu Leu Thr Ala
        215             220             225 gcc cag gtc cgg gtt gct gcg gcg gcc tac gag acg gcg tat ggg ctg    776
Ala Gln Val Arg Val Ala Ala Ala Ala Tyr Glu Thr Ala Tyr Gly Leu
230             235             240             245 acg gtg ccc ccg ccg gtg atc gcc gag aac cgt gct gaa ctg atg att    824
Thr Val Pro Pro Pro Val Ile Ala Glu Asn Arg Ala Glu Leu Met Ile
                250             255             260 ctg ata gcg acc aac ctc ttg ggg caa aac acc ccg gcg atc gcg gtc    872
Leu Ile Ala Thr Asn Leu Leu Gly Gln Asn Thr Pro Ala Ile Ala Val
            265             270             275 aac gag gcc gaa tac ggc gag atg tgg gcc caa gac gcc gcc gcg atg    920
Asn Glu Ala Glu Tyr Gly Glu Met Trp Ala Gln Asp Ala Ala Ala Met
        280             285             290 ttt ggc tac gcc gcg gcg acg gcg acg gcg acg gcg acg ttg ctg ccg    968
Phe Gly Tyr Ala Ala Ala Thr Ala Thr Ala Thr Ala Thr Leu Leu Pro
    295             300             305 ttc gag gag gcg ccg gag atg acc agc gcg ggt ggg ctc ctc gag cag    1016
Phe Glu Glu Ala Pro Glu Met Thr Ser Ala Gly Gly Leu Leu Glu Gln
310             315             320             325 gcc gcc gcg gtc gag gag gcc tcc gac acc gcc gcg aac cag ttg        1064
Ala Ala Ala Val Glu Glu Ala Ser Asp Thr Ala Ala Ala Asn Gln Leu
                330             335             340 atg aac aat gtg ccc cag gcg ctg caa cag ctg gcc cag ccc acg cag    1112
Met Asn Asn Val Pro Gln Ala Leu Gln Gln Leu Ala Gln Pro Thr Gln
            345             350             355 ggc acc acg cct tct tcc aag ctg ggt ggc ctg tgg aag acg gtc tcg    1160
Gly Thr Thr Pro Ser Ser Lys Leu Gly Gly Leu Trp Lys Thr Val Ser
        360             365             370 ccg cat cgg tcg ccg atc agc aac atg gtg tcg atg gcc aac aac cac    1208
Pro His Arg Ser Pro Ile Ser Asn Met Val Ser Met Ala Asn Asn His
    375             380             385 atg tcg atg acc aac tcg ggt gtg tcg atg acc aac acc ttg agc tcg    1256
Met Ser Met Thr Asn Ser Gly Val Ser Met Thr Asn Thr Leu Ser Ser
390             395             400             405 atg ttg aag ggc ttt gct ccg gcg gcg gcc cgc cag gcc gtg caa acc    1304
Met Leu Lys Gly Phe Ala Pro Ala Ala Ala Arg Gln Ala Val Gln Thr
                410             415             420 gcg gcg caa aac ggg gtc cgg gcg atg agc tcg ctg ggc agc tcg ctg    1352
Ala Ala Gln Asn Gly Val Arg Ala Met Ser Ser Leu Gly Ser Ser Leu
            425             430             435 ggt tct tcg ggt ctg ggc ggt ggg gtg gcc gcc aac ttg ggt cgg gcg    1400
Gly Ser Ser Gly Leu Gly Gly Gly Val Ala Ala Asn Leu Gly Arg Ala
        440             445             450 gcc tcg gtc ggt tcg ttg tcg gtg ccg cag gcc tgg gcc gcg gcc aac    1448
Ala Ser Val Gly Ser Leu Ser Val Pro Gln Ala Trp Ala Ala Ala Asn
    455             460             465 cag gca gtc acc ccg gcg gcg cgg gcg ctg ccg ctg acc agc ctg acc    1496
Gln Ala Val Thr Pro Ala Ala Arg Ala Leu Pro Leu Thr Ser Leu Thr
470             475             480             485 agc gcc gcg gaa aga ggg ccc ggg cag atg ctg ggc ggg ctg ccg gtg    1544
Ser Ala Ala Glu Arg Gly Pro Gly Gln Met Leu Gly Gly Leu Pro Val
                490             495             500 ggg cag atg ggc gcc agg gcc ggt ggg ctc agt ggt gtg ctg cgt        1592
Gly Gln Met Gly Ala Arg Ala Gly Gly Gly Leu Ser Gly Val Leu Arg
            505             510             515 gtt ccg ccg cga ccc tat gtg atg ccg cat tct ccg gca gcc ggc gat    1640
```

-continued

```
                Val Pro Pro Arg Pro Tyr Val Met Pro His Ser Pro Ala Ala Gly Asp
                    520                 525                 530 atc gcc ccg ccg gcc ttg tcg cag gac cgg ttc gcc gac ttc ccc gcg      1688
Ile Ala Pro Pro Ala Leu Ser Gln Asp Arg Phe Ala Asp Phe Pro Ala
535                 540                 545 ctg ccc ctc gac ccg tcc gcg atg gtc gcc caa gtg ggg cca cag gtg      1736
Leu Pro Leu Asp Pro Ser Ala Met Val Ala Gln Val Gly Pro Gln Val
550                 555                 560                 565 gtc aac atc aac acc aaa ctg ggc tac aac aac gcc gtg ggc gcc ggg      1784
Val Asn Ile Asn Thr Lys Leu Gly Tyr Asn Asn Ala Val Gly Ala Gly
                570                 575                 580 acc ggc atc gtc atc gat ccc aac ggt gtc gtg ctg acc aac aac cac      1832
Thr Gly Ile Val Ile Asp Pro Asn Gly Val Val Leu Thr Asn Asn His
            585                 590                 595 gtg atc gcg ggc gcc acc gac atc aat gcg ttc agc gtc ggc tcc ggc      1880
Val Ile Ala Gly Ala Thr Asp Ile Asn Ala Phe Ser Val Gly Ser Gly
        600                 605                 610 caa acc tac ggc gtc gat gtg gtc ggg tat gac cgc acc cag gat gtc      1928
Gln Thr Tyr Gly Val Asp Val Val Gly Tyr Asp Arg Thr Gln Asp Val
    615                 620                 625 gcg gtg ctg cag ctg cgc ggt gcc ggt ggc ctg ccg tcg gcg gcg atc      1976
Ala Val Leu Gln Leu Arg Gly Ala Gly Gly Leu Pro Ser Ala Ala Ile
630                 635                 640                 645 ggt ggc ggc gtc gcg gtt ggt gag ccc gtc gtc gcg atg ggc aac agc      2024
Gly Gly Gly Val Ala Val Gly Glu Pro Val Val Ala Met Gly Asn Ser
                650                 655                 660 ggt ggg cag ggc gga acg ccc cgt gcg gtg cct ggc agg gtg gtc gcg      2072
Gly Gly Gln Gly Gly Thr Pro Arg Ala Val Pro Gly Arg Val Val Ala
            665                 670                 675 ctc ggc caa acc gtg cag gcg tcg gat tcg ctg acc ggt gcc gaa gag      2120
Leu Gly Gln Thr Val Gln Ala Ser Asp Ser Leu Thr Gly Ala Glu Glu
        680                 685                 690 aca ttg aac ggg ttg atc cag ttc gat gcc gcg atc cag ccc ggt gat      2168
Thr Leu Asn Gly Leu Ile Gln Phe Asp Ala Ala Ile Gln Pro Gly Asp
    695                 700                 705 tcg ggc ggg ccc gtc gtc aac ggc cta gga cag gtg gtc ggt atg aac      2216
Ser Gly Gly Pro Val Val Asn Gly Leu Gly Gln Val Val Gly Met Asn
710                 715                 720                 725 acg gcc gcg tcc taggatatcc atcacactgg cggccgctcg agcagatccg          2268
Thr Ala Ala Ser gntgtaacaa agcccgaaa                                                  2287

<210> SEQ ID NO 2
<211> LENGTH: 729
<212> TYPE: PRT
<213> ORGANISM: Artificial Sequence
<220> FEATURE:
<223> OTHER INFORMATION: Description of Artificial Sequence:tri-fusion

<400> SEQUENCE: 2

Met His His His His His Thr Ala Ala Ser Asp Asn Phe Gln Leu
1               5                   10                  15

Ser Gln Gly Gly Gln Gly Phe Ala Ile Pro Ile Gly Gln Ala Met Ala
                20                  25                  30

Ile Ala Gly Gln Ile Arg Ser Gly Gly Ser Pro Thr Val His Ile
            35                  40                  45

Gly Pro Thr Ala Phe Leu Gly Leu Gly Val Val Asp Asn Asn Gly Asn
        50                  55                  60

Gly Ala Arg Val Gln Arg Val Val Gly Ser Ala Pro Ala Ala Ser Leu
65                  70                  75                  80
```

```
Gly Ile Ser Thr Gly Asp Val Ile Thr Ala Val Asp Gly Ala Pro Ile
                85                  90                  95

Asn Ser Ala Thr Ala Met Ala Asp Ala Leu Asn Gly His His Pro Gly
            100                 105                 110

Asp Val Ile Ser Val Thr Trp Gln Thr Lys Ser Gly Thr Arg Thr
        115                 120                 125

Gly Asn Val Thr Leu Ala Glu Gly Pro Pro Ala Glu Phe Met Val Asp
130                 135                 140

Phe Gly Ala Leu Pro Pro Glu Ile Asn Ser Ala Arg Met Tyr Ala Gly
145                 150                 155                 160

Pro Gly Ser Ala Ser Leu Val Ala Ala Gln Met Trp Asp Ser Val
                165                 170                 175

Ala Ser Asp Leu Phe Ser Ala Ala Ser Ala Phe Gln Ser Val Val Trp
            180                 185                 190

Gly Leu Thr Val Gly Ser Trp Ile Gly Ser Ser Ala Gly Leu Met Val
        195                 200                 205

Ala Ala Ala Ser Pro Tyr Val Ala Trp Met Ser Val Thr Ala Gly Gln
210                 215                 220

Ala Glu Leu Thr Ala Ala Gln Val Arg Val Ala Ala Ala Tyr Glu
225                 230                 235                 240

Thr Ala Tyr Gly Leu Thr Val Pro Pro Val Ile Ala Glu Asn Arg
                245                 250                 255

Ala Glu Leu Met Ile Leu Ile Ala Thr Asn Leu Leu Gly Gln Asn Thr
            260                 265                 270

Pro Ala Ile Ala Val Asn Glu Ala Glu Tyr Gly Glu Met Trp Ala Gln
        275                 280                 285

Asp Ala Ala Ala Met Phe Gly Tyr Ala Ala Ala Thr Ala Thr Ala Thr
290                 295                 300

Ala Thr Leu Leu Pro Phe Glu Glu Ala Pro Glu Met Thr Ser Ala Gly
305                 310                 315                 320

Gly Leu Leu Glu Gln Ala Ala Ala Val Glu Glu Ala Ser Asp Thr Ala
                325                 330                 335

Ala Ala Asn Gln Leu Met Asn Asn Val Pro Gln Ala Leu Gln Gln Leu
            340                 345                 350

Ala Gln Pro Thr Gln Gly Thr Thr Pro Ser Ser Lys Leu Gly Gly Leu
        355                 360                 365

Trp Lys Thr Val Ser Pro His Arg Ser Pro Ile Ser Asn Met Val Ser
370                 375                 380

Met Ala Asn Asn His Met Ser Met Thr Asn Ser Gly Val Ser Met Thr
385                 390                 395                 400

Asn Thr Leu Ser Ser Met Leu Lys Gly Phe Ala Pro Ala Ala Ala Arg
                405                 410                 415

Gln Ala Val Gln Thr Ala Ala Gln Asn Gly Val Arg Ala Met Ser Ser
            420                 425                 430

Leu Gly Ser Ser Leu Gly Ser Ser Gly Leu Gly Gly Val Ala Ala
        435                 440                 445

Asn Leu Gly Arg Ala Ala Ser Val Gly Ser Leu Ser Val Pro Gln Ala
450                 455                 460

Trp Ala Ala Ala Asn Gln Ala Val Thr Pro Ala Ala Arg Ala Leu Pro
465                 470                 475                 480

Leu Thr Ser Leu Thr Ser Ala Ala Glu Arg Gly Pro Gly Gln Met Leu
                485                 490                 495

Gly Gly Leu Pro Val Gly Gln Met Gly Ala Arg Ala Gly Gly Gly Leu
```

```
                    500                 505                 510
Ser Gly Val Leu Arg Val Pro Pro Arg Pro Tyr Val Met Pro His Ser
            515                 520                 525

Pro Ala Ala Gly Asp Ile Ala Pro Pro Ala Leu Ser Gln Asp Arg Phe
            530                 535                 540

Ala Asp Phe Pro Ala Leu Pro Leu Asp Pro Ser Ala Met Val Ala Gln
545                 550                 555                 560

Val Gly Pro Gln Val Val Asn Ile Asn Thr Lys Leu Gly Tyr Asn Asn
                565                 570                 575

Ala Val Gly Ala Gly Thr Gly Ile Val Ile Asp Pro Asn Gly Val Val
            580                 585                 590

Leu Thr Asn Asn His Val Ile Ala Gly Ala Thr Asp Ile Asn Ala Phe
            595                 600                 605

Ser Val Gly Ser Gly Gln Thr Tyr Gly Val Asp Val Gly Tyr Asp
            610                 615                 620

Arg Thr Gln Asp Val Ala Val Leu Gln Leu Arg Gly Ala Gly Gly Leu
625                 630                 635                 640

Pro Ser Ala Ala Ile Gly Gly Gly Val Ala Val Gly Glu Pro Val Val
                645                 650                 655

Ala Met Gly Asn Ser Gly Gly Gln Gly Gly Thr Pro Arg Ala Val Pro
                660                 665                 670

Gly Arg Val Val Ala Leu Gly Gln Thr Val Gln Ala Ser Asp Ser Leu
            675                 680                 685

Thr Gly Ala Glu Glu Thr Leu Asn Gly Leu Ile Gln Phe Asp Ala Ala
            690                 695                 700

Ile Gln Pro Gly Asp Ser Gly Gly Pro Val Val Asn Gly Leu Gly Gln
705                 710                 715                 720

Val Val Gly Met Asn Thr Ala Ala Ser
                725

<210> SEQ ID NO 3
<211> LENGTH: 1081
<212> TYPE: DNA
<213> ORGANISM: Artificial Sequence
<220> FEATURE:
<223> OTHER INFORMATION: Description of Artificial Sequence:tri-fusion
      protein Erd14-DPV-MTI
<221> NAME/KEY: CDS
<222> LOCATION: (10)..(1002)

<400> SEQUENCE: 3 gatatacat atg cat cac cat cac cat cac atg gcc acc acc ctt ccc gtt     51
          Met His His His His His His Met Ala Thr Thr Leu Pro Val
            1               5                  10 cag cgc cac ccg cgg tcc ctc ttc ccc gag ttt tct gag ctg ttc gcg       99
Gln Arg His Pro Arg Ser Leu Phe Pro Glu Phe Ser Glu Leu Phe Ala
 15                  20                  25                  30 gcc ttc ccg tca ttc gcc gga ctc cgg ccc acc ttc gac acc cgg ttg      147
Ala Phe Pro Ser Phe Ala Gly Leu Arg Pro Thr Phe Asp Thr Arg Leu
                 35                  40                  45 atg cgg ctg gaa gac gag atg aaa gag ggg cgc tac gag gta cgc gcg     195
Met Arg Leu Glu Asp Glu Met Lys Glu Gly Arg Tyr Glu Val Arg Ala
         50                  55                  60 gag ctt ccc ggg gtc gac ccc gac aag gac gtc gac att atg gtc cgc     243
Glu Leu Pro Gly Val Asp Pro Asp Lys Asp Val Asp Ile Met Val Arg
             65                  70                  75 gat ggt cag ctg acc atc aag gcc gag cgc acc gag cag aag gac ttc     291
Asp Gly Gln Leu Thr Ile Lys Ala Glu Arg Thr Glu Gln Lys Asp Phe
 80                  85                  90
```

```
gac ggt cgc tcg gaa ttc gcg tac ggt tcc ttc gtt cgc acg gtg tcg    339
Asp Gly Arg Ser Glu Phe Ala Tyr Gly Ser Phe Val Arg Thr Val Ser
 95             100                 105                 110 ctg ccg gta ggt gct gac gag gac gac att aag gcc acc tac gac aag    387
Leu Pro Val Gly Ala Asp Glu Asp Asp Ile Lys Ala Thr Tyr Asp Lys
                115                 120                 125 ggc att ctt act gtg tcg gtg gcg gtt tcg gaa ggg aag cca acc gaa    435
Gly Ile Leu Thr Val Ser Val Ala Val Ser Glu Gly Lys Pro Thr Glu
            130                 135                 140 aag cac att cag atc cgg tcc acc aac aag ctt gat ccc gtg gac gcg    483
Lys His Ile Gln Ile Arg Ser Thr Asn Lys Leu Asp Pro Val Asp Ala
        145                 150                 155 gtc att aac acc acc tgc aat tac ggg cag gta gta gct gcg ctc aac    531
Val Ile Asn Thr Thr Cys Asn Tyr Gly Gln Val Val Ala Ala Leu Asn
160                 165                 170 gcg acg gat ccg ggg gct gcc gca cag ttc aac gcc tca ccg gtg gcg    579
Ala Thr Asp Pro Gly Ala Ala Ala Gln Phe Asn Ala Ser Pro Val Ala
175                 180                 185                 190 cag tcc tat ttg cgc aat ttc ctc gcc gca ccg cca cct cag cgc gct    627
Gln Ser Tyr Leu Arg Asn Phe Leu Ala Ala Pro Pro Pro Gln Arg Ala
                195                 200                 205 gcc atg gcc gcg caa ttg caa gct gtg ccg ggg gcg gca cag tac atc    675
Ala Met Ala Ala Gln Leu Gln Ala Val Pro Gly Ala Ala Gln Tyr Ile
            210                 215                 220 ggc ctt gtc gag tcg gtt gcc ggc tcc tgc aac aac tat gag ctc atg    723
Gly Leu Val Glu Ser Val Ala Gly Ser Cys Asn Asn Tyr Glu Leu Met
        225                 230                 235 acg att aat tac cag ttc ggg gac gtc gac gct cat ggc gcc atg atc    771
Thr Ile Asn Tyr Gln Phe Gly Asp Val Asp Ala His Gly Ala Met Ile
    240                 245                 250 cgc gct cag gcg gcg tcg ctt gag gcg gag cat cag gcc atc gtt cgt    819
Arg Ala Gln Ala Ala Ser Leu Glu Ala Glu His Gln Ala Ile Val Arg
255                 260                 265                 270 gat gtg ttg gcc gcg ggt gac ttt tgg ggc ggc gcc ggt tcg gtg gct    867
Asp Val Leu Ala Ala Gly Asp Phe Trp Gly Gly Ala Gly Ser Val Ala
                275                 280                 285 tgc cag gag ttc att acc cag ttg ggc cgt aac ttc cag gtg atc tac    915
Cys Gln Glu Phe Ile Thr Gln Leu Gly Arg Asn Phe Gln Val Ile Tyr
            290                 295                 300 gag cag gcc aac gcc cac ggg cag aag gtg cag gct gcc ggc aac aac    963
Glu Gln Ala Asn Ala His Gly Gln Lys Val Gln Ala Ala Gly Asn Asn
        305                 310                 315 atg gcg caa acc gac agc gcc gtc ggc tcc agc tgg gcc actagtaacg   1012
Met Ala Gln Thr Asp Ser Ala Val Gly Ser Ser Trp Ala
    320                 325                 330 gccgccagtg tgctggaatt ctgcagatat ccatcacact ggcggccgct cgagcagatc   1072
cggctgcta                                                          1081

<210> SEQ ID NO 4
<211> LENGTH: 331
<212> TYPE: PRT
<213> ORGANISM: Artificial Sequence
<220> FEATURE:
<223> OTHER INFORMATION: Description of Artificial Sequence:tri-fusion

<400> SEQUENCE: 4

Met His His His His His Met Ala Thr Thr Leu Pro Val Gln Arg
 1               5                  10                  15

His Pro Arg Ser Leu Phe Pro Glu Phe Ser Glu Leu Phe Ala Ala Phe
                20                  25                  30
```

```
Pro Ser Phe Ala Gly Leu Arg Pro Thr Phe Asp Thr Arg Leu Met Arg
         35                  40                  45

Leu Glu Asp Glu Met Lys Glu Gly Arg Tyr Glu Val Arg Ala Glu Leu
 50                  55                  60

Pro Gly Val Asp Pro Asp Lys Asp Val Asp Ile Met Val Arg Asp Gly
 65                  70                  75                  80

Gln Leu Thr Ile Lys Ala Glu Arg Thr Glu Gln Lys Asp Phe Asp Gly
                 85                  90                  95

Arg Ser Glu Phe Ala Tyr Gly Ser Phe Val Arg Thr Val Ser Leu Pro
            100                 105                 110

Val Gly Ala Asp Glu Asp Asp Ile Lys Ala Thr Tyr Asp Lys Gly Ile
        115                 120                 125

Leu Thr Val Ser Val Ala Val Ser Glu Gly Lys Pro Thr Glu Lys His
    130                 135                 140

Ile Gln Ile Arg Ser Thr Asn Lys Leu Asp Pro Val Asp Ala Val Ile
145                 150                 155                 160

Asn Thr Thr Cys Asn Tyr Gly Gln Val Ala Ala Leu Asn Ala Thr
                165                 170                 175

Asp Pro Gly Ala Ala Gln Phe Asn Ala Ser Pro Val Ala Gln Ser
            180                 185                 190

Tyr Leu Arg Asn Phe Leu Ala Ala Pro Pro Gln Arg Ala Ala Met
        195                 200                 205

Ala Ala Gln Leu Gln Ala Val Pro Gly Ala Ala Gln Tyr Ile Gly Leu
    210                 215                 220

Val Glu Ser Val Ala Gly Ser Cys Asn Asn Tyr Glu Leu Met Thr Ile
225                 230                 235                 240

Asn Tyr Gln Phe Gly Asp Val Asp Ala His Gly Ala Met Ile Arg Ala
                245                 250                 255

Gln Ala Ala Ser Leu Glu Ala Glu His Gln Ala Ile Val Arg Asp Val
            260                 265                 270

Leu Ala Ala Gly Asp Phe Trp Gly Gly Ala Gly Ser Val Ala Cys Gln
        275                 280                 285

Glu Phe Ile Thr Gln Leu Gly Arg Asn Phe Gln Val Ile Tyr Glu Gln
    290                 295                 300

Ala Asn Ala His Gly Gln Lys Val Gln Ala Gly Asn Asn Met Ala
305                 310                 315                 320

Gln Thr Asp Ser Ala Val Gly Ser Ser Trp Ala
            325                 330
```

<210> SEQ ID NO 5
<211> LENGTH: 1993
<212> TYPE: DNA
<213> ORGANISM: Artificial Sequence
<220> FEATURE:
<223> OTHER INFORMATION: Description of Artificial Sequence:tri-fusion
      protein TbRa3-38kD-Tb38-1
<221> NAME/KEY: CDS
<222> LOCATION: (152)..(1276)

<400> SEQUENCE: 5

```
tgttcttcga cggcaggctg gtggaggaag ggcccaccga acagctgttc tcctcgccga    60
agcatgcgga aaccgcccga tacgtcgccg gactgtcggg gacgtcaag dacgccaagc   120 gcggaaattg aagagcacag aaaggtatgg c gtg aaa att cgt ttg cat acg     172
                                   Val Lys Ile Arg Leu His Thr
                                     1               5 ctg ttg gcc gtg ttg acc gct gcg ccg ctg ctg cta gca gcg gcg ggc    220
```

```
        Leu Leu Ala Val Leu Thr Ala Ala Pro Leu Leu Leu Ala Ala Ala Gly
                 10                  15                  20 tgt ggc tcg aaa cca ccg agc ggt tcg cct gaa acg ggc gcc ggc gcc         268
Cys Gly Ser Lys Pro Pro Ser Gly Ser Pro Glu Thr Gly Ala Gly Ala
         25                  30                  35 ggt act gtc gcg act acc ccc gcg tcg tcg ccg gtg acg ttg gcg gag         316
Gly Thr Val Ala Thr Thr Pro Ala Ser Ser Pro Val Thr Leu Ala Glu
 40                  45                  50                  55 acc ggt agc acg ctg ctc tac ccg ctg ttc aac ctg tgg ggt ccg gcc         364
Thr Gly Ser Thr Leu Leu Tyr Pro Leu Phe Asn Leu Trp Gly Pro Ala
                 60                  65                  70 ttt cac gag agg tat ccg aac gtc acg atc acc gct cag ggc acc ggt         412
Phe His Glu Arg Tyr Pro Asn Val Thr Ile Thr Ala Gln Gly Thr Gly
         75                  80                  85 tct ggt gcc ggg atc gcg cag gcc gcc gcc ggg acg gtc aac att ggg         460
Ser Gly Ala Gly Ile Ala Gln Ala Ala Ala Gly Thr Val Asn Ile Gly
 90                  95                 100 gcc tcc gac gcc tat ctg tcg gaa ggt gat atg gcc gcg cac aag ggg         508
Ala Ser Asp Ala Tyr Leu Ser Glu Gly Asp Met Ala Ala His Lys Gly
                105                 110                 115 ctg atg aac atc gcg cta gcc atc tcc gct cag cag gtc aac tac aac         556
Leu Met Asn Ile Ala Leu Ala Ile Ser Ala Gln Gln Val Asn Tyr Asn
120                 125                 130                 135 ctg ccc gga gtg agc gag cac ctc aag ctg aac gga aaa gtc ctg gcg         604
Leu Pro Gly Val Ser Glu His Leu Lys Leu Asn Gly Lys Val Leu Ala
                140                 145                 150 gcc atg tac cag ggc acc atc aaa acc tgg gac gac ccg cag atc gct         652
Ala Met Tyr Gln Gly Thr Ile Lys Thr Trp Asp Asp Pro Gln Ile Ala
         155                 160                 165 gcg ctc aac ccc ggc gtg aac ctg ccc ggc acc gcg gta gtt ccg ctg         700
Ala Leu Asn Pro Gly Val Asn Leu Pro Gly Thr Ala Val Val Pro Leu
 170                 175                 180 cac cgc tcc gac ggg tcc ggt gac acc ttc ttg ttc acc cag tac ctg         748
His Arg Ser Asp Gly Ser Gly Asp Thr Phe Leu Phe Thr Gln Tyr Leu
                185                 190                 195 tcc aag caa gat ccc gag ggc tgg ggc aag tcg ccc ggc ttc ggc acc         796
Ser Lys Gln Asp Pro Glu Gly Trp Gly Lys Ser Pro Gly Phe Gly Thr
200                 205                 210                 215 acc gtc gac ttc ccg gcg gtg ccg ggt gcg ctg ggt gag aac ggc aac         844
Thr Val Asp Phe Pro Ala Val Pro Gly Ala Leu Gly Glu Asn Gly Asn
                220                 225                 230 ggc ggc atg gtg acc ggt tgc gcc gag aca ccg ggc tgc gtg gcc tat         892
Gly Gly Met Val Thr Gly Cys Ala Glu Thr Pro Gly Cys Val Ala Tyr
         235                 240                 245 atc ggc atc agc ttc ctc gac cag gcc agt caa cgg gga ctc ggc gag         940
Ile Gly Ile Ser Phe Leu Asp Gln Ala Ser Gln Arg Gly Leu Gly Glu
 250                 255                 260 gcc caa cta ggc aat agc tct ggc aat ttc ttg ttg ccc gac gcg caa         988
Ala Gln Leu Gly Asn Ser Ser Gly Asn Phe Leu Leu Pro Asp Ala Gln
                265                 270                 275 agc att cag gcc gcg gcg gct ggc ttc gca tcg aaa acc ccg gcg aac        1036
Ser Ile Gln Ala Ala Ala Ala Gly Phe Ala Ser Lys Thr Pro Ala Asn
280                 285                 290                 295 cag gcg att tcg atg atc gac ggg ccc gcc ccg gac ggc tac ccg atc        1084
Gln Ala Ile Ser Met Ile Asp Gly Pro Ala Pro Asp Gly Tyr Pro Ile
                300                 305                 310 atc aac tac gag tac gcc atc gtc aac aac cgg caa aag gac gcc gcc        1132
Ile Asn Tyr Glu Tyr Ala Ile Val Asn Asn Arg Gln Lys Asp Ala Ala
         315                 320                 325 acc gcg cag acc ttg cag gca ttt ctg cac tgg gcg atc acc gac ggc        1180
```

```
Thr Ala Gln Thr Leu Gln Ala Phe Leu His Trp Ala Ile Thr Asp Gly
        330                 335                 340 aac aag gcc tcg ttc ctc gac cag gtt cat ttc cag ccg ctg ccg ccc    1228
Asn Lys Ala Ser Phe Leu Asp Gln Val His Phe Gln Pro Leu Pro Pro
        345                 350                 355 gcg gtg gtg aag ttg tct gac gcg ttg atc gcg acg att tcc agc        1273
Ala Val Val Lys Leu Ser Asp Ala Leu Ile Ala Thr Ile Ser Ser
360                 365                 370 tagcctcgtt gaccaccacg cgacagcaac ctccgtcggg ccatcgggct gctttgcgga   1333
gcatgctggc ccgtgccggt gaagtcggcc gcgctggccc ggccatccgg tggttgggtg   1393
ggataggtgc ggtgatcccg ctgcttgcgc tggtcttggt gctggtggtg ctggtcatcg   1453
aggcgatggg tgcgatcagg ctcaacgggt tgcatttctt caccgccacc gaatggaatc   1513
caggcaacac ctacggcgaa accgttgtca ccgacgcgtc gcccatccgg tcggcgccta   1573
ctacggggcg ttgccgctga tcgtcgggac gctggcgacc tcggcaatcg ccctgatcat   1633
cgcggtgccg gtctctgtag gagcggcgct ggtgatcgtg aacggctgcc gaaacggtt   1693 ggccgaggct gtgggaatag tcctggaatt gctcgccgga atccccagcg tggtcgtcgg   1753 tttgtgggg gcaatgacgt tcgggccgtt catcgctcat cacatcgctc cggtgatcgc   1813
tcacaacgct cccgatgtgc cggtgctgaa ctacttgcgc ggcgacccgg caacgggga   1873 gggcatgttg gtgtccggtc tggtgttggc ggtgatggtc gttcccatta tcgccaccac   1933
cactcatgac ctgttccggc aggtgccggt gttgccccgg gagggcgcga tcgggaattc   1993

<210> SEQ ID NO 6
<211> LENGTH: 374
<212> TYPE: PRT
<213> ORGANISM: Artificial Sequence
<220> FEATURE:
<223> OTHER INFORMATION: Description of Artificial Sequence:tri-fusion

<400> SEQUENCE: 6

Val Lys Ile Arg Leu His Thr Leu Leu Ala Val Leu Thr Ala Ala Pro
  1               5                  10                  15

Leu Leu Leu Ala Ala Ala Gly Cys Gly Ser Lys Pro Pro Ser Gly Ser
                 20                  25                  30

Pro Glu Thr Gly Ala Gly Ala Gly Thr Val Ala Thr Thr Pro Ala Ser
             35                  40                  45

Ser Pro Val Thr Leu Ala Glu Thr Gly Ser Thr Leu Leu Tyr Pro Leu
         50                  55                  60

Phe Asn Leu Trp Gly Pro Ala Phe His Glu Arg Tyr Pro Asn Val Thr
 65                  70                  75                  80

Ile Thr Ala Gln Gly Thr Gly Ser Gly Ala Gly Ile Ala Gln Ala Ala
                 85                  90                  95

Ala Gly Thr Val Asn Ile Gly Ala Ser Asp Ala Tyr Leu Ser Glu Gly
            100                 105                 110

Asp Met Ala Ala His Lys Gly Leu Met Asn Ile Ala Leu Ala Ile Ser
        115                 120                 125

Ala Gln Gln Val Asn Tyr Asn Leu Pro Gly Val Ser Glu His Leu Lys
    130                 135                 140

Leu Asn Gly Lys Val Leu Ala Ala Met Tyr Gln Gly Thr Ile Lys Thr
145                 150                 155                 160

Trp Asp Asp Pro Gln Ile Ala Ala Leu Asn Pro Gly Val Asn Leu Pro
                165                 170                 175

Gly Thr Ala Val Val Pro Leu His Arg Ser Asp Gly Ser Gly Asp Thr
            180                 185                 190
```

```
Phe Leu Phe Thr Gln Tyr Leu Ser Lys Gln Asp Pro Glu Gly Trp Gly
            195                 200                 205

Lys Ser Pro Gly Phe Gly Thr Thr Val Asp Phe Pro Ala Val Pro Gly
    210                 215                 220

Ala Leu Gly Glu Asn Gly Asn Gly Gly Met Val Thr Gly Cys Ala Glu
225                 230                 235                 240

Thr Pro Gly Cys Val Ala Tyr Ile Gly Ile Ser Phe Leu Asp Gln Ala
                245                 250                 255

Ser Gln Arg Gly Leu Gly Glu Ala Gln Leu Gly Asn Ser Ser Gly Asn
                260                 265                 270

Phe Leu Leu Pro Asp Ala Gln Ser Ile Gln Ala Ala Ala Ala Gly Phe
            275                 280                 285

Ala Ser Lys Thr Pro Ala Asn Gln Ala Ile Ser Met Ile Asp Gly Pro
    290                 295                 300

Ala Pro Asp Gly Tyr Pro Ile Ile Asn Tyr Glu Tyr Ala Ile Val Asn
305                 310                 315                 320

Asn Arg Gln Lys Asp Ala Ala Thr Ala Gln Thr Leu Gln Ala Phe Leu
                325                 330                 335

His Trp Ala Ile Thr Asp Gly Asn Lys Ala Ser Phe Leu Asp Gln Val
                340                 345                 350

His Phe Gln Pro Leu Pro Pro Ala Val Val Lys Leu Ser Asp Ala Leu
            355                 360                 365

Ile Ala Thr Ile Ser Ser
    370

<210> SEQ ID NO 7
<211> LENGTH: 1777
<212> TYPE: DNA
<213> ORGANISM: Artificial Sequence
<220> FEATURE:
<223> OTHER INFORMATION: Description of Artificial Sequence:bi-fusion
      protein TbH9-Tb38-1

<400> SEQUENCE: 7
ggtcttgacc accacctggg tgtcgaagtc ggtgcccgga ttgaagtcca ggtactcgtg      60
ggtggggcgg gcgaaacaat agcgacaagc atgcgagcag ccgcggtagc cgttgacggt    120
gtagcgaaac ggcaacgcgg ccgcgttggg caccttgttc agcgctgatt tgcacaacac    180
ctcgtggaag gtgatgccgt cgaattgtgg cgcgcgaacg ctgcggacca ggccgatccg    240
ctgcaacccg gcagcgcccg tcgtcaacgg catcccgtt caccgcgacg gcttgccggg    300
cccaacgcat accattattc gaacaaccgt tctatacttt gtcaacgctg gccgctaccg    360
agcgccgcac aggatgtgat atgccatctc tgcccgcaca gacaggagcc aggccttatg    420
acagcattcg gcgtcgagcc ctacgggcag ccgaagtacc tagaaatcgc cgggaagcgc    480
atggcgtata tcgacgaagg caaggtgac gccatcgtct ttcagcacgg caaccccacg    540
tcgtcttact tgtggcgcaa catcatgccg cacttggaag ggctgggccg ctggtggcc    600 tgcgatctga tcgggatggg cgcgtcggac aagctcagcc catcgggacc cgaccgctat    660
agctatggcg agcaacgaga cttttttgttc gcgctctggg atgcgctcga cctcggcgac    720
cacgtggtac tggtgctgca cgactggggc tcggcgctcg gcttcgactg gctaaccag    780 catcgcgacc gagtgcaggg gatcgcgttc atggaagcga tcgtcacccc gatgacgtgg    840
gcggactggc cgccggccgt gcggggtgtg ttccagggtt ccgatcgcc tcaaggcgag    900 ccaatggcgt tggagcacaa catctttgtc gaacgggtgc tgcccgggc gatcctgcga    960
```

-continued

```
cagctcagcg acgaggaaat gaaccactat cggcggccat cgtgaacgg cggcgaggac    1020 cgtcgcccca cgttgtcgtg gccacgaaac cttccaatcg acggtgagcc cgccgaggtc    1080
gtcgcgttgg tcaacgagta ccggagctgg ctcgaggaaa ccgacatgcc gaaactgttc    1140
atcaacgccg agcccggcgc gatcatcacc ggccgcatcc gtgactatgt caggagctgg    1200
cccaaccaga ccgaaatcac agtgcccggc gtgcatttcg ttcaggagga cagcgatggc    1260
gtcgtatcgt gggcgggcgc tcggcagcat cggcgacctg ggagcgctct catttcacga    1320
gaccaagaat gtgatttccg gcgaaggcgg cgccctgctt gtcaactcat aagacttcct    1380
gctccgggca gagattctca gggaaaaggg caccaatcgc agccgcttcc ttcgcaacga    1440
ggtcgacaaa tatacgtggc aggacaaagg tcttcctatt tgcccagcga attagtcgct    1500
gcctttctat gggctcagtt cgaggaagcc gagcggatca cgcgtatccg attggaccta    1560
tggaaccggt atcatgaaag cttcgaatca ttggaacagc ggggctcct gcgccgtccg    1620 atcatcccac agggctgctc tcacaacgcc cacatgtact acgtgttact agcgcccagc    1680
gccgatcggg aggaggtgct ggcgcgtctg acgagcgaag gtataggcgc ggtctttcat    1740
tacgtgccgc ttcacgattc gccggccggg cgtcgct    1777
```

<210> SEQ ID NO 8  
<211> LENGTH: 358  
<212> TYPE: PRT  
<213> ORGANISM: Artificial Sequence  
<220> FEATURE:  
<223> OTHER INFORMATION: Description of Artificial Sequence:bi-fusion protein TbH9-Tb38-1  
<221> NAME/KEY: MOD_RES  
<222> LOCATION: (254)  
<223> OTHER INFORMATION: Xaa = any amino acid

<400> SEQUENCE: 8

```
Val Ala Trp Met Ser Val Thr Ala Gly Gln Ala Glu Leu Thr Ala Ala
  1               5                  10                  15

Gln Val Arg Val Ala Ala Ala Ala Tyr Glu Thr Ala Tyr Gly Leu Thr
                 20                  25                  30

Val Pro Pro Pro Val Ile Ala Glu Asn Arg Ala Glu Leu Met Ile Leu
             35                  40                  45

Ile Ala Thr Asn Leu Leu Gly Gln Asn Thr Pro Ala Ile Ala Val Asn
         50                  55                  60

Glu Ala Glu Tyr Gly Glu Met Trp Ala Gln Asp Ala Ala Ala Met Phe
 65                  70                  75                  80

Gly Tyr Ala Ala Ala Thr Ala Thr Ala Thr Ala Leu Leu Pro Phe
                 85                  90                  95

Glu Glu Ala Pro Glu Met Thr Ser Ala Gly Gly Leu Leu Glu Gln Ala
            100                 105                 110

Ala Ala Val Glu Glu Ala Ser Asp Thr Ala Ala Ala Asn Gln Leu Met
        115                 120                 125

Asn Asn Val Pro Gln Ala Leu Lys Gln Leu Ala Gln Pro Thr Gln Gly
    130                 135                 140

Thr Thr Pro Ser Ser Lys Leu Gly Gly Leu Trp Lys Thr Val Ser Pro
145                 150                 155                 160

His Arg Ser Pro Ile Ser Asn Met Val Ser Met Ala Asn Asn His Met
                165                 170                 175

Ser Met Thr Asn Ser Gly Val Ser Met Thr Asn Thr Leu Ser Ser Met
            180                 185                 190

Leu Lys Gly Phe Ala Pro Ala Ala Ala Ala Gln Ala Val Gln Thr Ala
        195                 200                 205
```

```
Ala Gln Asn Gly Val Arg Ala Met Ser Ser Leu Gly Ser Ser Leu Gly
    210                 215                 220

Ser Ser Gly Leu Gly Gly Val Ala Ala Asn Leu Gly Arg Ala Ala
225                 230                 235                 240

Ser Val Arg Tyr Gly His Arg Asp Gly Lys Tyr Ala Xaa Ser Gly
                245                 250                 255

Arg Arg Asn Gly Gly Pro Ala Thr Asp Ala Ala Thr Leu Ala Gln Glu
            260                 265                 270

Ala Gly Asn Phe Glu Arg Ile Ser Gly Asp Leu Lys Thr Gln Ile Asp
        275                 280                 285

Gln Val Glu Ser Thr Ala Gly Ser Leu Gln Gly Gln Trp Arg Gly Ala
    290                 295                 300

Ala Gly Thr Ala Ala Gln Ala Ala Val Val Arg Phe Gln Glu Ala Ala
305                 310                 315                 320

Asn Lys Gln Lys Gln Glu Leu Asp Glu Ile Ser Thr Asn Ile Arg Gln
                325                 330                 335

Ala Gly Val Gln Tyr Ser Arg Ala Asp Glu Glu Gln Gln Ala Leu
            340                 345                 350

Ser Ser Gln Met Gly Phe
        355

<210> SEQ ID NO 9
<211> LENGTH: 7676
<212> TYPE: DNA
<213> ORGANISM: Artificial Sequence
<220> FEATURE:
<223> OTHER INFORMATION: Description of Artificial Sequence:tetra-fusion
      protein TbRa3-38kD-Tb38-1-DPEP (designated TbF-2)
<221> NAME/KEY: CDS
<222> LOCATION: (5072)..(7480)

<400> SEQUENCE: 9
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcggggggc tccctttagg     180
gttccgattt agtgctttac ggcacctcga ccccaaaaaa cttgattagg gtgatggttc     240
acgtagtggg ccatcgccct gatagacggt ttttcgccct tgacgttgg agtccacgtt     300 ctttaatagt ggactcttgt tccaaactgg aacaacactc aaccctatct cggtctattc     360
ttttgattta aagggatttt tgccgatttc ggcctattgg ttaaaaaatg agctgattta     420
acaaaaattt aacgcgaatt ttaacaaaat attaacgttt acaatttcag gtggcacttt     480
tcggggaaat gtgcgcggaa ccctattttg tttatttttc taaatacatt caaatatgta     540
tccgctcatg aattaattct tagaaaaact catcgagcat caaatgaaac tgcaatttat     600
tcatatcagg attatcaata ccatattttt gaaaagccg tttctgtaat gaaggagaaa      660
actcaccgag gcagttccat aggatggcaa gatcctggta tcggtctgcg attccgactc     720
gtccaacatc aatacaacct attaatttcc cctcgtcaaa aataaggtta tcaagtgaga     780
aatcaccatg agtgacgact gaatccggtg agaatggcaa aagtttatgc atttctttcc     840
agacttgttc aacaggccag ccattacgct cgtcatcaaa atcactcgca tcaaccaaac     900
cgttattcat tcgtgattgc gcctgagcga gacgaaatac gcgatcgctg ttaaaaggac     960
aattacaaac aggaatcgaa tgcaaccggc gcaggaacac tgccagcgca tcaacaatat    1020
tttcacctga atcaggatat tcttctaata cctggaatgc tgttttcccg gggatcgcag    1080
```

```
tggtgagtaa ccatgcatca tcaggagtac ggataaaatg cttgatggtc ggaagaggca    1140
taaattccgt cagccagttt agtctgacca tctcatctgt aacatcattg caacgctac    1200 ctttgccatg tttcagaaac aactctggcg catcgggctt cccatacaat cgatagattg    1260
tcgcacctga ttgcccgaca ttatcgcgag cccatttata cccatataaa tcagcatcca    1320
tgttggaatt taatcgcggc ctagagcaag acgtttcccg ttgaatatgg ctcataacac    1380
cccttgtatt actgtttatg taagcagaca gttttattgt tcatgaccaa aatcccttaa    1440
cgtgagtttt cgttccactg agcgtcagac cccgtagaaa agatcaaagg atcttcttga    1500
gatccttttt ttctgcgcgt aatctgctgc ttgcaaacaa aaaaaccacc gctaccagcg    1560
gtggtttgtt tgccggatca agagctacca actcttttc cgaaggtaac tggcttcagc    1620
agagcgcaga taccaaatac tgtccttcta gtgtagccg agttaggcca ccacttcaag    1680
aactctgtag caccgcctac atacctcgct ctgctaatcc tgttaccagt ggctgctgcc    1740
agtggcgata agtcgtgtct taccgggttg gactcaagac gatagttacc ggataaggcg    1800
cagcggtcgg gctgaacggg gggttcgtgc acacagccca gcttggagcg aacgacctac    1860
accgaactga gatacctaca gcgtgagcta tgagaaagcg ccacgcttcc cgaagggaga    1920
aaggcggaca ggtatccggt aagcggcagg gtcggaacag gagagcgcac gagggagctt    1980
ccagggggaa acgcctggta tctttatagt cctgtcgggt ttcgccacct ctgacttgag    2040
cgtcgatttt tgtgatgctc gtcagggggg cggagcctat ggaaaaacgc cagcaacgcg    2100
gcctttttac ggttcctggc cttttgctgg ccttttgctc acatgttctt tcctgcgtta    2160
tcccctgatt ctgtggataa ccgtattacc gcctttgagt gagctgatac cgctcgccgc    2220
agccgaacga ccgagcgcag cgagtcagtg agcgaggaag cggaagagcg cctgatgcgg    2280
tattttctcc ttacgcatct gtgcggtatt tcacaccgca tatatggtgc actctcagta    2340
caatctgctc tgatgccgca tagttaagcc agtatacact ccgctatcgc tacgtgactg    2400
ggtcatggct gcgccccgac acccgccaac acccgctgac gcgccctgac gggcttgtct    2460
gctcccggca tccgcttaca gacaagctgt gaccgtctcc gggagctgca tgtgtcagag    2520
gttttcaccg tcatcaccga aacgcgcgag gcagctgcgg taaagctcat cagcgtggtc    2580
gtgaagcgat tcacagatgt ctgcctgttc atccgcgtcc agctcgttga gtttctccag    2640
aagcgttaat gtctggcttc tgataaagcg ggccatgtta agggcggttt tttcctgttt    2700
ggtcactgat gcctccgtgt aagggggatt tctgttcatg ggggtaatga taccgatgaa    2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
```

```
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg cgcgcattg     3840 cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa agacaccgg     4560 catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa ctttaagaag gagatataca t atg ggc cat cat cat cat cat       5092
                                   Met Gly His His His His His
                                     1               5 cac gtg atc gac atc atc ggg acc agc ccc aca tcc tgg gaa cag gcg      5140
His Val Ile Asp Ile Ile Gly Thr Ser Pro Thr Ser Trp Glu Gln Ala
         10                  15                  20 gcg gcg gag gcg gtc cag cgg gcg cgg gat agc gtc gat gac atc cgc      5188
Ala Ala Glu Ala Val Gln Arg Ala Arg Asp Ser Val Asp Asp Ile Arg
     25                  30                  35 gtc gct cgg gtc att gag cag gac atg gcc gtg gac agc gcc ggc aag      5236
Val Ala Arg Val Ile Glu Gln Asp Met Ala Val Asp Ser Ala Gly Lys
 40                  45                  50                  55 atc acc tac cgc atc aag ctc gaa gtg tcg ttc aag atg agg ccg gcg      5284
Ile Thr Tyr Arg Ile Lys Leu Glu Val Ser Phe Lys Met Arg Pro Ala
                 60                  65                  70 caa ccg agg ggc tcg aaa cca ccg agc ggt tcg cct gaa acg ggc gcc      5332
Gln Pro Arg Gly Ser Lys Pro Pro Ser Gly Ser Pro Glu Thr Gly Ala
         75                  80                  85 ggc gcc ggt act gtc gcg act acc ccc gcg tcg tcg ccg gtg acg ttg      5380
Gly Ala Gly Thr Val Ala Thr Thr Pro Ala Ser Ser Pro Val Thr Leu
     90                  95                 100
```

-continued

| | |
|---|---|
| gcg gag acc ggt agc acg ctg ctc tac ccg ctg ttc aac ctg tgg ggt<br>Ala Glu Thr Gly Ser Thr Leu Leu Tyr Pro Leu Phe Asn Leu Trp Gly<br>105                  110                  115 | 5428 |
| ccg gcc ttt cac gag agg tat ccg aac gtc acg atc acc gct cag ggc<br>Pro Ala Phe His Glu Arg Tyr Pro Asn Val Thr Ile Thr Ala Gln Gly<br>120                  125                  130                  135 | 5476 |
| acc ggt tct ggt gcc ggg atc gcg cag gcc gcc gcc ggg acg gtc aac<br>Thr Gly Ser Gly Ala Gly Ile Ala Gln Ala Ala Ala Gly Thr Val Asn<br>                  140                  145                  150 | 5524 |
| att ggg gcc tcc gac gcc tat ctg tcg gaa ggt gat atg gcc gcg cac<br>Ile Gly Ala Ser Asp Ala Tyr Leu Ser Glu Gly Asp Met Ala Ala His<br>                  155                  160                  165 | 5572 |
| aag ggg ctg atg aac atc gcg cta gcc atc tcc gct cag cag gtc aac<br>Lys Gly Leu Met Asn Ile Ala Leu Ala Ile Ser Ala Gln Gln Val Asn<br>                  170                  175                  180 | 5620 |
| tac aac ctg ccc gga gtg agc gag cac ctc aag ctg aac gga aaa gtc<br>Tyr Asn Leu Pro Gly Val Ser Glu His Leu Lys Leu Asn Gly Lys Val<br>                  185                  190                  195 | 5668 |
| ctg gcg gcc atg tac cag ggc acc atc aaa acc tgg gac gac ccg cag<br>Leu Ala Ala Met Tyr Gln Gly Thr Ile Lys Thr Trp Asp Asp Pro Gln<br>200                  205                  210                  215 | 5716 |
| atc gct gcg ctc aac ccc ggc gtg aac ctg ccc ggc acc gcg gta gtt<br>Ile Ala Ala Leu Asn Pro Gly Val Asn Leu Pro Gly Thr Ala Val Val<br>                  220                  225                  230 | 5764 |
| ccg ctg cac cgc tcc gac ggg tcc ggt gac acc ttc ttg ttc acc cag<br>Pro Leu His Arg Ser Asp Gly Ser Gly Asp Thr Phe Leu Phe Thr Gln<br>                  235                  240                  245 | 5812 |
| tac ctg tcc aag caa gat ccc gag ggc tgg ggc aag tcg ccc ggc ttc<br>Tyr Leu Ser Lys Gln Asp Pro Glu Gly Trp Gly Lys Ser Pro Gly Phe<br>250                  255                  260 | 5860 |
| ggc acc acc gtc gac ttc ccg gcg gtg ccg ggt gcg ctg ggt gag aac<br>Gly Thr Thr Val Asp Phe Pro Ala Val Pro Gly Ala Leu Gly Glu Asn<br>    265                  270                  275 | 5908 |
| ggc aac ggc ggc atg gtg acc ggt tgc gcc gag aca ccg ggc tgc gtg<br>Gly Asn Gly Gly Met Val Thr Gly Cys Ala Glu Thr Pro Gly Cys Val<br>280                  285                  290                  295 | 5956 |
| gcc tat atc ggc atc agc ttc ctc gac cag gcc agt caa cgg gga ctc<br>Ala Tyr Ile Gly Ile Ser Phe Leu Asp Gln Ala Ser Gln Arg Gly Leu<br>                  300                  305                  310 | 6004 |
| ggc gag gcc caa cta ggc aat agc tct ggc aat ttc ttg ttg ccc gac<br>Gly Glu Ala Gln Leu Gly Asn Ser Ser Gly Asn Phe Leu Leu Pro Asp<br>                  315                  320                  325 | 6052 |
| gcg caa agc att cag gcc gcg gcg gct ggc ttc gca tcg aaa acc ccg<br>Ala Gln Ser Ile Gln Ala Ala Ala Ala Gly Phe Ala Ser Lys Thr Pro<br>            330                  335                  340 | 6100 |
| gcg aac cag gcg att tcg atg atc gac ggg ccc gcc ccg gac ggc tac<br>Ala Asn Gln Ala Ile Ser Met Ile Asp Gly Pro Ala Pro Asp Gly Tyr<br>345                  350                  355 | 6148 |
| ccg atc atc aac tac gag tac gcc atc gtc aac aac cgg caa aag gac<br>Pro Ile Ile Asn Tyr Glu Tyr Ala Ile Val Asn Asn Arg Gln Lys Asp<br>360                  365                  370                  375 | 6196 |
| gcc gcc acc gcg cag acc ttg cag gca ttt ctg cac tgg gcg atc acc<br>Ala Ala Thr Ala Gln Thr Leu Gln Ala Phe Leu His Trp Ala Ile Thr<br>                  380                  385                  390 | 6244 |
| gac ggc aac aag gcc tcg ttc ctc gac cag gtt cat ttc cag ccg ctg<br>Asp Gly Asn Lys Ala Ser Phe Leu Asp Gln Val His Phe Gln Pro Leu<br>                  395                  400                  405 | 6292 |
| ccg ccc gcg gtg gtg aag ttg tct gac gcg ttg atc gcg acg att tcc<br>Pro Pro Ala Val Val Lys Leu Ser Asp Ala Leu Ile Ala Thr Ile Ser<br>410                  415                  420 | 6340 |

```
agc gct gag atg aag acc gat gcc gct acc ctc gcg cag gag gca ggt    6388
Ser Ala Glu Met Lys Thr Asp Ala Ala Thr Leu Ala Gln Glu Ala Gly
    425                 430                 435 aat ttc gag cgg atc tcc ggc gac ctg aaa acc cag atc gac cag gtg    6436
Asn Phe Glu Arg Ile Ser Gly Asp Leu Lys Thr Gln Ile Asp Gln Val
440                 445                 450                 455 gag tcg acg gca ggt tcg ttg cag ggc cag tgg cgc ggc gcg gcg ggg    6484
Glu Ser Thr Ala Gly Ser Leu Gln Gly Gln Trp Arg Gly Ala Ala Gly
                460                 465                 470 acg gcc gcc cag gcc gcg gtg gtg cgc ttc caa gaa gca gcc aat aag    6532
Thr Ala Ala Gln Ala Ala Val Val Arg Phe Gln Glu Ala Ala Asn Lys
                475                 480                 485 cag aag cag gaa ctc gac gag atc tcg acg aat att cgt cag gcc ggc    6580
Gln Lys Gln Glu Leu Asp Glu Ile Ser Thr Asn Ile Arg Gln Ala Gly
                490                 495                 500 gtc caa tac tcg agg gcc gac gag gag cag cag cag gcg ctg tcc tcg    6628
Val Gln Tyr Ser Arg Ala Asp Glu Glu Gln Gln Gln Ala Leu Ser Ser
    505                 510                 515 caa atg ggc ttt gtg ccc aca acg gcc gcc tcg ccg ccg tcg acc gct    6676
Gln Met Gly Phe Val Pro Thr Thr Ala Ala Ser Pro Pro Ser Thr Ala
520                 525                 530                 535 gca gcg cca ccc gca ccg gcg aca cct gtt gcc ccc cca cca ccg gcc    6724
Ala Ala Pro Pro Ala Pro Ala Thr Pro Val Ala Pro Pro Pro Pro Ala
                540                 545                 550 gcc gcc aac acg ccg aat gcc cag ccg ggc gat ccc aac gca gca cct    6772
Ala Ala Asn Thr Pro Asn Ala Gln Pro Gly Asp Pro Asn Ala Ala Pro
                555                 560                 565 ccg ccg gcc gac ccg aac gca ccg ccg cca cct gtc att gcc cca aac    6820
Pro Pro Ala Asp Pro Asn Ala Pro Pro Pro Pro Val Ile Ala Pro Asn
                570                 575                 580 gca ccc caa cct gtc cgg atc gac aac ccg gtt gga gga ttc agc ttc    6868
Ala Pro Gln Pro Val Arg Ile Asp Asn Pro Val Gly Gly Phe Ser Phe
    585                 590                 595 gcg ctg cct gct ggc tgg gtg gag tct gac gcc gcc cac ttc gac tac    6916
Ala Leu Pro Ala Gly Trp Val Glu Ser Asp Ala Ala His Phe Asp Tyr
600                 605                 610                 615 ggt tca gca ctc ctc agc aaa acc acc ggg gac ccg cca ttt ccc gga    6964
Gly Ser Ala Leu Leu Ser Lys Thr Thr Gly Asp Pro Pro Phe Pro Gly
                620                 625                 630 cag ccg ccg ccg gtg gcc aat gac acc cgt atc gtg ctc ggc cgg cta    7012
Gln Pro Pro Pro Val Ala Asn Asp Thr Arg Ile Val Leu Gly Arg Leu
                635                 640                 645 gac caa aag ctt tac gcc agc gcc gaa gcc acc gac tcc aag gcc gcg    7060
Asp Gln Lys Leu Tyr Ala Ser Ala Glu Ala Thr Asp Ser Lys Ala Ala
                650                 655                 660 gcc cgg ttg ggc tcg gac atg ggt gag ttc tat atg ccc tac ccg ggc    7108
Ala Arg Leu Gly Ser Asp Met Gly Glu Phe Tyr Met Pro Tyr Pro Gly
    665                 670                 675 acc cgg atc aac cag gaa acc gtc tcg ctt gac gcc aac ggg gtg tct    7156
Thr Arg Ile Asn Gln Glu Thr Val Ser Leu Asp Ala Asn Gly Val Ser
680                 685                 690                 695 gga agc gcg tcg tat tac gaa gtc aag ttc agc gat ccg agt aag ccg    7204
Gly Ser Ala Ser Tyr Tyr Glu Val Lys Phe Ser Asp Pro Ser Lys Pro
                700                 705                 710 aac ggc cag atc tgg acg ggc gta atc ggc tcg ccc gcg gcg aac gca    7252
Asn Gly Gln Ile Trp Thr Gly Val Ile Gly Ser Pro Ala Ala Asn Ala
                715                 720                 725 ccg gac gcc ggg ccc cct cag cgc tgg ttt gtg gta tgg ctc ggg acc    7300
Pro Asp Ala Gly Pro Pro Gln Arg Trp Phe Val Val Trp Leu Gly Thr
                730                 735                 740
```

-continued

```
gcc aac aac ccg gtg gac aag ggc gcg gcc aag gcg ctg gcc gaa tcg      7348
Ala Asn Asn Pro Val Asp Lys Gly Ala Ala Lys Ala Leu Ala Glu Ser
    745                 750                 755 atc cgg cct ttg gtc gcc ccg ccg gcg ccg gca ccg gct cct gca          7396
Ile Arg Pro Leu Val Ala Pro Pro Ala Pro Ala Pro Ala Pro Ala
760                 765                 770                 775 gag ccc gct ccg gcg ccg gcg ccg gcc ggg gaa gtc gct cct acc ccg      7444
Glu Pro Ala Pro Ala Pro Ala Pro Ala Gly Glu Val Ala Pro Thr Pro
                780                 785                 790 acg aca ccg aca ccg cag cgg acc tta ccg gcc tgagaattct gcagatatcc    7497
Thr Thr Pro Thr Pro Gln Arg Thr Leu Pro Ala
            795                 800 atcacactgg cggccgctcg agcaccacca ccaccaccac tgagatccgg ctgctaacaa    7557
agcccgaaag gaagctgagt tggctgctgc caccgctgag caataactag cataaccct    7617 tggggcctct aaacgggtct tgagggttt tttgctgaaa ggaggaacta tatccggat      7676

<210> SEQ ID NO 10
<211> LENGTH: 802
<212> TYPE: PRT
<213> ORGANISM: Artificial Sequence
<220> FEATURE:
<223> OTHER INFORMATION: Description of Artificial Sequence:tetra-fusion

<400> SEQUENCE: 10

Met Gly His His His His His His Val Ile Asp Ile Gly Thr Ser
1               5                   10                  15

Pro Thr Ser Trp Glu Gln Ala Ala Glu Ala Val Gln Arg Ala Arg
            20                  25                  30

Asp Ser Val Asp Ile Arg Val Ala Arg Val Ile Glu Gln Asp Met
        35                  40                  45

Ala Val Asp Ser Ala Gly Lys Ile Thr Tyr Arg Ile Lys Leu Glu Val
    50                  55                  60

Ser Phe Lys Met Arg Pro Ala Gln Pro Arg Gly Ser Lys Pro Pro Ser
65                  70                  75                  80

Gly Ser Pro Glu Thr Gly Ala Gly Ala Gly Thr Val Ala Thr Thr Pro
                85                  90                  95

Ala Ser Ser Pro Val Thr Leu Ala Glu Thr Gly Ser Thr Leu Leu Tyr
            100                 105                 110

Pro Leu Phe Asn Leu Trp Gly Pro Ala Phe His Glu Arg Tyr Pro Asn
        115                 120                 125

Val Thr Ile Thr Ala Gln Gly Thr Gly Ser Gly Ala Gly Ile Ala Gln
    130                 135                 140

Ala Ala Ala Gly Thr Val Asn Ile Gly Ala Ser Asp Ala Tyr Leu Ser
145                 150                 155                 160

Glu Gly Asp Met Ala Ala His Lys Gly Leu Met Asn Ile Ala Leu Ala
                165                 170                 175

Ile Ser Ala Gln Gln Val Asn Tyr Asn Leu Pro Gly Val Ser Glu His
            180                 185                 190

Leu Lys Leu Asn Gly Lys Val Leu Ala Ala Met Tyr Gln Gly Thr Ile
        195                 200                 205

Lys Thr Trp Asp Asp Pro Gln Ile Ala Ala Leu Asn Pro Gly Val Asn
    210                 215                 220

Leu Pro Gly Thr Ala Val Val Pro Leu His Arg Ser Asp Gly Ser Gly
225                 230                 235                 240

Asp Thr Phe Leu Phe Thr Gln Tyr Leu Ser Lys Gln Asp Pro Glu Gly
                245                 250                 255
```

```
Trp Gly Lys Ser Pro Gly Phe Gly Thr Thr Val Asp Phe Pro Ala Val
            260                 265                 270

Pro Gly Ala Leu Gly Glu Asn Gly Asn Gly Gly Met Val Thr Gly Cys
            275                 280                 285

Ala Glu Thr Pro Gly Cys Val Ala Tyr Ile Gly Ile Ser Phe Leu Asp
290                 295                 300

Gln Ala Ser Gln Arg Gly Leu Gly Glu Ala Gln Leu Gly Asn Ser Ser
305                 310                 315                 320

Gly Asn Phe Leu Leu Pro Asp Ala Gln Ser Ile Gln Ala Ala Ala Ala
                325                 330                 335

Gly Phe Ala Ser Lys Thr Pro Ala Asn Gln Ala Ile Ser Met Ile Asp
                340                 345                 350

Gly Pro Ala Pro Asp Gly Tyr Pro Ile Ile Asn Tyr Glu Tyr Ala Ile
            355                 360                 365

Val Asn Asn Arg Gln Lys Asp Ala Ala Thr Ala Gln Thr Leu Gln Ala
370                 375                 380

Phe Leu His Trp Ala Ile Thr Asp Gly Asn Lys Ala Ser Phe Leu Asp
385                 390                 395                 400

Gln Val His Phe Gln Pro Leu Pro Pro Ala Val Val Lys Leu Ser Asp
                405                 410                 415

Ala Leu Ile Ala Thr Ile Ser Ser Ala Glu Met Lys Thr Asp Ala Ala
                420                 425                 430

Thr Leu Ala Gln Glu Ala Gly Asn Phe Glu Arg Ile Ser Gly Asp Leu
            435                 440                 445

Lys Thr Gln Ile Asp Gln Val Glu Ser Thr Ala Gly Ser Leu Gln Gly
            450                 455                 460

Gln Trp Arg Gly Ala Ala Gly Thr Ala Ala Gln Ala Ala Val Val Arg
465                 470                 475                 480

Phe Gln Glu Ala Ala Asn Lys Gln Lys Gln Glu Leu Asp Glu Ile Ser
                485                 490                 495

Thr Asn Ile Arg Gln Ala Gly Val Gln Tyr Ser Arg Ala Asp Glu Glu
            500                 505                 510

Gln Gln Gln Ala Leu Ser Ser Gln Met Gly Phe Val Pro Thr Thr Ala
            515                 520                 525

Ala Ser Pro Pro Ser Thr Ala Ala Pro Ala Pro Ala Thr Pro
530                 535                 540

Val Ala Pro Pro Pro Ala Ala Ala Asn Thr Pro Asn Ala Gln Pro
545                 550                 555                 560

Gly Asp Pro Asn Ala Ala Pro Pro Ala Asp Pro Asn Ala Pro Pro
                565                 570                 575

Pro Pro Val Ile Ala Pro Asn Ala Pro Gln Pro Val Arg Ile Asp Asn
            580                 585                 590

Pro Val Gly Gly Phe Ser Phe Ala Leu Pro Ala Gly Trp Val Glu Ser
            595                 600                 605

Asp Ala Ala His Phe Asp Tyr Gly Ser Ala Leu Leu Ser Lys Thr Thr
            610                 615                 620

Gly Asp Pro Pro Phe Pro Gly Gln Pro Pro Val Ala Asn Asp Thr
625                 630                 635                 640

Arg Ile Val Leu Gly Arg Leu Asp Gln Lys Leu Tyr Ala Ser Ala Glu
                645                 650                 655

Ala Thr Asp Ser Lys Ala Ala Ala Arg Leu Gly Ser Asp Met Gly Glu
                660                 665                 670

Phe Tyr Met Pro Tyr Pro Gly Thr Arg Ile Asn Gln Glu Thr Val Ser
            675                 680                 685
```

```
Leu Asp Ala Asn Gly Val Ser Gly Ser Ala Ser Tyr Tyr Glu Val Lys
    690                 695                 700

Phe Ser Asp Pro Ser Lys Pro Asn Gly Gln Ile Trp Thr Gly Val Ile
705                 710                 715                 720

Gly Ser Pro Ala Ala Asn Ala Pro Asp Ala Gly Pro Pro Gln Arg Trp
                725                 730                 735

Phe Val Val Trp Leu Gly Thr Ala Asn Asn Pro Val Asp Lys Gly Ala
            740                 745                 750

Ala Lys Ala Leu Ala Glu Ser Ile Arg Pro Leu Val Ala Pro Pro Pro
        755                 760                 765

Ala Pro Ala Pro Ala Pro Ala Glu Pro Ala Pro Ala Pro Ala Pro Ala
    770                 775                 780

Gly Glu Val Ala Pro Thr Pro Thr Thr Pro Thr Pro Gln Arg Thr Leu
785                 790                 795                 800

Pro Ala

<210> SEQ ID NO 11
<211> LENGTH: 2577
<212> TYPE: DNA
<213> ORGANISM: Artificial Sequence
<220> FEATURE:
<223> OTHER INFORMATION: Description of Artificial Sequence:penta-fusion
      protein Erd14-DPV-MTI-MSL-MTCC2 (designated
      Mtb88f)
<221> NAME/KEY: CDS
<222> LOCATION: (1)..(2571)

<400> SEQUENCE: 11 cat atg cat cac cat cac cat cac atg gcc acc acc ctt ccc gtt cag       48
His Met His His His His His His Met Ala Thr Thr Leu Pro Val Gln
  1               5                  10                  15 cgc cac ccg cgg tcc ctc ttc ccc gag ttt tct gag ctg ttc gcg gcc       96
Arg His Pro Arg Ser Leu Phe Pro Glu Phe Ser Glu Leu Phe Ala Ala
            20                  25                  30 ttc ccg tca ttc gcc gga ctc cgg ccc acc ttc gac acc cgg ttg atg      144
Phe Pro Ser Phe Ala Gly Leu Arg Pro Thr Phe Asp Thr Arg Leu Met
        35                  40                  45 cgg ctg gaa gac gag atg aaa gag ggg cgc tac gag gta cgc gcg gag      192
Arg Leu Glu Asp Glu Met Lys Glu Gly Arg Tyr Glu Val Arg Ala Glu
     50                  55                  60 ctt ccc ggg gtc gac ccc gac aag gac gtc gac att atg gtc cgc gat      240
Leu Pro Gly Val Asp Pro Asp Lys Asp Val Asp Ile Met Val Arg Asp
 65                  70                  75                  80 ggt cag ctg acc atc aag gcc gag cgc acc gag cag aag gac ttc gac      288
Gly Gln Leu Thr Ile Lys Ala Glu Arg Thr Glu Gln Lys Asp Phe Asp
                 85                  90                  95 ggt cgc tcg gaa ttc gcg tac ggt tcc ttc gtt cgc acg gtg tcg ctg      336
Gly Arg Ser Glu Phe Ala Tyr Gly Ser Phe Val Arg Thr Val Ser Leu
            100                 105                 110 ccg gta ggt gct gac gag gac gac att aag gcc acc tac gac aag ggc      384
Pro Val Gly Ala Asp Glu Asp Asp Ile Lys Ala Thr Tyr Asp Lys Gly
        115                 120                 125 att ctt act gtg tcg gtg gcg gtt tcg gaa ggg aag cca acc gaa aag      432
Ile Leu Thr Val Ser Val Ala Val Ser Glu Gly Lys Pro Thr Glu Lys
    130                 135                 140 cac att cag atc cgg tcc acc aac aag ctt gat ccc gtg gac gcg gtc      480
His Ile Gln Ile Arg Ser Thr Asn Lys Leu Asp Pro Val Asp Ala Val
145                 150                 155                 160 att aac acc acc tgc aat tac ggg cag gta gta gct gcg ctc aac gcg      528
Ile Asn Thr Thr Cys Asn Tyr Gly Gln Val Val Ala Ala Leu Asn Ala
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     | 165 |     |     |     | 170 |     |     |     | 175 |     |     |     |     |      |
| acg | gat | ccg | ggg | gct | gcc | gca | cag | ttc | aac | gcc | tca | ccg | gtg | gcg | cag | 576  |
| Thr | Asp | Pro | Gly | Ala | Ala | Ala | Gln | Phe | Asn | Ala | Ser | Pro | Val | Ala | Gln |      |
|     |     |     | 180 |     |     |     | 185 |     |     |     | 190 |     |     |     |     |      |
| tcc | tat | ttg | cgc | aat | ttc | ctc | gcc | gca | ccg | cca | cct | cag | cgc | gct | gcc | 624  |
| Ser | Tyr | Leu | Arg | Asn | Phe | Leu | Ala | Ala | Pro | Pro | Pro | Gln | Arg | Ala | Ala |      |
|     |     | 195 |     |     |     | 200 |     |     |     | 205 |     |     |     |     |     |      |
| atg | gcc | gcg | caa | ttg | caa | gct | gtg | ccg | ggc | gcg | gca | cag | tac | atc | ggc | 672  |
| Met | Ala | Ala | Gln | Leu | Gln | Ala | Val | Pro | Gly | Ala | Ala | Gln | Tyr | Ile | Gly |      |
|     | 210 |     |     |     | 215 |     |     |     | 220 |     |     |     |     |     |     |      |
| ctt | gtc | gag | tcg | gtt | gcc | ggc | tcc | tgc | aac | aac | tat | gag | ctc | atg | acg | 720  |
| Leu | Val | Glu | Ser | Val | Ala | Gly | Ser | Cys | Asn | Asn | Tyr | Glu | Leu | Met | Thr |      |
| 225 |     |     |     | 230 |     |     |     | 235 |     |     |     | 240 |     |     |     |      |
| att | aat | tac | cag | ttc | ggg | gac | gtc | gac | gct | cat | ggc | gcc | atg | atc | cgc | 768  |
| Ile | Asn | Tyr | Gln | Phe | Gly | Asp | Val | Asp | Ala | His | Gly | Ala | Met | Ile | Arg |      |
|     |     |     | 245 |     |     |     | 250 |     |     |     | 255 |     |     |     |     |      |
| gct | cag | gcg | gcg | tcg | ctt | gag | gcg | gag | cat | cag | gcc | atc | gtt | cgt | gat | 816  |
| Ala | Gln | Ala | Ala | Ser | Leu | Glu | Ala | Glu | His | Gln | Ala | Ile | Val | Arg | Asp |      |
|     |     | 260 |     |     |     | 265 |     |     |     | 270 |     |     |     |     |     |      |
| gtg | ttg | gcc | gcg | ggt | gac | ttt | tgg | ggc | ggc | gcc | ggt | tcg | gtg | gct | tgc | 864  |
| Val | Leu | Ala | Ala | Gly | Asp | Phe | Trp | Gly | Gly | Ala | Gly | Ser | Val | Ala | Cys |      |
|     | 275 |     |     |     | 280 |     |     |     | 285 |     |     |     |     |     |     |      |
| cag | gag | ttc | att | acc | cag | ttg | ggc | cgt | aac | ttc | cag | gtg | atc | tac | gag | 912  |
| Gln | Glu | Phe | Ile | Thr | Gln | Leu | Gly | Arg | Asn | Phe | Gln | Val | Ile | Tyr | Glu |      |
| 290 |     |     |     | 295 |     |     |     | 300 |     |     |     |     |     |     |     |      |
| cag | gcc | aac | gcc | cac | ggg | cag | aag | gtg | cag | gct | gcc | ggc | aac | aac | atg | 960  |
| Gln | Ala | Asn | Ala | His | Gly | Gln | Lys | Val | Gln | Ala | Ala | Gly | Asn | Asn | Met |      |
| 305 |     |     |     | 310 |     |     |     | 315 |     |     |     | 320 |     |     |     |      |
| gcg | caa | acc | gac | agc | gcc | gtc | ggc | tcc | agc | tgg | gcc | act | agt | atg | agc | 1008 |
| Ala | Gln | Thr | Asp | Ser | Ala | Val | Gly | Ser | Ser | Trp | Ala | Thr | Ser | Met | Ser |      |
|     |     |     | 325 |     |     |     | 330 |     |     |     | 335 |     |     |     |     |      |
| ctt | ttg | gat | gct | cat | atc | cca | cag | ttg | gtg | gcc | tcc | cag | tcg | gcg | ttt | 1056 |
| Leu | Leu | Asp | Ala | His | Ile | Pro | Gln | Leu | Val | Ala | Ser | Gln | Ser | Ala | Phe |      |
|     |     |     | 340 |     |     |     | 345 |     |     |     | 350 |     |     |     |     |      |
| gcc | gcc | aag | gcg | ggg | ctg | atg | cgg | cac | acg | atc | ggt | cag | gcc | gag | cag | 1104 |
| Ala | Ala | Lys | Ala | Gly | Leu | Met | Arg | His | Thr | Ile | Gly | Gln | Ala | Glu | Gln |      |
|     |     | 355 |     |     |     | 360 |     |     |     | 365 |     |     |     |     |     |      |
| gcg | gcg | atg | tcg | gct | cag | gcg | ttt | cac | cag | ggg | gag | tcg | tcg | gcg | gcg | 1152 |
| Ala | Ala | Met | Ser | Ala | Gln | Ala | Phe | His | Gln | Gly | Glu | Ser | Ser | Ala | Ala |      |
|     | 370 |     |     |     | 375 |     |     |     | 380 |     |     |     |     |     |     |      |
| ttt | cag | gcc | gcc | cat | gcc | cgg | ttt | gtg | gcg | gcg | gcc | aaa | gtc | aac | 1200 |      |
| Phe | Gln | Ala | Ala | His | Ala | Arg | Phe | Val | Ala | Ala | Ala | Lys | Val | Asn |      |      |
| 385 |     |     |     | 390 |     |     |     | 395 |     |     |     | 400 |     |     |     |      |
| acc | ttg | ttg | gat | gtc | gcg | cag | gcg | aat | ctg | ggt | gag | gcc | gcc | ggt | acc | 1248 |
| Thr | Leu | Leu | Asp | Val | Ala | Gln | Ala | Asn | Leu | Gly | Glu | Ala | Ala | Gly | Thr |      |
|     |     |     | 405 |     |     |     | 410 |     |     |     | 415 |     |     |     |     |      |
| tat | gtg | gcc | gcc | gat | gct | gcg | gcc | gcg | tcg | acc | tat | acc | ggg | ttc | gat | 1296 |
| Tyr | Val | Ala | Ala | Asp | Ala | Ala | Ala | Ala | Ser | Thr | Tyr | Thr | Gly | Phe | Asp |      |
|     |     |     | 420 |     |     |     | 425 |     |     |     | 430 |     |     |     |     |      |
| atc | atg | gat | ttc | ggg | ctt | tta | cct | ccg | gaa | gtg | aat | tca | agc | cga | atg | 1344 |
| Ile | Met | Asp | Phe | Gly | Leu | Leu | Pro | Pro | Glu | Val | Asn | Ser | Ser | Arg | Met |      |
|     |     | 435 |     |     |     | 440 |     |     |     | 445 |     |     |     |     |     |      |
| tat | tcc | ggt | ccg | ggg | ccg | gag | tcg | atg | cta | gcc | gcc | gcg | gcc | gcc | tgg | 1392 |
| Tyr | Ser | Gly | Pro | Gly | Pro | Glu | Ser | Met | Leu | Ala | Ala | Ala | Ala | Ala | Trp |      |
|     | 450 |     |     |     | 455 |     |     |     | 460 |     |     |     |     |     |     |      |
| gac | ggt | gtg | gcc | gcg | gag | ttg | act | tcc | gcc | gcg | gtc | tcg | tat | gga | tcg | 1440 |
| Asp | Gly | Val | Ala | Ala | Glu | Leu | Thr | Ser | Ala | Ala | Val | Ser | Tyr | Gly | Ser |      |
| 465 |     |     |     | 470 |     |     |     | 475 |     |     |     | 480 |     |     |     |      |
| gtg | gtg | tcg | acg | ctg | atc | gtt | gag | ccg | tgg | atg | ggg | ccg | gcg | gcg | gcc | 1488 |
| Val | Val | Ser | Thr | Leu | Ile | Val | Glu | Pro | Trp | Met | Gly | Pro | Ala | Ala | Ala |      |

-continued

```
             485                      490                      495
gcg atg gcg gcc gcg gca acg ccg tat gtg ggg tgg ctg gcc gcc acg      1536
Ala Met Ala Ala Ala Ala Thr Pro Tyr Val Gly Trp Leu Ala Ala Thr
            500                      505                      510 gcg gcg ctg gcg aag gag acg gcc aca cag gcc agg gca gcg gcg gaa      1584
Ala Ala Leu Ala Lys Glu Thr Ala Thr Gln Ala Arg Ala Ala Ala Glu
            515                      520                      525 gcg ttt ggg acg gcg ttc gcg atg acg gtg cca cca tcc ctc gtc gcg      1632
Ala Phe Gly Thr Ala Phe Ala Met Thr Val Pro Pro Ser Leu Val Ala
            530                      535                      540 gcc aac cgc agc cgg ttg atg tcg ctg gtc gcg gcg aac att ctg ggg      1680
Ala Asn Arg Ser Arg Leu Met Ser Leu Val Ala Ala Asn Ile Leu Gly
545                      550                      555                      560 caa aac agt gcg gcg atc gcg gct acc cag gcc gag tat gcc gaa atg      1728
Gln Asn Ser Ala Ala Ile Ala Ala Thr Gln Ala Glu Tyr Ala Glu Met
            565                      570                      575 tgg gcc caa gac gct gcc gtg atg tac agc tat gag ggg gca tct gcg      1776
Trp Ala Gln Asp Ala Ala Val Met Tyr Ser Tyr Glu Gly Ala Ser Ala
            580                      585                      590 gcc gcg tcg gcg ttg ccg ccg ttc act cca ccc gtg caa ggc acc ggc      1824
Ala Ala Ser Ala Leu Pro Pro Phe Thr Pro Pro Val Gln Gly Thr Gly
            595                      600                      605 ccg gcc ggg ccc gcg gcc gca gcc gcg gcg acc caa gcc gcc ggt gcg      1872
Pro Ala Gly Pro Ala Ala Ala Ala Ala Thr Gln Ala Ala Gly Ala
            610                      615                      620 ggc gcc gtt gcg gat gca cag gcg aca ctg gcc cag ctg ccc ccg ggg      1920
Gly Ala Val Ala Asp Ala Gln Ala Thr Leu Ala Gln Leu Pro Pro Gly
625                      630                      635                      640 atc ctg agc gac att ctg tcc gca ttg gcc gcc aac gct gat ccg ctg      1968
Ile Leu Ser Asp Ile Leu Ser Ala Leu Ala Ala Asn Ala Asp Pro Leu
            645                      650                      655 aca tcg gga ctg ttg ggg atc gcg tcg acc ctc aac ccg caa gtc gga      2016
Thr Ser Gly Leu Leu Gly Ile Ala Ser Thr Leu Asn Pro Gln Val Gly
            660                      665                      670 tcc gct cag ccg ata gtg atc ccc acc ccg ata ggg gaa ttg gac gtg      2064
Ser Ala Gln Pro Ile Val Ile Pro Thr Pro Ile Gly Glu Leu Asp Val
            675                      680                      685 atc gcg ctc tac att gca tcc atc gcg acc ggc agc att gcg ctc gcg      2112
Ile Ala Leu Tyr Ile Ala Ser Ile Ala Thr Gly Ser Ile Ala Leu Ala
            690                      695                      700 atc acg aac acg gcc aga ccc tgg cac atc ggc cta tac ggg aac gcc      2160
Ile Thr Asn Thr Ala Arg Pro Trp His Ile Gly Leu Tyr Gly Asn Ala
705                      710                      715                      720 ggc ggg ctg gga ccg acg cag ggc cat cca ctg agt tcg gcg acc gac      2208
Gly Gly Leu Gly Pro Thr Gln Gly His Pro Leu Ser Ser Ala Thr Asp
            725                      730                      735 gag ccg gag ccg cac tgg ggc ccc ttc ggg ggc gcg gcg ccg gtg tcc      2256
Glu Pro Glu Pro His Trp Gly Pro Phe Gly Gly Ala Ala Pro Val Ser
            740                      745                      750 gcg ggc gtc ggc cac gca gca tta gtc gga gcg ttg tcg gtg ccg cac      2304
Ala Gly Val Gly His Ala Ala Leu Val Gly Ala Leu Ser Val Pro His
            755                      760                      765 agc tgg acc acg gcc gcc ccg gag atc cag ctc gcc gtt cag gca aca      2352
Ser Trp Thr Thr Ala Ala Pro Glu Ile Gln Leu Ala Val Gln Ala Thr
            770                      775                      780 ccc acc ttc agc tcc agc gcc ggc gcc gac ccg acg gcc cta aac ggg      2400
Pro Thr Phe Ser Ser Ser Ala Gly Ala Asp Pro Thr Ala Leu Asn Gly
785                      790                      795                      800 atg ccg gca ggc ctg ctc agc ggg atg gct ttg gcg agc ctg gcc gca      2448
Met Pro Ala Gly Leu Leu Ser Gly Met Ala Leu Ala Ser Leu Ala Ala
```

-continued

```
                805                 810                 815
cgc ggc acg acg ggc ggt ggc ggc acc cgt agc ggc acc agc act gac      2496
Arg Gly Thr Thr Gly Gly Gly Gly Thr Arg Ser Gly Thr Ser Thr Asp
        820                 825                 830 ggc caa gag gac ggc cgc aaa ccc ccg gta gtt gtg att aga gag cag      2544
Gly Gln Glu Asp Gly Arg Lys Pro Pro Val Val Val Ile Arg Glu Gln
835                 840                 845 ccg ccg ccc gga aac ccc ccg cgg taagatatc                            2577
Pro Pro Pro Gly Asn Pro Pro Arg
    850                 855

<210> SEQ ID NO 12
<211> LENGTH: 856
<212> TYPE: PRT
<213> ORGANISM: Artificial Sequence
<220> FEATURE:
<223> OTHER INFORMATION: Description of Artificial Sequence:penta-fusion

<400> SEQUENCE: 12

His Met His His His His His His Met Ala Thr Thr Leu Pro Val Gln
 1               5                  10                  15

Arg His Pro Arg Ser Leu Phe Pro Glu Phe Ser Glu Leu Phe Ala Ala
             20                  25                  30

Phe Pro Ser Phe Ala Gly Leu Arg Pro Thr Phe Asp Thr Arg Leu Met
         35                  40                  45

Arg Leu Glu Asp Glu Met Lys Glu Gly Arg Tyr Glu Val Arg Ala Glu
     50                  55                  60

Leu Pro Gly Val Asp Pro Asp Lys Asp Val Asp Ile Met Val Arg Asp
 65                  70                  75                  80

Gly Gln Leu Thr Ile Lys Ala Glu Arg Thr Glu Gln Lys Asp Phe Asp
                 85                  90                  95

Gly Arg Ser Glu Phe Ala Tyr Gly Ser Phe Val Arg Thr Val Ser Leu
            100                 105                 110

Pro Val Gly Ala Asp Glu Asp Ile Lys Ala Thr Tyr Asp Lys Gly
        115                 120                 125

Ile Leu Thr Val Ser Val Ala Val Ser Glu Gly Lys Pro Thr Glu Lys
    130                 135                 140

His Ile Gln Ile Arg Ser Thr Asn Lys Leu Asp Pro Val Asp Ala Val
145                 150                 155                 160

Ile Asn Thr Thr Cys Asn Tyr Gly Gln Val Val Ala Ala Leu Asn Ala
                165                 170                 175

Thr Asp Pro Gly Ala Ala Ala Gln Phe Asn Ala Ser Pro Val Ala Gln
            180                 185                 190

Ser Tyr Leu Arg Asn Phe Leu Ala Ala Pro Pro Gln Arg Ala Ala
        195                 200                 205

Met Ala Ala Gln Leu Gln Ala Val Pro Gly Ala Ala Gln Tyr Ile Gly
    210                 215                 220

Leu Val Glu Ser Val Ala Gly Ser Cys Asn Asn Tyr Glu Leu Met Thr
225                 230                 235                 240

Ile Asn Tyr Gln Phe Gly Asp Val Asp Ala His Gly Ala Met Ile Arg
                245                 250                 255

Ala Gln Ala Ala Ser Leu Glu Ala Glu His Gln Ala Ile Val Arg Asp
            260                 265                 270

Val Leu Ala Ala Gly Asp Phe Trp Gly Gly Ala Gly Ser Val Ala Cys
        275                 280                 285

Gln Glu Phe Ile Thr Gln Leu Gly Arg Asn Phe Gln Val Ile Tyr Glu
    290                 295                 300
```

-continued

```
Gln Ala Asn Ala His Gly Gln Lys Val Gln Ala Gly Asn Asn Met
305                 310                 315                 320

Ala Gln Thr Asp Ser Ala Val Gly Ser Ser Trp Ala Thr Ser Met Ser
            325                 330                 335

Leu Leu Asp Ala His Ile Pro Gln Leu Val Ala Ser Gln Ser Ala Phe
                340                 345                 350

Ala Ala Lys Ala Gly Leu Met Arg His Thr Ile Gly Gln Ala Glu Gln
        355                 360                 365

Ala Ala Met Ser Ala Gln Ala Phe His Gln Gly Glu Ser Ser Ala Ala
    370                 375                 380

Phe Gln Ala Ala His Ala Arg Phe Val Ala Ala Ala Lys Val Asn
385                 390                 395                 400

Thr Leu Leu Asp Val Ala Gln Ala Asn Leu Gly Glu Ala Ala Gly Thr
                405                 410                 415

Tyr Val Ala Ala Asp Ala Ala Ala Ser Thr Tyr Thr Gly Phe Asp
        420                 425                 430

Ile Met Asp Phe Gly Leu Leu Pro Pro Glu Val Asn Ser Ser Arg Met
    435                 440                 445

Tyr Ser Gly Pro Gly Pro Glu Ser Met Leu Ala Ala Ala Ala Ala Trp
    450                 455                 460

Asp Gly Val Ala Ala Glu Leu Thr Ser Ala Ala Val Ser Tyr Gly Ser
465                 470                 475                 480

Val Val Ser Thr Leu Ile Val Glu Pro Trp Met Gly Pro Ala Ala Ala
                485                 490                 495

Ala Met Ala Ala Ala Thr Pro Tyr Val Gly Trp Leu Ala Ala Thr
        500                 505                 510

Ala Ala Leu Ala Lys Glu Thr Ala Thr Gln Ala Arg Ala Ala Ala Glu
    515                 520                 525

Ala Phe Gly Thr Ala Phe Ala Met Thr Val Pro Pro Ser Leu Val Ala
    530                 535                 540

Ala Asn Arg Ser Arg Leu Met Ser Leu Val Ala Ala Asn Ile Leu Gly
545                 550                 555                 560

Gln Asn Ser Ala Ala Ile Ala Ala Thr Gln Ala Glu Tyr Ala Glu Met
                565                 570                 575

Trp Ala Gln Asp Ala Ala Val Met Tyr Ser Tyr Glu Gly Ala Ser Ala
        580                 585                 590

Ala Ala Ser Ala Leu Pro Pro Phe Thr Pro Val Gln Gly Thr Gly
    595                 600                 605

Pro Ala Gly Pro Ala Ala Ala Ala Ala Thr Gln Ala Ala Gly Ala
    610                 615                 620

Gly Ala Val Ala Asp Ala Gln Ala Thr Leu Ala Gln Leu Pro Pro Gly
625                 630                 635                 640

Ile Leu Ser Asp Ile Leu Ser Ala Leu Ala Ala Asn Ala Asp Pro Leu
                645                 650                 655

Thr Ser Gly Leu Leu Gly Ile Ala Ser Thr Leu Asn Pro Gln Val Gly
        660                 665                 670

Ser Ala Gln Pro Ile Val Ile Pro Thr Pro Ile Gly Glu Leu Asp Val
    675                 680                 685

Ile Ala Leu Tyr Ile Ala Ser Ile Ala Thr Gly Ser Ile Ala Leu Ala
    690                 695                 700

Ile Thr Asn Thr Ala Arg Pro Trp His Ile Gly Leu Tyr Gly Asn Ala
705                 710                 715                 720

Gly Gly Leu Gly Pro Thr Gln Gly His Pro Leu Ser Ser Ala Thr Asp
```

```
                        725                 730                 735
Glu Pro Glu Pro His Trp Gly Pro Phe Gly Gly Ala Ala Pro Val Ser
            740                 745                 750

Ala Gly Val Gly His Ala Ala Leu Val Gly Ala Leu Ser Val Pro His
        755                 760                 765

Ser Trp Thr Thr Ala Ala Pro Glu Ile Gln Leu Ala Val Gln Ala Thr
    770                 775                 780

Pro Thr Phe Ser Ser Ala Gly Ala Asp Pro Thr Ala Leu Asn Gly
785                 790                 795                 800

Met Pro Ala Gly Leu Leu Ser Gly Met Ala Leu Ala Ser Leu Ala Ala
            805                 810                 815

Arg Gly Thr Thr Gly Gly Gly Thr Arg Ser Gly Thr Ser Thr Asp
        820                 825                 830

Gly Gln Glu Asp Gly Arg Lys Pro Val Val Val Ile Arg Glu Gln
        835                 840                 845

Pro Pro Pro Gly Asn Pro Pro Arg
    850                 855

<210> SEQ ID NO 13
<211> LENGTH: 1299
<212> TYPE: DNA
<213> ORGANISM: Artificial Sequence
<220> FEATURE:
<223> OTHER INFORMATION: Description of Artificial Sequence:tetra-fusion
      protein Erd14-DPV-MTI-MSL (designated Mtb46f)
<221> NAME/KEY: CDS
<222> LO

```
            Ile Asn Thr Thr Cys Asn Tyr Gly Gln Val Val Ala Ala Leu Asn Ala
                            165                 170                 175 acg gat ccg ggg gct gcc gca cag ttc aac gcc tca ccg gtg gcg cag                576
Thr Asp Pro Gly Ala Ala Ala Gln Phe Asn Ala Ser Pro Val Ala Gln
                180                 185                 190 tcc tat ttg cgc aat ttc ctc gcc gca ccg cca cct cag cgc gct gcc                624
Ser Tyr Leu Arg Asn Phe Leu Ala Ala Pro Pro Pro Gln Arg Ala Ala
            195                 200                 205 atg gcc gcg caa ttg caa gct gtg ccg ggg gcg gca cag tac atc ggc                672
Met Ala Ala Gln Leu Gln Ala Val Pro Gly Ala Ala Gln Tyr Ile Gly
        210                 215                 220 ctt gtc gag tcg gtt gcc ggc tcc tgc aac aac tat gag ctc atg acg                720
Leu Val Glu Ser Val Ala Gly Ser Cys Asn Asn Tyr Glu Leu Met Thr
225                 230                 235                 240 att aat tac cag ttc ggg gac gtc gac gct cat ggc gcc atg atc cgc                768
Ile Asn Tyr Gln Phe Gly Asp Val Asp Ala His Gly Ala Met Ile Arg
                245                 250                 255 gct cag gcg gcg tcg ctt gag gcg gag cat cag gcc atc gtt cgt gat                816
Ala Gln Ala Ala Ser Leu Glu Ala Glu His Gln Ala Ile Val Arg Asp
                260                 265                 270 gtg ttg gcc gcg ggt gac ttt tgg ggc ggc gcc ggt tcg gtg gct tgc                864
Val Leu Ala Ala Gly Asp Phe Trp Gly Gly Ala Gly Ser Val Ala Cys
            275                 280                 285 cag gag ttc att acc cag ttg ggc cgt aac ttc cag gtg atc tac gag                912
Gln Glu Phe Ile Thr Gln Leu Gly Arg Asn Phe Gln Val Ile Tyr Glu
        290                 295                 300 cag gcc aac gcc cac ggg cag aag gtg cag gct gcc ggc aac aac atg                960
Gln Ala Asn Ala His Gly Gln Lys Val Gln Ala Ala Gly Asn Asn Met
305                 310                 315                 320 gcg caa acc gac agc gcc gtc ggc tcc agc tgg gcc act agt atg agc                1008
Ala Gln Thr Asp Ser Ala Val Gly Ser Ser Trp Ala Thr Ser Met Ser
                325                 330                 335 ctt ttg gat gct cat atc cca cag ttg gtg gcc tcc cag tcg gcg ttt                1056
Leu Leu Asp Ala His Ile Pro Gln Leu Val Ala Ser Gln Ser Ala Phe
                340                 345                 350 gcc gcc aag gcg ggg ctg atg cgg cac acg atc ggt cag gcc gag cag                1104
Ala Ala Lys Ala Gly Leu Met Arg His Thr Ile Gly Gln Ala Glu Gln
            355                 360                 365 gcg gcg atg tcg gct cag gcg ttt cac cag ggg gag tcg tcg gcg gcg                1152
Ala Ala Met Ser Ala Gln Ala Phe His Gln Gly Glu Ser Ser Ala Ala
        370                 375                 380 ttt cag gcc gcc cat gcc cgg ttt gtg gcg gcg gcc aaa gtc aac                    1200
Phe Gln Ala Ala His Ala Arg Phe Val Ala Ala Ala Lys Val Asn
385                 390                 395                 400 acc ttg ttg gat gtc gcg cag gcg aat ctg ggt gag gcc gcc ggt acc                1248
Thr Leu Leu Asp Val Ala Gln Ala Asn Leu Gly Glu Ala Ala Gly Thr
                405                 410                 415 tat gtg gcc gcc gat gct gcg gcc gcg tcg acc tat acc ggg ttc gat                1296
Tyr Val Ala Ala Asp Ala Ala Ala Ala Ser Thr Tyr Thr Gly Phe Asp
                420                 425                 430 atc                                                                            1299
Ile <210> SEQ ID NO 14
<211> LENGTH: 433
<212> TYPE: PRT
<213> ORGANISM: Artificial Sequence
<220> FEATURE:
<223> OTHER INFORMATION: Description of Artificial Sequence:tetra-fusion

<400> SEQUENCE: 14
```

-continued

```
His Met His His His His His Met Ala Thr Thr Leu Pro Val Gln
  1               5                   10                  15

Arg His Pro Arg Ser Leu Phe Pro Glu Phe Ser Glu Leu Phe Ala Ala
                 20                  25                  30

Phe Pro Ser Phe Ala Gly Leu Arg Pro Thr Phe Asp Thr Arg Leu Met
             35                  40                  45

Arg Leu Glu Asp Glu Met Lys Glu Gly Arg Tyr Glu Val Arg Ala Glu
         50                  55                  60

Leu Pro Gly Val Asp Pro Asp Lys Asp Val Asp Ile Met Val Arg Asp
 65                  70                  75                  80

Gly Gln Leu Thr Ile Lys Ala Glu Arg Thr Gln Lys Asp Phe Asp
                 85                  90                  95

Gly Arg Ser Glu Phe Ala Tyr Gly Ser Phe Val Arg Thr Val Ser Leu
                100                 105                 110

Pro Val Gly Ala Asp Glu Asp Ile Lys Ala Thr Tyr Asp Lys Gly
             115                 120                 125

Ile Leu Thr Val Ser Val Ala Val Ser Glu Gly Lys Pro Thr Glu Lys
    130                 135                 140

His Ile Gln Ile Arg Ser Thr Asn Lys Leu Asp Pro Val Asp Ala Val
145                 150                 155                 160

Ile Asn Thr Thr Cys Asn Tyr Gly Gln Val Val Ala Ala Leu Asn Ala
                165                 170                 175

Thr Asp Pro Gly Ala Ala Ala Gln Phe Asn Ala Ser Pro Val Ala Gln
                180                 185                 190

Ser Tyr Leu Arg Asn Phe Leu Ala Ala Pro Pro Gln Arg Ala Ala
    195                 200                 205

Met Ala Ala Gln Leu Gln Ala Val Pro Gly Ala Ala Gln Tyr Ile Gly
210                 215                 220

Leu Val Glu Ser Val Ala Gly Ser Cys Asn Asn Tyr Glu Leu Met Thr
225                 230                 235                 240

Ile Asn Tyr Gln Phe Gly Asp Val Asp Ala His Gly Ala Met Ile Arg
                245                 250                 255

Ala Gln Ala Ala Ser Leu Glu Ala Glu His Gln Ala Ile Val Arg Asp
                260                 265                 270

Val Leu Ala Ala Gly Asp Phe Trp Gly Gly Ala Gly Ser Val Ala Cys
    275                 280                 285

Gln Glu Phe Ile Thr Gln Leu Gly Arg Asn Phe Gln Val Ile Tyr Glu
    290                 295                 300

Gln Ala Asn Ala His Gly Gln Lys Val Gln Ala Gly Asn Asn Met
305                 310                 315                 320

Ala Gln Thr Asp Ser Ala Val Gly Ser Ser Trp Ala Thr Ser Met Ser
                325                 330                 335

Leu Leu Asp Ala His Ile Pro Gln Leu Val Ala Ser Gln Ser Ala Phe
                340                 345                 350

Ala Ala Lys Ala Gly Leu Met Arg His Thr Ile Gly Gln Ala Glu Gln
            355                 360                 365

Ala Ala Met Ser Ala Gln Ala Phe His Gln Gly Glu Ser Ser Ala Ala
            370                 375                 380

Phe Gln Ala Ala His Ala Arg Phe Val Ala Ala Ala Lys Val Asn
385                 390                 395                 400

Thr Leu Leu Asp Val Ala Gln Ala Asn Leu Gly Glu Ala Ala Gly Thr
                405                 410                 415

Tyr Val Ala Ala Asp Ala Ala Ala Ser Thr Tyr Thr Gly Phe Asp
            420                 425                 430
```

Ile

```
<210> SEQ ID NO 15
<211> LENGTH: 2168
<212> TYPE: DNA
<213> ORGANISM: Artificial Sequence
<220> FEATURE:
<223> OTHER INFORMATION: Description of Artificial Sequence:tetra-fusion
      protein DPV-MTI-MSL-MTCC2 (designated Mtb71f)
<221> NAME/KEY: CDS
<222> LOCATION: (1

```
ttg gat gtc gcg cag gcg aat ctg ggt gag gcc gcc ggt acc tat gtg      816
Leu Asp Val Ala Gln Ala Asn Leu Gly Glu Ala Ala Gly Thr Tyr Val
            260                 265                 270 gcc gcc gat gct gcg gcc gcg tcg acc tat acc ggg ttc gat atc atg      864
Ala Ala Asp Ala Ala Ala Ala Ser Thr Tyr Thr Gly Phe Asp Ile Met
        275                 280                 285 gat ttc ggg ctt tta cct ccg gaa gtg aat tca agc cga atg tat tcc      912
Asp Phe Gly Leu Leu Pro Pro Glu Val Asn Ser Ser Arg Met Tyr Ser
    290                 295                 300 ggt ccg ggg ccg gag tcg atg cta gcc gcc gcg gcc tgg gac ggt          960
Gly Pro Gly Pro Glu Ser Met Leu Ala Ala Ala Ala Trp Asp Gly
305                 310                 315                 320 gtg gcc gcg gag ttg act tcc gcc gcg gtc tcg tat gga tcg gtg gtg     1008
Val Ala Ala Glu Leu Thr Ser Ala Ala Val Ser Tyr Gly Ser Val Val
            325                 330                 335 tcg acg ctg atc gtt gag ccg tgg atg ggg ccg gcg gcg gcc gcg atg     1056
Ser Thr Leu Ile Val Glu Pro Trp Met Gly Pro Ala Ala Ala Ala Met
        340                 345                 350 gcg gcc gcg gca acg ccg tat gtg ggg tgg ctg gcc gcc acg gcg gcg     1104
Ala Ala Ala Ala Thr Pro Tyr Val Gly Trp Leu Ala Ala Thr Ala Ala
    355                 360                 365 ctg gcg aag gag acg gcc aca cag gcg agg gca gcg gcg gaa gcg ttt     1152
Leu Ala Lys Glu Thr Ala Thr Gln Ala Arg Ala Ala Ala Glu Ala Phe
370                 375                 380 ggg acg gcg ttc gcg atg acg gtg cca cca tcc ctc gtc gcg gcc aac     1200
Gly Thr Ala Phe Ala Met Thr Val Pro Pro Ser Leu Val Ala Ala Asn
385                 390                 395                 400 cgc agc cgg ttg atg tcg ctg gtc gcg gcg aac att ctg ggg caa aac     1248
Arg Ser Arg Leu Met Ser Leu Val Ala Ala Asn Ile Leu Gly Gln Asn
            405                 410                 415 agt gcg gcg atc gcg gct acc cag gcc gag tat gcc gaa atg tgg gcc     1296
Ser Ala Ala Ile Ala Ala Thr Gln Ala Glu Tyr Ala Glu Met Trp Ala
        420                 425                 430 caa gac gct gcc gtg atg tac agc tat gag ggg gca tct gcg gcc gcg     1344
Gln Asp Ala Ala Val Met Tyr Ser Tyr Glu Gly Ala Ser Ala Ala Ala
    435                 440                 445 tcg gcg ttg ccg ccg ttc act cca ccc gtg caa ggc acc ggc ccg gcc     1392
Ser Ala Leu Pro Pro Phe Thr Pro Pro Val Gln Gly Thr Gly Pro Ala
450                 455                 460 ggg ccc gcg gcc gca gcc gcg gcg acc caa gcc gcc ggt gcg ggc gcc     1440
Gly Pro Ala Ala Ala Ala Ala Thr Gln Ala Ala Gly Ala Gly Ala
465                 470                 475                 480 gtt gcg gat gca cag gcg aca ctg gcc cag ctg ccc ccg ggg atc ctg     1488
Val Ala Asp Ala Gln Ala Thr Leu Ala Gln Leu Pro Pro Gly Ile Leu
            485                 490                 495 agc gac att ctg tcc gca ttg gcc gcc aac gct gat ccg ctg aca tcg     1536
Ser Asp Ile Leu Ser Ala Leu Ala Ala Asn Ala Asp Pro Leu Thr Ser
        500                 505                 510 gga ctg ttg ggg atc gcg tcg acc ctc aac ccg caa gtc gga tcc gct     1584
Gly Leu Leu Gly Ile Ala Ser Thr Leu Asn Pro Gln Val Gly Ser Ala
    515                 520                 525 cag ccg ata gtg atc ccc acc ccg ata ggg gaa ttg gac gtg atc gcg     1632
Gln Pro Ile Val Ile Pro Thr Pro Ile Gly Glu Leu Asp Val Ile Ala
530                 535                 540 ctc tac att gca tcc atc gcg acc ggc agc att gcg ctc gcg atc acg     1680
Leu Tyr Ile Ala Ser Ile Ala Thr Gly Ser Ile Ala Leu Ala Ile Thr
545                 550                 555                 560 aac acg gcc aga ccc tgg cac atc ggc cta tac ggg aac gcc ggc ggg     1728
Asn Thr Ala Arg Pro Trp His Ile Gly Leu Tyr Gly Asn Ala Gly Gly
            565                 570                 575
```

```
ctg gga ccg acg cag ggc cat cca ctg agt tcg gcg acc gac gag ccg    1776
Leu Gly Pro Thr Gln Gly His Pro Leu Ser Ser Ala Thr Asp Glu Pro
            580                 585                 590 gag ccg cac tgg ggc ccc ttc ggg ggc gcg gcg ccg gtg tcc gcg ggc    1824
Glu Pro His Trp Gly Pro Phe Gly Gly Ala Ala Pro Val Ser Ala Gly
        595                 600                 605 gtc ggc cac gca gca tta gtc gga gcg ttg tcg gtg ccg cac agc tgg    1872
Val Gly His Ala Ala Leu Val Gly Ala Leu Ser Val Pro His Ser Trp
610                 615                 620 acc acg gcc gcc ccg gag atc cag ctc gcc gtt cag gca aca ccc acc    1920
Thr Thr Ala Ala Pro Glu Ile Gln Leu Ala Val Gln Ala Thr Pro Thr
625                 630                 635                 640 ttc agc tcc agc gcc ggc gcc gac ccg acg gcc cta aac ggg atg ccg    1968
Phe Ser Ser Ser Ala Gly Ala Asp Pro Thr Ala Leu Asn Gly Met Pro
                645                 650                 655 gca ggc ctg ctc agc ggg atg gct ttg gcg agc ctg gcc gca cgc ggc    2016
Ala Gly Leu Leu Ser Gly Met Ala Leu Ala Ser Leu Ala Ala Arg Gly
            660                 665                 670 acg acg ggc ggt ggc ggc acc cgt agc ggc acc agc act gac ggc caa    2064
Thr Thr Gly Gly Gly Gly Thr Arg Ser Gly Thr Ser Thr Asp Gly Gln
        675                 680                 685 gag gac ggc cgc aaa ccc ccg gta gtt gtg att aga gag cag ccg ccg    2112
Glu Asp Gly Arg Lys Pro Pro Val Val Val Ile Arg Glu Gln Pro Pro
690                 695                 700 ccc gga aac ccc ccg cgg taagatttct aaatccatca cactggcggc cgctcgag  2168
Pro Gly Asn Pro Pro Arg
705                 710

<210> SEQ ID NO 16
<211> LENGTH: 710
<212> TYPE: PRT
<213> ORGANISM: Artificial Sequence
<220> FEATURE:
<223> OTHER INFORMATION: Description of Artificial Sequence:tetra-fusion

<400> SEQUENCE: 16

His Met His His His His His His Asp Pro Val Asp Ala Val Ile Asn
 1               5                  10                  15

Thr Thr Cys Asn Tyr Gly Gln Val Val Ala Ala Leu Asn Ala Thr Asp
                20                  25                  30

Pro Gly Ala Ala Gln Phe Asn Ala Ser Pro Val Ala Gln Ser Tyr
            35                  40                  45

Leu Arg Asn Phe Leu Ala Ala Pro Pro Gln Arg Ala Ala Met Ala
    50                  55                  60

Ala Gln Leu Gln Ala Val Pro Gly Ala Ala Gln Tyr Ile Gly Leu Val
65                  70                  75                  80

Glu Ser Val Ala Gly Ser Cys Asn Asn Tyr Glu Leu Met Thr Ile Asn
                85                  90                  95

Tyr Gln Phe Gly Asp Val Asp Ala His Gly Ala Met Ile Arg Ala Gln
            100                 105                 110

Ala Ala Ser Leu Glu Ala Glu His Gln Ala Ile Val Arg Asp Val Leu
        115                 120                 125

Ala Ala Gly Asp Phe Trp Gly Ala Gly Ser Val Ala Cys Gln Glu
    130                 135                 140

Phe Ile Thr Gln Leu Gly Arg Asn Phe Gln Val Ile Tyr Glu Gln Ala
145                 150                 155                 160

Asn Ala His Gly Gln Lys Val Gln Ala Ala Gly Asn Asn Met Ala Gln
                165                 170                 175

Thr Asp Ser Ala Val Gly Ser Ser Trp Ala Thr Ser Met Ser Leu Leu
```

```
            180                 185                 190
Asp Ala His Ile Pro Gln Leu Val Ala Ser Gln Ser Ala Phe Ala Ala
            195                 200                 205

Lys Ala Gly Leu Met Arg His Thr Ile Gly Gln Ala Glu Gln Ala Ala
            210                 215                 220

Met Ser Ala Gln Ala Phe His Gln Gly Glu Ser Ser Ala Ala Phe Gln
225                 230                 235                 240

Ala Ala His Ala Arg Phe Val Ala Ala Ala Lys Val Asn Thr Leu
                    245                 250                 255

Leu Asp Val Ala Gln Ala Asn Leu Gly Glu Ala Gly Thr Tyr Val
            260                 265                 270

Ala Ala Asp Ala Ala Ala Ser Thr Tyr Thr Gly Phe Asp Ile Met
            275                 280                 285

Asp Phe Gly Leu Leu Pro Pro Glu Val Asn Ser Ser Arg Met Tyr Ser
            290                 295                 300

Gly Pro Gly Pro Glu Ser Met Leu Ala Ala Ala Ala Trp Asp Gly
305                 310                 315                 320

Val Ala Ala Glu Leu Thr Ser Ala Ala Val Ser Tyr Gly Ser Val Val
                    325                 330                 335

Ser Thr Leu Ile Val Glu Pro Trp Met Gly Pro Ala Ala Ala Met
            340                 345                 350

Ala Ala Ala Ala Thr Pro Tyr Val Gly Trp Leu Ala Ala Thr Ala Ala
            355                 360                 365

Leu Ala Lys Glu Thr Ala Thr Gln Ala Arg Ala Ala Ala Glu Ala Phe
            370                 375                 380

Gly Thr Ala Phe Ala Met Thr Val Pro Pro Ser Leu Val Ala Ala Asn
385                 390                 395                 400

Arg Ser Arg Leu Met Ser Leu Val Ala Ala Asn Ile Leu Gly Gln Asn
                    405                 410                 415

Ser Ala Ala Ile Ala Ala Thr Gln Ala Glu Tyr Ala Glu Met Trp Ala
                    420                 425                 430

Gln Asp Ala Ala Val Met Tyr Ser Tyr Glu Gly Ala Ser Ala Ala Ala
            435                 440                 445

Ser Ala Leu Pro Pro Phe Thr Pro Pro Val Gln Gly Thr Gly Pro Ala
450                 455                 460

Gly Pro Ala Ala Ala Ala Ala Thr Gln Ala Gly Ala Gly Ala
465                 470                 475                 480

Val Ala Asp Ala Gln Ala Thr Leu Ala Gln Leu Pro Pro Gly Ile Leu
                    485                 490                 495

Ser Asp Ile Leu Ser Ala Leu Ala Ala Asn Ala Asp Pro Leu Thr Ser
            500                 505                 510

Gly Leu Leu Gly Ile Ala Ser Thr Leu Asn Pro Gln Val Gly Ser Ala
            515                 520                 525

Gln Pro Ile Val Ile Pro Thr Pro Ile Gly Glu Leu Asp Val Ile Ala
            530                 535                 540

Leu Tyr Ile Ala Ser Ile Ala Thr Gly Ser Ile Ala Leu Ala Ile Thr
545                 550                 555                 560

Asn Thr Ala Arg Pro Trp His Ile Gly Leu Tyr Gly Asn Ala Gly Gly
                    565                 570                 575

Leu Gly Pro Thr Gln Gly His Pro Leu Ser Ser Ala Thr Asp Glu Pro
                    580                 585                 590

Glu Pro His Trp Gly Pro Phe Gly Gly Ala Ala Pro Val Ser Ala Gly
            595                 600                 605
```

```
Val Gly His Ala Ala Leu Val Gly Ala Leu Ser Val Pro His Ser Trp
    610                 615                 620

Thr Th

-continued

```
              115                 120                 125
gcc gcg ggt gac ttt tgg ggc ggc gcc ggt tcg gtg gct tgc cag gag       432
Ala Ala Gly Asp Phe Trp Gly Gly Ala Gly Ser Val Ala Cys Gln Glu
        130                 135                 140 ttc att acc cag ttg ggc cgt aac ttc cag gtg atc tac gag cag gcc       480
Phe Ile Thr Gln Leu Gly Arg Asn Phe Gln Val Ile Tyr Glu Gln Ala
145                 150                 155                 160 aac gcc cac ggg cag aag gtg cag gct gcc ggc aac aac atg gcg caa       528
Asn Ala His Gly Gln Lys Val Gln Ala Ala Gly Asn Asn Met Ala Gln
                165                 170                 175 acc gac agc gcc gtc ggc tcc agc tgg gcc act agt atg agc ctt ttg       576
Thr Asp Ser Ala Val Gly Ser Ser Trp Ala Thr Ser Met Ser Leu Leu
        180                 185                 190 gat gct cat atc cca cag ttg gtg gcc tcc cag tcg gcg ttt gcc gcc       624
Asp Ala His Ile Pro Gln Leu Val Ala Ser Gln Ser Ala Phe Ala Ala
    195                 200                 205 aag gcg ggg ctg atg cgg cac acg atc ggt cag gcc gag cag gcg gcg       672
Lys Ala Gly Leu Met Arg His Thr Ile Gly Gln Ala Glu Gln Ala Ala
210                 215                 220 atg tcg gct cag gcg ttt cac cag ggg gag tcg tcg gcg gcg ttt cag       720
Met Ser Ala Gln Ala Phe His Gln Gly Glu Ser Ser Ala Ala Phe Gln
225                 230                 235                 240 gcc gcc cat gcc cgg ttt gtg gcg gcg gcc gcc aaa gtc aac acc ttg       768
Ala Ala His Ala Arg Phe Val Ala Ala Ala Ala Lys Val Asn Thr Leu
                245                 250                 255 ttg gat gtc gcg cag gcg aat ctg ggt gag gcc gcc ggt acc tat gtg       816
Leu Asp Val Ala Gln Ala Asn Leu Gly Glu Ala Ala Gly Thr Tyr Val
        260                 265                 270 gcc gcc gat gct gcg gcc gcg tcg acc tat acc ggg ttc gat atc cat       864
Ala Ala Asp Ala Ala Ala Ala Ser Thr Tyr Thr Gly Phe Asp Ile His
    275                 280                 285 cac act ggc ggc cgc tcg agc aga tcc ggc tgc taacaaagcc cgaaggaag     917
His Thr Gly Gly Arg Ser Ser Arg Ser Gly Cys
290                 295 ctga                                                                  921

<210> SEQ ID NO 19
<211> LENGTH: 299
<212> TYPE: PRT
<213> ORGANISM: Artificial Sequence
<220> FEATURE:
<223> OTHER INFORMATION: Description of Artificial Sequence:tri-fusion

<400> SEQUENCE: 19

His Met His His His His His Asp Pro Val Asp Ala Val Ile Asn
1               5                   10                  15

Thr Thr Cys Asn Tyr Gly Gln Val Val Ala Ala Leu Asn Ala Thr Asp
            20                  25                  30

Pro Gly Ala Ala Ala Gln Phe Asn Ala Ser Pro Val Ala Gln Ser Tyr
        35                  40                  45

Leu Arg Asn Phe Leu Ala Ala Pro Pro Gln Arg Ala Ala Met Ala
    50                  55                  60

Ala Gln Leu Gln Ala Val Pro Gly Ala Ala Gln Tyr Ile Gly Leu Val
65                  70                  75                  80

Glu Ser Val Ala Gly Ser Cys Asn Asn Tyr Glu Leu Met Thr Ile Asn
                85                  90                  95

Tyr Gln Phe Gly Asp Val Asp Ala His Gly Ala Met Ile Arg Ala Gln
            100                 105                 110

Ala Ala Ser Leu Glu Ala Glu His Gln Ala Ile Val Arg Asp Val Leu
```

```
                    115                 120                 125
Ala Ala Gly Asp Phe Trp Gly Ala Gly Ser Val Ala Cys Gln Glu
    130                 135                 140

Phe Ile Thr Gln Leu Gly Arg Asn Phe Gln Val Ile Tyr Glu Gln Ala
145                 150                 155                 160

Asn Ala His Gly Gln Lys Val Gln Ala Ala Gly Asn Asn Met Ala Gln
                165                 170                 175

Thr Asp Ser Ala Val Gly Ser Ser Trp Ala Thr Ser Met Ser Leu Leu
            180                 185                 190

Asp Ala His Ile Pro Gln Leu Val Ala Ser Gln Ser Ala Phe Ala Ala
        195                 200                 205

Lys Ala Gly Leu Met Arg His Thr Ile Gly Gln Ala Glu Gln Ala Ala
    210                 215                 220

Met Ser Ala Gln Ala Phe His Gln Gly Glu Ser Ser Ala Ala Phe Gln
225                 230                 235                 240

Ala Ala His Ala Arg Phe Val Ala Ala Ala Lys Val Asn Thr Leu
                245                 250                 255

Leu Asp Val Ala Gln Ala Asn Leu Gly Glu Ala Ala Gly Thr Tyr Val
            260                 265                 270

Ala Ala Asp Ala Ala Ala Ala Ser Thr Tyr Thr Gly Phe Asp Ile His
        275                 280                 285

His Thr Gly Gly Arg Ser Ser Arg Ser Gly Cys
    290                 295

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence:peptide
      transcribed from positions 901-918 of
      SEQ ID NO:18

<400> SEQUENCE: 20

Gln Ser Pro Lys Gly Ser
  1               5

<210> SEQ ID NO 21
<211> LENGTH: 1801
<212> TYPE: DNA
<213> ORGANISM: Artificial Sequence
<220> FEATURE:
<223> OTHER INFORMATION: Description of Artificial Sequence:tri-fusion
      protein TbH9-DPV-MTI (designated Mtb61f)
<221> NAME/KEY: CDS
<222> LOCATION: (1)..(1800)

<400> SEQUENCE: 21 cat atg cat cac cat cac c

-continued

| | | |
|---|---|---|
| Ser Trp Ile Gly Ser Ser Ala Gly Leu Met Val Ala Ala Ser Pro<br>65                        70                    75                  80 | |
| tat gtg gcg tgg atg agc gtc acc gcg ggg cag gcc gag ctg acc gcc<br>Tyr Val Ala Trp Met Ser Val Thr Ala Gly Gln Ala Glu Leu Thr Ala<br>                  85                        90                        95 | 288 |
| gcc cag gtc cgg gtt gct gcg gcg gcc tac gag acg gcg tat ggg ctg<br>Ala Gln Val Arg Val Ala Ala Ala Ala Tyr Glu Thr Ala Tyr Gly Leu<br>            100                        105                      110 | 336 |
| acg gtg ccc ccg ccg gtg atc gcc gag aac cgt gct gaa ctg atg att<br>Thr Val Pro Pro Pro Val Ile Ala Glu Asn Arg Ala Glu Leu Met Ile<br>        115                        120                      125 | 384 |
| ctg ata gcg acc aac ctc ttg ggg caa aac acc ccg gcg atc gcg gtc<br>Leu Ile Ala Thr Asn Leu Leu Gly Gln Asn Thr Pro Ala Ile Ala Val<br>130                        135                      140 | 432 |
| aac gag gcc gaa tac ggc gag atg tgg gcc caa gac gcc gcc gcg atg<br>Asn Glu Ala Glu Tyr Gly Glu Met Trp Ala Gln Asp Ala Ala Ala Met<br>145                      150                      155                160 | 480 |
| ttt ggc tac gcc gcg gcg acg gcg acg gcg acg gcg acg ttg ctg ccg<br>Phe Gly Tyr Ala Ala Ala Thr Ala Thr Ala Thr Ala Thr Leu Leu Pro<br>                  165                        170                      175 | 528 |
| ttc gag gag gcg ccg gag atg acc agc gcg ggt ggg ctc ctc gag cag<br>Phe Glu Glu Ala Pro Glu Met Thr Ser Ala Gly Gly Leu Leu Glu Gln<br>        180                        185                      190 | 576 |
| gcc gcc gcg gtc gag gag gcc tcc gac acc gcc gcg aac cag ttg<br>Ala Ala Ala Val Glu Glu Ala Ser Asp Thr Ala Ala Asn Gln Leu<br>                195                        200                      205 | 624 |
| atg aac aat gtg ccc cag gcg ctg caa cag ctg gcc cag ccc acg cag<br>Met Asn Asn Val Pro Gln Ala Leu Gln Gln Leu Ala Gln Pro Thr Gln<br>210                        215                      220 | 672 |
| ggc acc acg cct tct tcc aag ctg ggt ggc ctg tgg aag acg gtc tcg<br>Gly Thr Thr Pro Ser Ser Lys Leu Gly Gly Leu Trp Lys Thr Val Ser<br>225                      230                      235                  240 | 720 |
| ccg cat cgg tcg ccg atc agc aac atg gtg tcg atg gcc aac aac cac<br>Pro His Arg Ser Pro Ile Ser Asn Met Val Ser Met Ala Asn Asn His<br>                245                        250                      255 | 768 |
| atg tcg atg acc aac tcg ggt gtg tcg atg acc aac acc ttg agc tcg<br>Met Ser Met Thr Asn Ser Gly Val Ser Met Thr Asn Thr Leu Ser Ser<br>        260                        265                      270 | 816 |
| atg ttg aag ggc ttt gct ccg gcg gcg gcc gcc cag gcc gtg caa acc<br>Met Leu Lys Gly Phe Ala Pro Ala Ala Ala Ala Gln Ala Val Gln Thr<br>275                        280                      285 | 864 |
| gcg gcg caa aac ggg gtc cgg gcg atg agc tcg ctg ggc agc tcg ctg<br>Ala Ala Gln Asn Gly Val Arg Ala Met Ser Ser Leu Gly Ser Ser Leu<br>290                        295                      300 | 912 |
| ggt tct tcg ggt ctg ggc ggt ggg gtg gcc gcc aac ttg ggt cgg gcg<br>Gly Ser Ser Gly Leu Gly Gly Gly Val Ala Ala Asn Leu Gly Arg Ala<br>305                      310                      315                  320 | 960 |
| gcc tcg gtc ggt tcg ttg tcg gtg ccg cag gcc tgg gcc gcg gcc aac<br>Ala Ser Val Gly Ser Leu Ser Val Pro Gln Ala Trp Ala Ala Ala Asn<br>                325                        330                      335 | 1008 |
| cag gca gtc acc ccg gcg gcg cgg gcg ctg ccg ctg acc agc ctg acc<br>Gln Ala Val Thr Pro Ala Ala Arg Ala Leu Pro Leu Thr Ser Leu Thr<br>        340                        345                      350 | 1056 |
| agc gcc gcg gaa aga ggg ccc ggg cag atg ctg ggc ggg ctg ccg gtg<br>Ser Ala Ala Glu Arg Gly Pro Gly Gln Met Leu Gly Gly Leu Pro Val<br>                355                        360                      365 | 1104 |
| ggg cag atg ggc gcc agg gcc ggt ggg ctc agt ggt gtg ctg cgt<br>Gly Gln Met Gly Ala Arg Ala Gly Gly Gly Leu Ser Gly Val Leu Arg<br>370                        375                      380 | 1152 |
| gtt ccg ccg cga ccc tat gtg atg ccg cat tct ccg gca gcc ggc aag | 1200 |

```
Val Pro Pro Arg Pro Tyr Val Met Pro His Ser Pro Ala Ala Gly Lys
385                 390                 395                 400 ctt gat ccc gtg gac gcg gtc att aac acc acc tgc aat tac ggg cag      1248
Leu Asp Pro Val Asp Ala Val Ile Asn Thr Thr Cys Asn Tyr Gly Gln
                405                 410                 415 gta gta gct gcg ctc aac gcg acg gat ccg ggg gct gcc gca cag ttc      1296
Val Val Ala Ala Leu Asn Ala Thr Asp Pro Gly Ala Ala Gln Phe
                420                 425                 430 aac gcc tca ccg gtg gcg cag tcc tat ttg cgc aat ttc ctc gcc gca      1344
Asn Ala Ser Pro Val Ala Gln Ser Tyr Leu Arg Asn Phe Leu Ala Ala
                435                 440                 445 ccg cca cct cag cgc gct gcc atg gcc gcg caa ttg caa gct gtg ccg      1392
Pro Pro Pro Gln Arg Ala Ala Met Ala Ala Gln Leu Gln Ala Val Pro
            450                 455                 460 ggg gcg gca cag tac atc ggc ctt gtc gag tcg gtt gcc ggc tcc tgc      1440
Gly Ala Ala Gln Tyr Ile Gly Leu Val Glu Ser Val Ala Gly Ser Cys
465                 470                 475                 480 aac aac tat gag ctc atg acg att aat tac cag ttc ggg gac gtc gac      1488
Asn Asn Tyr Glu Leu Met Thr Ile Asn Tyr Gln Phe Gly Asp Val Asp
                485                 490                 495 gct cat ggc gcc atg atc cgc gct cag gcg gcg tcg ctt gag gcg gag      1536
Ala His Gly Ala Met Ile Arg Ala Gln Ala Ala Ser Leu Glu Ala Glu
                500                 505                 510 cat cag gcc atc gtt cgt gat gtg ttg gcc gcg ggt gac ttt tgg ggc      1584
His Gln Ala Ile Val Arg Asp Val Leu Ala Ala Gly Asp Phe Trp Gly
            515                 520                 525 ggc gcc ggt tcg gtg gct tgc cag gag ttc att acc cag ttg ggc cgt      1632
Gly Ala Gly Ser Val Ala Cys Gln Glu Phe Ile Thr Gln Leu Gly Arg
530                 535                 540 aac ttc cag gtg atc tac gag cag gcc aac gcc cac ggg cag aag gtg      1680
Asn Phe Gln Val Ile Tyr Glu Gln Ala Asn Ala His Gly Gln Lys Val
545                 550                 555                 560 cag gct gcc ggc aac aac atg gcg caa acc gac agc gcc gtc ggc tcc      1728
Gln Ala Ala Gly Asn Asn Met Ala Gln Thr Asp Ser Ala Val Gly Ser
                565                 570                 575 agc tgg gcc act agt aac ggc cgc cag tgt gct gga att ctg cag ata      1776
Ser Trp Ala Thr Ser Asn Gly Arg Gln Cys Ala Gly Ile Leu Gln Ile
                580                 585                 590 tcc atc aca ctg gcg gcc gct cga g                                    1801
Ser Ile Thr Leu Ala Ala Ala Arg
            595                 600

<210> SEQ ID NO 22
<211> LENGTH: 600
<212> TYPE: PRT
<213> ORGANISM: Artificial Sequence
<220> FEATURE:
<223> OTHER INFORMATION: Description of Artificial Sequence:tri-fusion

<400> SEQUENCE: 22

His Met His His His His His Met Val Asp Phe Gly Ala Leu Pro
1               5                   10                  15

Pro Glu Ile Asn Ser Ala Arg Met Tyr Ala Gly Pro Gly Ser Ala Ser
                20                  25                  30

Leu Val Ala Ala Ala Gln Met Trp Asp Ser Val Ala Ser Asp Leu Phe
            35                  40                  45

Ser Ala Ala Ser Ala Phe Gln Ser Val Val Trp Gly Leu Thr Val Gly
        50                  55                  60

Ser Trp Ile Gly Ser Ser Ala Gly Leu Met Val Ala Ala Ala Ser Pro
65              70                  75                  80
```

-continued

```
Tyr Val Ala Trp Met Ser Val Thr Ala Gly Gln Ala Glu Leu Thr Ala
                 85                  90                  95

Ala Gln Val Arg Val Ala Ala Ala Tyr Glu Thr Ala Tyr Gly Leu
            100                 105                 110

Thr Val Pro Pro Val Ile Ala Glu Asn Arg Ala Glu Leu Met Ile
            115                 120                 125

Leu Ile Ala Thr Asn Leu Leu Gly Gln Asn Thr Pro Ala Ile Ala Val
        130                 135                 140

Asn Glu Ala Glu Tyr Gly Glu Met Trp Ala Gln Asp Ala Ala Ala Met
145                 150                 155                 160

Phe Gly Tyr Ala Ala Ala Thr Ala Thr Ala Thr Ala Thr Leu Leu Pro
                165                 170                 175

Phe Glu Glu Ala Pro Glu Met Thr Ser Ala Gly Gly Leu Leu Glu Gln
            180                 185                 190

Ala Ala Ala Val Glu Glu Ala Ser Asp Thr Ala Ala Ala Asn Gln Leu
        195                 200                 205

Met Asn Asn Val Pro Gln Ala Leu Gln Gln Leu Ala Gln Pro Thr Gln
210                 215                 220

Gly Thr Thr Pro Ser Ser Lys Leu Gly Gly Leu Trp Lys Thr Val Ser
225                 230                 235                 240

Pro His Arg Ser Pro Ile Ser Asn Met Val Ser Met Ala Asn Asn His
                245                 250                 255

Met Ser Met Thr Asn Ser Gly Val Ser Met Thr Asn Thr Leu Ser Ser
                260                 265                 270

Met Leu Lys Gly Phe Ala Pro Ala Ala Ala Gln Ala Val Gln Thr
            275                 280                 285

Ala Ala Gln Asn Gly Val Arg Ala Met Ser Ser Leu Gly Ser Ser Leu
        290                 295                 300

Gly Ser Ser Gly Leu Gly Gly Val Ala Ala Asn Leu Gly Arg Ala
305                 310                 315                 320

Ala Ser Val Gly Ser Leu Ser Val Pro Gln Ala Trp Ala Ala Ala Asn
                325                 330                 335

Gln Ala Val Thr Pro Ala Ala Arg Ala Leu Pro Leu Thr Ser Leu Thr
                340                 345                 350

Ser Ala Ala Glu Arg Gly Pro Gly Gln Met Leu Gly Gly Leu Pro Val
        355                 360                 365

Gly Gln Met Gly Ala Arg Ala Gly Gly Leu Ser Gly Val Leu Arg
370                 375                 380

Val Pro Pro Arg Pro Tyr Val Met Pro His Ser Pro Ala Ala Gly Lys
385                 390                 395                 400

Leu Asp Pro Val Asp Ala Val Ile Asn Thr Thr Cys Asn Tyr Gly Gln
                405                 410                 415

Val Val Ala Ala Leu Asn Ala Thr Asp Pro Gly Ala Ala Ala Gln Phe
            420                 425                 430

Asn Ala Ser Pro Val Ala Gln Ser Tyr Leu Arg Asn Phe Leu Ala Ala
        435                 440                 445

Pro Pro Pro Gln Arg Ala Ala Met Ala Ala Gln Leu Gln Ala Val Pro
        450                 455                 460

Gly Ala Ala Gln Tyr Ile Gly Leu Val Glu Ser Val Ala Gly Ser Cys
465                 470                 475                 480

Asn Asn Tyr Glu Leu Met Thr Ile Asn Tyr Gln Phe Gly Asp Val Asp
                485                 490                 495

Ala His Gly Ala Met Ile Arg Ala Gln Ala Ala Ser Leu Glu Ala Glu
            500                 505                 510
```

His Gln Ala Ile Val Arg Asp Val Leu Ala Ala Gly Asp Phe Trp Gly
            515                 520                 525

Gly Ala Gly Ser Val Ala Cys Gln Glu Phe Ile Thr Gln Leu Gly Arg
        530                 535                 540

Asn Phe Gln Val Ile Tyr Glu Gln Ala Asn Ala His Gly Gln Lys Val
545                 550                 555                 560

Gln Ala Ala Gly Asn Asn Met Ala Gln Thr Asp Ser Ala Val Gly Ser
            565                 570                 575

Ser Trp Ala Thr Ser Asn Gly Arg Gln Cys Ala Gly Ile Leu Gln Ile
            580                 585                 590

Ser Ile Thr Leu Ala Ala Ala Arg
            595                 600

<210> SEQ ID NO 23
<211> LENGTH: 1104
<212> TYPE: DNA
<213> ORGANISM: Artificial Sequence
<220> FEATURE:
<223> OTHER INFORMATION: Description of Artificial Sequence:tri-fusion
      Erd14-DPV-MTI (designated Mtb36f)
<221> NAME/KEY: CDS
<222> LOCATION: (1)..(1104)

<400> SEQUENCE: 23 cat atg cat cac cat cac cat cac atg gcc acc acc ctt ccc gtt cag      48
His Met His His His His His His Met Ala Thr Thr Leu Pro Val Gln
 1               5                  10                  15 cgc cac ccg cgg tcc ctc ttc ccc gag ttt tct gag ctg ttc gcg gcc      96
Arg His Pro Arg Ser Leu Phe Pro Glu Phe Ser Glu Leu Phe Ala Ala
             20                  25                  30 ttc ccg tca ttc gcc gga ctc cgg ccc acc ttc gac acc cgg ttg atg     144
Phe Pro Ser Phe Ala Gly Leu Arg Pro Thr Phe Asp Thr Arg Leu Met
         35                  40                  45 cgg ctg gaa gac gag atg aaa gag ggg cgc tac gag gta cgc gcg gag     192
Arg Leu Glu Asp Glu Met Lys Glu Gly Arg Tyr Glu Val Arg Ala Glu
     50                  55                  60 ctt ccc ggg gtc gac ccc gac aag gac gtc gac att atg gtc cgc gat     240
Leu Pro Gly Val Asp Pro Asp Lys Asp Val Asp Ile Met Val Arg Asp
 65                  70                  75                  80 ggt cag ctg acc atc aag gcc gag cgc acc gag cag aag gac ttc gac     288
Gly Gln Leu Thr Ile Lys Ala Glu Arg Thr Glu Gln Lys Asp Phe Asp
                 85                  90                  95 ggt cgc tcg gaa ttc gcg tac ggt tcc ttc gtt cgc acg gtg tcg ctg     336
Gly Arg Ser Glu Phe Ala Tyr Gly Ser Phe Val Arg Thr Val Ser Leu
            100                 105                 110 ccg gta ggt gct gac gag gac gac att aag gcc acc tac gac aag ggc     384
Pro Val Gly Ala Asp Glu Asp Asp Ile Lys Ala Thr Tyr Asp Lys Gly
        115                 120                 125 att ctt act gtg tcg gtg gcg gtt tcg gaa ggg aag cca acc gaa aag     432
Ile Leu Thr Val Ser Val Ala Val Ser Glu Gly Lys Pro Thr Glu Lys
    130                 135                 140 cac att cag atc cgg tcc acc aac aag ctt gat ccc gtg gac gcg gtc     480
His Ile Gln Ile Arg Ser Thr Asn Lys Leu Asp Pro Val Asp Ala Val
145                 150                 155                 160 att aac acc acc tgc aat tac ggg cag gta gta gct gcg ctc aac gcg     528
Ile Asn Thr Thr Cys Asn Tyr Gly Gln Val Val Ala Ala Leu Asn Ala
                165                 170                 175 acg gat ccg ggg gct gcc gca cag ttc aac gcc tca ccg gtg gcg cag     576
Thr Asp Pro Gly Ala Ala Ala Gln Phe Asn Ala Ser Pro Val Ala Gln
            180                 185                 190

```
tcc tat ttg cgc aat ttc ctc gcc gca ccg cca cct cag cgc gct gcc    624
Ser Tyr Leu Arg Asn Phe Leu Ala Ala Pro Pro Pro Gln Arg Ala Ala
        195                 200                 205 atg gcc gcg caa ttg caa gct gtg ccg ggg gcg gca cag tac atc ggc    672
Met Ala Ala Gln Leu Gln Ala Val Pro Gly Ala Ala Gln Tyr Ile Gly
210                 215                 220 ctt gtc gag tcg gtt gcc ggc tcc tgc aac aac tat gag ctc atg acg    720
Leu Val Glu Ser Val Ala Gly Ser Cys Asn Asn Tyr Glu Leu Met Thr
225                 230                 235                 240 att aat tac cag ttc ggg gac gtc gac gct cat ggc gcc atg atc cgc    768
Ile Asn Tyr Gln Phe Gly Asp Val Asp Ala His Gly Ala Met Ile Arg
                245                 250                 255 gct cag gcg gcg tcg ctt gag gcg gag cat cag gcc atc gtt cgt gat    816
Ala Gln Ala Ala Ser Leu Glu Ala Glu His Gln Ala Ile Val Arg Asp
            260                 265                 270 gtg ttg gcc gcg ggt gac ttt tgg ggc ggc gcc ggt tcg gtg gct tgc    864
Val Leu Ala Ala Gly Asp Phe Trp Gly Gly Ala Gly Ser Val Ala Cys
        275                 280                 285 cag gag ttc att acc cag ttg ggc cgt aac ttc cag gtg atc tac gag    912
Gln Glu Phe Ile Thr Gln Leu Gly Arg Asn Phe Gln Val Ile Tyr Glu
290                 295                 300 cag gcc aac gcc cac ggg cag aag gtg cag gct gcc ggc aac aac atg    960
Gln Ala Asn Ala His Gly Gln Lys Val Gln Ala Ala Gly Asn Asn Met
305                 310                 315                 320 gcg caa acc gac agc gcc gtc ggc tcc agc tgg gcc act agt aac ggc    1008
Ala Gln Thr Asp Ser Ala Val Gly Ser Ser Trp Ala Thr Ser Asn Gly
                325                 330                 335 cgc cag tgt gct gga att ctg cag ata tcc atc aca ctg gcg gcc gct    1056
Arg Gln Cys Ala Gly Ile Leu Gln Ile Ser Ile Thr Leu Ala Ala Ala
            340                 345                 350 cga gca gat ccg gct gct aac aaa gcc cga aag gaa gct gag ttg gct    1104
Arg Ala Asp Pro Ala Ala Asn Lys Ala Arg Lys Glu Ala Glu Leu Ala
        355                 360                 365
```

<210> SEQ ID NO 24
<211> LENGTH: 368
<212> TYPE: PRT
<213> ORGANISM: Artificial Sequence
<220> FEATURE:
<223> OTHER INFORMATION: Description of Artificial Sequence:tri-fusion

<400> SEQUENCE: 24

```
His Met His His His His His Met Ala Thr Thr Leu Pro Val Gln
1               5                   10                  15

Arg His Pro Arg Ser Leu Phe Pro Glu Phe Ser Glu Leu Phe Ala Ala
            20                  25                  30

Phe Pro Ser Phe Ala Gly Leu Arg Pro Thr Phe Asp Thr Arg Leu Met
        35                  40                  45

Arg Leu Glu Asp Glu Met Lys Glu Gly Arg Tyr Glu Val Arg Ala Glu
    50                  55                  60

Leu Pro Gly Val Asp Pro Asp Lys Asp Val Asp Ile Met Val Arg Asp
65                  70                  75                  80

Gly Gln Leu Thr Ile Lys Ala Glu Arg Thr Glu Gln Lys Asp Phe Asp
                85                  90                  95

Gly Arg Ser Glu Phe Ala Tyr Gly Ser Phe Val Arg Thr Val Ser Leu
            100                 105                 110

Pro Val Gly Ala Asp Glu Asp Asp Ile Lys Ala Thr Tyr Asp Lys Gly
        115                 120                 125

Ile Leu Thr Val Ser Val Ala Val Ser Glu Gly Lys Pro Thr Glu Lys
    130                 135                 140
```

```
His Ile Gln Ile Arg Ser Thr Asn Lys Leu Asp Pro Val Asp Ala Val
145                 150                 155                 160

Ile Asn Thr Thr Cys Asn Tyr Gly Gln Val Val Ala Ala Leu Asn Ala
                165                 170                 175

Thr Asp Pro Gly Ala Ala Ala Gln Phe Asn Ala Ser Pro Val Ala Gln
            180                 185                 190

Ser Tyr Leu Arg Asn Phe Leu Ala Ala Pro Pro Gln Arg Ala Ala
        195                 200                 205

Met Ala Ala Gln Leu Gln Ala Val Pro Gly Ala Ala Gln Tyr Ile Gly
    210                 215                 220

Leu Val Glu Ser Val Ala Gly Ser Cys Asn Asn Tyr Glu Leu Met Thr
225                 230                 235                 240

Ile Asn Tyr Gln Phe Gly Asp Val Asp Ala His Gly Ala Met Ile Arg
                245                 250                 255

Ala Gln Ala Ala Ser Leu Glu Ala Glu His Gln Ala Ile Val Arg Asp
            260                 265                 270

Val Leu Ala Ala Gly Asp Phe Trp Gly Gly Ala Gly Ser Val Ala Cys
        275                 280                 285

Gln Glu Phe Ile Thr Gln Leu Gly Arg Asn Phe Gln Val Ile Tyr Glu
    290                 295                 300

Gln Ala Asn Ala His Gly Gln Lys Val Gln Ala Ala Gly Asn Asn Met
305                 310                 315                 320

Ala Gln Thr Asp Ser Ala Val Gly Ser Ser Trp Ala Thr Ser Asn Gly
                325                 330                 335

Arg Gln Cys Ala Gly Ile Leu Gln Ile Ser Ile Thr Leu Ala Ala Ala
            340                 345                 350

Arg Ala Asp Pro Ala Ala Asn Lys Ala Arg Lys Glu Ala Glu Leu Ala
        355                 360                 365

<210> SEQ ID NO 25
<211> LENGTH: 1797
<212> TYPE: DNA
<213> ORGANISM: Artificial Sequence
<220> FEATURE:
<223> OTHER INFORMATION: Description of Artificial Sequence:bi-fusion
      protein TbH9-Ra35 (designated Mtb59f)
<221> NAME/KEY: CDS
<222> LOCATION: (1)..(1791)

<400> SEQUENCE: 25 cat atg cat cac cat cac cat cac atg gtg gat ttc ggg gcg tta cca        48
His Met His His His His His His Met Val Asp Phe Gly Ala Leu Pro
  1               5

| | | |
|---|---|---|
| gcc cag gtc cgg gtt gct gcg gcg gcc tac gag acg gcg tat ggg ctg<br>Ala Gln Val Arg Val Ala Ala Ala Ala Tyr Glu Thr Ala Tyr Gly Leu<br>            100                          105                      110 | 336 |
| acg gtg ccc ccg ccg gtg atc gcc gag aac cgt gct gaa ctg atg att<br>Thr Val Pro Pro Pro Val Ile Ala Glu Asn Arg Ala Glu Leu Met Ile<br>        115                        120                      125 | 384 |
| ctg ata gcg acc aac ctc ttg ggg caa aac acc ccg gcg atc gcg gtc<br>Leu Ile Ala Thr Asn Leu Leu Gly Gln Asn Thr Pro Ala Ile Ala Val<br>130                        135                        140 | 432 |
| aac gag gcc gaa tac ggc gag atg tgg gcc caa gac gcc gcc gcg atg<br>Asn Glu Ala Glu Tyr Gly Glu Met Trp Ala Gln Asp Ala Ala Ala Met<br>145                      150                        155                      160 | 480 |
| ttt ggc tac gcc gcg gcg acg gcg acg gcg acg gcg acg ttg ctg ccg<br>Phe Gly Tyr Ala Ala Ala Thr Ala Thr Ala Thr Ala Thr Leu Leu Pro<br>                    165                        170                      175 | 528 |
| ttc gag gag gcg ccg gag atg acc agc gcg ggt ggg ctc ctc gag cag<br>Phe Glu Glu Ala Pro Glu Met Thr Ser Ala Gly Gly Leu Leu Glu Gln<br>        180                        185                      190 | 576 |
| gcc gcc gcg gtc gag gag gcc tcc gac acc gcg gcg aac cag ttg<br>Ala Ala Ala Val Glu Glu Ala Ser Asp Thr Ala Ala Ala Asn Gln Leu<br>                195                        200                      205 | 624 |
| atg aac aat gtg ccc cag gcg ctg caa cag ctg gcc cag ccc acg cag<br>Met Asn Asn Val Pro Gln Ala Leu Gln Gln Leu Ala Gln Pro Thr Gln<br>210                        215                        220 | 672 |
| ggc acg acg cct tct tcc aag ctg ggt ggc tgg aag acg gtc tcg<br>Gly Thr Thr Pro Ser Ser Lys Leu Gly Gly Leu Trp Lys Thr Val Ser<br>225                        230                        235                      240 | 720 |
| ccg cat cgg tcg ccg atc agc aac atg gtg tcg atg gcc aac aac cac<br>Pro His Arg Ser Pro Ile Ser Asn Met Val Ser Met Ala Asn Asn His<br>                    245                        250                      255 | 768 |
| atg tcg atg acc aac tcg ggt gtg tcg atg acc aac acc ttg agc tcg<br>Met Ser Met Thr Asn Ser Gly Val Ser Met Thr Asn Thr Leu Ser Ser<br>        260                        265                      270 | 816 |
| atg ttg aag ggc ttt gct ccg gcg gcg gcc gcc cag gcc gtg caa acc<br>Met Leu Lys Gly Phe Ala Pro Ala Ala Ala Ala Gln Ala Val Gln Thr<br>275                        280                        285 | 864 |
| gcg gcg caa aac ggg gtc cgg gcg atg agc tcg ctg ggc agc tcg ctg<br>Ala Ala Gln Asn Gly Val Arg Ala Met Ser Ser Leu Gly Ser Ser Leu<br>290                        295                        300 | 912 |
| ggt tct tcg ggt ctg ggc ggt ggg gtg gcc gcc aac ttg ggt cgg gcg<br>Gly Ser Ser Gly Leu Gly Gly Gly Val Ala Ala Asn Leu Gly Arg Ala<br>305                        310                        315                      320 | 960 |
| gcc tcg gtc ggt tcg ttg tcg gtg ccg cag gcc tgg gcc gcg gcc aac<br>Ala Ser Val Gly Ser Leu Ser Val Pro Gln Ala Trp Ala Ala Ala Asn<br>                    325                        330                      335 | 1008 |
| cag gca gtc acc ccg gcg gcg cgg gcg ctg ccg ctg acc agc ctg acc<br>Gln Ala Val Thr Pro Ala Ala Arg Ala Leu Pro Leu Thr Ser Leu Thr<br>        340                        345                      350 | 1056 |
| agc gcc gcg gaa aga ggg ccc ggg cag atg ctg ggc ggg ctg ccg gtg<br>Ser Ala Ala Glu Arg Gly Pro Gly Gln Met Leu Gly Gly Leu Pro Val<br>                355                        360                      365 | 1104 |
| ggg cag atg ggc gcc agg gcc ggt ggt ggg ctc agt ggt gtg ctg cgt<br>Gly Gln Met Gly Ala Arg Ala Gly Gly Gly Leu Ser Gly Val Leu Arg<br>        370                        375                      380 | 1152 |
| gtt ccg ccg cga ccc tat gtg atg ccg cat tct ccg gca gcc ggc gat<br>Val Pro Pro Arg Pro Tyr Val Met Pro His Ser Pro Ala Ala Gly Asp<br>385                        390                        395                      400 | 1200 |
| atc gcc ccg ccg gcc ttg tcg cag gac cgg ttc gcc gac ttc ccc gcg<br>Ile Ala Pro Pro Ala Leu Ser Gln Asp Arg Phe Ala Asp Phe Pro Ala<br>                    405                        410                      415 | 1248 |

```
ctg ccc ctc gac ccg tcc gcg atg gtc gcc caa gtg ggg cca cag gtg      1296
Leu Pro Leu Asp Pro Ser Ala Met Val Ala Gln Val Gly Pro Gln Val
            420                 425                 430 gtc aac atc aac acc aaa ctg ggc tac aac aac gcc gtg ggc gcc ggg      1344
Val Asn Ile Asn Thr Lys Leu Gly Tyr Asn Asn Ala Val Gly Ala Gly
        435                 440                 445 acc ggc atc gtc atc gat ccc aac ggt gtc gtg ctg acc aac aac cac      1392
Thr Gly Ile Val Ile Asp Pro Asn Gly Val Val Leu Thr Asn Asn His
450                 455                 460 gtg atc gcg ggc gcc acc gac atc aat gcg ttc agc gtc ggc tcc ggc      1440
Val Ile Ala Gly Ala Thr Asp Ile Asn Ala Phe Ser Val Gly Ser Gly
465                 470                 475                 480 caa acc tac ggc gtc gat gtg gtc ggg tat gac cgc acc cag gat gtc      1488
Gln Thr Tyr Gly Val Asp Val Val Gly Tyr Asp Arg Thr Gln Asp Val
                485                 490                 495 gcg gtg ctg cag ctg cgc ggt gcc ggt ggc ctg ccg tcg gcg gcg atc      1536
Ala Val Leu Gln Leu Arg Gly Ala Gly Gly Leu Pro Ser Ala Ala Ile
            500                 505                 510 ggt ggc ggc gtc gcg gtt ggt gag ccc gtc gtc gcg atg ggc aac agc      1584
Gly Gly Gly Val Ala Val Gly Glu Pro Val Val Ala Met Gly Asn Ser
        515                 520                 525 ggt ggg cag ggc gga acg ccc cgt gcg gtg cct ggc agg gtg gtc gcg      1632
Gly Gly Gln Gly Gly Thr Pro Arg Ala Val Pro Gly Arg Val Val Ala
530                 535                 540 ctc ggc caa acc gtg cag gcg tcg gat tcg ctg acc ggt gcc gaa gag      1680
Leu Gly Gln Thr Val Gln Ala Ser Asp Ser Leu Thr Gly Ala Glu Glu
545                 550                 555                 560 aca ttg aac ggg ttg atc cag ttc gat gcc gcg atc cag ccc ggt gat      1728
Thr Leu Asn Gly Leu Ile Gln Phe Asp Ala Ala Ile Gln Pro Gly Asp
                565                 570                 575 tcg ggc ggg ccc gtc gtc aac ggc cta gga cag gtg gtc ggt atg aac      1776
Ser Gly Gly Pro Val Val Asn Gly Leu Gly Gln Val Val Gly Met Asn
            580                 585                 590 acg gcc gcg tcc taggatatc                                            1797
Thr Ala Ala Ser
        595

<210> SEQ ID NO 26
<211> LENGTH: 596
<212> TYPE: PRT
<213> ORGANISM: Artificial Sequence
<220> FEATURE:
<223> OTHER INFORMATION: Description of Artificial Sequence:bi-fusion

<400> SEQUENCE: 26

His Met His His His His His His Met Val Asp Phe Gly Ala Leu Pro
1               5                   10                  15

Pro Glu Ile Asn Ser Ala Arg Met Tyr Ala Gly Pro Gly Ser Ala Ser
            20                  25                  30

Leu Val Ala Ala Ala Gln Met Trp Asp Ser Val Ala Ser Asp Leu Phe
        35                  40                  45

Ser Ala Ala Ser Ala Phe Gln Ser Val Val Trp Gly Leu Thr Val Gly
    50                  55                  60

Ser Trp Ile Gly Ser Ser Ala Gly Leu Met Val Ala Ala Ser Pro
65                  70                  75                  80

Tyr Val Ala Trp Met Ser Val Thr Ala Gly Gln Ala Glu Leu Thr Ala
                85                  90                  95

Ala Gln Val Arg Val Ala Ala Ala Ala Tyr Glu Thr Ala Tyr Gly Leu
            100                 105                 110

Thr Val Pro Pro Pro Val Ile Ala Glu Asn Arg Ala Glu Leu Met Ile
```

```
            115                 120                 125
Leu Ile Ala Thr Asn Leu Leu Gly Gln Asn Thr Pro Ala Ile Ala Val
130                 135                 140

Asn Glu Ala Glu Tyr Gly Glu Met Trp Ala Gln Asp Ala Ala Ala Met
145                 150                 155                 160

Phe Gly Tyr Ala Ala Ala Thr Ala Thr Ala Thr Ala Thr Leu Leu Pro
                165                 170                 175

Phe Glu Glu Ala Pro Glu Met Thr Ser Ala Gly Gly Leu Leu Glu Gln
                180                 185                 190

Ala Ala Ala Val Glu Glu Ala Ser Asp Thr Ala Ala Ala Asn Gln Leu
                195                 200                 205

Met Asn Asn Val Pro Gln Ala Leu Gln Gln Leu Ala Gln Pro Thr Gln
210                 215                 220

Gly Thr Thr Pro Ser Ser Lys Leu Gly Gly Leu Trp Lys Thr Val Ser
225                 230                 235                 240

Pro His Arg Ser Pro Ile Ser Asn Met Val Ser Met Ala Asn Asn His
                245                 250                 255

Met Ser Met Thr Asn Ser Gly Val Ser Met Thr Asn Thr Leu Ser Ser
                260                 265                 270

Met Leu Lys Gly Phe Ala Pro Ala Ala Ala Gln Ala Val Gln Thr
                275                 280                 285

Ala Ala Gln Asn Gly Val Arg Ala Met Ser Ser Leu Gly Ser Ser Leu
290                 295                 300

Gly Ser Ser Gly Leu Gly Gly Val Ala Ala Asn Leu Gly Arg Ala
305                 310                 315                 320

Ala Ser Val Gly Ser Leu Ser Val Pro Gln Ala Trp Ala Ala Ala Asn
                325                 330                 335

Gln Ala Val Thr Pro Ala Ala Arg Ala Leu Pro Leu Thr Ser Leu Thr
                340                 345                 350

Ser Ala Ala Glu Arg Gly Pro Gly Gln Met Leu Gly Gly Leu Pro Val
                355                 360                 365

Gly Gln Met Gly Ala Arg Ala Gly Gly Gly Leu Ser Gly Val Leu Arg
                370                 375                 380

Val Pro Pro Arg Pro Tyr Val Met Pro His Ser Pro Ala Ala Gly Asp
385                 390                 395                 400

Ile Ala Pro Pro Ala Leu Ser Gln Asp Arg Phe Ala Asp Phe Pro Ala
                405                 410                 415

Leu Pro Leu Asp Pro Ser Ala Met Val Ala Gln Val Gly Pro Gln Val
                420                 425                 430

Val Asn Ile Asn Thr Lys Leu Gly Tyr Asn Asn Ala Val Gly Ala Gly
                435                 440                 445

Thr Gly Ile Val Ile Asp Pro Asn Gly Val Val Leu Thr Asn Asn His
                450                 455                 460

Val Ile Ala Gly Ala Thr Asp Ile Asn Ala Phe Ser Val Gly Ser Gly
465                 470                 475                 480

Gln Thr Tyr Gly Val Asp Val Val Gly Tyr Asp Arg Thr Gln Asp Val
                485                 490                 495

Ala Val Leu Gln Leu Arg Gly Ala Gly Gly Leu Pro Ser Ala Ala Ile
                500                 505                 510

Gly Gly Gly Val Ala Val Gly Glu Pro Val Val Ala Met Gly Asn Ser
                515                 520                 525

Gly Gly Gln Gly Gly Thr Pro Arg Ala Val Pro Gly Arg Val Val Ala
530                 535                 540
```

```
Leu Gly Gln Thr Val Gln Ala Ser Asp Ser Leu Thr Gly Ala Glu Glu
545                 550                 555                 560

Thr Leu Asn Gly Leu Ile Gln Phe Asp Ala Ala Ile Gln Pro Gly Asp
                565                 570                 575

Ser Gly Gly Pro Val Val Asn Gly Leu Gly Gln Val Val Gly Met Asn
            580                 585                 590

Thr Ala Ala Ser
        595

<210> SEQ ID NO 27
<211> LENGTH: 702
<212> TYPE: DNA
<213> ORGANISM: Artificial Sequence
<220> FEATURE:
<223> OTHER INFORMATION: Description of Artificial Sequence:bi-fusion
      protein Ra12-DPPD (designated Mtb24), reading
      frame 1
<221> NAME/KEY: CDS
<222> LOCATION: (1)..(693)
<223> OTHER INFORMATION: bi-fusion protein Ra12-DPPD (designated Mtb24),
      reading frame 1
<221> NAME/KEY: CDS
<222> LOCATION: (2)..(700)
<223> OTHER INFORMATION: reading frame 2
<221> NAME/KEY: CDS
<222> LOCATION: (3)..(701)
<223> OTHER INFORMATION: reading frame 3

<400> SEQUENCE: 27 cat atg cat cac cat cac cat cac acg gcc gcg tcc gat aac ttc cag      48
His Met His His His His His His Thr Ala Ala Ser Asp Asn Phe Gln
  1               5                  10                  15 ctg tcc cag ggt ggg cag gga ttc gcc att ccg atc ggg cag gcg atg      96
Leu Ser Gln Gly Gly Gln Gly Phe Ala Ile Pro Ile Gly Gln Ala Met
             20                  25                  30 gcg atc gcg ggc cag atc cga tcg ggt ggg ggg tca ccc acc gtt cat     144
Ala Ile Ala Gly Gln Ile Arg Ser Gly Gly Gly Ser Pro Thr Val His
         35                  40                  45 atc ggg cct acc gcc ttc ctc ggc ttg ggt gtt gtc gac aac aac ggc     192
Ile Gly Pro Thr Ala Phe Leu Gly Leu Gly Val Val Asp Asn Asn Gly
     50                  55                  60 aac ggc gca cga gtc caa cgc gtg gtc ggg agc gct ccg gcg gca agt     240
Asn Gly Ala Arg Val Gln Arg Val Val Gly Ser Ala Pro Ala Ala Ser
 65                  70                  75                  80 ctc ggc atc tcc acc ggc gac gtg atc acc gcg gtc gac ggc gct ccg     288
Leu Gly Ile Ser Thr Gly Asp Val Ile Thr Ala Val Asp Gly Ala Pro
                 85                  90                  95 atc aac tcg gcc acc gcg atg gcg gac gcg ctt aac ggg cat cat ccc     336
Ile Asn Ser Ala Thr Ala Met Ala Asp Ala Leu Asn Gly His His Pro
            100                 105                 110 ggt gac gtc atc tcg gtg acc tgg caa acc aag tcg ggc ggc acg cgt     384
Gly Asp Val Ile Ser Val Thr Trp Gln Thr Lys Ser Gly Gly Thr Arg
        115                 120                 125 aca ggg aac gtg aca ttg gcc gag gga ccc ccg gcc gaa ttc gac gac     432
Thr Gly Asn Val Thr Leu Ala Glu Gly Pro Pro Ala Glu Phe Asp Asp
    130                 135                 140 gac gac aag gat cca cct gac ccg cat cag ccg gac atg acg aaa ggc     480
Asp Asp Lys Asp Pro Pro Asp Pro His Gln Pro Asp Met Thr Lys Gly
145                 150                 155                 160 tat tgc ccg ggt ggc cga tgg ggt ttt ggc gac ttg gcc gtg tgc gac     528
Tyr Cys Pro Gly Gly Arg Trp Gly Phe Gly Asp Leu Ala Val Cys Asp
                165                 170                 175 ggc gag aag tac ccc gac ggc tcg ttt tgg cac cag tgg atg caa acg     576
Gly Glu Lys Tyr Pro Asp Gly Ser Phe Trp His Gln Trp Met Gln Thr
```

```
                180                 185                 190
tgg ttt acc ggc cca cag ttt tac ttc gat tgt gtc agc ggc ggt gag    624
Trp Phe Thr Gly Pro Gln Phe Tyr Phe Asp Cys Val Ser Gly Gly Glu
        195                 200                 205 ccc ctc ccc ggc ccg ccg cca ccg ggt ggt tgc ggt ggg gca att ccg    672
Pro Leu Pro Gly Pro Pro Pro Pro Gly Gly Cys Gly Gly Ala Ile Pro
    210                 215                 220 tcc gag cag ccc aac gct ccc tgagaattc                              702
Ser Glu Gln Pro Asn Ala Pro
225                 230

<210> SEQ ID NO 28
<211> LENGTH: 231
<212> TYPE: PRT
<213> ORGANISM: Artificial Sequence
<220> FEATURE:
<223> OTHER INFORMATION: Description of Artificial Sequence:bi-fusion

<400> SEQUENCE: 28

His Met His His His His His Thr Ala Ala Ser Asp Asn Phe Gln
  1               5                  10                  15

Leu Ser Gln Gly Gly Gln Gly Phe Ala Ile Pro Ile Gly Gln Ala Met
             20                  25                  30

Ala Ile Ala Gly Gln Ile Arg Ser Gly Gly Ser Pro Thr Val His
         35                  40                  45

Ile Gly Pro Thr Ala Phe Leu Gly Leu Gly Val Val Asp Asn Asn Gly
     50                  55                  60

Asn Gly Ala Arg Val Gln Arg Val Val Gly Ser Ala Pro Ala Ala Ser
 65                  70                  75                  80

Leu Gly Ile Ser Thr Gly Asp Val Ile Thr Ala Val Asp Gly Ala Pro
                 85                  90                  95

Ile Asn Ser Ala Thr Ala Met Ala Asp Ala Leu Asn Gly His His Pro
            100                 105                 110

Gly Asp Val Ile Ser Val Thr Trp Gln Thr Lys Ser Gly Gly Thr Arg
        115                 120                 125

Thr Gly Asn Val Thr Leu Ala Glu Gly Pro Pro Ala Glu Phe Asp Asp
    130                 135                 140

Asp Asp Lys Asp Pro Pro Asp Pro His Gln Pro Asp Met Thr Lys Gly
145                 150                 155                 160

Tyr Cys Pro Gly Gly Arg Trp Gly Phe Gly Asp Leu Ala Val Cys Asp
                165                 170                 175

Gly Glu Lys Tyr Pro Asp Gly Ser Phe Trp His Gln Trp Met Gln Thr
            180                 185                 190

Trp Phe Thr Gly Pro Gln Phe Tyr Phe Asp Cys Val Ser Gly Gly Glu
        195                 200                 205

Pro Leu Pro Gly Pro Pro Pro Pro Gly Gly Cys Gly Gly Ala Ile Pro
    210                 215                 220

Ser Glu Gln Pro Asn Ala Pro
225                 230

<210> SEQ ID NO 29
<211> LENGTH: 87
<212> TYPE: PRT
<213> ORGANISM: Artificial Sequence
<220> FEATURE:
<223> OTHER INFORMATION: Description of Artificial Sequence:peptide of

<400> SEQUENCE: 29

Ile Cys Ile Thr Ile Thr Ile Thr Arg Pro Arg Pro Ile Thr Ser Ser
```

-continued

```
                1               5                  10                 15
Cys Pro Arg Val Gly Arg Asp Ser Pro Phe Arg Ser Gly Arg Arg Trp
                20                 25                 30

Arg Ser Arg Ala Arg Ser Asp Arg Val Gly Gly His Pro Pro Phe Ile
            35                 40                 45

Ser Gly Leu Pro Pro Ser Ser Ala Trp Val Leu Ser Thr Thr Thr Ala
        50                 55                 60

Thr Ala His Glu Ser Asn Ala Trp Ser Gly Ala Leu Arg Arg Gln Val
65                  70                 75                 80

Ser Ala Ser Pro Pro Ala Thr
                85

<210> SEQ ID NO 30
<211> LENGTH: 29
<212> TYPE: PRT
<213> ORGANISM: Artificial Sequence
<220> FEATURE:
<223> OTHER INFORMATION: Description of Artificial Sequence:peptide of

<400> SEQUENCE: 30

Ser Pro Arg Ser Thr Ala Leu Arg Ser Thr Arg Pro Pro Arg Trp Arg
1               5                  10                 15

Thr Arg Leu Thr Gly Ile Ile Pro Val Thr Ser Ser Arg
            20                 25

<210> SEQ ID NO 31
<211> LENGTH: 13
<212> TYPE: PRT
<213> ORGANISM: Artificial Sequence
<220> FEATURE:
<223> OTHER INFORMATION: Description of Artificial Sequence:peptide of

<400> SEQUENCE: 31

Pro Gly Lys Pro Ser Arg Ala Ala Arg Val Gln Gly Thr
1               5                  10

<210> SEQ ID NO 32
<211> LENGTH: 24
<212> TYPE: PRT
<213> ORGANISM: Artificial Sequence
<220> FEATURE:
<223> OTHER INFORMATION: Description of Artificial Sequence:peptide of

<400> SEQUENCE: 32

His Trp Pro Arg Asp Pro Arg Pro Asn Ser Thr Thr Thr Thr Arg Ile
1               5                  10                 15

His Leu Thr Arg Ile Ser Arg Thr
            20

<210> SEQ ID NO 33
<211> LENGTH: 77
<212> TYPE: PRT
<213> ORGANISM: Artificial Sequence
<220> FEATURE:
<223> OTHER INFORMATION: Description of Artificial Sequence:peptide of

<400> SEQUENCE: 33

Arg Lys Ala Ile Ala Arg Val Ala Asp Gly Val Leu Ala Thr Trp Pro
1               5                  10                 15

Cys Ala Thr Ala Arg Ser Thr Pro Thr Ala Arg Phe Gly Thr Ser Gly
            20                 25                 30

Cys Lys Arg Gly Leu Pro Ala His Ser Phe Thr Ser Ile Val Ser Ala
        35                 40                 45
```

Ala Val Ser Pro Ser Pro Ala Arg Arg His Arg Val Val Ala Val Gly
        50                  55                  60

Gln Phe Arg Pro Ser Ser Pro Thr Leu Pro Glu Asn Ser
 65                  70                  75

<210> SEQ ID NO 34
<211> LENGTH: 13
<212> TYPE: PRT
<213> ORGANISM: Artificial Sequence
<220> FEATURE:
<223> OTHER INFORMATION: Description of Artificial Sequence:peptide of

<400> SEQUENCE: 34

Pro Tyr Ala Ser Pro Ser Pro Ser His Gly Arg Val Arg
 1               5                  10

<210> SEQ ID NO 35
<211> LENGTH: 93
<212> TYPE: PRT
<213> ORGANISM: Artificial Sequence
<220> FEATURE:
<223> OTHER INFORMATION: Description of Artificial Sequence:peptide of

<400> SEQUENCE: 35

Leu Pro Ala Val Pro Gly Trp Ala Gly Ile Arg His Ser Asp Arg Ala
 1               5                  10                  15

Gly Asp Gly Asp Arg Gly Pro Asp Pro Ile Gly Trp Gly Val Thr His
                20                  25                  30

Arg Ser Tyr Arg Ala Tyr Arg Leu Pro Arg Leu Gly Cys Cys Arg Gln
            35                  40                  45

Gln Arg Gln Arg Arg Thr Ser Pro Thr Arg Gly Arg Glu Arg Ser Gly
        50                  55                  60

Gly Lys Ser Arg His Leu His Arg Arg Asp His Arg Gly Arg Arg
 65                  70                  75                  80

Arg Ser Asp Gln Leu Gly His Arg Asp Gly Arg Ala
                85                  90

<210> SEQ ID NO 36
<211> LENGTH: 5
<212> TYPE: PRT
<213> ORGANISM: Artificial Sequence
<220> FEATURE:
<223> OTHER INFORMATION: Description of Artificial Sequence:peptide of

<400> SEQUENCE: 36

Arg Ala Ser Ser Arg
 1               5

<210> SEQ ID NO 37
<211> LENGTH: 36
<212> TYPE: PRT
<213> ORGANISM: Artificial Sequence
<220> FEATURE:
<223> OTHER INFORMATION: Description of Artificial Sequence:peptide of

<400> SEQUENCE: 37

Arg His Leu Gly Asp Leu Ala Asn Gln Val Gly Arg His Ala Tyr Arg
 1               5                  10                  15

Glu Arg Asp Ile Gly Arg Gly Thr Pro Gly Arg Ile Arg Arg Arg
                20                  25                  30

Gln Gly Ser Thr
            35

```
<210> SEQ ID NO 38
<211> LENGTH: 56
<212> TYPE: PRT
<213> ORGANISM: Artificial Sequence
<220> FEATURE:
<223> OTHER INFORMATION: Description of Artificial Sequence:peptide of

<400> SEQUENCE: 38

Pro Ala Ser Ala Gly His Asp Glu Arg Leu Leu Pro Gly Trp Pro Met
 1               5                  10                  15

Gly Phe Trp Arg Leu Gly Arg Val Arg Arg Glu Val Pro Arg Arg
             20                  25                  30

Leu Val Leu Ala Pro Val Asp Ala Asn Val Val Tyr Arg Pro Thr Val
         35                  40                  45

Leu Leu Arg Leu Cys Gln Arg Arg
     50                  55

<210> SEQ ID NO 39
<211> LENGTH: 26
<212> TYPE: PRT
<213> ORGANISM: Artificial Sequence
<220> FEATURE:
<223> OTHER INFORMATION: Description of Artificial Sequence:peptide of

<400> SEQUENCE: 39

Ala Pro Pro Arg Pro Ala Ala Thr Gly Trp Leu Arg Trp Gly Asn Ser
 1               5                  10                  15

Val Arg Ala Ala Gln Arg Ser Leu Arg Ile
             20                  25

<210> SEQ ID NO 40
<211> LENGTH: 374
<212> TYPE: PRT
<213> ORGANISM: Mycobacterium tuberculosis
<220> FEATURE:
<223> OTHER INFORMATION: 38 kD antigen

<400> SEQUENCE: 40

Met Lys Ile Arg Leu His Thr Leu Leu Ala Val Leu Thr Ala Ala Pro
 1               5                  10                  15

Leu Leu Leu Ala Ala Ala Gly Cys Gly Ser Lys Pro Pro Ser Gly Ser
             20                  25                  30

Pro Glu Thr Gly Ala Gly Ala Gly Thr Val Ala Thr Thr Pro Ala Ser
         35                  40                  45

Ser Pro Val Thr Leu Ala Glu Thr Gly Ser Thr Leu Leu Tyr Pro Leu
     50                  55                  60

Phe Asn Leu Trp Gly Pro Ala Phe His Glu Arg Tyr Pro Asn Val Thr
 65                  70                  75                  80

Ile Thr Ala Gln Gly Thr Gly Ser Gly Ala Gly Ile Ala Gln Ala Ala
                 85                  90                  95

Ala Gly Thr Val Asn Ile Gly Ala Ser Asp Ala Tyr Leu Ser Glu Gly
            100                 105                 110

Asp Met Ala Ala His Lys Gly Leu Met Asn Ile Ala Leu Ala Ile Ser
        115                 120                 125

Ala Gln Gln Val Asn Tyr Asn Leu Pro Gly Val Ser Glu His Leu Lys
    130                 135                 140

Leu Asn Gly Lys Val Leu Ala Ala Met Tyr Gln Gly Thr Ile Lys Thr
145                 150                 155                 160

Trp Asp Asp Pro Gln Ile Ala Ala Leu Asn Pro Gly Val Asn Leu Pro
                165                 170                 175
```

```
Gly Thr Ala Val Val Pro Leu His Arg Ser Asp Gly Ser Gly Asp Thr
            180                 185                 190

Phe Leu Phe Thr Gln Tyr Leu Ser Lys Gln Asp Pro Glu Gly Trp Gly
        195                 200                 205

Lys Ser Pro Gly Phe Gly Thr Thr Val Asp Phe Pro Ala Val Pro Gly
210                 215                 220

Ala Leu Gly Glu Asn Gly Asn Gly Gly Met Val Thr Gly Cys Ala Glu
225                 230                 235                 240

Thr Pro Gly Cys Val Ala Tyr Ile Gly Ile Ser Phe Leu Asp Gln Ala
                245                 250                 255

Ser Gln Arg Gly Leu Gly Glu Ala Gln Leu Gly Asn Ser Ser Gly Asn
            260                 265                 270

Phe Leu Leu Pro Asp Ala Gln Ser Ile Gln Ala Ala Ala Gly Phe
        275                 280                 285

Ala Ser Lys Thr Pro Ala Asn Gln Ala Ile Ser Met Ile Asp Gly Pro
290                 295                 300

Ala Pro Asp Gly Tyr Pro Ile Ile Asn Tyr Glu Tyr Ala Ile Val Asn
305                 310                 315                 320

Asn Arg Gln Lys Asp Ala Ala Thr Ala Gln Thr Leu Gln Ala Phe Leu
                325                 330                 335

His Trp Ala Ile Thr Asp Gly Asn Lys Ala Ser Phe Leu Asp Gln Val
            340                 345                 350

His Phe Gln Pro Leu Pro Pro Ala Val Val Lys Leu Ser Asp Ala Leu
        355                 360                 365

Ile Ala Thr Ile Ser Ser
    370

<210> SEQ ID NO 41
<211> LENGTH: 3
<212> TYPE: PRT
<213> ORGANISM: Artificial Sequence
<220> FEATURE:
<223> OTHER INFORMATION: Description of Artificial Sequence:flexible
      polylinker

<400> SEQUENCE: 41

Gly Cys Gly
  1

<210> SEQ ID NO 42
<211> LENGTH: 6
<212> TYPE: PRT
<213> ORGANISM: Artificial Sequence
<220> FEATURE:
<223> OTHER INFORMATION: Description of Artificial Sequence:flexible
      polylinker

<400> SEQUENCE: 42

Gly Cys Gly Gly Cys Gly
  1               5

<210> SEQ ID NO 43
<211> LENGTH: 9
<212> TYPE: PRT
<213> ORGANISM: Artificial Sequence
<220> FEATURE:
<223> OTHER INFORMATION: Description of Artificial Sequence:flexible
      polylinker

<400> SEQUENCE: 43

Gly Cys Gly Gly Cys Gly Gly Cys Gly
```

```
<210> SEQ ID NO 44
<211> LENGTH: 5
<212> TYPE: PRT
<213> ORGANISM: Artificial Sequence
<220> FEATURE:
<223> OTHER INFORMATION: Description of Artificial Sequence:flexible
      polylinker

<400> SEQUENCE: 44

Gly Gly Gly Gly Ser
  1               5

<210> SEQ ID NO 45
<211> LENGTH: 10
<212> TYPE: PRT
<213> ORGANISM: Artificial Sequence
<220> FEATURE:
<223> OTHER INFORMATION: Description of Artificial Sequence:flexible
      polylinker

<400> SEQUENCE: 45

Gly Gly Gly Gly Ser Gly Gly Gly Gly Ser
  1               5                  10

<210> SEQ ID NO 46
<211> LENGTH: 15
<212> TYPE: PRT
<213> ORGANISM: Artificial Sequence
<220> FEATURE:
<223> OTHER INFORMATION: Description of Artificial Sequence:flexible
      polylinker

<400> SEQUENCE: 46

Gly Gly Gly Gly Ser Gly Gly Gly Gly Ser Gly Gly Gly Gly Ser
  1               5                  10                  15
```

What is claimed is:

1. A polynucleotide comprising a nucleotide sequence encoding a fusion protein comprising:
 (i) a DPV antigen consisting of residues 9 to 90 of SEQ ID NO:16, or an immunogenic fragment thereof;
 (ii) a MTI antigen consisting of residues 93 to 186 of SEQ ID NO:16, or an immunogenic fragment thereof;
- (iii) a MSL antigen consisting of residues 189 to 285 of SEQ ID NO:16, or an immunogenic fragment thereof; and
- (iv) a MTCC2 antigen consisting of residues 288 to 710 of SEQ ID NO:16, or an immunogenic fragment thereof.

2. The polynucleotide of claim 1, comprising a nucleotide sequence encoding a fusion protein comprising:
- (i) a DPV antigen consisting of residues 9 to 90 of SEQ ID NO:16;
- (ii) a MTI antigen consisting of residues 93 to 186 of SEQ ID NO:16;
- (iii) a MSL antigen consisting of residues 189 to 285 of SEQ ID NO:16; and
- (iv) a MTCC2 antigen consisting of residues 288 to 710 of SEQ ID NO:16.

3. The polynucleotide of claim 1, comprising a nucleotide sequence encoding a fusion protein consisting of:
- (i) a DPV antigen consisting of residues 9 to 90 of SEQ ID NO:16, or an immunogenic fragment thereof;
- (ii) a Mu antigen consisting of residues 93 to 186 of SEQ ID NO:16, or an immunogenic fragment thereof;
- (iii) a MSL antigen consisting of residues 189 to 285 of SEQ ID NO:16, or an immunogenic fragment thereof; and
- (iv) a MTCC2 antigen consisting of residues 288 to 710 of SEQ ID NO:16, or an immunogenic fragment thereof.

4. The polynucleotide of claim 3, comprising a nucleotide sequence encoding a fusion protein consisting of:
- (i) a DPV antigen consisting of residues 9 to 90 of SEQ ID NO:16;
- (ii) a MTI antigen consisting of residues 93 to 186 of SEQ ID NO:16;
- (iii) a MSL antigen consisting of residues 189 to 285 of SEQ ID NO:16; and
- (iv) a MTCC2 antigen consisting of residues 288 to 710 of SEQ ID NO:16.

5. The polynucleotide of claim 1, consisting of a nucleotide sequence encoding a fusion protein consisting of:
- (i) a DPV antigen consisting of residues 9 to 90 of SEQ ID NO:16, or an immunogenic fragment thereof;
- (ii) a Mu antigen consisting of residues 93 to 186 of SEQ ID NO:16, or an immunogenic fragment thereof; (iii) a MSL antigen consisting of residues 189 to 285 of SEQ ID NO:16, or an immunogenic fragment thereof; and
- (iv) a MTCC2 antigen consisting of residues 288 to 710 of SEQ ID NO:16, or an immunogenic fragment thereof.

6. The polynucleotide of claim 5, comprising a nucleotide sequence encoding a fusion protein consisting of:
- (i) a DPV antigen consisting of residues 9 to 90 of SEQ ID NO:16;

(ii) a Mu antigen consisting of residues 93 to 186 of SEQ ID NO:16;

(iii) a MSL antigen consisting of residues 189 to 285 of SEQ ID NO:16; and (iv) a MTCC2 antigen consisting of residues 288 to 710 of SEQ ID NO:16.

7. The polynucleotide of claim 1, wherein the antigens or immunogenic fragments thereof in the encoded fusion are joined at the amino- or carboxy-termini via peptide bonds.

8. The polynucleotide of claim 1, wherein the antigens or immunogenic fragments thereof in the encoded fusion are joined via peptide linkers from 1 to about 50 amino acids in length.

9. The polynucleotide of claim 1, comprising a nucleotide sequence encoding a fusion protein comprising residues 9 to 710 of SEQ ID NO:16.

10. The polynucleotide of claim 9, comprising a nucleotide sequence encoding a fusion protein comprising residues 3 to 710 of SEQ ID NO:16.

11. The polynucleotide of claim 1, comprising a nucleotide sequence encoding a fusion protein consisting of residues 9 to 710 of SEQ ID NO:16.

12. The polynucleotide of claim 1, comprising a nucleotide sequence encoding a fusion protein consisting of residues 3 to 710 of SEQ ID NO:16.

13. The polynucleotide of claim 1, consisting of a nucleotide sequence encoding a fusion protein consisting of residues 9 to 710 of SEQ ID NO:16.

14. The polynucleotide of claim 1, consisting of a nucleotide sequence encoding a fusion protein consisting of residues 3 to 710 of SEQ ID NO:16.

15. The polynucleotide of claim 1, which is in an expression vector.

16. The polynucleotide of claim 9, which is in an expression vector.

17. An isolated host cell transfected with the polynucleotide of claim 15.

18. The host cell of claim 17, wherein the host cell is a *Bacillus*-Calmette-Guerrin.

19. A pharmaceutical composition comprising the polynucleotide of claim 1 and a physiologically acceptable carrier.

20. The pharmaceutical composition of claim 19, wherein the polynucleotide comprises a nucleotide sequence encoding a fusion protein comprising residues 9 to 710 of SEQ ID NO:16.

21. A method to induce protective immunity against *M. tuberculosis*, comprising administering an effective amount of the polynucleotide of claim 2.

22. The method of claim 21, wherein the polynucleotide comprises a nucleotide sequence encoding a fusion protein comprising residues 9 to 710 of SEQ ID NO:16.

23. A method of recombinantly making a fusion protein, comprising the step of expressing the polynucleotide of claim 1 in a host cell.

* * * * *